US010385382B2

(12) United States Patent
Moysey et al.

(10) Patent No.: US 10,385,382 B2
(45) Date of Patent: Aug. 20, 2019

(54) ENZYME METHOD

(71) Applicant: OXFORD NANOPORE TECHNOLOGIES LIMITED, Oxford (GB)

(72) Inventors: Ruth Moysey, Oxford (GB); Andrew John Heron, Oxford (GB); Szabolcs Soeroes, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 359 days.

(21) Appl. No.: 14/369,072

(22) PCT Filed: Dec. 28, 2012

(86) PCT No.: PCT/GB2012/053274
§ 371 (c)(1),
(2) Date: Jun. 26, 2014

(87) PCT Pub. No.: WO2013/098562
PCT Pub. Date: Jul. 4, 2013

(65) Prior Publication Data
US 2014/0335512 A1 Nov. 13, 2014

Related U.S. Application Data

(60) Provisional application No. 61/581,332, filed on Dec. 29, 2011.

(51) Int. Cl.
| | |
|---|---|
| G01N 33/00 | (2006.01) |
| G01N 25/18 | (2006.01) |
| C12Q 1/68 | (2018.01) |
| C12Q 1/6869 | (2018.01) |
| C12N 9/14 | (2006.01) |

(52) U.S. Cl.
CPC ............... *C12Q 1/68* (2013.01); *C12N 9/14* (2013.01); *C12Q 1/6869* (2013.01); *C12Y 306/04012* (2013.01)

(58) Field of Classification Search
None
See application file for complete search history.

(56) References Cited

U.S. PATENT DOCUMENTS

| | | | |
|---|---|---|---|
| 7,338,807 B2 | 3/2008 | Harris et al. | |
| 7,625,706 B2 | 12/2009 | Akeson et al. | |
| 7,745,116 B2 | 6/2010 | Williams | |
| 7,851,203 B2 | 12/2010 | Letant et al. | |
| 7,947,454 B2 | 5/2011 | Akeson et al. | |
| 8,105,846 B2 | 1/2012 | Bayley et al. | |
| 8,785,211 B2 | 7/2014 | Bayley et al. | |
| 8,828,208 B2 | 9/2014 | Canas et al. | |
| 9,617,591 B2 | 4/2017 | Moysey et al. | |
| 9,758,823 B2 | 9/2017 | Moysey et al. | |
| 9,797,009 B2 | 10/2017 | Heron et al. | |
| 2003/0010638 A1 | 1/2003 | Hansford et al. | |
| 2004/0058378 A1* | 3/2004 | Kong | C12Q 1/6844 435/6.12 |
| 2004/0248114 A1 | 12/2004 | Taira et al. | |
| 2006/0063171 A1* | 3/2006 | Akeson | B01L 3/502707 435/6.11 |
| 2008/0293045 A1 | 11/2008 | Piepenburg et al. | |
| 2009/0256116 A1 | 10/2009 | Shumaker-Parry et al. | |
| 2010/0035260 A1* | 2/2010 | Olasagasti | C12Q 1/6869 435/6.16 |
| 2010/0092960 A1 | 4/2010 | Fehr | |
| 2010/0120098 A1 | 5/2010 | Grunenwald et al. | |
| 2010/0221212 A1 | 9/2010 | Stagliano et al. | |
| 2011/0177748 A1 | 7/2011 | Clarke et al. | |
| 2011/0229877 A1 | 9/2011 | Jayasinghe et al. | |
| 2011/0311965 A1* | 12/2011 | Maglia | C07K 14/245 435/6.1 |
| 2012/0058468 A1 | 3/2012 | Mckeown | |
| 2012/0107802 A1 | 5/2012 | Stoddart et al. | |
| 2013/0149769 A1 | 6/2013 | Kizaki et al. | |
| 2013/0225421 A1 | 8/2013 | Li et al. | |
| 2014/0051069 A1 | 2/2014 | Jayasinghe et al. | |
| 2014/0186823 A1 | 7/2014 | Clarke et al. | |
| 2014/0255921 A1 | 9/2014 | Moysey et al. | |
| 2014/0262784 A1 | 9/2014 | Clarke et al. | |
| 2015/0008126 A1 | 1/2015 | Maglia et al. | |
| 2015/0031020 A1 | 1/2015 | Jayasinghe et al. | |
| 2015/0065354 A1 | 3/2015 | Moysey et al. | |
| 2015/0152492 A1 | 6/2015 | Brown et al. | |
| 2015/0191709 A1 | 7/2015 | Heron et al. | |
| 2015/0197796 A1 | 7/2015 | White et al. | |

(Continued)

FOREIGN PATENT DOCUMENTS

| | | |
|---|---|---|
| JP | 2006-500028 A | 1/2006 |
| WO | 00/28312 A1 | 5/2000 |

(Continued)

OTHER PUBLICATIONS

U.S. Appl. No. 13/002,709, filed May 13, 2011, Lakmal Jayasinghe.
U.S. Appl. No. 13/968,778, filed Aug. 16, 2013, Lakmal Jayasinghe.
U.S. Appl. No. 14/455,394, filed Aug. 8, 2014, Lakmal Jayasinghe.
U.S. Appl. No. 13/002,717, filed Mar. 30, 2011, James Clarke.
U.S. Appl. No. 13/147,171, filed Nov. 10, 2011, Ruth Moysey.
U.S. Appl. No. 14/071,731, filed Nov. 5, 2013, Ruth Moysey.
U.S. Appl. No. 13/260,178, filed Jan. 17, 2012, David Stoddart.
U.S. Appl. No. 13/265,448, filed Feb. 10, 2012, Antonio Canas.
U.S. Appl. No. 13/512,937, filed Sep. 6, 2012, Clive Gavin Brown.
U.S. Appl. No. 14/302,303, filed Jun. 11, 2014, Clive Gavin Brown.
U.S. Appl. No. 12/339,956, filed Dec. 19, 2008, Stuart William Reid.

(Continued)

*Primary Examiner* — Bradley L. Sisson
(74) *Attorney, Agent, or Firm* — Wolf, Greenfield & Sacks, P.C.

(57) ABSTRACT

The invention relates to a new method of characterizing a target polynucleotide. The method uses a pore and a RecD helicase. The helicase controls the movement of the target polynucleotide through the pore.

10 Claims, 13 Drawing Sheets

Specification includes a Sequence Listing.

(56) References Cited

U.S. PATENT DOCUMENTS

| | | |
|---|---|---|
| 2015/0218629 A1 | 8/2015 | Heron et al. |
| 2016/0257942 A1 | 9/2016 | Bruce et al. |
| 2017/0002406 A1 | 1/2017 | Bowen et al. |
| 2018/0030530 A1 | 2/2018 | Moysey et al. |
| 2018/0037874 A9 | 2/2018 | Bruce et al. |
| 2018/0179500 A1 | 6/2018 | Heron et al. |
| 2018/0230526 A1 | 8/2018 | Heron et al. |

FOREIGN PATENT DOCUMENTS

| | | |
|---|---|---|
| WO | WO 2002/092821 | 11/2002 |
| WO | WO 2004/027025 A2 | 4/2004 |
| WO | 2005/124888 A1 | 12/2005 |
| WO | 2006/028508 A2 | 3/2006 |
| WO | 2006/100484 A2 | 9/2006 |
| WO | WO 2007/057668 | 5/2007 |
| WO | 2008/102120 A1 | 8/2008 |
| WO | 2008/102121 A1 | 8/2008 |
| WO | 2009/035647 A1 | 3/2009 |
| WO | WO 2009/044170 A1 | 4/2009 |
| WO | 2009/077734 A2 | 6/2009 |
| WO | 2010/004265 A1 | 1/2010 |
| WO | 2010/004273 A1 | 1/2010 |
| WO | 2010/086603 A1 | 8/2010 |
| WO | WO 2010/086602 A1 | 8/2010 |
| WO | WO 2010/086622 | 8/2010 |
| WO | 2010/109197 A2 | 9/2010 |
| WO | 2010/122293 A1 | 10/2010 |
| WO | 2011/067559 A1 | 6/2011 |
| WO | WO 2012/033524 A2 | 3/2012 |
| WO | WO 2012/164270 A1 | 12/2012 |
| WO | WO 2013/014451 A1 | 1/2013 |
| WO | WO 2013/041878 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/153359 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/135838 A1 | 9/2014 |
| WO | WO 2014/158665 A1 | 10/2014 |
| WO | WO 2015/055981 A2 | 4/2015 |
| WO | WO 2015/110777 A1 | 7/2015 |

OTHER PUBLICATIONS

U.S. Appl. No. 14/302,287, filed Jun. 11, 2014, Stuart William Reid.
U.S. Appl. No. 13/002,709, dated Mar. 10, 2014.
U.S. Appl. No. 13/002,709, dated Jun. 27, 2013.
U.S. Appl. No. 13/002,709, dated Dec. 21, 2012.
U.S. Appl. No. 13/968,778, dated Jul. 9, 2014.
U.S. Appl. No. 13/002,717, dated Apr. 3, 2014.
U.S. Appl. No. 13/002,717, dated Dec. 20, 2012.
U.S. Appl. No. 13/147,171, dated May 6, 2013.
U.S. Appl. No. 13/147,171, dated Jan. 3, 2013.
U.S. Appl. No. 13/260,178, dated Jan. 14, 2014.
U.S. Appl. No. 13/260,178, dated May 9, 2013.
U.S. Appl. No. 13/260,178, dated Feb. 20, 2013.
U.S. Appl. No. 13/265,448, dated Apr. 28, 2014.
U.S. Appl. No. 13/265,448, dated Jan. 10, 2014.
U.S. Appl. No. 12/339,956, dated Feb. 27, 2014.
U.S. Appl. No. 12/339,956, dated Jun. 12, 2013.
U.S. Appl. No. 12/339,956, dated Oct. 10, 2012.
U.S. Appl. No. 12/339,956, dated Mar. 28, 2012.
U.S. Appl. No. 12/339,956, dated Sep. 8, 2011.
U.S. Appl. No. 12/339,956, dated Apr. 25, 2011.
Altschul, Stephen F. et al., "Basic Local Alignment Search Tool," J. Mol. Biol., vol. 215:403-410 (1990).
Altschul, Stephen F., "A Protein Alignment Scoring System Sensitive at All Evolutionary Distances," J. Mol. Evol., vol. 36:290-300 (1993).
Braha, Orit et al., "Designed protein pores as components for biosensors," Chemistry & Biology, vol. 4:497-505 (1997).
Cheng, Yuan et al., "Functional Characterization of the Multidomain F Plasmid TraI Relaxase-Helicase," The Journal of Biological Chemistry, vol. 286(14):12670-12682 (2011).
Devereux, John et al., "A comprehensive set of sequence analysis programs for the VAX," Nucleic Acids Research, vol. 12(1):387-395 (1984).
Garcillan-Barcia, Maria Pilar et al., "The diversity of conjugative relaxases and its application in plasmid classification," FEMS Microbiol. Rev., vol. 33:657-687 (2009).
Grant, Gian Paola G. et al., "A facile method for attaching nitroxide spin labels at the 5' terminus of nucleic acids," Nucleic Acids Research, vol. 35(10):e77, doi:10.1093/nar/gkm240, 8 pages (2007).
Holden, Matthew A. et al., "Direct Introduction of Single Protein Channels and Pores into Lipid Bilayers," J. Am. Chem. Soc., vol. 127:6502-6503 (2005).
Holden, Matthew A. et al., "Functional Bionetworks from Nanoliter Water Droplets," J. Am. Chem. Soc., vol. 129:8650-8655 (2007).
Ivanov, Aleksandar P. et al., "DNA Tunneling Detector Embedded in a Nanopore," Nano Letters, vol. 11:279-285 (2011).
Kafri, Yariv et al., "Dynamics of Molecular Motors and Polymer Translocation with Sequence Heterogeneity," Biophysical Journal, vol. 86:3373-3391 (2004).
Kumar, Abhay et al., "Nonradioactive Labeling of Synthetic Oligonucleotide Probes with Terminal Deoxynucleotidyl Transferase," Analytical Biochemistry, vol. 169:376-382 (1988).
Lieberman, Kate R. et al., "Processive Replication of Single DNA Molecules in a Nanopore Catalyzed by phi29 DNA Polymerase," J. Am. Chem. Soc., vol. 132:17961-17972 (2010).
Montal, M. et al., "Formation of Biomolecular Membranes from Lipid Monolayers and a Study of Their Electrical Properties," Proc. Natl. Acad. Sci. USA, vol. 69(12):3561-3566 (1972).
Nikolov, Vesselin et al., "Behavior of Giant Vesicles with Anchored DNA Molecules," Biophysical Journal, vol. 92:4356-4368 (2007).
Pfeiffer, Indriati et al., "Bivalent Cholesterol-Based Coupling of Oligonucleotides to Lipid Membrane Assemblies," J. Am. Chem. Soc., vol. 126:10224-10225 (2004).
Satapathy, Ajit K. et al., "ATPase activity of RecD is essential for growth of the Antarctic Pseudomonas syringae Lz4W at low temperature," The FEBS Journal, vol. 275:1835-1851 (2008).
Soni, Gautam V. et al., "Synchronous optical and electrical detection of biomolecules traversing through solid-state nanopores," Review of Scientific Instruments, vol. 81:014301-1-014301-7 (2010).
Stoddart, David et al., "Single-nucleotide discimination in immobilized DNA oligonucleotides with a biological nanopore," PNAS, vol. 106(19):7702-7707 (2009).
Troutt, Anthony B. et al., "Ligation-anchored PCR: a simple amplification technique with single-sided specificity," Proc. Natl. Acad. Sci. USA, vol. 89:9823-9825 (1992).
Van Lengerich, Bettina et al., "Covalent attachment of lipid vesicles to a fluid supported bilayer allows observation of DNA-mediated vesicle interactions," Langmuir, vol. 26(11):8666-8672 (2010).
Yoshina-Ishii, Chiaki et al., "Arrays of Mobile Tethered Vesicles on Supported Lipid Bilayers," J. Am. Chem. Soc., vol. 125:3696-3697 (2003).
Blast® NCBI. Sequence ID No. 10; ZSYBNHWV114. Sep. 18, 2015.
Blast® NCBI. Sequence ID No. 52; ZT1133A811N. Sep. 18, 2015.
Genbank Submission. NCBI; Accession No. AM778123. Richards et al.; Sep. 18, 2008.
GenPept Accession No. XP 003728286. Jun. 7, 2012.
Press release: Oxford Nanopore introduces DNA 'strand sequencing' on the high-throughput GridION platform and presents MinION, a sequencer the size of a USB memory stick, Feb 2012.
UniProt Database accession No. b4kac8 sequence. Sep. 23, 2008.
UniProt Database accession No. Q7Y5C3 sequence. Oct. 1, 2003.
UniProt Database accession No. a4s1e1 sequence. May 15, 2007.
UniProt Database accession No. elqus6 sequence. Nov. 30, 2010.
UniProt Database accession No. i3d0e7 sequence. Jul. 11, 2012.
UniProt Database accession No. I7J3V8 sequence. Oct. 3, 2012.
UniProt Database accession No. k0im99 sequence. Nov. 28, 2012.
UniProt Database accession No. k7nri8 sequence. Feb. 6, 2013.

(56) References Cited

OTHER PUBLICATIONS

Sequence ID No. 2 Search Results. US-14-351-038-2. Sep. 16, 2015. 69 pages.
[No Author Listed] Antibodies bind specific molecules through their hypervariable loops. 33.3 Antibody Binding. 6$^{th}$ edition. 2007;953-954.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Comer et al., Microscopic mechanics of hairpin DNA translocation through synthetic nanopores. Biophys J. Jan. 2009;96(2):593-608. doi: 10.1016/j.bpj.2008.09.023.
Deamer, Nanopore analysis of nucleic acids bound to exonucleases and polymerases. Annu Rev Biophys. 2010;39:79-90. doi:10.1146/annurev.biophys.093008.131250.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Dostál et al., Tracking F plasmid TraI relaxase processing reactions provides insight into F plasmid transfer. Nucleic Acids Res. Apr. 2011;39(7):2658-70. doi: 10.1093/nar/gkq1137. Epub Nov. 24, 2010.
Dou et al., The DNA binding properties of the *Escherichia coli* RecQ helicase. J Biol Chem. Feb. 20, 2004;279(8):6354-63. Epub Dec. 9, 2003.
Fairman-Williams et al., SF1 and SF2 helicases: family matters. Curr Opin Struct Biol. Jun. 2010;20(3):313-24. doi:10.1016/j.sbi.2010.03.011. Epub Apr. 22, 2010.
Gonzalez-Perez et al., Biomimetic triblock copolymer membrane arrays: a stable template for functional membrane proteins. Langmuir. Sep. 15, 2009;25(18):10447-50. doi: 10.1021/1a902417m.
Green et al., Quantitative evaluation of the lengths of homobifunctional protein cross-linking reagents used as molecular rulers. Protein Sci. Jul. 2001;10(7):1293-304.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
He et al, The T4 phage SF1B helicase Dda is structurally optimized to perform DNA strand separation. Structure. Jul. 3, 2012;20(7):1189-200. doi:10.1016/j.str.2012.04.013. Epub May 31, 2012.
Hopfner et al., Mechanisms of nucleic acid translocases: lessons from structural biology and single-molecule biophysics. Curr Opin Struct Biol. Feb. 2007;17(1):87-95. Epub Dec. 6, 2006.
Hornblower et al., Single-molecule analysis of DNA-protein complexes using nanopores. Nat Methods. Apr. 2007;4(4):315-7. Epub Mar. 4, 2007.
Howorka et al., Nanopore analytics: sensing of single molecules. Chem Soc Rev. Aug. 2009;38(8):2360-84. doi: 10.1039/b813796j. Epub Jun. 15, 2009.
James, Aptamers. Encyclopedia of Analytical Chemistry. R.A. Meyers (Ed.). 4848-4871. John Wiley & Sons Ltd, Chichester, 2000.
Kar et al., Defining the structure-function relationships of bluetongue virus helicase protein VP6. J Virol. Nov. 2003;77(21):11347-56.
Keyser, Controlling molecular transport through nanopores. J R Soc Interface. Oct. 7, 2011;8(63):1369-78. doi: 10.1098/rsif.2011.0222. Epub Jun. 29, 2011.
Khafizov, Single Molecule Force Spectroscopy of Single Stranded Dna Binding Protein and Rep Helicase. University of Illinois at Urbana-Champaign Dissertation. 2012.

Liu et al., Adding new chemistries to the genetic code. Annu Rev Biochem. 2010;79:413-44. doi: 10.1146/annurev.biochem.052308.105824.
Liu et al., Structure of the DNA repair helicase XPD. Cell. May 30, 2008;133(5):801-12. doi: 10.1016/j.cell.2008.04.029.
Lohman et al., Non-hexameric DNA helicases and translocases:mechanisms and regulation. Nat Rev Mol Cell Biol. May 2008;9(5):391-401. doi:10.1038/nrm2394.
Ma et al., Bright functional rotaxanes. Chem Soc Rev. Jan. 2010;39(1):70-80. doi: 10.1039/b901710k. Epub Jul. 21, 2009.
Marini et al., A human DNA helicase homologous to the DNA cross-link sensitivity protein Mus308. J Biol Chem. Mar. 8, 2002;277(10):8716-23. Epub Dec. 18, 2001.
Morris et al., Evidence for a functional monomeric form of the bacteriophage T4 DdA helicase. Dda does not form stable oligomeric structures. J Biol Chem. Jun. 8, 2001;276(23):19691-8. Epub Feb. 27, 2001.
O'Shea et al., X-ray structure of the GCN4 leucine zipper, a two-stranded, parallel coiled coil. Science. Oct. 25, 1991;254(5031):539-44.
Pinero-Fernandez et al., Indole transport across *Escherichia coli* membranes. J Bacteriol. Apr. 2011;193(8):1793-8. doi:10.1128/JB.01477-10. Epub Feb. 4, 2011.
Remaut et al., Protein-protein interaction through beta-strand addition. Trends Biochem Sci. Aug. 2006;31(8):436-44. Epub Jul. 7, 2006.
Richards et al., Structure of the DNA repair helicase hel308 reveals DNA binding and autoinhibitory domains. J Biol Chem. Feb. 22, 2008;283(8):5118-26. Epub Dec. 4, 2007.
Saariaho et al., Characteristics of MuA transposase-catalyzed processing of model transposon end DNA hairpin substrates. Nucleic Acids Res. Jun. 6, 2006;34(10):3139-49. Print 2006.
Schneider et al., DNA sequencing with nanopores. Nat Biotechnol. Apr. 10, 2012;30(4):326-8. doi: 10.1038/nbt.2181.
Singleton et al., Structure and mechanism of helicases and nucleic acid translocases. Annu Rev Biochem. 2007;76:23-50.
Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.
Van Heel et al., Single-particle electron cryo-microscopy:towards atomic resolution. Q Rev Biophys. Nov. 2000;33(4):307-69.
Venkatesan et al., Nanopore sensors for nucleic acid analysis. Nat Nanotechnol. Sep. 18, 2011;6(10):615-24. doi: 10.1038/nnano.2011.129.
Vinson, Proteins in motion. Introduction. Science. Apr. 10, 2009;324(5924):197. doi: 10.1126/science.324.5924.197.
Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.
Korolev et al., Major domain swiveling revealed by the crystal structures of complexes of *E. coli* Rep helicase bound to single-stranded DNA and ADP. Cell. Aug. 22, 1997;90(4):635-47.
Raney et al., Structure and Mechanisms of SF1 DNA Helicases. Adv Exp Med Biol. 2013;767:17-46. doi: 10.1007/978-1-4614-5037-5_2.
U.S. Appl. No. 15/517,592, filed Apr. 7, 2017, Heron et al.
U.S. Appl. No. 15/674,653, filed Aug. 11, 2017, Moysey et al.
U.S. Appl. No. 15/704,395, filed Sep. 14, 2017, Heron et al.
Bennett et al., Association of yeast DNA topoisomerase III and Sgs1 DNA helicase: studies of fusion proteins. Proc Natl Acad Sci U S A. Sep. 25, 2001;98(20):11108-13.
Bessler et al., The amino terminus of the *Saccharomyces cerevisiae* DNA helicase Rrm3p modulates protein function ltering replication and checkpoint activity. Genetics. Nov. 2004;168(3):1205-18.
Data sheet SERO ID No. 10 search results from STIC, printed on Oct. 29, 2018, pp. 1-38 (Year: 2018).
Data sheet SERO ID No. 2 search results from STIC, printed on Oct. 29, 2018, pp. 1-24 (Year: 2018).
Durrieu et al., Interactions between neuronal fusion proteins explored by molecular dynamics. Biophys J. May 1, 2008;94(9):3436-46. doi:10.1529/biophysj.107.123117.

(56) References Cited

OTHER PUBLICATIONS

Guo et al., The linker region between the helicase and primase domains of the bacteriophage T7 gene 4 protein is critical for hexamer formation. J Biol Chem. Oct. 15, 1999;274(42):30303-9.

Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Marsault et al., Macrocycles are great cycles: applications, opportunities, and challenges of synthetic macrocycles in drug discovery. J Med Chem. Apr. 14, 2011;54(7):1961-2004. doi: 10.1021/jm1012374.

Mechanic et al., *Escherichia coli* DNA helicase II is active as a monomer. J Biol Chem. Apr. 30, 1999;274(18):12488-98.

Miles et al., Properties of Bacillus cereus hemolysin II: a heptameric transmembrane pore. Protein Sci. Jul. 2002;11(7):1813-24.

Ngo et al., Computational complexity, protein structure prediction, and the levinthal paradox. 14. The protein folding problem teritary structure prediction. Ed(s):Merz et al. Birkhauser, Boston, Ma. 1994. 433, 492-5.

Allen et al., The genome sequence of the psychrophilic archaeon, Methanococcoides burtonii: the role of genome evolution in cold adaptation. ISME J. Sep. 2009;3(9):1012-35. doi: 10.1038/ismej.2009.45.

Arslan et al., Protein structure. Engineering of a superhelicase through conformational control. Science. Apr. 17, 2015;348(6232):344-7. doi: 10.1126/science.aaa0445.

Balci et al., Single-molecule nanopositioning: structural transitions of a helicase-DNA complex during ATP hydrolysis. Biophys J. Aug. 17, 2011;101(4):976-84. doi: 10.1016/j.bpj.2011.07.010.

Buttner et al., Structural basis for DNA duplex separation by a superfamily-2 helicase. Nat Struct Mol Biol. Jul. 2007;14(7):647-52.

Colas et al., Microscopical investigations of nisin-loaded nanoliposomes prepared by Mozafari method and their bacterial targeting. Micron. 2007;38(8):841-7.

Eliseev et al., Molecular Recognition of Nucleotides, Nucleosides, and Sugars by Aminocyclodextrins. J. Am. Chem. Soc., vol. 116:6081-6088 (1994).

Garalde et al., Highly parallel direct RNA sequencing on an array of nanopores. bioRxiv. 2016. doi: http://dx.doi.org/10.1101/068809.

Genbank accession No. AEA72977 sequence. Apr. 6, 2011.

Kuper et al., Functional and structural studies of the nucleotide excision repair helicase XPD suggest a polarity for DNA translocation. EMBO J. Jan. 18, 2012;31(2):494-502. doi: 10.1038/emboj.2011.374.

Langecker et al., Synthetic lipid membrane channels formed by designed DNA nanostructures. Science. Nov. 16, 2012;338(6109):932-6. doi: 10.1126/science.1225624.

Maddox et al., Elevated serum levels in human pregnancy of a molecule immunochemically similar to eosinophil granule major basic protein. J Exp Med. Oct. 1, 1983;158(4):1211-26.

Portakal et al., Construction of recB-recD genetic fusion and functional analysis of RecBDC fusion enzyme in *Escherichia coli*. BMC Biochem. Oct. 10, 2008;9:27. doi: 10.1186/1471-2091-9-27.

Rudolf et al., The DNA repair helicases XPD and FancJ have essential iron-sulfur domains. Mol Cell. Sep. 15, 2006;23(6):801-8.

Rudolf et al., The helicase XPD unwinds bubble structures and is not stalled by DNA lesions removed by the nucleotide excision repair pathway. Nucleic Acids Res. Jan. 2010;38(3):931-41. doi:10.1093/nar/gkp1058.

Sathiyamoorthy et al., The crystal structure of *Escherichia coli* group 4 capsule protein GfcC reveals a domain organization resembling that of Wza. Biochemistry. Jun. 21, 2011;50(24):5465-76. doi: 10.1021/bi101869h.

UniProt Database accession No. D7RM26 sequence. Aug. 10, 2010.

UniProt Database accession No. I6ZR75 sequence. Oct. 3, 2012.

UniProt Database accession No. Q12WZ6 sequence. Apr. 12, 2017.

Wang et al., DNA helicase activity of the RecD protein from Deinococcus radiodurans. J Biol Chem. Dec. 10, 2004;279(50):52024-32.

White, Structure, function and evolution of the XPD family of iron-sulfur-containing 5'→3' DNA helicases. Biochem Soc Trans. 2009;37:547-551.

Woodman et al., Molecular biology of Hel308 helicase in archaea. Biochem Soc Trans. Feb. 2009;37(Pt 1):74-8. doi: 10.1042/BST0370074.

Woodman et al., Winged helix domains with unknown function in Hel308 and related helicases. Biochem Soc Trans. Jan. 2011;39(1):140-4. doi:10.1042/BST0390140.

Zhang et al., Structural evidence for consecutive Hel308-like modules in the spliceosomal ATPase Brr2. Nat Struct Mol Biol. Jul. 2009;16(7):731-9. doi: 10.1038/nsmb.1625.

* cited by examiner

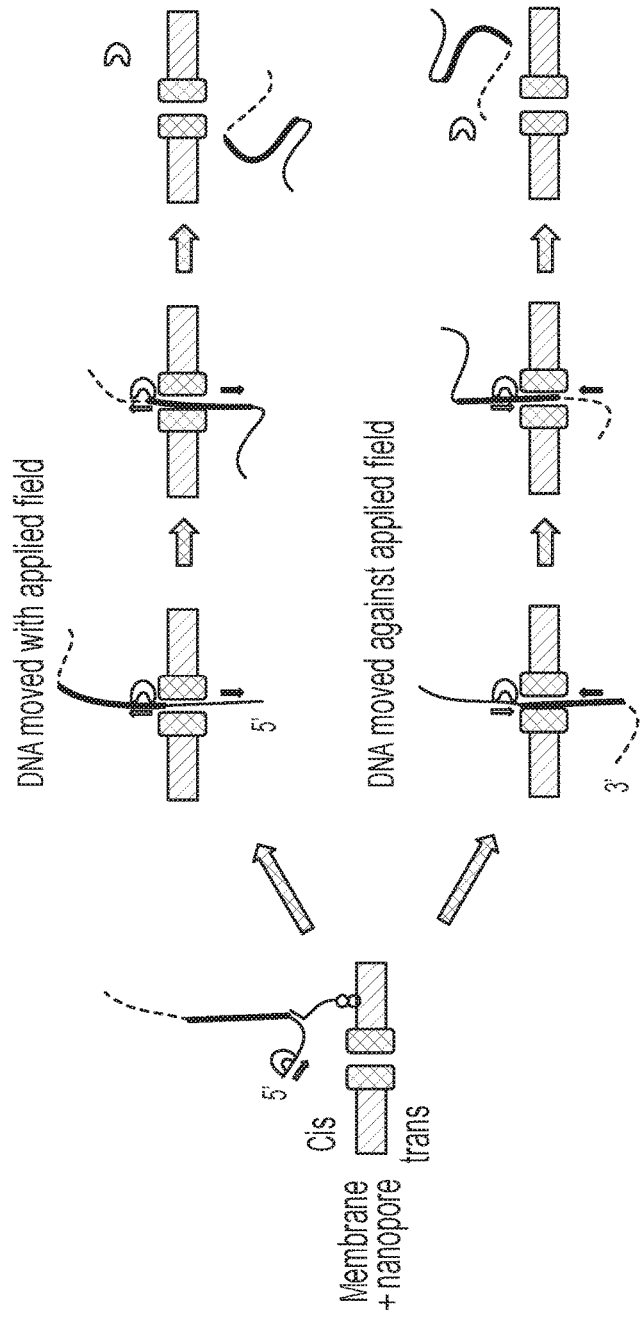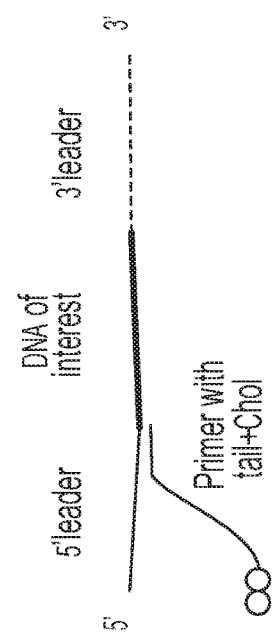
FIG. 1A
FIG. 1B

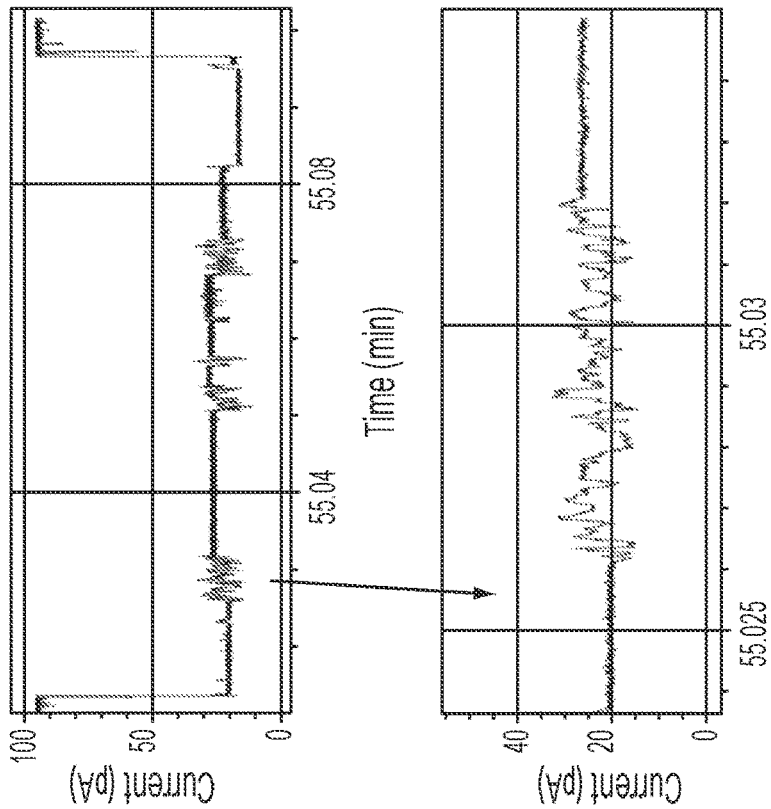
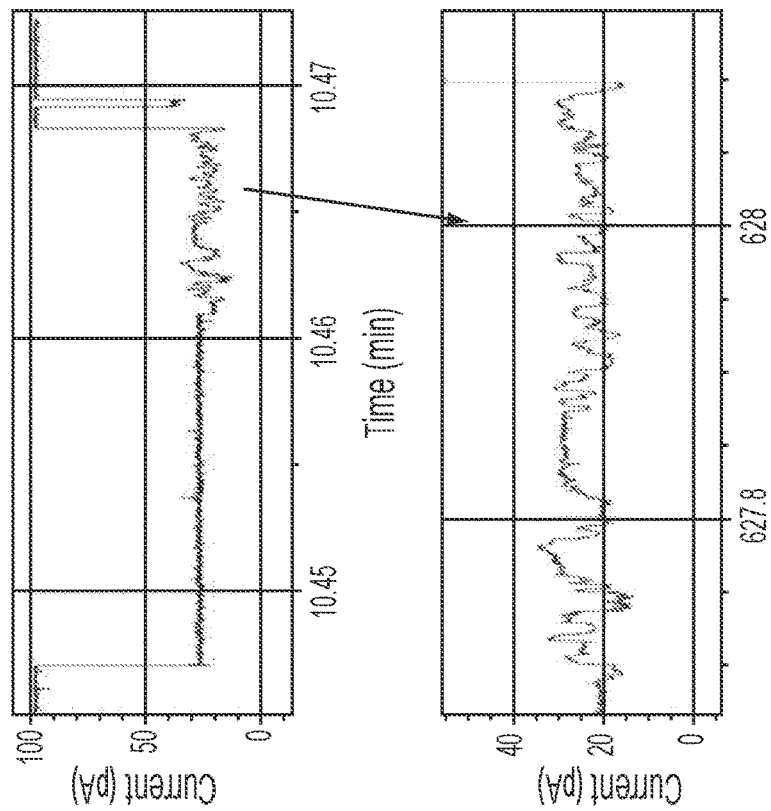
FIG. 5A
FIG. 5B

```
                       SEQUENCE LISTING

<160> NUMBER OF SEQ ID NOS: 182

<210> SEQ ID NO 1
<211> LENGTH: 558
<212> TYPE: DNA
<213> ORGANISM: Artificial sequence
<220> FEATURE:
<223> OTHER INFORMATION: MspA (D90N, D91N, D93N, D118R, D134R and E139K)

<400> SEQUENCE: 1
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                  558

<210> SEQ ID NO 2
<211> LENGTH: 184
<212> TYPE: PRT
<213> ORGANISM: Artificial sequence
<220> FEATURE:
<223> OTHER INFORMATION: MspA (D90N, D91N, D93N, D118R, D134R and E139K)

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
        50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175
```

Tyr Gly Glu Pro Trp Asn Met Asn
              180

<210> SEQ ID NO 3
<211> LENGTH: 885
<212> TYPE: DNA
<213> ORGANISM: Artificial sequence
<220> FEATURE:
<223> OTHER INFORMATION: a-hemolysin-E111N/K147N

<400> SEQUENCE: 3

```
atggcagatt ctgatattaa tattaaaacc ggtactacag atattggaag caatactaca      60
gtaaaaacag gtgatttagt cacttatgat aagaaaatg gcatgcacaa aaagtatt       120
tatagtttta tcgatgataa aaatcacaat aaaaaactgc tagttattag aacaaaaggt    180
accattgctg gtcaatatag agtttatagc gaagaaggtg ctaacaaaag tggtttagcc    240
tggccttcag cctttaaggt acagttgcaa ctacctgata tgaagtagc tcaaatatct     300
gattactatc caagaaattc gattgataca aaaaactata tgagtacttt aacttatgga    360
ttcaacggta atgttactgg tgatgataca ggaaaaattg gcggccttat tggtgcaaat    420
gtttcgattg gtcatacact gaactatgtt caacctgatt tcaaaacaat tttagagagc    480
ccaactgata aaaagtagg ctggaaagtg atatttaaca atatggtgaa tcaaaattgg    540
ggaccatacg atcgagattc ttggaacccg gtatatggca atcaactttt catgaaaact   600
agaaatggtt ctatgaaagc agcagataac ttccttgatc ctaacaaagc aagttctcta   660
ttatcttcag gttttcacc agacttcgct acagttatta ctatggatag aaaagcatcc    720
aaacaacaaa caaatataga tgtaatatac gaacgagttc gtgatgatta ccaattgcat   780
tggacttcaa caaattggaa aggtaccaat actaaagata aatggacaga tcgttcttca   840
gaaagatata aaatcgattg ggaaaaagaa gaatgacaa attaa                    885
```

<210> SEQ ID NO 4
<211> LENGTH: 293
<212> TYPE: PRT
<213> ORGANISM: Artificial sequence
<220> FEATURE:
<223> OTHER INFORMATION: a-hemolysin-E111N/K147N

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
        50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 6
<211> LENGTH: 184

<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
            165                 170                 175

Gly Glu Pro Trp Asn Met Asn
            180

<210> SEQ ID NO 8
<211> LENGTH: 8
<212> TYPE: PRT
<213> ORGANISM: Artificial sequence
<220> FEATURE:
<223> OTHER INFORMATION: RecD-like motif I
<220> FEATURE:
<221> NAME/KEY: MISC_FEATURE
<222> LOCATION: (1)..(1)
<223> OTHER INFORMATION: Xaa = G, S or A
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = P, A, S or G
<220> FEATURE:
<221> NAME/KEY: MISC_FEATURE
<222> LOCATION: (5)..(5)
<223> OTHER INFORMATION: Xaa = T, A, V, S or C
<220> FEATURE:
<221> NAME/KEY: MISC_FEATURE
<222> LOCATION: (6)..(6)
<223> OTHER INFORMATION: Xaa = G or A
<220> FEATURE:
<221> NAME/KEY: MISC_FEATURE
<222> LOCATION: (7)..(7)
<223> OTHER INFORMATION: Xaa = K or R
<220> FEATURE:
<221> NAME/KEY: MISC_FEATURE
<222> LOCATION: (8)..(8)
<223> OTHER INFORMATION: Xaa = T or S

<400> SEQUENCE: 8

Xaa Xaa Xaa Gly Xaa Xaa Xaa Xaa
1               5

<210> SEQ ID NO 9
<211> LENGTH: 25
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(17)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = G, S or A
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = P, A, S or G
<220> FEATURE:
<221> NAME/KEY: MISC_FEATURE
<222> LOCATION: (22)..(22)
<223> OTHER INFORMATION: Xaa = T, A, V, S or C
<220> FEATURE:
<221> NAME/KEY: MISC_FEATURE
<222> LOCATION: (23)..(23)
<223> OTHER INFORMATION: Xaa = G or A
<220> FEATURE:

```
<221> NAME/KEY: MISC_FEATURE
<222> LOCATION: (24)..(24)
<223> OTHER INFORMATION: Xaa = K or R
<220> FEATURE:
<221> NAME/KEY: MISC_FEATURE
<222> LOCATION: (25)..(25)
<223> OTHER INFORMATION: Xaa = T or S

<400> SEQUENCE: 9

Gln Xaa Xaa Xaa Xaa Xaa Xaa Xaa Xaa Xaa Xaa Xaa Xaa Xaa Xaa
1               5                   10                  15

Xaa Xaa Xaa Xaa Gly Xaa Xaa Xaa Xaa
            20                  25

<210> SEQ ID NO 10
<211> LENGTH: 26
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = G, S or A
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = P, A, S or G
<220> FEATURE:
<221> NAME/KEY: MISC_FEATURE
<222> LOCATION: (23)..(23)
<223> OTHER INFORMATION: Xaa = T, A, V, S or C
<220> FEATURE:
<221> NAME/KEY: MISC_FEATURE
<222> LOCATION: (24)..(24)
<223> OTHER INFORMATION: Xaa = G or A
<220> FEATURE:
<221> NAME/KEY: MISC_FEATURE
<222> LOCATION: (25)..(25)
<223> OTHER INFORMATION: Xaa = K or A
<220> FEATURE:
<221> NAME/KEY: MISC_FEATURE
<222> LOCATION: (26)..(26)
<223> OTHER INFORMATION: Xaa = T or S

<400> SEQUENCE: 10

Gln Xaa Xaa Xaa Xaa Xaa Xaa Xaa Xaa Xaa Xaa Xaa Xaa Xaa Xaa
1               5                   10                  15

Xaa Xaa Xaa Xaa Xaa Gly Xaa Xaa Xaa Xaa
            20                  25

<210> SEQ ID NO 11
<211> LENGTH: 27
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = G, S or A
```

```
<220> FEATURE:
<221> NAME/KEY: MISC_FEATURE
<222> LOCATION: (21)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = P, A, S or G
<220> FEATURE:
<221> NAME/KEY: MISC_FEATURE
<222> LOCATION: (24)..(24)
<223> OTHER INFORMATION: Xaa = T, A, V, S or C
<220> FEATURE:
<221> NAME/KEY: MISC_FEATURE
<222> LOCATION: (25)..(25)
<223> OTHER INFORMATION: Xaa = G or A
<220> FEATURE:
<221> NAME/KEY: MISC_FEATURE
<222> LOCATION: (26)..(26)
<223> OTHER INFORMATION: Xaa = K or R
<220> FEATURE:
<221> NAME/KEY: MISC_FEATURE
<222> LOCATION: (27)..(27)
<223> OTHER INFORMATION: Xaa = T or S

<400> SEQUENCE: 11

Gln Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Gly Xaa Xaa Xaa Xaa
            20                  25

<210> SEQ ID NO 12
<211> LENGTH: 8
<212> TYPE: PRT
<213> ORGANISM: Artificial sequence
<220> FEATURE:
<223> OTHER INFORMATION: RecD motif I
<220> FEATURE:
<221> NAME/KEY: MISC_FEATURE
<222> LOCATION: (5)..(5)
<223> OTHER INFORMATION: Xaa = T, V or C
<220> FEATURE:
<221> NAME/KEY: MISC_FEATURE
<222> LOCATION: (8)..(8)
<223> OTHER INFORMATION: Xaa = T or S

<400> SEQUENCE: 12

Gly Gly Pro Gly Xaa Gly Lys Xaa
1               5

<210> SEQ ID NO 13
<211> LENGTH: 25
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(17)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = T, V or C
<220> FEATURE:
<221> NAME/KEY: MISC_FEATURE
<222> LOCATION: (25)..(25)
<223> OTHER INFORMATION: Xaa = T or S

<400> SEQUENCE: 13

Gln Xaa Xaa Xaa Xaa Xaa Xaa Xaa Xaa Xaa Xaa Xaa Xaa Xaa Xaa
1               5                   10                  15
```

Xaa Gly Gly Pro Gly Xaa Gly Lys Xaa
            20              25

<210> SEQ ID NO 14
<211> LENGTH: 26
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(18)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = T, V or C
<220> FEATURE:
<221> NAME/KEY: MISC_FEATURE
<222> LOCATION: (26)..(26)
<223> OTHER INFORMATION: Xaa = T or S

<400> SEQUENCE: 14

Gln Xaa Xaa Xaa Xaa Xaa Xaa Xaa Xaa Xaa Xaa Xaa Xaa Xaa Xaa
1               5                   10                  15

Xaa Xaa Gly Gly Pro Gly Xaa Gly Lys Xaa
            20                  25

<210> SEQ ID NO 15
<211> LENGTH: 27
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(19)
<223> OTHER INFORMATION: Xaa = any amino acid
<220> FEATURE:
<221> NAME/KEY: MISC_FEATURE
<222> LOCATION: (24)..(24)
<223> OTHER INFORMATION: Xaa = T, V or C
<220> FEATURE:
<221> NAME/KEY: MISC_FEATURE
<222> LOCATION: (27)..(27)
<223> OTHER INFORMATION: Xaa = T or S

<400> SEQUENCE: 15

Gln Xaa Xaa Xaa Xaa Xaa Xaa Xaa Xaa Xaa Xaa Xaa Xaa Xaa Xaa
1               5                   10                  15

Xaa Xaa Xaa Gly Gly Pro Gly Xaa Gly Lys Xaa
            20                  25

<210> SEQ ID NO 16
<211> LENGTH: 10
<212> TYPE: PRT
<213> ORGANISM: Artificial sequence
<220> FEATURE:
<223> OTHER INFORMATION: RecD-like motif V
<220> FEATURE:
<221> NAME/KEY: MISC_FEATURE
<222> LOCATION: (1)..(1)
<223> OTHER INFORMATION: Xaa = Y, W or F
<220> FEATURE:
<221> NAME/KEY: MISC_FEATURE
<222> LOCATION: (2)..(2)
<223> OTHER INFORMATION: Xaa = A, T, S, M, C or V
<220> FEATURE:
<221> NAME/KEY: MISC_FEATURE
<222> LOCATION: (3)..(3)
<223> OTHER INFORMATION: Xaa = any amino acid
<220> FEATURE:

-continued

```
<221> NAME/KEY: MISC_FEATURE
<222> LOCATION: (4)..(4)
<223> OTHER INFORMATION: Xaa = T, N or S
<220> FEATURE:
<221> NAME/KEY: MISC_FEATURE
<222> LOCATION: (5)..(5)
<223> OTHER INFORMATION: Xaa = A, T, G, S, V or I
<220> FEATURE:
<221> NAME/KEY: MISC_FEATURE
<222> LOCATION: (6)..(8)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = G or S

<400> SEQUENCE: 16

Xaa Xaa Xaa Xaa Xaa Xaa Xaa Xaa Gln Xaa
1               5                   10

<210> SEQ ID NO 17
<211> LENGTH: 10
<212> TYPE: PRT
<213> ORGANISM: Artificial sequence
<220> FEATURE:
<223> OTHER INFORMATION: RecD motif V
<220> FEATURE:
<221> NAME/KEY: MISC_FEATURE
<222> LOCATION: (1)..(1)
<223> OTHER INFORMATION: Xaa = Y, W or F
<220> FEATURE:
<221> NAME/KEY: MISC_FEATURE
<222> LOCATION: (2)..(2)
<223> OTHER INFORMATION: Xaa = A, M, C or V
<220> FEATURE:
<221> NAME/KEY: MISC_FEATURE
<222> LOCATION: (3)..(3)
<223> OTHER INFORMATION: Xaa = I, M or L
<220> FEATURE:
<221> NAME/KEY: MISC_FEATURE
<222> LOCATION: (4)..(4)
<223> OTHER INFORMATION: Xaa = T or S
<220> FEATURE:
<221> NAME/KEY: MISC_FEATURE
<222> LOCATION: (5)..(5)
<223> OTHER INFORMATION: Xaa = V or I

<400> SEQUENCE: 17

Xaa Xaa Xaa Xaa Xaa His Lys Ser Gln Gly
1               5                   10

<210> SEQ ID NO 18
<211> LENGTH: 753
<212> TYPE: PRT
<213> ORGANISM: Acaryochloris marina

<400> SEQUENCE: 18

Met Pro Ser Ser Ser Ala His Pro Gly Ser Pro Pro Ile Glu Gln Leu
1               5                   10                  15

Gln Gly Val Val Glu Arg Leu Thr Phe His Ser Asp Glu Ser Gly Tyr
            20                  25                  30

Thr Val Ala Arg Leu Lys Ala Pro Arg Thr Arg Glu Leu Ile Thr Ile
        35                  40                  45

Val Gly Ser Phe Ala Asn Ile Gln Ala Gly Thr Leu Gln Leu Gln
    50                  55                  60

Gly Ile Trp Arg Asp His Pro Lys Tyr Gly Pro Gln Phe Gln Val Lys
65                  70                  75                  80

Gln Tyr Lys Glu Thr Lys Pro Ala Thr Leu Thr Gly Ile Glu Lys Tyr
                85                  90                  95
```

```
Leu Gly Ser Gly Leu Ile Lys Gly Val Gly Val Thr Ala Lys Arg
            100                 105                 110

Ile Val Ala His Phe Gly Leu Asp Thr Leu Asp Ile Glu Thr His
            115                 120                 125

Ile Glu Arg Leu Ile Glu Val Pro Gly Ile Ala Lys Lys Arg Val Lys
            130                 135                 140

Leu Ile Gln Thr Ala Leu Asp Ser Gln Lys Ala Ile Lys Glu Val Met
145                 150                 155                 160

Val Phe Leu Gln Gly His Gly Val Ser Thr Thr Tyr Ala Val Lys Ile
                    165                 170                 175

Phe Lys Gln Tyr Gly Asp Glu Ser Ile Glu Thr Val Thr His Asn Pro
                    180                 185                 190

Tyr Arg Leu Ala Thr Asp Val Tyr Gly Ile Gly Phe Val Thr Ala Asp
            195                 200                 205

Glu Ile Ala Arg Ser Leu Gly Ile Ser Pro His Ser Glu Tyr Arg Tyr
            210                 215                 220

Arg Ser Gly Leu Leu His Val Leu Ser Glu Ser Ala Glu Glu Gly His
225                 230                 235                 240

Cys Tyr Leu Pro Gln Pro Glu Leu Ile Asp Arg Ala Val Lys Arg Leu
                    245                 250                 255

Ala Leu Pro Asp Tyr Gln Pro Lys Pro Asp Gln Val Glu Tyr Leu Ile
                    260                 265                 270

His Ala Met Ile Ser Asp Ala Glu Leu Ile Val Glu Arg Leu Thr His
            275                 280                 285

Glu Gly Ser Thr Lys Leu Leu Cys Tyr Ala Pro Pro Phe Phe Gln Ala
            290                 295                 300

Glu Phe His Leu Ser Arg Arg Val Leu Gln Leu Leu Ala Ser Ser Leu
305                 310                 315                 320

Val Val Asp Asn Glu Arg Val Arg Ala Trp Leu Asp Arg Phe Met Ala
                    325                 330                 335

Gln Thr Asp Val Ser Leu Ser Lys Gln Gln Gln Ala Val Glu Met
                    340                 345                 350

Ala Ala Ser Gln Arg Val Val Ile Leu Thr Gly Gly Pro Gly Thr Gly
            355                 360                 365

Lys Thr Phe Thr Thr Arg Thr Ile Val Ala Leu Trp Lys Ala Met Gly
            370                 375                 380

Lys Asp Ile Val Leu Ala Ser Pro Thr Gly Arg Ala Ala Gln Arg Leu
385                 390                 395                 400

Ser Glu Val Thr Gly His Glu Ala Lys Thr Ile His Arg Leu Leu Glu
                    405                 410                 415

Phe Asp Pro Lys Thr Met Lys Phe Gln Arg Asn Ser Asn Pro Ile
                    420                 425                 430

Pro Ala Asp Ala Val Val Ile Asp Glu Ala Ser Met Leu Asp Leu Phe
            435                 440                 445

Leu Ala Asn Ser Leu Ile Lys Ala Ile Asp Thr Asn Ala Gln Leu Leu
            450                 455                 460

Leu Val Gly Asp Thr Asp Gln Leu Pro Ser Val Gly Pro Gly Asn Val
465                 470                 475                 480

Leu Leu Asp Leu Ile Thr Ser Gly Arg Ile Pro Ile Glu Leu Thr
                    485                 490                 495

Glu Val Phe Arg Gln Ala Gln Ala Ser His Ile Ile Arg Asn Ala His
            500                 505                 510
```

-continued

```
Arg Ile Asn Gln Gly Gln Phe Pro Asn Leu Glu Ser Val Ser Pro Ser
            515                 520                 525

Pro Lys Thr Asp Cys Leu Trp Leu Gly Ala Pro Glu Pro Glu Asn Gly
    530                 535                 540

Val Gln Ala Ile Gln Glu Leu Ile Asn Asp Leu Leu Pro Glu Leu Gly
545                 550                 555                 560

Phe Gln Pro Ala Arg Asp Val Gln Val Leu Cys Pro Met Thr Arg Gly
                565                 570                 575

Glu Val Gly Thr Arg Lys Leu Asn Gln Val Leu Gln Ala Leu Ile Asn
            580                 585                 590

Pro Pro Cys Pro Asp Lys Pro Glu Leu Thr Arg Gly Gly Leu Ile Leu
        595                 600                 605

Arg Val Gly Asp Arg Val Leu Gln Gln Val Asn Asp Tyr Asn Arg Glu
    610                 615                 620

Val Phe Asn Gly Asp Met Gly Val Ile Glu Asp Ile Asn Leu Glu Glu
625                 630                 635                 640

Ile Glu Val Thr Val His Tyr Ala Glu Arg Ser Val Ser Tyr Asp Leu
                645                 650                 655

Ala Asp Leu Asn Glu Ile Gly Leu Ala Trp Ala Val Thr Ile His Lys
            660                 665                 670

Ser Gln Gly Ser Glu Tyr Pro Val Val Ile Leu Pro Leu Tyr Met Gln
        675                 680                 685

His Tyr Ile Met Leu Ser Arg Asn Leu Leu Tyr Thr Gly Leu Thr Arg
    690                 695                 700

Ala Lys Lys Leu Ala Ile Leu Val Gly Pro Lys Asn Ala Ile Ser Met
705                 710                 715                 720

Ala Ile Arg Gln Ile Lys Asp Arg Gln Arg Tyr Thr Leu Leu Glu Arg
                725                 730                 735

Arg Leu Gly Gly Val Pro Lys Ala Asn Glu Ser Leu Ala Ser Ala Ile
            740                 745                 750

Leu

<210> SEQ ID NO 19
<211> LENGTH: 8
<212> TYPE: PRT
<213> ORGANISM: Artificial sequence
<220> FEATURE:
<223> OTHER INFORMATION: RecD motif I of RecD2 Ama

<400> SEQUENCE: 19

Gly Gly Pro Gly Thr Gly Lys Thr
1               5

<210> SEQ ID NO 20
<211> LENGTH: 10
<212> TYPE: PRT
<213> ORGANISM: Artificial sequence
<220> FEATURE:
<223> OTHER INFORMATION: RecD-like motif V of RecD2 Ama

<400> SEQUENCE: 20

Trp Ala Val Thr Ile His Lys Ser Gln Gly
1               5                   10

<210> SEQ ID NO 21
<211> LENGTH: 710
<212> TYPE: PRT
<213> ORGANISM: Deinococcus deserti
```

<400> SEQUENCE: 21

```
Met Ser His Ala Leu Pro Asn Glu Pro Phe Arg Val Thr Gly Gly Val
1               5                   10                  15

Asn Lys Val Arg Phe Arg Ala Glu Ser Gly Phe Thr Val Met Thr Ala
            20                  25                  30

Arg Leu Arg Asn Asn Asp Gly Glu Asp Pro Asp Ala Thr Val Ile Gly
        35                  40                  45

Met Met Pro Pro Leu Asp Ala Gly Asp Ser Phe Ser Ala Asp Val Leu
    50                  55                  60

Met Glu Glu His Arg Glu Tyr Gly Tyr Gln Tyr Arg Val Leu Asn Leu
65                  70                  75                  80

Val Leu Glu Ala Thr Pro Ala Asp Leu Thr Glu Ala Gly Val Ala Ala
                85                  90                  95

Tyr Leu Glu Ala Arg Val Gly Gly Val Gly Lys Val Leu Ala Gly Arg
            100                 105                 110

Ile Ala Lys Ala Phe Gly Pro Ala Thr Phe Asp Leu Leu Glu Thr Glu
        115                 120                 125

Pro Asp Lys Leu Leu Gln Val Pro Gly Val Thr Ala Ser Thr Leu His
    130                 135                 140

Lys Met Val Gln Ser Trp Ser Gln Gln Gly Leu Glu Arg Arg Leu Leu
145                 150                 155                 160

Ala Gly Leu Gln Gly Leu Gly Leu Thr Ile Ser Gln Ala Gln Arg Ala
                165                 170                 175

Val Lys His Phe Gly Glu Ala Ala Leu Glu Arg Leu Thr Ala Asp Leu
            180                 185                 190

Phe Ala Leu Thr Glu Val Glu Gly Ile Gly Phe Leu Thr Ala Asp Lys
        195                 200                 205

Leu Trp Gln Ser Gln Gly Gly Ala Leu Asp Asp Ala Arg Arg Leu Thr
    210                 215                 220

Ala Ala Ala Val Tyr Ala Leu Gln Gln Ala Gln Gln Gly Gly His
225                 230                 235                 240

Ser Tyr Leu Pro Arg Ser Arg Ala Glu Arg Gly Val Ala His Tyr Thr
                245                 250                 255

Arg Val Thr Gln Ala Gln Ala Gln Met Ala Val Asp Thr Ala Val Glu
            260                 265                 270

Leu Gly Arg Leu Ser Asp Asp Thr Pro Pro Leu Leu Asp Thr Gln Asp
        275                 280                 285

Pro Leu His Asp Gly Thr Arg Ile Tyr Leu Pro His Val Leu Arg Ala
    290                 295                 300

Glu Lys Lys Leu Ala Gly Leu Ile Arg Thr Leu Leu Ala Thr Pro Pro
305                 310                 315                 320

Ser Gly Glu Trp Ser Val Pro Ala Gly Ala Ser Lys Gly Leu Ser Glu
                325                 330                 335

Glu Gln Ala Gln Ile Leu Asp Leu Leu Glu Asp His Arg Leu Val Val
            340                 345                 350

Leu Thr Gly Gly Pro Gly Thr Gly Lys Ser Thr Thr Arg Ala Val
        355                 360                 365

Ala Asp Leu Ala Glu Arg Leu Gly Leu Glu Val Gly Leu Cys Ala Pro
    370                 375                 380

Thr Gly Lys Ala Ala Arg Arg Leu Gly Glu Val Thr Gly Arg Thr Ala
385                 390                 395                 400

Ser Thr Ile His Arg Leu Leu Gly Tyr Gly Pro Ala Gly Phe Arg His
                405                 410                 415
```

Asn His Leu Glu Pro Ala Pro Tyr Asp Leu Leu Ile Val Asp Glu Val
            420                 425                 430

Ser Met Cys Gly Asp Gly Leu Met Leu Ser Leu Leu Ala Ala Val Pro
        435                 440                 445

Pro Gly Ser Arg Val Leu Leu Val Gly Asp Thr Asp Gln Leu Pro Pro
    450                 455                 460

Val Asp Ala Gly Leu Pro Leu His Ala Leu Thr His Ala Ala Pro Thr
465                 470                 475                 480

Val Arg Leu Thr Gln Val Tyr Arg Gln Ala Ala Glu Asn Pro Ile Ile
            485                 490                 495

Arg Ala Ala His Gly Leu Leu Gln Gly Gln Ala Pro Ala Trp Gly Asp
                500                 505                 510

Pro Arg Leu Asn Leu Ile Glu Thr Glu Pro Asp Gly Gly Ala Arg Arg
            515                 520                 525

Val Ala Leu Thr Val Arg Glu Leu Gly Pro Thr Gln Val Gln Val
    530                 535                 540

Leu Thr Pro Met Arg Lys Gly Pro Leu Gly Val Glu Met Leu Asn His
545                 550                 555                 560

Gln Leu Gln Ser Leu Phe Asn Pro Gly Gln Gly Val Arg Ile Gly
                565                 570                 575

Asp Ser Glu Ala Arg Ala Gly Asp Val Val Val Gln Thr Lys Asn Asp
                580                 585                 590

Tyr Thr Asn Glu Ile Phe Asn Gly Thr Leu Gly Thr Val Leu Lys Ala
            595                 600                 605

Glu Gly Gly Arg Leu Thr Val Asp Phe Asp Gly Asn Ile Val Asp Leu
    610                 615                 620

Ala Gly Ala Glu Leu Phe Asn Leu Gln Leu Gly Tyr Ala Leu Thr Val
625                 630                 635                 640

His Arg Ala Gln Gly Ser Glu Trp Gly Thr Val Leu Gly Val Leu His
                645                 650                 655

Glu Ala His Met Pro Met Leu Ser Arg Asn Leu Val Tyr Thr Ala Leu
            660                 665                 670

Thr Arg Ala Arg Glu Arg Phe Tyr Ala Val Gly Ser Ala Thr Ser Trp
    675                 680                 685

Gln Lys Ala Ala Val Arg Gln Arg Glu Arg Asn Thr Ala Leu Leu
690                 695                 700

Glu Arg Ile Lys Ala Arg
705                 710

<210> SEQ ID NO 22
<211> LENGTH: 8
<212> TYPE: PRT
<213> ORGANISM: Artificial sequence
<220> FEATURE:
<223> OTHER INFORMATION: RecD motif I of RecD2 Dde

<400> SEQUENCE: 22

Gly Gly Pro Gly Thr Gly Lys Ser
1               5

<210> SEQ ID NO 23
<211> LENGTH: 10
<212> TYPE: PRT
<213> ORGANISM: Artificial sequence
<220> FEATURE:
<223> OTHER INFORMATION: RecD-like motif V of RecD2 Dde

```
<400> SEQUENCE: 23

Tyr Ala Leu Thr Val His Arg Ala Gln Gly
1               5                   10

<210> SEQ ID NO 24
<211> LENGTH: 726
<212> TYPE: PRT
<213> ORGANISM: Deinococcus geothermalis

<400> SEQUENCE: 24

Met Arg Glu Pro Pro Gly Val Phe Pro Ser Arg Gly Val Arg Ala Arg
1               5                   10                  15

Lys Gly Ala Ile Leu Ala Gly Met Ser Ala Gly Leu Pro Thr Glu Pro
                20                  25                  30

Phe Arg Val Thr Gly Gly Val Asn Lys Val Arg Phe Arg Ala Glu Ser
            35                  40                  45

Gly Phe Thr Val Met Ser Ala Arg Leu Arg Asn Ala Glu Gly Glu Asp
        50                  55                  60

Pro Asp Ala Thr Val Ile Gly Val Met Pro Pro Leu Glu Val Gly Asp
65                  70                  75                  80

Ser Phe Ser Ala Glu Val Leu Met Glu Glu His Arg Glu Tyr Gly His
                85                  90                  95

Gln Tyr Arg Val Leu Asn Met Val Leu Glu Ala Gln Pro Ala Asp Leu
            100                 105                 110

Thr Glu Ala Gly Val Ala Ala Tyr Leu Glu Ala Arg Val Gly Gly Val
        115                 120                 125

Gly Lys Val Leu Ala Gly Arg Ile Ala Arg Thr Phe Gly Pro Ala Thr
130                 135                 140

Phe Asp Val Leu Glu Gln Glu Pro Glu Lys Leu Leu Gln Val Pro Gly
145                 150                 155                 160

Val Thr Ala Ser Thr Leu His Lys Met Val Ser Ser Trp Ser Gln Gln
                165                 170                 175

Gly Leu Glu Arg Arg Leu Leu Ala Gly Leu Gln Gly Leu Gly Leu Ser
            180                 185                 190

Ile Ser Gln Ala Gln Arg Ala Val Lys His Phe Gly Glu Ala Ala Leu
        195                 200                 205

Glu Arg Leu Gln Ala Asp Leu Phe Ala Leu Thr Glu Val Glu Gly Ile
210                 215                 220

Gly Phe Leu Thr Ala Asp Arg Leu Trp Gln Ala Gln Gly Gly Ala Gln
225                 230                 235                 240

Asp Asp Pro Arg Arg Leu Thr Ala Ala Val Tyr Ala Leu Gln Gln
                245                 250                 255

Ala Gly Gln Gln Gly Gly His Ala Phe Leu Pro Arg Ala Arg Ala Glu
            260                 265                 270

Arg Gly Val Leu His Tyr Thr Arg Val Ser Pro Glu Gln Ala Arg Leu
        275                 280                 285

Ala Val Glu Thr Ala Thr Glu Leu Gly Arg Leu Ala Asp Asp Pro Thr
290                 295                 300

Pro Ala Gly Glu Ser Arg Ile Tyr Leu Pro His Val Leu Arg Thr Glu
305                 310                 315                 320

Lys Lys Leu Ala Gly Leu Ile Arg Thr Leu Leu Ala Thr Pro Pro Ala
                325                 330                 335

Gly Ala Glu Trp Ala Val Pro Val Gly Ala Ala Gln Gly Leu Ser Glu
            340                 345                 350
```

Glu Gln Ala Arg Val Leu Gln Leu Leu Glu Asp His Arg Leu Val Val
            355                 360                 365

Leu Thr Gly Gly Pro Gly Thr Gly Lys Ser Thr Ala Thr Arg Ala Val
370                 375                 380

Ala Asp Leu Ala Glu Arg Leu Gly Leu Glu Val Gly Leu Cys Ala Pro
385                 390                 395                 400

Thr Gly Lys Ala Ala Arg Arg Leu Gly Glu Val Thr Gly Arg Pro Ala
            405                 410                 415

Ser Thr Ile His Arg Leu Leu Gly Tyr Gly Pro Ala Gly Phe Arg His
            420                 425                 430

Asn His Leu Glu Pro Ala Pro Tyr Asp Leu Leu Ile Val Asp Glu Val
            435                 440                 445

Ser Met Thr Gly Asp Ala Leu Met Leu Ser Leu Leu Ala Ala Val Ala
        450                 455                 460

Pro Gly Ala Arg Val Leu Leu Val Gly Asp Thr Asp Gln Leu Pro Pro
465                 470                 475                 480

Val Asp Ser Gly Leu Pro Leu Leu Ala Ile Ala Gln Thr Ala Pro Thr
                485                 490                 495

Val Arg Leu Ser Thr Val Tyr Arg Gln Ala Ala Glu Asn Pro Ile Ile
                500                 505                 510

Arg Ala Ala His Gly Leu Leu His Gly Gln Ala Pro Ser Trp Gly Asp
                515                 520                 525

Pro Arg Leu Asp Leu Thr Glu Thr Glu Pro Asp Val Gly Ala Arg Arg
            530                 535                 540

Val Ala Leu Met Val Arg Asp Leu Gly Gly Pro Gly Arg Val Gln Val
545                 550                 555                 560

Leu Thr Pro Met Arg Lys Gly Pro Leu Gly Val Glu Thr Leu Asn Arg
                565                 570                 575

His Leu Gln Ala Leu Phe Asn Pro Gly Glu Gly Thr Arg Ile Ala
            580                 585                 590

Asp Gly Glu Ala Arg Pro Gly Asp Val Val Gln Thr Lys Asn Asp
            595                 600                 605

Tyr Gln Asn Glu Val Phe Asn Gly Thr Val Gly Thr Val Leu Lys Ala
            610                 615                 620

Glu Gly Gly Arg Leu Thr Val Asp Phe Asp Gly Asn Ile Val Glu Leu
625                 630                 635                 640

Ala Gly Ala Glu Leu Phe Asn Leu Gln Leu Gly Tyr Ala Leu Thr Val
                645                 650                 655

His Arg Ala Gln Gly Ser Glu Trp Pro Thr Val Leu Gly Val Leu His
            660                 665                 670

Glu Val His Met Pro Met Leu Ser Arg Asn Leu Ala Tyr Thr Ala Leu
        675                 680                 685

Thr Arg Ala Arg Glu Arg Phe Leu Ala Val Gly Ser Ala Ser Ala Trp
    690                 695                 700

Glu Lys Ala Ala Gly Arg Gln Arg Glu Glu Arg Asn Thr Ala Leu Leu
705                 710                 715                 720

Glu Arg Ile Arg Arg Arg
                725

<210> SEQ ID NO 25
<211> LENGTH: 768
<212> TYPE: PRT
<213> ORGANISM: Haliangium ochraceum DSM

<400> SEQUENCE: 25

```
Met Ala Gly Ser Pro Gly Asn Gly Pro Arg Thr Glu Arg His Arg Gln
1               5                   10                  15

Arg Arg Thr Pro Val Ala Asp Asp Pro Ala Gln Thr Gly Ser Val Val
            20                  25                  30

Glu Gly Thr Leu Thr Arg Ile Val Tyr Glu Asn Ala Asp Thr His Trp
                35                  40                  45

Thr Val Ala Arg Val Arg Val Gly Asp Asp Glu Ala Gly Thr Thr Arg
    50                  55                  60

Asp Pro Ala Ala Arg Ala Glu Gly Glu Ile Thr Val Val Gly Ser Met
65                  70                  75                  80

Val Gly Val Ala Pro Gly Thr Pro Leu Arg Leu Arg Gly Thr Trp Glu
                85                  90                  95

Gln His Asn Ser Tyr Gly Arg Gln Phe Arg Val His Ser Tyr Gln Ala
                100                 105                 110

Arg Met Pro Glu Thr Ile Ala Gly Leu Glu Arg Tyr Leu Gly Ser Gly
            115                 120                 125

Glu Phe Arg Gly Ile Gly Pro Glu Leu Ala Lys Arg Ile Val Glu His
            130                 135                 140

Phe Gly Leu Glu Ala Leu Ser Val Ile Glu Lys Ala Pro Lys Arg Leu
145                 150                 155                 160

Gln Glu Val Asp Gly Ile Gly Ala Ala Arg Ala Glu Lys Ile Ala Glu
                165                 170                 175

Ala Trp Thr Ala Gln Arg Asp Val His Asp Val Met Val Phe Leu Arg
            180                 185                 190

Gly Tyr Gly Val Thr Ala Ser Gln Ala Ala Arg Ile His Lys Arg Tyr
            195                 200                 205

Gly Asn Arg Ala Glu Ala Ile Val Arg Glu Asn Pro Tyr Arg Leu Ala
210                 215                 220

Leu Asp Ile Trp Gly Ile Gly Phe Lys Thr Ala Asp Ser Ile Ala Gln
225                 230                 235                 240

Asn Leu Gly Met Ala Arg Asp Ala Pro Glu Arg Leu Glu Ala Gly Leu
            245                 250                 255

Ile His Val Leu Gly Lys Leu Ala Glu Asp Gly His Val His Val Pro
            260                 265                 270

Glu Pro Asn Leu Leu Asp Thr Ala Ala Gly Ile Leu Glu Val Asp Ala
            275                 280                 285

Met Leu Leu Pro Glu Ala Leu Asp Arg Leu Glu Thr Ser Gln Leu Val
            290                 295                 300

Val Cys Glu Ala Leu Gly Asp Arg Gly Thr Cys Val Ser Leu Thr Phe
305                 310                 315                 320

Leu Trp Gln His Glu Ser Asp Ala Ala Ala Arg Tyr Ala Ala Leu Val
                325                 330                 335

Glu Thr Pro Met Arg Pro Arg Lys Leu Asp Leu Asp Gln Ala Leu Ala
            340                 345                 350

Ala Phe Glu Ala Glu Ala Glu Leu Ala Leu Thr Ala Glu Gln Arg Arg
            355                 360                 365

Ala Ala Leu Ala Ala Val Met Asp Lys Ser Val Val Leu Thr Gly Gly
            370                 375                 380

Pro Gly Val Gly Lys Thr Thr Ile Val Arg Ala Ile Val Phe Leu Phe
385                 390                 395                 400

Glu Arg Leu Gly Arg Ser Val Thr Leu Ala Ala Pro Thr Gly Arg Ala
                405                 410                 415
```

```
Ala Lys Arg Leu Ala Glu Ser Thr Ala Arg Asp Ala Thr Ile His
            420                 425                 430
Arg Leu Leu Glu Phe Gln Pro Ala Gly Gly Gly Phe Phe Arg Ser Ala
            435                 440                 445
Asp Asn Pro Leu Asp Ser Asp Val Val Ile Ile Asp Glu Thr Ser Met
        450                 455                 460
Val Asp Ile Ala Leu Leu Ala Ala Leu Leu Asp Ala Met Pro Ala Ser
465                 470                 475                 480
Ala Gln Leu Val Leu Val Gly Asp Ile Asp Gln Leu Pro Ser Val Gly
                485                 490                 495
Pro Gly Ala Val Leu Ala Asp Leu Ile Ala Ser Arg Ala Ala Thr Val
            500                 505                 510
Val Arg Leu Thr Glu Ile Phe Arg Gln Ala Arg Glu Ser Arg Ile Val
        515                 520                 525
Met Ala Ala His Glu Ile Asn Ser Gly Met Val Pro Gln Leu Ala Pro
530                 535                 540
Pro Gln Gly Thr Ser Ala His Arg Ser Asp Phe Tyr Phe Ile Ser Arg
545                 550                 555                 560
Glu Gln Pro Val Arg Ala Arg Glu Thr Ile Val Asp Leu Val Ala Glu
                565                 570                 575
Arg Ile Pro Glu Ala Phe Gly Phe Asp Pro Leu Ala Asp Ile Gln Val
            580                 585                 590
Leu Cys Pro Val His Arg Gly Glu Leu Gly Thr Ile Ala Leu Asn Arg
        595                 600                 605
Ala Leu Gln Glu Arg Leu Thr Pro Ala Val Asp Glu Gln His Gln Val
610                 615                 620
Thr Arg Gly Glu Arg Ser Tyr Arg Val Gly Asp Lys Val Met Gln Leu
625                 630                 635                 640
Glu Asn Asp Tyr Asp Arg Gly Val Phe Asn Gly Asp Ile Gly Val Ile
                645                 650                 655
Phe Glu Ile Ala Gly Glu Arg Lys Lys Val Leu Val Asp Tyr Met Asp
            660                 665                 670
Gly Arg Val Val Gly Tyr Glu Ala Arg Asp Leu Asp Gln Leu Thr His
        675                 680                 685
Ala Tyr Ala Ile Ser Val His Lys Ser Gln Gly Ser Glu Tyr Pro Val
690                 695                 700
Val Val Leu Pro Leu Ala Thr Gln His Tyr Ile Met Leu Gln Arg Asn
705                 710                 715                 720
Leu Leu Tyr Thr Ala Val Thr Arg Gly Lys Ser Leu Val Val Ile Val
                725                 730                 735
Gly Ser Ala Lys Ala Val Arg Arg Ala Val Glu Asn Gln Thr Asn Thr
            740                 745                 750
Ala Arg Trp Thr Trp Leu Ala Glu Arg Ile Arg Glu Gln Leu Gly Glu
        755                 760                 765

<210> SEQ ID NO 26
<211> LENGTH: 8
<212> TYPE: PRT
<213> ORGANISM: Artificial sequence
<220> FEATURE:
<223> OTHER INFORMATION: RecD motif I of RecD2 Hoc

<400> SEQUENCE: 26

Gly Gly Pro Gly Val Gly Lys Thr
1               5
```

```
<210> SEQ ID NO 27
<211> LENGTH: 10
<212> TYPE: PRT
<213> ORGANISM: Artificial sequence
<220> FEATURE:
<223> OTHER INFORMATION: RecD-like motif V of RecD2 Hoc

<400> SEQUENCE: 27

Tyr Ala Ile Ser Val His Lys Ser Gln Gly
1               5                   10

<210> SEQ ID NO 28
<211> LENGTH: 726
<212> TYPE: PRT
<213> ORGANISM: Natranaerobius thermophilus

<400> SEQUENCE: 28

Met Glu Met Ala Gln Ile Glu Gly Ile Ile Lys Arg Val Thr Tyr His
1               5                   10                  15

Asn Pro Glu Asn Met Phe Thr Val Ala Lys Leu Val Thr Gln Glu Thr
            20                  25                  30

Arg Asn Glu Ile Thr Ile Val Gly Asn Met Pro His Leu Thr Pro Gly
        35                  40                  45

Glu Arg Leu Asp Leu Ser Gly Glu Tyr Val Asp His Lys Lys Phe Gly
    50                  55                  60

Lys Gln Phe Gln Val Asp Ser Tyr Glu Ile Lys Leu Pro Val Thr Val
65                  70                  75                  80

Asp Gly Leu Ile Lys Phe Leu Ser Ser Gly Met Ile Lys Gly Ile Gly
                85                  90                  95

Pro Lys Thr Ala Glu Ser Leu Val Glu His Phe Gly Lys Glu Val Leu
            100                 105                 110

Gln Val Ile Glu Asn Thr Pro Glu Lys Leu Gln Glu Val Pro Gly Ile
        115                 120                 125

Gly Lys Glu Lys Ala Ala Gln Ile Ser Arg Gly Phe Gln Glu His Lys
    130                 135                 140

Gln Ile Lys Asp Ile Met Val Phe Leu Gln Glu Phe Gly Val Ser Pro
145                 150                 155                 160

Ala Phe Ala Leu Lys Ile Tyr Arg Arg Phe Gly Asp Asn Thr Ile Gln
                165                 170                 175

Lys Val Ser Glu Asn Pro Tyr Ser Leu Ala Arg Glu Val Phe Gly Ile
            180                 185                 190

Gly Phe Lys Thr Ala Asp Lys Ile Ala Arg Glu Met Gly Val Ser Val
        195                 200                 205

Asp Ser Glu Glu Arg Ala Lys Ala Ala Val Val Tyr Leu Leu Glu Glu
    210                 215                 220

Lys Ser Gln Asp Gly Asn Thr Phe Leu Lys Arg Glu Glu Leu Ile Glu
225                 230                 235                 240

Ala Leu Lys Glu Leu Glu Val Glu Asn Val Asn Leu Asn Ser Val Leu
                245                 250                 255

Glu Glu Leu Val Glu Glu Lys Glu Ile Val Val Glu Asn Ile Pro Glu
            260                 265                 270

Ala Gly Glu Leu Ile Tyr Pro Ala Pro Phe Phe Ala Glu Gln Gly
        275                 280                 285

Ile Ala Ser Arg Leu Lys Arg Leu Lys Asp Gly Val Asp Arg Glu Leu
    290                 295                 300

Phe Pro Arg Ile Gln Lys Ile Ala Glu Lys Tyr Leu Glu Glu Gln Ala
```

```
305                 310                 315                 320
Asn Leu Val Leu Ser Pro Glu Gln His Gln Val Ile Lys Gln Val Pro
                325                 330                 335

Glu Thr Gly Leu Met Val Val Thr Gly Pro Gly Thr Gly Lys Thr
            340                 345                 350

Thr Val Ile Lys Cys Leu Met Asp Ile Phe Gln Lys Ala Gly Gln Lys
                355                 360                 365

Val Met Leu Ala Ala Pro Thr Gly Arg Ala Ala Lys Arg Met Ser Glu
    370                 375                 380

Ala Thr Gly Asp Glu Ala Lys Thr Ile His Arg Leu Leu Glu Phe Thr
385                 390                 395                 400

Tyr Asp Lys Glu Glu Gly Met Lys Phe Gln Arg Asn Gln Asp Arg Pro
                405                 410                 415

Leu Lys Gly Asp Leu Leu Ile Val Asp Glu Ala Ser Met Ile Asp Thr
            420                 425                 430

Ile Leu Met Asn Asn Leu Leu Lys Ala Ile Ser Pro Gly Thr Arg Leu
        435                 440                 445

Val Leu Val Gly Asp Thr Asp Gln Leu Pro Ser Val Gly Ala Gly Asn
    450                 455                 460

Val Leu Gln Asp Ile Ile Glu Ser Gly Arg Ile Pro Leu Val Arg Leu
465                 470                 475                 480

Lys Arg Val Phe Arg Gln Ala Arg Glu Ser Met Val Val Asn Ala
                485                 490                 495

His Arg Ile Asn Glu Gly Lys Phe Pro Ile Leu Asn Ala Lys Gly Lys
            500                 505                 510

Asp Phe Tyr Phe Leu Pro Arg Glu Glu Pro Glu Asp Val Val Lys Thr
        515                 520                 525

Ile Ile Ser Leu Cys Ala Lys Arg Leu Pro Asn Tyr Asn Gly Tyr His
    530                 535                 540

Pro Val Asn Asp Ile Gln Val Leu Ser Pro Met Arg Arg Thr Val Thr
545                 550                 555                 560

Gly Val Glu Asn Leu Asn Gln Ser Leu Gln Lys Val Leu Asn Pro Pro
                565                 570                 575

Gln Lys Asn Lys Ala Glu Ile Asn Phe Gly Gly Ala Cys Tyr Arg Thr
            580                 585                 590

Gly Asp Lys Val Met Gln Val Lys Asn Asp Tyr Glu Lys Asn Val Phe
        595                 600                 605

Asn Gly Asp Thr Gly Ile Val Thr Lys Val Asp Ala Glu Glu Asn Val
    610                 615                 620

Val Asn Val Arg Tyr Gly His Gly Glu Glu Ile Ala Tyr Glu Gly Arg
625                 630                 635                 640

Glu Leu Asp Ala Leu Val His Ala Tyr Cys Ile Ser Val His Lys Ser
                645                 650                 655

Gln Gly Ser Glu Tyr Pro Val Val Leu Pro Val Thr Thr Gln His
            660                 665                 670

Tyr Ile Met Leu Gln Arg Asn Leu Leu Tyr Thr Ala Val Thr Arg Ala
        675                 680                 685

Lys Ser Leu Val Val Leu Val Gly Thr Lys Lys Ser Ile Gly Ile Ala
    690                 695                 700

Ile Ser Asn Lys Lys Thr Asp Glu Arg Asn Thr Phe Leu Gln His Arg
705                 710                 715                 720

Ile Ala Val Tyr Glu Val
                725
```

```
<210> SEQ ID NO 29
<211> LENGTH: 10
<212> TYPE: PRT
<213> ORGANISM: Artificial sequence
<220> FEATURE:
<223> OTHER INFORMATION: RecD-like motif V of RecD2 Nth

<400> SEQUENCE: 29

Tyr Cys Ile Ser Val His Lys Ser Gln Gly
1               5                   10

<210> SEQ ID NO 30
<211> LENGTH: 729
<212> TYPE: PRT
<213> ORGANISM: Octadecabacter antarcticus

<400> SEQUENCE: 30

Met Lys Gln Ser Ala Glu Asn Ser Lys Gln Glu Val Leu Ala Gly Leu
1               5                   10                  15

Val Glu Arg Val Thr Phe His Ser Leu Glu Ser Gly Phe Cys Val Leu
                20                  25                  30

Arg Leu Lys Ala Arg Gly His Arg Asp Leu Val Thr Thr Ile Gly His
            35                  40                  45

Ala Ala Met Ile Ser Ala Gly Glu Trp Val Thr Ala Ser Gly Asp Trp
        50                  55                  60

Ile Asn Asp Arg Asp His Gly Leu Gln Phe Lys Ala Arg Phe Leu Arg
65                  70                  75                  80

Thr Ser Ala Pro Ser Ser Leu Glu Gly Ile Glu Lys Tyr Leu Gly Ser
                85                  90                  95

Gly Met Ile Arg Gly Ile Gly Pro Val Tyr Ala Lys Arg Met Val Lys
            100                 105                 110

Lys Phe Gly Lys Asp Val Phe Asp Leu Ile Glu Ala Glu Pro Glu Arg
        115                 120                 125

Leu Arg Glu Val Glu Gly Ile Gly Pro Lys Arg Ala Asp Lys Ile Thr
130                 135                 140

Ser Ala Trp Ala Asp Gln Lys Val Ile Arg Glu Ile Met Val Phe Leu
145                 150                 155                 160

His Glu His Ser Val Gly Thr Ala Arg Ala Val Arg Ile Phe Lys Thr
                165                 170                 175

Tyr Gly Thr Asp Ala Val Gln Val Met Ser Glu Asn Pro Tyr Gln Leu
            180                 185                 190

Ala Arg Asp Ile Arg Gly Ile Gly Phe Arg Thr Ala Asp Met Ile Ala
        195                 200                 205

Glu Lys Leu Gly Ile Glu Lys Thr Ala Met Ile Arg Val Arg Ala Gly
    210                 215                 220

Ile Ser Tyr Ala Leu Thr Glu Ala Met Gly Asn Gly His Cys Gly Leu
225                 230                 235                 240

Pro Arg Gln Glu Leu Ile Pro Leu Ala Ile Lys Leu Leu Asp Val Pro
                245                 250                 255

Asp Glu Leu Ile His Thr Ala Ile Glu Phe Glu Ile Thr Asp Gly Thr
            260                 265                 270

Val Thr Ala Asp Thr Val Ser Asp Thr Pro Cys Val Phe Leu Ser Gly
        275                 280                 285

Leu Tyr His Ala Glu Lys Gly Ile Ala Gly Arg Phe Arg Ala Leu Ile
    290                 295                 300
```

```
Ser Gly Ser Leu Pro Trp Pro Lys Ile Asp Ala Asp Lys Ala Leu Pro
305                 310                 315                 320

Trp Val Glu Lys Lys Thr Gly Leu Ala Leu Ala Glu Ser Gln Val Glu
                325                 330                 335

Ala Ile Arg Leu Ala Leu Cys Ser Lys Val Thr Val Ile Thr Gly Gly
                340                 345                 350

Pro Gly Val Gly Lys Thr Thr Ile Val Asn Ser Ile Leu Gln Ile Leu
            355                 360                 365

Ala Ala Lys Ala Val Thr Leu Leu Cys Ala Pro Thr Gly Arg Ala
370                 375                 380

Ala Lys Arg Met Lys Glu Ala Thr Gly Met Glu Ala Lys Thr Ile His
385             390                 395                 400

Arg Leu Leu Glu Ile Asp Pro Asn Ser Phe Gly Phe Lys Arg Asn Glu
                405                 410                 415

Glu Asn Pro Leu Glu Cys Asp Leu Leu Val Ile Asp Glu Ser Ser Met
            420                 425                 430

Val Asp Val Ser Leu Met Gln Ser Leu Leu Arg Ala Val Pro Asp His
            435                 440                 445

Ala Ala Val Leu Ile Val Gly Asp Ile Asp Gln Leu Pro Ser Val Gly
450                 455                 460

Pro Gly Gln Val Leu Ala Asp Ile Ile Gly Ser Asn Ala Ile Pro Ile
465                 470                 475                 480

Val Arg Leu Thr Glu Val Phe Arg Gln Ala Lys Ser Arg Ile Ile
                485                 490                 495

Thr Asn Ala His Leu Ile Asn Lys Gly Lys Thr Pro Asp Leu Ser Thr
            500                 505                 510

Pro Asp Ser Glu Thr Asp Phe Tyr Phe Val Pro Ala Glu Asp Pro Glu
            515                 520                 525

Gln Ala Val Ser Arg Ile Ile Thr Leu Val Gln Ser Arg Ile Pro Lys
            530                 535                 540

Arg Phe Gly Leu Asp Pro Ile Arg Asp Ile Gln Val Leu Cys Pro Met
545                 550                 555                 560

Asn Arg Ser Gly Val Gly Ala Arg Ser Leu Asn Ile Glu Leu Gln Ala
                565                 570                 575

Ala Leu Asn Thr Pro Gly Glu Asn Lys Val Glu Arg Phe Gly Ser Thr
            580                 585                 590

Phe Ala Pro Gly Asp Lys Val Met Gln Ile Glu Asn Asp Tyr Asp Lys
            595                 600                 605

Glu Val Tyr Asn Gly Asp Ile Gly Tyr Val Glu Ser Val Asp Val Asn
            610                 615                 620

Glu Gly Glu Leu Thr Ala Ser Phe Asp Gly Arg Ala Val Ser Tyr Leu
625                 630                 635                 640

Phe Gly Glu Leu Asp Thr Leu Val Leu Ala Tyr Ala Ala Thr Ile His
                645                 650                 655

Lys Ser Gln Gly Ser Glu Tyr Pro Ala Val Val Ile Pro Val Leu Thr
            660                 665                 670

Gln His Tyr Val Met Leu Gln Arg Asn Leu Leu Tyr Thr Gly Ile Thr
            675                 680                 685

Arg Gly Lys Arg Leu Val Leu Val Gly Gln Arg Lys Ala Val Ala
            690                 695                 700

Ile Ala Val Lys Asn Val Ser Gly Arg Gln Arg Trp Ser Lys Leu Asn
705                 710                 715                 720

Glu Trp Leu Val Glu Gly Glu Gly Thr
```

<210> SEQ ID NO 31
<211> LENGTH: 10
<212> TYPE: PRT
<213> ORGANISM: Artificial sequence
<220> FEATURE:
<223> OTHER INFORMATION: RecD-like motif V of RecD2 Oan

<400> SEQUENCE: 31

Tyr Ala Ala Thr Ile His Lys Ser Gln Gly
1               5                   10

<210> SEQ ID NO 32
<211> LENGTH: 741
<212> TYPE: PRT
<213> ORGANISM: Salinispora tropica

<400> SEQUENCE: 32

Met Ala Asp Val Thr Ala Ala Pro Arg Pro Ala Leu Ala Thr Leu Asp
1               5                   10                  15

Ala Val Leu Glu Arg Leu Thr Tyr Val Asn Glu Glu Ser Gly Tyr Thr
                20                  25                  30

Val Ala Arg Val Ala Thr Asp Arg Gly Ser Asp Leu Leu Thr Val Val
            35                  40                  45

Gly Ala Leu Leu Gly Ala Gln Pro Gly Glu Ser Leu Arg Leu His Gly
        50                  55                  60

Arg Trp Ser Ser His Pro Lys Tyr Gly Arg Gln Phe Glu Val Asp Ser
65                  70                  75                  80

Tyr Thr Thr Val Leu Pro Ala Thr Ile Gln Gly Ile Gln Arg Tyr Leu
                85                  90                  95

Gly Ser Gly Leu Val Lys Gly Ile Gly Pro Val Phe Ala Glu Arg Ile
                100                 105                 110

Val Ala His Phe Gly Leu Glu Thr Leu Arg Ile Ile Glu Glu Glu Pro
            115                 120                 125

Ala Arg Leu Val Glu Val Pro Gly Leu Gly Pro Lys Arg Thr Ala Lys
        130                 135                 140

Ile Thr Ala Ala Trp Glu Glu Gln Gln Ala Ile Lys Glu Val Met Val
145                 150                 155                 160

Phe Leu Gln Gly Val Gly Val Ser Thr Ser Leu Ala Val Arg Ile Tyr
                165                 170                 175

Lys Gln Tyr Gly Asp Thr Ser Thr Asp Val Val Thr Lys Glu Pro Tyr
                180                 185                 190

Arg Leu Ala Ala Asp Val Trp Gly Ile Gly Phe Lys Thr Ala Asp Thr
            195                 200                 205

Ile Ala Gln Ser Val Gly Ile Pro His Asp Ser Pro Gln Arg Val Met
        210                 215                 220

Ala Gly Leu Gln Tyr Thr Leu Ser Glu Ala Thr Asp Asn Gly His Cys
225                 230                 235                 240

Tyr Leu Pro Glu Pro Glu Leu Ile Ala Asp Ala Thr Lys Ile Leu Asp
                245                 250                 255

Val Pro Ala Asp Leu Val Thr Arg Cys Leu Asp Asp Leu Val Ala Glu
                260                 265                 270

Glu Gly Val Val Arg Glu Ser Leu Pro Gly Gly Asp Ala Glu Pro Val
            275                 280                 285

Arg Ala Val Tyr Leu Val Pro Phe His Arg Ala Glu Arg Ser Leu Ala
        290                 295                 300

```
Thr Ser Leu Leu Arg Leu Leu Asp Asp Gly Thr Asp Arg Leu Pro His
305                 310                 315                 320

Phe Ala Gly Val Asp Trp Ala Lys Ala Leu Thr Trp Leu Lys Ala Arg
            325                 330                 335

Thr Gly Asn Asp Leu Ala Pro Glu Gln Glu Gln Ala Val Arg Leu Ala
            340                 345                 350

Leu Thr Ser Lys Val Ala Val Leu Thr Gly Gly Pro Gly Cys Gly Lys
            355                 360                 365

Ser Phe Thr Val Arg Ser Ile Val Glu Leu Ala Ala Ala Lys Arg Ala
370                 375                 380

Lys Val Thr Leu Val Ala Pro Thr Gly Arg Ala Ala Lys Arg Leu Ser
385                 390                 395                 400

Glu Leu Thr Gly His Pro Ala Ala Thr Val His Arg Leu Leu Gln Leu
                405                 410                 415

Arg Pro Gly Gly Asp Ala Ser Tyr Asp Arg Asp Asn Pro Leu Asp Val
                420                 425                 430

Asp Leu Leu Val Val Asp Glu Ala Ser Met Leu Asp Leu Ile Leu Ala
            435                 440                 445

Asn Lys Leu Val Lys Ala Val Pro Pro Gly Ala His Leu Leu Leu Val
450                 455                 460

Gly Asp Val Asp Gln Leu Pro Ser Val Gly Ala Gly Glu Val Leu Arg
465                 470                 475                 480

Asp Leu Leu Ala Ala Pro Ala Ile Pro Arg Val Arg Leu Thr Gln Ile
                485                 490                 495

Phe Arg Gln Ala Ala Gln Ser Gly Val Val Thr Asn Ala His Arg Ile
            500                 505                 510

Asn Ala Gly Arg Pro Pro Leu Leu Gln Gly Leu Pro Asp Phe Phe Leu
            515                 520                 525

Phe Ala Cys Asp Asp Thr Glu Ala Thr Ala Glu Arg Thr Val Asp Val
530                 535                 540

Ala Cys Ser Arg Ile Pro Ala Lys Phe Arg Leu Asp Pro Arg Arg Asp
545                 550                 555                 560

Val Gln Val Leu Thr Pro Met His Arg Gly Pro Ala Gly Ser Gly Ala
                565                 570                 575

Leu Asn Thr Leu Leu Gln Gln Arg Leu Thr Pro His Arg Glu Gly Gln
            580                 585                 590

Pro Glu Arg Arg Ala Gly Gly Arg Val Phe Arg Ile Gly Asp Lys Val
            595                 600                 605

Thr Gln Ile Arg Asn Asn Tyr Asp Lys Gly Glu Ala Gly Val Phe Asn
610                 615                 620

Gly Thr Leu Gly Ile Val Thr Gln Leu Ser Thr Glu Glu Gln Thr Leu
625                 630                 635                 640

Thr Val Arg Thr Asp Glu Asp Glu Ser Ile Asp Tyr Asp Phe Asp Glu
                645                 650                 655

Leu Asp Glu Leu Ala His Ala Tyr Ala Met Thr Ile His Arg Ser Gln
            660                 665                 670

Gly Ser Glu Tyr Pro Ala Val Val Ile Pro Leu Thr Thr Ser Ala Trp
            675                 680                 685

Met Met Leu Gln Arg Asn Leu Leu Tyr Thr Ala Val Thr Arg Ala Lys
            690                 695                 700

Gln Leu Val Val Leu Val Gly Ser Arg Arg Ala Leu Ala Ala Ala Val
705                 710                 715                 720
```

```
Arg Thr Val Gly Ala Gly Arg Arg His Thr Ala Leu Asn His Arg Leu
            725                 730                 735
Ala Ala Ala Thr Pro
            740

<210> SEQ ID NO 33
<211> LENGTH: 8
<212> TYPE: PRT
<213> ORGANISM: Artificial sequence
<220> FEATURE:
<223> OTHER INFORMATION: RecD motif I of RecD2 Str

<400> SEQUENCE: 33

Gly Gly Pro Gly Cys Gly Lys Ser
1               5

<210> SEQ ID NO 34
<211> LENGTH: 10
<212> TYPE: PRT
<213> ORGANISM: Artificial sequence
<220> FEATURE:
<223> OTHER INFORMATION: RecD-like motif V of RecD2 Str

<400> SEQUENCE: 34

Tyr Ala Met Thr Ile His Arg Ser Gln Gly
1               5                   10

<210> SEQ ID NO 35
<211> LENGTH: 732
<212> TYPE: PRT
<213> ORGANISM: Desulfonatronospira thiodismutans

<400> SEQUENCE: 35

Met Asn Thr Ser Asn Thr Thr Ser Leu Glu Tyr Leu Gln Gly Gln Ile
1               5                   10                  15
Glu Arg Ile Thr Tyr Thr Asn Glu Glu Asn Gly Tyr Thr Val Ala Lys
            20                  25                  30
Val Lys Val Arg Gly Arg Arg Asp Leu Val Thr Val Val Gly Ser Ile
        35                  40                  45
Ala Ser Pro Leu Ala Gly Gln Val Leu Lys Met Lys Gly Glu Trp Ser
    50                  55                  60
Asn His Pro Lys Phe Gly Glu Gln Phe Lys Ala Val Phe Cys Glu Cys
65                  70                  75                  80
Ala Val Pro Ala Thr Ser Ala Gly Ile Gln Arg Tyr Leu Gly Ser Gly
                85                  90                  95
Leu Ile Lys Gly Ile Gly Pro Val Met Ala Lys Lys Ile Val Ser Leu
            100                 105                 110
Phe Gly Asp Lys Thr Leu Asp Ile Ile Glu His Glu Thr Asp Arg Leu
        115                 120                 125
Thr Glu Val Asp Gly Ile Gly Gln Lys Arg Ile Glu Lys Ile Lys Lys
    130                 135                 140
Ala Trp Glu Glu Gln Lys Glu Ile Arg Glu Val Met Leu Phe Leu Gln
145                 150                 155                 160
Gly His Gly Val Ser Ser Thr Tyr Ala Ser Lys Ile Phe Lys Thr Tyr
                165                 170                 175
Gly Lys Asp Ser Ile Lys Val Val Gln Asp Asn Pro Tyr Arg Leu Ala
            180                 185                 190
Thr Asp Ile Phe Gly Ile Gly Phe Ile Thr Ala Asp Asn Ile Ala Gln
        195                 200                 205
```

Lys Leu Gly Phe Ser Leu Glu Ser Glu Phe Arg Ile Gln Ala Gly Ile
    210                 215                 220

Leu Tyr Val Leu His Gln Leu Ser Asp Glu Gly His Val Tyr Tyr Pro
225                 230                 235                 240

Arg Gln Asp Leu Ala Arg Lys Ala Ala Glu Ile Leu Lys Val Asp Ala
                245                 250                 255

Glu Leu Val Asp Gln Gln Ile Asp Ser Leu Glu Thr Leu Gln Tyr Ile
                260                 265                 270

Val Met Glu Ser Leu Pro Gln Gln Gln Lys Ala Val Tyr Leu Ala
            275                 280                 285

Lys Tyr Phe Tyr Ser Glu Thr Ser Ile Ala Ala Lys Leu Lys Leu
290                 295                 300

Ile Lys Ala Pro Lys Ser Ile Arg Gln Val Asp Thr Asp Lys Ala Leu
305                 310                 315                 320

Asp Trp Val Gln Lys Thr Tyr Gly Leu Asn Leu Ala Glu Lys Gln Ala
                325                 330                 335

Glu Ala Val Arg Lys Ala Leu Leu Asp Lys Ile Leu Val Ile Thr Gly
                340                 345                 350

Gly Pro Gly Thr Gly Lys Ser Phe Leu Leu Asn Ala Ile Leu Lys Ile
        355                 360                 365

Val Ser Arg Leu Lys Val Lys Ile Leu Leu Ala Ala Pro Thr Gly Arg
    370                 375                 380

Ala Ala Lys Arg Met Gln Glu Ser Thr Gly Tyr Glu Ala Lys Thr Ile
385                 390                 395                 400

His Arg Leu Leu Glu Phe Asp Phe Gln Lys Gly Gly Phe Lys Lys Asn
                405                 410                 415

Asp Glu His Pro Leu Asn Cys Asp Leu Leu Ile Val Asp Glu Met Ser
                420                 425                 430

Met Val Asp Thr Val Leu Met His His Leu Leu Lys Ala Val Arg Met
            435                 440                 445

Asp Thr Thr Leu Ile Met Val Gly Asp Val Asn Gln Leu Pro Ser Val
        450                 455                 460

Gly Pro Gly Asn Val Leu Lys Asp Ile Ile Asn Ser Gly Ser Val Pro
465                 470                 475                 480

Val Val Glu Leu Asn Glu Ile Phe Arg Gln Ala Arg Glu Ser Ser Ile
                485                 490                 495

Ile Val Asn Ala His Met Ile Asn Gln Gly Arg Leu Pro Val Leu Gln
                500                 505                 510

Pro Arg Gln Asp Lys Leu Asp Asp Phe Phe Phe Met Gln Glu Glu Asp
            515                 520                 525

Pro His Lys Val Leu Glu Lys Ile Lys Tyr Ile Val Met Glu Arg Ile
        530                 535                 540

Pro Gln Arg Phe Lys Leu Asn Pro Ile Asp His Val Gln Val Ile Ser
545                 550                 555                 560

Pro Met Asn Arg Gly Val Val Gly Val Ser Asn Leu Asn Thr Glu Leu
                565                 570                 575

Gln Ala Cys Leu Asn Pro Gln Gly Gln Glu Ile Ile Arg Gly Gly Lys
                580                 585                 590

Thr Phe Arg Gln Gly Asp Lys Val Met Gln Ile Arg Asn Asn Tyr Asp
                595                 600                 605

Lys Glu Val Phe Asn Gly Asp Ile Gly Val Ile Thr Gly Leu Asp Leu
            610                 615                 620

Glu Glu Gln Glu Ile Lys Val Arg Phe Tyr Asp Arg Gln Val Val Tyr

```
                625                 630                 635                 640
Glu Tyr Ser Asp Leu Asp Glu Leu Val Leu Ala Tyr Ala Val Ser Ile
                    645                 650                 655
His Lys Ser Gln Gly Ser Asp Tyr Pro Ala Val Val Ile Pro Leu Leu
                660                 665                 670
Thr Gln His Tyr Ile Met Leu Gln Lys Asn Leu Val Tyr Thr Gly Ile
                675                 680                 685
Thr Arg Gly Lys Asn Leu Val Val Ile Gly Thr Lys Lys Ala Leu
            690                 695                 700
Ala Ile Ala Val Lys Asn Ala Gly Thr Asn Glu Arg Tyr Thr His Leu
705                 710                 715                 720
Ala Gly Arg Leu Asn His Lys Ile Gln Glu Ile Thr
                725                 730
```

<210> SEQ ID NO 36
<211> LENGTH: 10
<212> TYPE: PRT
<213> ORGANISM: Artificial sequence
<220> FEATURE:
<223> OTHER INFORMATION: RecD-like motif V of RecD2 Dth

<400> SEQUENCE: 36

```
Tyr Ala Val Ser Ile His Lys Ser Gln Gly
1               5                   10
```

<210> SEQ ID NO 37
<211> LENGTH: 730
<212> TYPE: PRT
<213> ORGANISM: Nitrosococcus halophilus

<400> SEQUENCE: 37

```
Met Lys Pro Pro Leu His Ser Glu Thr Pro Pro Glu Phe Leu Thr Gly
1               5                   10                  15
Ala Val Glu Arg Val Thr Phe His Ser Glu Glu Asn Gly Phe Cys Val
                20                  25                  30
Leu Arg Ile Lys Val Arg Gly Glu Arg Asp Leu Ile Thr Val Val Gly
            35                  40                  45
Asn Thr Pro Thr Val Thr Pro Gly Glu Tyr Val Glu Cys His Gly Glu
    50                  55                  60
Trp Val Asn Asp Arg Thr His Gly Leu Gln Phe Lys Thr Lys His Leu
65                  70                  75                  80
Arg Val Ile Pro Pro Ser Thr Leu Glu Gly Ile Glu Lys Tyr Leu Gly
                85                  90                  95
Ser Gly Met Val Lys Gly Ile Gly Pro His Phe Ala Lys Lys Leu Val
                100                 105                 110
Gln Ala Phe Gly Glu Gln Val Phe Glu Val Ile Glu His Glu Ser Glu
            115                 120                 125
Arg Leu Thr Glu Leu Asp Gly Ile Gly Pro Lys Arg Lys Glu Gln Val
    130                 135                 140
Ile Gln Ala Trp Ala Glu Gln Arg Val Ile Arg Ala Ile Met Val Phe
145                 150                 155                 160
Leu Gln Ser His Gly Val Gly Ser Ala Arg Ala Val Arg Ile Tyr Lys
                165                 170                 175
Thr Tyr Gly Asp Lys Ala Ile Glu Arg Val Arg Glu Asn Pro Tyr Arg
                180                 185                 190
Leu Ala Leu Asp Ile His Gly Ile Gly Phe Lys Thr Ala Asp Arg Ile
            195                 200                 205
```

```
Ala Gln Arg Leu Gly Ile Pro Ala Asp Ser Leu Ile Arg Ala Gln Ala
    210                 215                 220
Gly Val Arg His Val Leu Gln Glu Phe Ala Asn Glu Gly His Cys Ala
225                 230                 235                 240
Met Glu Gln Gly Arg Leu Val Glu Thr Ala Ser Gln Leu Leu Glu Ile
                245                 250                 255
Pro Ala Pro Ile Ile Glu Gln Ala Ile Thr Gln Glu Val Ala Glu Gly
                260                 265                 270
Gln Leu Ile Ala Glu Ile Ile Ala Gly Lys Pro Cys Leu Phe Leu Ala
            275                 280                 285
Pro Leu Tyr Arg Ser Glu Ile Gly Val Ala Lys His Leu Gln Arg Leu
        290                 295                 300
Leu Arg Gly Val Pro Pro Trp Gly Gln Ile Asn Ala Asp Lys Ala Ile
305                 310                 315                 320
Pro Trp Val Glu Ala Lys Thr Gly Leu Leu Leu Ser Pro Ser Gln Arg
                325                 330                 335
Val Ala Leu Ile Gln Thr Ile Asn Asn Lys Ile Thr Val Ile Thr Gly
            340                 345                 350
Gly Pro Gly Val Gly Lys Thr Thr Val Val Asn Ser Ile Leu Arg Ile
        355                 360                 365
Val Arg Ala Lys Gln Thr Gln Val Leu Leu Gly Ala Pro Thr Gly Arg
370                 375                 380
Ala Ala Lys Arg Leu Ala Glu Ser Thr Gly Leu Glu Ala Lys Thr Ile
385                 390                 395                 400
His Arg Leu Leu Glu Phe Asp Pro His Ala Met Gly Phe Lys His His
                405                 410                 415
Ala Ala Asn Pro Leu Gln Ala Asp Leu Ile Val Ile Asp Glu Val Ser
            420                 425                 430
Met Val Asp Val Gly Leu Met Asn Gln Leu Leu Gln Ala Ile Pro Asn
        435                 440                 445
His Ala Ala Cys Ile Leu Ile Gly Asp Lys Asp Gln Leu Pro Ser Val
    450                 455                 460
Gly Pro Gly Gln Ile Leu Ala Asp Ile Ile Ala Ser Gln Lys Ile Ser
465                 470                 475                 480
Thr Val His Leu Ser Glu Val Phe Arg Gln Ala Ala Ser Ser Lys Ile
                485                 490                 495
Val Val Asn Ala His Arg Ile Asn Gln Gly Lys Met Pro Glu Lys Ala
            500                 505                 510
Asp Glu Ala Ala Thr Leu Ser Asp Phe Tyr Phe Ile Pro Thr Lys Ser
        515                 520                 525
Pro Glu Thr Ile Gln Asp Arg Val Leu Glu Leu Val Thr Ser Arg Ile
    530                 535                 540
Pro Lys Arg Phe Gly Phe Asp Ser Thr Arg Asp Ile Gln Val Leu Thr
545                 550                 555                 560
Pro Met Asn Arg Gly Ser Leu Gly Ala Arg Ala Leu Asn Gly Leu Leu
                565                 570                 575
Gln Gln Gln Leu Asn Gly Gln Ser Gln Pro Lys Ile Asn Arg Phe Gly
            580                 585                 590
Trp Ser Phe Ala Pro Gly Asp Lys Val Ile Gln Thr Val Asn Asn Tyr
        595                 600                 605
Asp Lys Glu Val Phe Asn Gly Asp Ile Gly Arg Ile Thr Arg Ile Ala
    610                 615                 620
```

```
Leu Glu Glu Gly Leu Val His Ile Asp Phe Asp Gly Arg Glu Ile Glu
625                 630                 635                 640

Tyr Glu Leu Gly Glu Leu Asp Glu Ile Ala Leu Ala Tyr Ala Thr Ser
            645                 650                 655

Val His Lys Ser Gln Gly Ser Glu Tyr Pro Ala Val Val Ile Pro Leu
            660                 665                 670

Ala Ile Gln His Tyr Thr Leu Leu Gln Arg Asn Leu Leu Tyr Thr Gly
            675                 680                 685

Ile Thr Arg Gly Lys Arg Leu Val Val Leu Val Gly Gln Pro Lys Ala
            690                 695                 700

Leu Ala Ile Ala Val Lys Arg Ile Asn Ser Thr Ala Arg Leu Thr His
705                 710                 715                 720

Leu Ser Ala Arg Leu Ala Asn Ser Gln Ile
            725                 730
```

<210> SEQ ID NO 38
<211> LENGTH: 10
<212> TYPE: PRT
<213> ORGANISM: Artificial sequence
<220> FEATURE:
<223> OTHER INFORMATION: RecD-like motif V of RecD2 Nha

<400> SEQUENCE: 38

```
Tyr Ala Thr Ser Val His Lys Ser Gln Gly
1               5                   10
```

<210> SEQ ID NO 39
<211> LENGTH: 728
<212> TYPE: PRT
<213> ORGANISM: Desulfohalobium retbaense

<400> SEQUENCE: 39

```
Met Ser Ala Thr Thr Leu Gln Ala Glu Ile Val Ser Ile Val Phe His
1               5                   10                  15

Asn Pro Glu Asn Asp Tyr Val Val Ala Arg Ala Arg Ala Glu Gly Glu
            20                  25                  30

Pro Gly Gln Ser Thr Val Val Gly Ile Met Pro Gln Val Met Pro Gly
        35                  40                  45

Glu Gln Val Arg Leu Glu Gly Glu Trp Arg Glu His Pro Lys Phe Gly
    50                  55                  60

Arg Gln Phe His Ala Val Ser His Thr Arg Glu Leu Pro Ala Thr Ile
65                  70                  75                  80

Asn Gly Ile Arg Arg Tyr Leu Ala Ser Gly Arg Ile Lys Gly Val Gly
            85                  90                  95

Pro Val Met Ala Glu Arg Leu Val Gln Phe Phe Gly Lys Asp Val Leu
            100                 105                 110

Asp Ile Leu Asp Asn Ala Pro Glu Arg Leu Leu Glu Val Glu Gly Leu
        115                 120                 125

Gly Lys Lys Thr Leu Glu Gly Ile Lys Ala Ser Trp Asp Gln Gln Arg
    130                 135                 140

Glu Val Arg Asn Val Met Leu Phe Leu Gln Ser His Asp Val Pro Pro
145                 150                 155                 160

Thr Tyr Ala Gly Arg Ile Phe Ala Arg Tyr Gly Asn Gln Ala Val Glu
                165                 170                 175

Lys Leu Gln Gln Asn Pro Tyr Glu Leu Ala Tyr Glu Ile Arg Gly Ile
            180                 185                 190

Gly Phe Lys Thr Ala Asp Thr Met Ala Leu Lys Leu Gly Phe Gln Glu
```

-continued

```
            195                 200                 205
Asp Ser Pro Glu Arg Leu Glu Ala Gly Leu Val Tyr Thr Leu Phe Gln
210                 215                 220

Phe Ala Glu Gln Gly His Met Phe Tyr Pro Gly Asp Glu Leu Val His
225                 230                 235                 240

Lys Val Thr Glu Thr Leu Gly Val Gly Asp Thr Gly Lys Val Asp Gly
                    245                 250                 255

Ala Leu Ala Arg Leu Glu Glu Arg Lys Arg Val Val Glu Asp Leu
                260                 265                 270

Pro Glu Gln Ala Val Leu Arg Ala Val Phe Leu Arg His Phe His Asn
                275                 280                 285

Trp Glu Ala Glu Ile Ala Ser Arg Leu Thr Ala Leu Val Ser His Pro
                290                 295                 300

Ala Pro Val Asn Glu Gly Lys Leu Asp Ser Ile Leu Pro Gly Leu Glu
305                 310                 315                 320

Gln Lys Ile Gly Val Ala Leu Ser Ser Glu Gln Lys Glu Ala Val Phe
                325                 330                 335

Glu Ala Cys Ala Asn Lys Thr Phe Ile Leu Thr Gly Gly Pro Gly Thr
                340                 345                 350

Gly Lys Thr Thr Ile Thr Gln Ala Val Val Arg Gly Leu Gly Lys Leu
                355                 360                 365

Gly Tyr Lys Ile Lys Leu Ala Ala Pro Thr Gly Arg Ala Ala Lys Arg
370                 375                 380

Leu Ser Glu Ala Thr Gly Ala Ser Ala Ser Thr Leu His Arg Leu Leu
385                 390                 395                 400

Gly Phe Ser Pro Asp Gly Ala Phe Ala Tyr Asn Glu Lys Lys Leu
                405                 410                 415

Lys Val Asp Ala Leu Val Val Asp Glu Ala Ser Met Leu Asp Cys Gln
                420                 425                 430

Leu Cys Val His Leu Leu Arg Ala Leu Pro Leu Thr Cys Arg Leu Ile
                435                 440                 445

Leu Val Gly Asp Val His Gln Leu Pro Ser Val Gly Ala Gly Asn Ile
                450                 455                 460

Leu Glu Asp Leu Leu Glu Ser Arg Ala Val Pro Ser Arg His Leu Thr
465                 470                 475                 480

His Ile Phe Arg Gln Ala Gln Glu Ser Leu Ile Val Val Asn Ala His
                485                 490                 495

Arg Phe Asn Glu Gly Leu Phe Pro Thr Thr Ser Ala Lys Glu Pro Pro
                500                 505                 510

Glu Ala Asp Phe Phe Trp Val Glu Gln Asp Pro Ala Arg Val Gln
                515                 520                 525

Glu Ile Ile Arg Gln Leu Val Cys Glu Arg Ile Pro Ala Ile Tyr Gly
                530                 535                 540

Leu Asp Pro Leu Arg Asp Val Gln Val Leu Ser Pro Met His Lys Gly
545                 550                 555                 560

Glu Val Gly Thr Gln Gln Leu Asn Thr Leu Leu Gln Gln Glu Leu Asn
                565                 570                 575

Pro Ser Gly Pro Thr Leu Thr Arg Gly Asn Arg Met Phe Arg Gln Gly
                580                 585                 590

Asp Arg Val Leu Gln Thr Arg Asn Asn Tyr Glu Lys Asp Val Phe Asn
                595                 600                 605

Gly Asp Leu Gly Trp Ile Thr Ala Ile Asn Ala Asp Ser Gln Thr Met
610                 615                 620
```

Gln Ile Asp Phe Glu Gly Arg Asp Leu Thr Tyr Glu Gln Gly Glu Leu
625                 630                 635                 640

Asp Glu Leu Thr Leu Ala Tyr Ala Val Ser Val His Lys Ser Gln Gly
                645                 650                 655

Ser Glu Tyr Pro Ala Val Val Leu Pro Val Val Thr Gln His Phe Met
                660                 665                 670

Leu Leu Gln Arg Asn Leu Ile Tyr Thr Ala Leu Thr Arg Ala Lys Ser
                675                 680                 685

Leu Ala Val Leu Val Gly Ser Ser Lys Ala Leu Gly Ile Ala Leu Asn
            690                 695                 700

His Lys Arg Gly Ala Glu Arg Tyr Thr His Leu Arg Tyr Arg Leu Gln
705                 710                 715                 720

Asp Ala Ala Asn Asp Ile Pro Tyr
                725

<210> SEQ ID NO 40
<211> LENGTH: 10
<212> TYPE: PRT
<213> ORGANISM: Artificial sequence
<220> FEATURE:
<223> OTHER INFORMATION: RecD-like motif V of RecD2 Dre

<400> SEQUENCE: 40

Tyr Ala Val Ser Val His Lys Ser Gln Gly
1               5                   10

<210> SEQ ID NO 41
<211> LENGTH: 715
<212> TYPE: PRT
<213> ORGANISM: Deinococcus radiidurans

<400> SEQUENCE: 41

Met Ser Ala Ala Leu Pro Ala Glu Pro Phe Arg Val Ser Gly Gly Val
1               5                   10                  15

Asn Lys Val Arg Phe Arg Ser Asp Thr Gly Phe Thr Val Met Ser Ala
                20                  25                  30

Thr Leu Arg Asn Glu Gln Gly Glu Asp Pro Asp Ala Thr Val Ile Gly
            35                  40                  45

Val Met Pro Pro Leu Asp Val Gly Asp Thr Phe Ser Ala Glu Val Leu
        50                  55                  60

Met Glu Glu His Arg Glu Tyr Gly Tyr Gln Tyr Arg Val Val Asn Met
65                  70                  75                  80

Val Leu Glu Ala Met Pro Ala Asp Leu Ser Glu Gly Val Ala Ala
                85                  90                  95

Tyr Phe Glu Ala Arg Val Gly Val Gly Lys Val Leu Ala Gly Arg
                100                 105                 110

Ile Ala Lys Thr Phe Gly Ala Ala Phe Asp Leu Leu Glu Asp Asp
            115                 120                 125

Pro Gln Lys Phe Leu Gln Val Pro Gly Ile Thr Glu Ser Thr Leu His
        130                 135                 140

Lys Met Val Ser Ser Trp Ser Gln Gln Gly Leu Glu Arg Arg Leu Leu
145                 150                 155                 160

Ala Gly Leu Gln Gly Leu Gly Leu Thr Ile Asn Gln Ala Gln Arg Ala
                165                 170                 175

Val Lys His Phe Gly Ala Asp Ala Leu Asp Arg Leu Glu Lys Asp Leu
                180                 185                 190

```
Phe Thr Leu Thr Glu Val Glu Gly Ile Gly Phe Leu Thr Ala Asp Lys
            195                 200                 205

Leu Trp Gln Ala Arg Gly Gly Ala Leu Asp Asp Pro Arg Arg Leu Thr
    210                 215                 220

Ala Ala Ala Val Tyr Ala Leu Gln Leu Ala Gly Thr Gln Ala Gly His
225                 230                 235                 240

Ser Phe Leu Pro Arg Ser Arg Ala Glu Lys Gly Val Val His Tyr Thr
                245                 250                 255

Arg Val Thr Pro Gly Gln Ala Arg Leu Ala Val Glu Thr Ala Val Glu
                260                 265                 270

Leu Gly Arg Leu Ser Glu Asp Asp Ser Pro Leu Phe Ala Ala Glu Ala
            275                 280                 285

Ala Ala Thr Gly Glu Gly Arg Ile Tyr Leu Pro His Val Leu Arg Ala
290                 295                 300

Glu Lys Lys Leu Ala Ser Leu Ile Arg Thr Leu Leu Ala Thr Pro Pro
305                 310                 315                 320

Ala Asp Gly Ala Gly Asn Asp Asp Trp Ala Val Pro Lys Lys Ala Arg
                325                 330                 335

Lys Gly Leu Ser Glu Glu Gln Ala Ser Val Leu Asp Gln Leu Ala Gly
                340                 345                 350

His Arg Leu Val Val Leu Thr Gly Gly Pro Gly Thr Gly Lys Ser Thr
            355                 360                 365

Thr Thr Lys Ala Val Ala Asp Leu Ala Glu Ser Leu Gly Leu Glu Val
    370                 375                 380

Gly Leu Cys Ala Pro Thr Gly Lys Ala Ala Arg Arg Leu Gly Glu Val
385                 390                 395                 400

Thr Gly Arg Thr Ala Ser Thr Val His Arg Leu Leu Gly Tyr Gly Pro
                405                 410                 415

Gln Gly Phe Arg His Asn His Leu Glu Pro Ala Pro Tyr Asp Leu Leu
                420                 425                 430

Ile Val Asp Glu Val Ser Met Met Gly Asp Ala Leu Met Leu Ser Leu
            435                 440                 445

Leu Ala Ala Val Pro Pro Gly Ala Arg Val Leu Leu Val Gly Asp Thr
450                 455                 460

Asp Gln Leu Pro Pro Val Asp Ala Gly Leu Pro Leu Leu Ala Leu Ala
465                 470                 475                 480

Gln Ala Ala Pro Thr Ile Lys Leu Thr Gln Val Tyr Arg Gln Ala Ala
                485                 490                 495

Lys Asn Pro Ile Ile Gln Ala Ala His Gly Leu Leu His Gly Glu Ala
                500                 505                 510

Pro Ala Trp Gly Asp Lys Arg Leu Asn Leu Thr Glu Ile Glu Pro Asp
            515                 520                 525

Gly Gly Ala Arg Arg Val Ala Leu Met Val Arg Glu Leu Gly Gly Pro
530                 535                 540

Gly Ala Val Gln Val Leu Thr Pro Met Arg Lys Gly Pro Leu Gly Met
545                 550                 555                 560

Asp His Leu Asn Tyr His Leu Gln Ala Leu Phe Asn Pro Gly Glu Gly
                565                 570                 575

Gly Val Arg Ile Ala Glu Gly Glu Ala Arg Pro Gly Asp Thr Val Val
                580                 585                 590

Gln Thr Lys Asn Asp Tyr Asn Asn Glu Ile Phe Asn Gly Thr Leu Gly
            595                 600                 605

Met Val Leu Lys Ala Glu Gly Ala Arg Leu Thr Val Asp Phe Asp Gly
```

```
Asn Val Val Glu Leu Thr Gly Ala Glu Leu Phe Asn Leu Gln Leu Gly
625                 630                 635                 640

Tyr Ala Leu Thr Val His Arg Ala Gln Gly Ser Glu Trp Gly Thr Val
                645                 650                 655

Leu Gly Val Leu His Glu Ala His Met Pro Met Leu Ser Arg Asn Leu
                660                 665                 670

Val Tyr Thr Ala Leu Thr Arg Ala Arg Asp Arg Phe Phe Ser Ala Gly
                675                 680                 685

Ser Ala Ser Ala Trp Gln Ile Ala Ala Ala Arg Gln Arg Glu Ala Arg
                690                 695                 700

Asn Thr Ala Leu Leu Glu Arg Ile Arg Ala His
705                 710                 715

<210> SEQ ID NO 42
<211> LENGTH: 738
<212> TYPE: PRT
<213> ORGANISM: Chlorobium chlorochromatii

<400> SEQUENCE: 42

Met Ser Val Gln Asp Gly Gln Glu Ser Tyr Tyr Ser Pro Lys Glu
1               5                   10                  15

Arg Leu Ser Gly Ala Val Glu Arg Val Thr Phe His Ser Gln Lys Asn
                20                  25                  30

Gly Phe Ser Val Leu Arg Ile Lys Val Lys Gly Arg Arg Asp Leu Val
                35                  40                  45

Thr Val Val Gly Ala Thr Pro Ser Ile Ala Pro Gly Glu Phe Val Glu
                50                  55                  60

Cys Leu Gly Glu Trp His Asn Asp Ser Thr Tyr Gly Leu Gln Phe Arg
65              70                  75                  80

Ala Thr Glu Leu Thr Val Val Pro Pro Glu Thr Ile Asp Gly Ile Glu
                85                  90                  95

Lys Tyr Leu Ala Ser Gly Met Val Lys Gly Ile Gly Pro His Phe Ala
                100                 105                 110

Lys Thr Leu Val Tyr Ala Phe Arg Glu Asp Val Phe Thr Val Ile Glu
                115                 120                 125

Glu Glu Pro Glu Arg Leu Leu Glu Leu Pro Gly Ile Gly Gln Lys Arg
                130                 135                 140

Met Glu Met Val Thr Ser Ala Trp Ala Asp Gln Lys Val Ile Arg Asp
145                 150                 155                 160

Ile Met Val Phe Leu Gln Ser His Gly Leu Gly Thr Ser Arg Ala Val
                165                 170                 175

Arg Ile Phe Lys Thr Tyr Gly Asn Glu Ser Ile Leu Arg Val Lys Glu
                180                 185                 190

Asn Pro Tyr Arg Leu Val Leu Asp Ile Tyr Gly Val Gly Phe Lys Thr
                195                 200                 205

Ala Asp Ala Leu Ala Met Gln Leu Gly Ile Ala Pro Asp Ser Leu Ile
                210                 215                 220

Arg Ala Gln Ala Gly Val His His Val Leu Gln Glu Ile Ala Ser Ser
225                 230                 235                 240

Gly His Cys Ala Ala Pro Arg Glu Gln Leu Val Ala Glu Ala Ser Arg
                245                 250                 255

Leu Leu Ser Ile Pro Glu Glu Arg Thr His Glu Ala Ile Asp Ala Glu
                260                 265                 270
```

```
Leu Arg Ala Gly Asn Leu Val Arg Glu Glu Leu Arg Gly Val Glu Thr
            275                 280                 285
Leu Tyr Leu Leu Ser Leu His Arg Ala Glu Leu Gly Val Ala Thr Ser
        290                 295                 300
Leu Met Arg Leu Leu Glu Gly Glu Ile Pro Trp Arg His Leu Ala Ile
305                 310                 315                 320
Glu Glu Ala Leu Pro Trp Val Glu Ala Gln Asn Asn Ile Thr Leu Ser
                325                 330                 335
Pro Ser Gln Lys Glu Ala Leu His Thr Ala Leu Thr Asn Lys Val Thr
            340                 345                 350
Val Ile Thr Gly Gly Pro Gly Val Gly Lys Thr Thr Leu Val Lys Ser
        355                 360                 365
Ile Leu Leu Ile Leu Gln Ala Gln Lys Val Arg Val Ala Leu Cys Ala
    370                 375                 380
Pro Thr Gly Arg Ala Ala Lys Arg Leu Ser Glu Ser Thr Gly Leu Glu
385                 390                 395                 400
Ala Lys Thr Ile His Arg Leu Leu Glu Phe Asp Pro Leu Thr Gly Gly
                405                 410                 415
Phe Lys His Gln Arg Asp Asn Pro Leu Glu Cys Asp Leu Val Val Val
            420                 425                 430
Asp Glu Ser Ser Met Val Asp Val Leu Met Asn Arg Leu Leu Ala
        435                 440                 445
Ala Val Pro Glu Lys Ala Ala Leu Leu Leu Ile Gly Asp Val Asp Gln
    450                 455                 460
Leu Pro Ser Val Gly Ala Gly Ala Val Leu Ala Asp Ile Ile Arg Ser
465                 470                 475                 480
Glu Thr Ile Pro Thr Ile Arg Leu Thr Glu Ile Phe Arg Gln Ala Ala
                485                 490                 495
Ser Ser Arg Ile Ile Met Asn Ala His Arg Ile Asn Lys Gly Glu Leu
            500                 505                 510
Pro Leu Arg Asp Glu Ser Asn Thr Leu Ser Asp Phe Tyr Leu Ile Ala
        515                 520                 525
Ala Asn Thr Pro Glu Glu Ile Tyr Asn Arg Leu Leu Thr Val Ile Thr
    530                 535                 540
Glu Arg Ile Pro Ala Arg Phe Gly Leu His Pro Val Arg Asp Val Gln
545                 550                 555                 560
Val Leu Thr Pro Met Asn Arg Gly Leu Gly Ala Arg Ala Leu Asn
                565                 570                 575
Val Glu Leu Gln Lys Val Leu Asn Gly Gln Val Glu Pro Ser Val Thr
            580                 585                 590
Arg Phe Gly Thr Arg Tyr Ala Ala Gly Asp Lys Val Ile Gln Met Val
        595                 600                 605
Asn Asn Tyr Asp Lys Glu Val Phe Asn Gly Asp Ile Gly His Ile Ser
    610                 615                 620
Ala Val Glu Arg Glu Asp Gly Ala Val Leu Val Asp Phe Asp Gly Thr
625                 630                 635                 640
Leu Val Ser Tyr Glu Phe Gly Glu Leu Asp Glu Leu Ser Leu Ala Tyr
                645                 650                 655
Ala Thr Ser Ile His Lys Ser Gln Gly Ser Glu Tyr Pro Ala Val Val
            660                 665                 670
Ile Pro Leu Ala Met Gln His Tyr Asn Leu Leu Glu Arg Asn Leu Ile
        675                 680                 685
Tyr Thr Ala Val Thr Arg Gly Lys Lys Leu Val Val Ile Ile Gly Glu
```

```
            690                 695                 700
Thr Arg Ala Leu Ala Met Ala Val Lys Asn His Lys Ala Met Arg Arg
705                 710                 715                 720

Leu Thr Gly Leu Ala Glu Arg Leu Ser Ala Leu Ala Arg Tyr Glu Ala
                    725                 730                 735

Asn Leu

<210> SEQ ID NO 43
<211> LENGTH: 10
<212> TYPE: PRT
<213> ORGANISM: Artificial sequence
<220> FEATURE:
<223> OTHER INFORMATION: RecD-like motif V of RecD2 Cch

<400> SEQUENCE: 43

Tyr Ala Thr Ser Ile His Lys Ser Gln Gly
1               5                   10

<210> SEQ ID NO 44
<211> LENGTH: 715
<212> TYPE: PRT
<213> ORGANISM: Deinococcus maricopensis

<400> SEQUENCE: 44

Met Leu Asp Thr Ser Ser Pro His Pro Ala Leu Cys Cys Thr Arg Asn
1               5                   10                  15

Val Thr Glu Arg Thr Pro Thr Ala Gln Pro His Leu Gln Val Thr Gly
                20                  25                  30

Thr Val Gln Lys Val Arg Tyr Arg Ala Asp Ser Gly Phe Ala Val Leu
            35                  40                  45

Thr Ala Ser Ile Arg Asn Asp His Gly Glu Asp Pro Asp Ala Thr Leu
        50                  55                  60

Val Gly Pro Val Pro Pro Leu Glu Ala Gly Asp Ala Phe Thr Ala Thr
65                  70                  75                  80

Val Val Val Glu Glu His Arg Glu Tyr Gly Pro Gln Tyr Lys Val Ile
                85                  90                  95

Gly Met Ile Leu Asp Ala His Pro Thr Asp Leu Asn Glu Ala Gly Val
            100                 105                 110

Ala Ala Tyr Leu Glu Ala Arg Val Gly Gly Val Gly Arg Val Leu Ala
        115                 120                 125

Gly Arg Ile Ala Arg Ala Phe Gly Ser Ala Thr Phe Asp Ile Leu Thr
130                 135                 140

Asp Asp Pro Lys Arg Leu Leu Gln Val Pro Gly Val Thr Gln Ser Thr
145                 150                 155                 160

Leu His Lys Ile Leu Val Ser Trp Glu Glu Gln Gly Gly Glu Arg Arg
                165                 170                 175

Thr Leu Ala Ala Leu Gln Gly Met Gly Leu Ser Val Gly Gln Ala Gln
            180                 185                 190

Arg Ala Leu Lys His Phe Gly Val Ala Ala Ile Glu Arg Leu Gln Thr
        195                 200                 205

Asp Leu Tyr Ala Leu Thr Glu Val Glu Gly Ile Gly Phe Leu Thr Ala
    210                 215                 220

Asp Lys Leu Ala Gln Glu Gln Gly Met Pro Gln Asp Asp Pro Arg Arg
225                 230                 235                 240

Leu Thr Ala Ala Ala Val Tyr Ala Leu Gln Leu Ala Gly Thr Ser Gly
                245                 250                 255
```

```
Gly His Thr Tyr Leu Pro Arg Pro Arg Ala Val Arg Gly Leu Met His
                260                 265                 270

Tyr Thr Arg Val Asn Glu Gly Leu Ala Glu Ala Ala Leu Glu Asn Ala
        275                 280                 285

Thr Thr Phe Gly Arg Leu Ala Asp Asp Gly Arg Ile Tyr Leu Pro
    290                 295                 300

His Ala Leu Arg Ala Glu Lys Lys Leu Ala Gln Thr Val Arg Thr Leu
305                 310                 315                 320

Leu Ala Thr Pro Pro Gln Asp Glu Trp Thr Val Lys Arg Gly Ala Ala
                325                 330                 335

Lys Gly Leu Ser Asp Glu Gln Glu Gln Val Leu His Leu Leu Glu His
                340                 345                 350

His Arg Leu Val Val Leu Thr Gly Gly Pro Gly Thr Gly Lys Ser Thr
                355                 360                 365

Thr Thr Arg Ala Val Ala Asp Leu Ala Glu Lys Leu Gly Leu Glu Val
    370                 375                 380

Gly Leu Cys Ala Pro Thr Gly Lys Ala Ala Arg Arg Leu Gly Glu Val
385                 390                 395                 400

Thr Gly Arg Thr Ala Ser Thr Val His Arg Leu Leu Gly Tyr Gly Pro
                405                 410                 415

Glu Gly Phe Arg Phe Gly Ala Met Glu Pro Val Met Phe Asp Leu Ile
                420                 425                 430

Ile Val Asp Glu Val Ser Met Met Gly Asp Thr Leu Met Leu Ala Leu
            435                 440                 445

Leu Gln Ala Val Pro Pro Gly Ala Arg Ile Leu Leu Val Gly Asp Ser
    450                 455                 460

Asp Gln Leu Pro Pro Val Asp Ala Gly Leu Pro Leu Ala Ala Leu Thr
465                 470                 475                 480

Ala Ala Ala Pro Thr Val Arg Leu Ser Arg Val Tyr Arg Gln Ala Met
                485                 490                 495

Asp Asn Pro Ile Ile Gly Ala Ala His Ala Ile Met His Ala Gln Ala
                500                 505                 510

Pro Thr Phe Gly Asp Pro Arg Leu Gln Phe His Ala Val Glu Thr Asp
                515                 520                 525

Thr Gly Ala Arg Arg Val Ala Leu Leu Val Arg Glu Leu Gly Gly Pro
    530                 535                 540

Gly Lys Val Gln Val Leu Thr Pro Met Arg Lys Gly Pro Leu Gly Met
545                 550                 555                 560

Asp Thr Leu Asn Thr His Leu Gln Thr Leu Phe Asn Pro Gly Asp Gly
                565                 570                 575

Gly Val Arg Ile Gly Asp Thr His Ala Arg Pro Gly Asp Leu Val Val
                580                 585                 590

Gln Thr Lys Asn Asp Tyr Gln Asn Glu Ile Phe Asn Gly Thr Val Gly
                595                 600                 605

Thr Val Leu Asp Met Glu Gly Asn Thr Leu Thr Ile Asp Phe Asp Ser
    610                 615                 620

Asn Val Val Thr Leu Ser Gly Ala Glu Leu Trp Asn Leu Asn Leu Ala
625                 630                 635                 640

Tyr Ala Leu Thr Val His Arg Gly Gln Gly Ser Glu Trp Pro Thr Val
                645                 650                 655

Leu Gly Val Leu His Glu Ala His Gly Pro Met Leu Asn Arg Asn Leu
                660                 665                 670

Ala Tyr Thr Ala Leu Thr Arg Ala Arg Glu Arg Phe Ile Gly Val Gly
```

675                 680                 685
Ser Glu Ser Ala Trp Arg Ala Ala Ala Thr Arg Ala Arg Asp Ala Arg
            690                 695                 700

His Thr His Leu Leu Glu Arg Ile Gln Ala Lys
705                 710                 715

<210> SEQ ID NO 45
<211> LENGTH: 10
<212> TYPE: PRT
<213> ORGANISM: Artificial sequence
<220> FEATURE:
<223> OTHER INFORMATION: RecD-like motif V of RecD2 Dma

<400> SEQUENCE: 45

Tyr Ala Leu Thr Val His Arg Gly Gln Gly
1               5                   10

<210> SEQ ID NO 46
<211> LENGTH: 13
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(10)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = any amino acid except D, E, R and K

<400> SEQUENCE: 46

His Xaa Xaa Xaa Arg Xaa Xaa Xaa Xaa Xaa His Xaa His
1               5                   10

<210> SEQ ID NO 47
<211> LENGTH: 14
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(11)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid except D, E, R and K

<400> SEQUENCE: 47

His Xaa Xaa Xaa Arg Xaa Xaa Xaa Xaa Xaa Xaa His Xaa His
1               5                   10

```
<210> SEQ ID NO 48
<211> LENGTH: 15
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(12)
<223> OTHER INFORMATION: Xaa = any amino acid
<220> FEATURE:
<221> NAME/KEY: MISC_FEATURE
<222> LOCATION: (14)..(14)
<223> OTHER INFORMATION: Xaa = any amino acid except D, E, R and K

<400> SEQUENCE: 48

His Xaa Xaa Xaa Arg Xaa Xaa Xaa Xaa Xaa Xaa Xaa His Xaa His
1               5                   10                  15

<210> SEQ ID NO 49
<211> LENGTH: 16
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(13)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid except D, E, R and K

<400> SEQUENCE: 49

His Xaa Xaa Xaa Arg Xaa Xaa Xaa Xaa Xaa Xaa Xaa His Xaa His
1               5                   10                  15

<210> SEQ ID NO 50
<211> LENGTH: 17
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(14)
<223> OTHER INFORMATION: Xaa = any amino acid
<220> FEATURE:
<221> NAME/KEY: MISC_FEATURE
```

```
<222> LOCATION: (16)..(16)
<223> OTHER INFORMATION: Xaa = any amino acid except D, E, R and K

<400> SEQUENCE: 50

His Xaa Xaa Xaa Arg Xaa Xaa Xaa Xaa Xaa Xaa Xaa Xaa Xaa His Xaa
1               5                   10                  15

His

<210> SEQ ID NO 51
<211> LENGTH: 18
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(15)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid except D, E, R and K

<400> SEQUENCE: 51

His Xaa Xaa Xaa Arg Xaa Xaa Xaa Xaa Xaa Xaa Xaa Xaa Xaa Xaa His
1               5                   10                  15

Xaa His

<210> SEQ ID NO 52
<211> LENGTH: 19
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid except D, E, R and K

<400> SEQUENCE: 52

His Xaa Xaa Xaa Arg Xaa Xaa Xaa Xaa Xaa Xaa Xaa Xaa Xaa Xaa
1               5                   10                  15

His Xaa His

<210> SEQ ID NO 53
<211> LENGTH: 20
<212> TYPE: PRT
<213> ORGANISM: Artificial sequence
<220> FEATURE:
<223> OTHER INFORMATION: MobF motif III
```

```
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(17)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid

<400> SEQUENCE: 53

His Xaa Xaa Xaa Arg Xaa Xaa Xaa Xaa Xaa Xaa Xaa Xaa Xaa Xaa
1               5                   10                  15

Xaa His Xaa His
        20

<210> SEQ ID NO 54
<211> LENGTH: 17
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(15)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid except D, E, K and R

<400> SEQUENCE: 54

Gly Xaa Xaa Xaa Xaa Xaa Xaa Xaa His Xaa Xaa Xaa Xaa Xaa His
1               5                   10                  15

Xaa

<210> SEQ ID NO 55
<211> LENGTH: 18
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
```

```
<220> FEATURE:
<221> NAME/KEY: MISC_FEATURE
<222> LOCATION: (10)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid except D, E, K and R

<400> SEQUENCE: 55

Gly Xaa Xaa Xaa Xaa Xaa Xaa Xaa His Xaa Xaa Xaa Xaa Xaa Xaa Xaa
1               5                   10                  15

His Xaa

<210> SEQ ID NO 56
<211> LENGTH: 19
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(17)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid except D, E, K and R

<400> SEQUENCE: 56

Gly Xaa Xaa Xaa Xaa Xaa Xaa Xaa His Xaa Xaa Xaa Xaa Xaa Xaa Xaa
1               5                   10                  15

Xaa His Xaa

<210> SEQ ID NO 57
<211> LENGTH: 20
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(18)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid except D, E, K and R
```

```
<400> SEQUENCE: 57

Gly Xaa Xaa Xaa Xaa Xaa Xaa Xaa His Xaa Xaa Xaa Xaa Xaa Xaa
1               5                   10                  15

Xaa Xaa His Xaa
            20

<210> SEQ ID NO 58
<211> LENGTH: 21
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(19)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = any amino acid

<400> SEQUENCE: 58

Gly Xaa Xaa Xaa Xaa Xaa Xaa Xaa His Xaa Xaa Xaa Xaa Xaa Xaa
1               5                   10                  15

Xaa Xaa Xaa His Xaa
            20

<210> SEQ ID NO 59
<211> LENGTH: 22
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(20)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except D, E, K and R

<400> SEQUENCE: 59

Gly Xaa Xaa Xaa Xaa Xaa Xaa Xaa His Xaa Xaa Xaa Xaa Xaa Xaa
1               5                   10                  15

Xaa Xaa Xaa Xaa His Xaa
            20
```

<210> SEQ ID NO 60
<211> LENGTH: 23
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = any amino acid except D, E, K and R

<400> SEQUENCE: 60

Gly Xaa Xaa Xaa Xaa Xaa Xaa His Xaa Xaa Xaa Xaa Xaa Xaa
1               5                   10                  15

Xaa Xaa Xaa Xaa Xaa His Xaa
            20

<210> SEQ ID NO 61
<211> LENGTH: 1756
<212> TYPE: PRT
<213> ORGANISM: Escherichia coli

<400> SEQUENCE: 61

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn

```
                180                 185                 190
Gln Ile Ala Phe Gly Arg Leu Tyr Arg Glu Lys Leu Lys Glu Gln Val
            195                 200                 205
Glu Ala Leu Gly Tyr Glu Thr Glu Val Val Gly Lys His Gly Met Trp
        210                 215                 220
Glu Met Pro Gly Val Pro Val Glu Ala Phe Ser Gly Arg Ser Gln Ala
225                 230                 235                 240
Ile Arg Glu Ala Val Gly Glu Asp Ala Ser Leu Lys Ser Arg Asp Val
                245                 250                 255
Ala Ala Leu Asp Thr Arg Lys Ser Lys Gln His Val Asp Pro Glu Ile
            260                 265                 270
Arg Met Ala Glu Trp Met Gln Thr Leu Lys Glu Thr Gly Phe Asp Ile
        275                 280                 285
Arg Ala Tyr Arg Asp Ala Ala Asp Gln Arg Thr Glu Ile Arg Thr Gln
    290                 295                 300
Ala Pro Gly Pro Ala Ser Gln Asp Gly Pro Asp Val Gln Gln Ala Val
305                 310                 315                 320
Thr Gln Ala Ile Ala Gly Leu Ser Glu Arg Lys Val Gln Phe Thr Tyr
                325                 330                 335
Thr Asp Val Leu Ala Arg Thr Val Gly Ile Leu Pro Pro Glu Asn Gly
            340                 345                 350
Val Ile Glu Arg Ala Arg Ala Gly Ile Asp Glu Ala Ile Ser Arg Glu
        355                 360                 365
Gln Leu Ile Pro Leu Asp Arg Glu Lys Gly Leu Phe Thr Ser Gly Ile
    370                 375                 380
His Val Leu Asp Glu Leu Ser Val Arg Ala Leu Ser Arg Asp Ile Met
385                 390                 395                 400
Lys Gln Asn Arg Val Thr Val His Pro Glu Lys Ser Val Pro Arg Thr
                405                 410                 415
Ala Gly Tyr Ser Asp Ala Val Ser Val Leu Ala Gln Asp Arg Pro Ser
            420                 425                 430
Leu Ala Ile Val Ser Gly Gln Gly Gly Ala Ala Gly Gln Arg Glu Arg
        435                 440                 445
Val Ala Glu Leu Val Met Met Ala Arg Glu Gln Gly Arg Glu Val Gln
    450                 455                 460
Ile Ile Ala Ala Asp Arg Arg Ser Gln Met Asn Leu Lys Gln Asp Glu
465                 470                 475                 480
Arg Leu Ser Gly Glu Leu Ile Thr Gly Arg Arg Gln Leu Leu Glu Gly
                485                 490                 495
Met Ala Phe Thr Pro Gly Ser Thr Val Ile Val Asp Gln Gly Glu Lys
            500                 505                 510
Leu Ser Leu Lys Glu Thr Leu Thr Leu Leu Asp Gly Ala Ala Arg His
        515                 520                 525
Asn Val Gln Val Leu Ile Thr Asp Ser Gly Gln Arg Thr Gly Thr Gly
    530                 535                 540
Ser Ala Leu Met Ala Met Lys Asp Ala Gly Val Asn Thr Tyr Arg Trp
545                 550                 555                 560
Gln Gly Gly Glu Gln Arg Pro Ala Thr Ile Ile Ser Glu Pro Asp Arg
                565                 570                 575
Asn Val Arg Tyr Ala Arg Leu Ala Gly Asp Phe Ala Ala Ser Val Lys
            580                 585                 590
Ala Gly Glu Glu Ser Val Ala Gln Val Ser Gly Val Arg Glu Gln Ala
        595                 600                 605
```

```
Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
                660                 665                 670

Arg Val Thr Ala Gln Ser His Ser Leu Thr Leu Arg Asp Ala Gln Gly
            675                 680                 685

Glu Thr Gln Val Val Arg Ile Ser Ser Leu Asp Ser Ser Trp Ser Leu
    690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Pro Gly Arg
            740                 745                 750

Ala Glu Pro Ala Ser Leu Pro Val Ser Asp Ser Pro Phe Thr Ala Leu
            755                 760                 765

Lys Leu Glu Asn Gly Trp Val Glu Thr Pro Gly His Ser Val Ser Asp
    770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
            835                 840                 845

Leu Glu Thr Ala Ile Ser Leu Gln Lys Ala Gly Leu His Thr Pro Ala
    850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
            915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Val Gln Gly
            980                 985                 990

Tyr Ala Gly Val Gly Lys Thr Thr Gln Phe Arg Ala Val Met Ser Ala
            995                 1000                1005

Val Asn Met Leu Pro Ala Ser Glu Arg Pro Arg Val Val Gly Leu
    1010                1015                1020
```

```
Gly Pro Thr His Arg Ala Val Gly Glu Met Arg Ser Ala Gly Val
    1025                1030                1035

Asp Ala Gln Thr Leu Ala Ser Phe Leu His Asp Thr Gln Leu Gln
    1040                1045                1050

Gln Arg Ser Gly Glu Thr Pro Asp Phe Ser Asn Thr Leu Phe Leu
    1055                1060                1065

Leu Asp Glu Ser Ser Met Val Gly Asn Thr Glu Met Ala Arg Ala
    1070                1075                1080

Tyr Ala Leu Ile Ala Ala Gly Gly Gly Arg Ala Val Ala Ser Gly
    1085                1090                1095

Asp Thr Asp Gln Leu Gln Ala Ile Ala Pro Gly Gln Ser Phe Arg
    1100                1105                1110

Leu Gln Gln Thr Arg Ser Ala Ala Asp Val Val Ile Met Lys Glu
    1115                1120                1125

Ile Val Arg Gln Thr Pro Glu Leu Arg Glu Ala Val Tyr Ser Leu
    1130                1135                1140

Ile Asn Arg Asp Val Glu Arg Ala Leu Ser Gly Leu Glu Ser Val
    1145                1150                1155

Lys Pro Ser Gln Val Pro Arg Leu Glu Gly Ala Trp Ala Pro Glu
    1160                1165                1170

His Ser Val Thr Glu Phe Ser His Ser Gln Glu Ala Lys Leu Ala
    1175                1180                1185

Glu Ala Gln Gln Lys Ala Met Leu Lys Gly Glu Ala Phe Pro Asp
    1190                1195                1200

Ile Pro Met Thr Leu Tyr Glu Ala Ile Val Arg Asp Tyr Thr Gly
    1205                1210                1215

Arg Thr Pro Glu Ala Arg Glu Gln Thr Leu Ile Val Thr His Leu
    1220                1225                1230

Asn Glu Asp Arg Arg Val Leu Asn Ser Met Ile His Asp Ala Arg
    1235                1240                1245

Glu Lys Ala Gly Glu Leu Gly Lys Glu Gln Val Met Val Pro Val
    1250                1255                1260

Leu Asn Thr Ala Asn Ile Arg Asp Gly Glu Leu Arg Arg Leu Ser
    1265                1270                1275

Thr Trp Glu Lys Asn Pro Asp Ala Leu Ala Leu Val Asp Asn Val
    1280                1285                1290

Tyr His Arg Ile Ala Gly Ile Ser Lys Asp Asp Gly Leu Ile Thr
    1295                1300                1305

Leu Gln Asp Ala Glu Gly Asn Thr Arg Leu Ile Ser Pro Arg Glu
    1310                1315                1320

Ala Val Ala Glu Gly Val Thr Leu Tyr Thr Pro Asp Lys Ile Arg
    1325                1330                1335

Val Gly Thr Gly Asp Arg Met Arg Phe Thr Lys Ser Asp Arg Glu
    1340                1345                1350

Arg Gly Tyr Val Ala Asn Ser Val Trp Thr Val Thr Ala Val Ser
    1355                1360                1365

Gly Asp Ser Val Thr Leu Ser Asp Gly Gln Gln Thr Arg Val Ile
    1370                1375                1380

Arg Pro Gly Gln Glu Arg Ala Glu Gln His Ile Asp Leu Ala Tyr
    1385                1390                1395

Ala Ile Thr Ala His Gly Ala Gln Gly Ala Ser Glu Thr Phe Ala
    1400                1405                1410

Ile Ala Leu Glu Gly Thr Glu Gly Asn Arg Lys Leu Met Ala Gly
```

```
            1415                1420                1425

Phe Glu Ser Ala Tyr Val Ala Leu Ser Arg Met Lys Gln His Val
        1430                1435                1440

Gln Val Tyr Thr Asp Asn Arg Gln Gly Trp Thr Asp Ala Ile Asn
    1445                1450                1455

Asn Ala Val Gln Lys Gly Thr Ala His Asp Val Leu Glu Pro Lys
1460                1465                1470

Pro Asp Arg Glu Val Met Asn Ala Gln Arg Leu Phe Ser Thr Ala
1475                1480                1485

Arg Glu Leu Arg Asp Val Ala Ala Gly Arg Ala Val Leu Arg Gln
1490                1495                1500

Ala Gly Leu Ala Gly Gly Asp Ser Pro Ala Arg Phe Ile Ala Pro
1505                1510                1515

Gly Arg Lys Tyr Pro Gln Pro Tyr Val Ala Leu Pro Ala Phe Asp
1520                1525                1530

Arg Asn Gly Lys Ser Ala Gly Ile Trp Leu Asn Pro Leu Thr Thr
1535                1540                1545

Asp Asp Gly Asn Gly Leu Arg Gly Phe Ser Gly Glu Gly Arg Val
1550                1555                1560

Lys Gly Ser Gly Asp Ala Gln Phe Val Ala Leu Gln Gly Ser Arg
1565                1570                1575

Asn Gly Glu Ser Leu Leu Ala Asp Asn Met Gln Asp Gly Val Arg
1580                1585                1590

Ile Ala Arg Asp Asn Pro Asp Ser Gly Val Val Arg Ile Ala
1595                1600                1605

Gly Glu Gly Arg Pro Trp Asn Pro Gly Ala Ile Thr Gly Gly Arg
1610                1615                1620

Val Trp Gly Asp Ile Pro Asp Asn Ser Val Gln Pro Gly Ala Gly
1625                1630                1635

Asn Gly Glu Pro Val Thr Ala Glu Val Leu Ala Gln Arg Gln Ala
1640                1645                1650

Glu Glu Ala Ile Arg Arg Glu Thr Glu Arg Arg Ala Asp Glu Ile
1655                1660                1665

Val Arg Lys Met Ala Glu Asn Lys Pro Asp Leu Pro Asp Gly Lys
1670                1675                1680

Thr Glu Leu Ala Val Arg Asp Ile Ala Gly Gln Glu Arg Asp Arg
1685                1690                1695

Ser Ala Ile Ser Glu Arg Glu Thr Ala Leu Pro Glu Ser Val Leu
1700                1705                1710

Arg Glu Ser Gln Arg Glu Arg Glu Ala Val Arg Glu Val Ala Arg
1715                1720                1725

Glu Asn Leu Leu Gln Glu Arg Leu Gln Gln Met Glu Arg Asp Met
1730                1735                1740

Val Arg Asp Leu Gln Lys Glu Lys Thr Leu Gly Gly Asp
1745                1750                1755

<210> SEQ ID NO 62
<211> LENGTH: 8
<212> TYPE: PRT
<213> ORGANISM: Artificial sequence
<220> FEATURE:
<223> OTHER INFORMATION: RecD-like motif I of TraI Eco

<400> SEQUENCE: 62

Gly Tyr Ala Gly Val Gly Lys Thr
```

<210> SEQ ID NO 63
<211> LENGTH: 10
<212> TYPE: PRT
<213> ORGANISM: Artificial sequence
<220> FEATURE:
<223> OTHER INFORMATION: RecD-like motif V of TraI Eco

<400> SEQUENCE: 63

```
Tyr Ala Ile Thr Ala His Gly Ala Gln Gly
1               5                   10
```

<210> SEQ ID NO 64
<211> LENGTH: 14
<212> TYPE: PRT
<213> ORGANISM: Artificial sequence
<220> FEATURE:
<223> OTHER INFORMATION: MobF motif III of TraI Eco

<400> SEQUENCE: 64

```
His Asp Thr Ser Arg Asp Gln Glu Pro Gln Leu His Thr His
1               5                   10
```

<210> SEQ ID NO 65
<211> LENGTH: 970
<212> TYPE: PRT
<213> ORGANISM: Citromicrobium bathyomarinum

<400> SEQUENCE: 65

```
Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Ile Gly Asp Gly Ala Lys Arg Leu Gly Leu Glu Gly Lys Val
            35                  40                  45

Glu Ala Arg Ala Phe Asp Ala Leu Leu Arg Gly Glu Leu Pro Asp Gly
        50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
                100                 105                 110

His Trp Ala Glu Lys Asn Ala Ala Glu Thr Arg Val Val Glu Lys Gly
            115                 120                 125

Met Val Val Thr Gln Ala Thr Gly Asn Leu Ala Ile Gly Leu Phe Gln
        130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
                180                 185                 190

Ala Arg Phe Arg Val Ala Val Glu Lys Leu Gly Tyr Glu Pro Gly Pro
            195                 200                 205

Val Leu Lys His Gly Asn Phe Glu Ala Arg Gly Ile Ser Arg Glu Gln
        210                 215                 220

Val Met Ala Phe Ser Thr Arg Arg Lys Glu Val Leu Glu Ala Arg Arg
```

```
                225                 230                 235                 240
Gly Pro Gly Leu Asp Ala Gly Arg Ile Ala Ala Leu Asp Thr Arg Ala
                    245                 250                 255

Ser Lys Glu Gly Ile Glu Asp Arg Ala Thr Leu Ser Lys Gln Trp Ser
                    260                 265                 270

Glu Ala Ala Gln Ser Ile Gly Leu Asp Leu Lys Pro Leu Val Asp Arg
                    275                 280                 285

Ala Arg Thr Lys Ala Leu Gly Gln Gly Met Glu Ala Thr Arg Ile Gly
                    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Ser Val Leu Lys
                    325                 330                 335

Gln Asp Arg Gln Thr Ile Ala Ala Ala Gln Ala Val Ala Ser Ala Val
                    340                 345                 350

Arg His Leu Ser Gln Arg Glu Ala Ala Phe Glu Arg Thr Ala Leu Tyr
                    355                 360                 365

Lys Ala Ala Leu Asp Phe Gly Leu Pro Thr Thr Ile Ala Asp Val Glu
370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                    405                 410                 415

Gln Arg Ile Leu Ser Glu Val Ala Ala Gly Lys Gly Asp Ser Ser Pro
                    420                 425                 430

Ala Ile Thr Pro Gln Lys Ala Ala Ser Val Gln Ala Ala Ala Leu
                    435                 440                 445

Thr Gly Gln Gly Phe Arg Leu Asn Glu Gly Gln Leu Ala Ala Ala Arg
                    450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                    485                 490                 495

Asp Glu Gly His Pro Val Ile Gly Leu Ala Ile Gln Asn Thr Leu Val
                    500                 505                 510

Gln Met Leu Glu Arg Asp Thr Gly Ile Gly Ser Gln Thr Leu Ala Arg
                    515                 520                 525

Phe Leu Gly Gly Trp Asn Lys Leu Leu Asp Asp Pro Gly Asn Val Ala
                    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                    565                 570                 575

Leu Ala Asn Leu Ala Gly Val His Arg Leu Val Leu Ile Gly Asp Arg
                    580                 585                 590

Lys Gln Leu Gly Ala Val Asp Ala Gly Lys Pro Phe Ala Leu Leu Gln
                    595                 600                 605

Arg Ala Gly Ile Ala Arg Ala Glu Met Ala Thr Asn Leu Arg Ala Arg
                    610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
                    645                 650                 655
```

```
Asp Gly Ala Gln Val Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
            675                 680                 685

Ala Val Asn Ala Ala Val Gln Gln Gly Leu Leu Ala Ser Arg Glu Ile
            690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
            740                 745                 750

Arg Val Ile Gly Gln Asp Arg Lys Gly Lys Leu Val Glu Val Glu Asp
            755                 760                 765

Lys Arg Gly Lys Arg Phe Arg Phe Asp Pro Ala Arg Ile Arg Ala Gly
            770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
            820                 825                 830

Val Thr Phe Glu Thr Ser Lys Gly Asp Leu Val Glu Leu Lys Lys Asp
            835                 840                 845

Asp Pro Met Leu Lys Arg Ile Asp Leu Ala Tyr Ala Leu Asn Val His
            850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
            900                 905                 910

Gly Ala Ala Val Ala Arg Asn Lys Gly Glu Lys Ala Ser Ala Ile Glu
            915                 920                 925

Val Thr Gly Ser Val Lys Pro Thr Ala Thr Lys Gly Ser Gly Val Asp
            930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970

<210> SEQ ID NO 66
<211> LENGTH: 8
<212> TYPE: PRT
<213> ORGANISM: Artificial sequence
<220> FEATURE:
<223> OTHER INFORMATION: RecD-like motif I of TrwC Cba

<400> SEQUENCE: 66

Gly Ile Ala Gly Ala Gly Lys Ser
1               5

<210> SEQ ID NO 67
<211> LENGTH: 10
<212> TYPE: PRT
<213> ORGANISM: Artificial sequence
```

```
<220> FEATURE:
<223> OTHER INFORMATION: RecD-like motif V of TrwC Cba

<400> SEQUENCE: 67

Tyr Ala Leu Asn Val His Met Ala Gln Gly
1               5                   10

<210> SEQ ID NO 68
<211> LENGTH: 14
<212> TYPE: PRT
<213> ORGANISM: Artificial sequence
<220> FEATURE:
<223> OTHER INFORMATION: MobF motif III of TrwC Cba

<400> SEQUENCE: 68

His Asp Thr Asn Arg Asn Gln Glu Pro Asn Leu His Phe His
1               5                   10

<210> SEQ ID NO 69
<211> LENGTH: 943
<212> TYPE: PRT
<213> ORGANISM: Halothiobacillus neapolitanus c2

<400> SEQUENCE: 69

Met Leu Arg Ile Lys Asn Leu Lys Gly Asp Pro Ser Ala Ile Ile Asp
1               5                   10                  15

Tyr Ala Glu Asn Lys Lys Asn His Pro Asp Gln Lys Ser Gly Tyr Tyr
                20                  25                  30

Asp Ala Lys Gly Ala Pro Ser Ala Trp Gly Gly Ala Leu Ala Ala Asp
            35                  40                  45

Leu Gly Leu Ser Gly Ser Val Gln Ala Ala Asp Leu Lys Lys Leu Leu
        50                  55                  60

Ser Gly Glu Leu Ser Asp Gly Thr Arg Phe Ala Lys Glu Asp Pro Asp
65                  70                  75                  80

Arg Arg Leu Gly Ile Asp Met Ser Phe Ser Ala Pro Lys Ser Val Ser
                85                  90                  95

Leu Ala Ala Leu Val Gly Gly Asp Glu Arg Ile Ile Gln Ala His Asp
            100                 105                 110

Ala Ala Val Arg Thr Ala Met Ser Met Ile Glu Gln Glu Tyr Ala Thr
        115                 120                 125

Ala Arg Phe Gly His Ala Gly Arg Asn Val Val Cys Ser Gly Lys Leu
    130                 135                 140

Val Tyr Ala Ala Tyr Arg His Glu Asp Ala Arg Thr Val Asp Asp Ile
145                 150                 155                 160

Ala Asp Pro Gln Leu His Thr His Cys Ile Val Ser Asn Ile Thr Ile
                165                 170                 175

Asp Pro Glu Thr Gly Lys Pro Arg Ser Ile Asp Phe Ala Trp Gly Gln
            180                 185                 190

Asp Gly Ile Lys Leu Ala Gly Ala Met Tyr Arg Ala Glu Leu Ala Arg
        195                 200                 205

Arg Leu Lys Glu Met Gly Tyr Glu Leu Arg Lys Ser Glu Glu Gly Phe
    210                 215                 220

Glu Leu Ala Gln Ile Ser Asp Glu Gln Val Thr Phe Ser Arg Arg
225                 230                 235                 240

Arg Val Gln Val Asp Gln Ala Leu Glu Gln Gln Gly Thr Asp Arg Glu
                245                 250                 255

His Ala Ser Ser Glu Leu Lys Thr Ala Val Thr Leu Ala Thr Arg Gln
            260                 265                 270
```

```
Gly Lys Ala Gln Leu Ser Ala Glu Asp Gln Tyr Glu Trp Gln Gln
        275                 280                 285

Arg Ala Ala Glu Ala Glu Leu Asp Leu Ser Gln Pro Val Gly Pro Arg
    290                 295                 300

Val Ser Val Thr Pro Pro Glu Ile Asp Leu Asp His Thr Phe Glu His
305                 310                 315                 320

Leu Ser Glu Arg Ala Ser Val Ile Asn Lys Asp Ala Val Arg Leu Asp
                325                 330                 335

Ala Leu Ile Asn His Met Ser Glu Gly Ala Thr Leu Ser Thr Val Asp
                340                 345                 350

Lys Ala Ile Gln Gly Ala Ala Val Thr Gly Asp Val Phe Glu Ile Glu
                355                 360                 365

Asp Gly Ile Lys Arg Lys Ile Ile Thr Arg Glu Thr Leu Lys Arg Glu
            370                 375                 380

Gln Gln Ile Leu Leu Ala Gln Gly Arg Gly Val Asn Ser Val
385                 390                 395                 400

Leu Ile Gly Val Gly Asp Thr Lys His Leu Ile Glu Asp Ala Glu Gln
                    405                 410                 415

Ala Gln Gly Phe Arg Phe Ser Glu Gly Gln Arg Ala Ile Asn Leu
                420                 425                 430

Thr Ala Thr Thr Thr Asp Gln Val Ser Gly Ile Val Gly Ala Ala Gly
            435                 440                 445

Ala Gly Lys Thr Thr Ala Met Lys Thr Val Ala Asp Leu Ala Lys Ser
450                 455                 460

Gln Gly Leu Thr Val Val Gly Ile Ala Pro Ser Ala Ala Ala Asp
465                 470                 475                 480

Glu Leu Lys Ser Ala Gly Ala Asp Asp Thr Met Thr Leu Ala Thr Phe
                485                 490                 495

Asn Leu Lys Gly Glu Ala Ala Gly Pro Arg Leu Leu Ile Leu Asp Glu
            500                 505                 510

Ala Gly Met Val Ser Ala Arg Asp Gly Glu Ala Leu Leu Lys Lys Leu
        515                 520                 525

Gly Lys Glu Asp Arg Leu Ile Phe Val Gly Asp Pro Lys Gln Leu Ala
    530                 535                 540

Ala Val Glu Ala Gly Ser Pro Phe Ala Gln Leu Met Arg Ser Gly Ala
545                 550                 555                 560

Ile Gln Tyr Ala Glu Ile Thr Glu Ile Asn Arg Gln Lys Asp Gln Lys
                565                 570                 575

Leu Leu Asp Ile Ala Gln His Phe Ala Lys Gly Lys Ala Glu Glu Ala
                580                 585                 590

Val Ala Leu Ala Thr Lys Tyr Val Thr Glu Val Pro Val Thr Leu Pro
                595                 600                 605

Asp Lys Pro Glu His Lys Ile Thr Arg Gln Ala Lys Thr Glu Ala Arg
            610                 615                 620

Arg Leu Ala Ile Ala Ser Ala Thr Ala Lys Arg Tyr Leu Glu Leu Ser
625                 630                 635                 640

Gln Glu Glu Arg Ala Thr Thr Leu Val Leu Ser Gly Thr Asn Ala Val
                645                 650                 655

Arg Lys Gln Val Asn Glu Gln Val Arg Lys Gly Leu Ile Asp Lys Gly
            660                 665                 670

Glu Ile Asn Gly Glu Ser Phe Thr Val Ser Thr Leu Asp Lys Ala Asp
            675                 680                 685
```

```
Met Thr Arg Ala Lys Met Arg Lys Ala Gly Asn Tyr Lys Pro Gly Gln
    690                 695                 700
Val Ile Lys Thr Ala Gly Lys Gln Ala Glu Gln Ser Glu Val Val Ala
705                 710                 715                 720
Val Asn Leu Asp Gln Asn Leu Ile Gln Val Lys Leu Ser Asp Gly Thr
                725                 730                 735
Leu Lys Ser Ile Asp Ala Ser Arg Phe Asp Val Lys Lys Thr Gln Val
            740                 745                 750
Phe Asn Pro Arg Gln Ile Asp Ile Ala Ala Gly Asp Lys Ile Ile Phe
        755                 760                 765
Thr Asn Asn Asp Gln Ala Thr Glu Thr Lys Asn Asn Gln Ile Gly Leu
    770                 775                 780
Ile Glu Glu Ile Lys Asp Gly Lys Ala Ile Ile Asn Ser Asn Gly Ala
785                 790                 795                 800
Lys Val Glu Ile Asp Ile Gln Arg Lys Leu His Ile Asp His Ala Tyr
                805                 810                 815
Cys Ile Thr Ile His Arg Ser Gln Gly Gln Thr Val Asp Ser Val Ile
            820                 825                 830
Val Ala Gly Glu Ala Ser Arg Thr Thr Thr Ala Glu Ala Ala Tyr Val
        835                 840                 845
Ala Cys Thr Arg Glu Arg Tyr Lys Leu Glu Ile Ile Thr Asp Asn Thr
    850                 855                 860
Glu Arg Leu Ser Lys Asn Trp Val Arg Tyr Ala Asp Arg Gln Thr Ala
865                 870                 875                 880
Ala Glu Ala Leu Lys Ser Ser Glu Glu Lys Tyr Pro His Leu Asp Glu
                885                 890                 895
Ile Arg Glu Glu Leu Arg Arg Glu Leu Gln Gln Glu Leu Glu Arg Gln
            900                 905                 910
Glu Pro Thr Asn Ile Thr Pro Glu Leu Glu Ile Glu Met Glu Arg Ser
        915                 920                 925
Met Phe Asp Gln Tyr Thr Leu His Ser Arg Gln Pro Arg Ser Tyr
    930                 935                 940

<210> SEQ ID NO 70
<211> LENGTH: 8
<212> TYPE: PRT
<213> ORGANISM: Artificial sequence
<220> FEATURE:
<223> OTHER INFORMATION: RecD-like motif I of TrwC Hne

<400> SEQUENCE: 70

Gly Ala Ala Gly Ala Gly Lys Thr
1               5

<210> SEQ ID NO 71
<211> LENGTH: 10
<212> TYPE: PRT
<213> ORGANISM: Artificial sequence
<220> FEATURE:
<223> OTHER INFORMATION: RecD-like motif V of TrwC Hne

<400> SEQUENCE: 71

Tyr Cys Ile Thr Ile His Arg Ser Gln Gly
1               5                   10

<210> SEQ ID NO 72
<211> LENGTH: 18
<212> TYPE: PRT
<213> ORGANISM: Artificial sequence
```

<220> FEATURE:
<223> OTHER INFORMATION: MobF motif III of TrwC Hne

<400> SEQUENCE: 72

His Glu Asp Ala Arg Thr Val Asp Asp Ile Ala Asp Pro Gln Leu His
1               5                   10                  15

Thr His

<210> SEQ ID NO 73
<211> LENGTH: 960
<212> TYPE: PRT
<213> ORGANISM: Erythrobacter litoralis HTCC2594

<400> SEQUENCE: 73

Met Leu Ser Val Ala Asn Val Arg Ser Pro Thr Ala Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Ile Gly Gly Gly Ala Lys Arg Leu Gly Leu Glu Gly Lys Val
            35                  40                  45

Glu Ala Lys Ala Phe Asp Ala Leu Leu Arg Gly Glu Leu Pro Asp Gly
        50                  55                  60

Ser Ser Val Gly Asn Pro Gly Gln Ala His Arg Pro Gly Thr Asp Leu
65                  70                  75                  80

Ser Phe Ser Val Pro Lys Ser Trp Ser Leu Ala Leu Val Gly Lys
                85                  90                  95

Asp Glu Arg Ile Ile Ala Ala Tyr Arg Glu Ala Val Val Glu Ala Leu
                100                 105                 110

Gln Trp Ala Glu Lys Asn Ala Ala Glu Thr Arg Ile Val Glu Lys Gly
            115                 120                 125

Lys Met Val Thr Gln Ala Thr Gly Asn Leu Ala Val Gly Leu Phe Gln
130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
                180                 185                 190

Ala Arg Phe Arg Val Ala Val Glu Lys Leu Gly Tyr Glu Pro Gly Pro
            195                 200                 205

Val Leu Lys His Gly Asn Phe Glu Ala Arg Gly Ile Ser Arg Glu Gln
        210                 215                 220

Ile Met Ala Phe Ser Thr Arg Arg Lys Glu Val Leu Glu Ala Arg Arg
225                 230                 235                 240

Gly Pro Gly Leu Glu Ala Gly Arg Ile Ala Ala Leu Asp Thr Arg Ala
                245                 250                 255

Ser Lys Glu Glu Ile Glu Asp Arg Ala Thr Leu Gly Lys Gln Trp Ser
                260                 265                 270

Glu Thr Ala Gln Ser Ile Gly Leu Asp Leu Thr Pro Leu Val Asp Arg
            275                 280                 285

Ala Arg Thr Asn Ala Leu Gly Gln Ser Met Glu Ala Thr Arg Ile Gly
        290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys

-continued

```
                325                 330                 335
Gln Asp Arg Gln Thr Ile Ala Ala Ala Gln Ala Val Ala Ser Ala Ile
            340                 345                 350
Arg His Leu Ser Gln Arg Glu Ala Ala Phe Glu Arg Thr Ala Leu Tyr
            355                 360                 365
Lys Ala Ala Leu Asp Phe Gly Leu Pro Ala Thr Ile Ala Asp Val Glu
            370                 375                 380
Lys Arg Thr Arg Ala Leu Val Arg Ser Gly Asp Leu Ile Ser Gly Lys
385                 390                 395                 400
Gly Glu His Lys Gly Trp Leu Ala Ser Arg Glu Ala Val Val Thr Glu
                405                 410                 415
Gln Arg Ile Leu Ser Glu Val Ala Ala Gly Lys Gly Asn Ser Ser Pro
            420                 425                 430
Ala Ile Glu Pro Gln Lys Ala Ala Ala Ser Val Gln Ala Ala Ala Ala
            435                 440                 445
Thr Gly Gln Gly Phe Arg Leu Asn Glu Gly Gln Leu Ala Ala Ala Glu
            450                 455                 460
Leu Ile Leu Thr Ser Lys Asp Arg Thr Ile Ala Ile Gln Gly Ile Ala
465                 470                 475                 480
Gly Ala Gly Lys Ser Ser Val Leu Lys Pro Val Ala Glu Val Leu Arg
                485                 490                 495
Asp Glu Gly His Pro Val Ile Gly Leu Ala Ile Gln Asn Thr Leu Val
            500                 505                 510
Gln Met Leu Glu Arg Glu Thr Gly Ile Gly Ser Gln Thr Leu Ala Arg
            515                 520                 525
Phe Leu Arg Gly Trp Thr Lys Leu Leu Gly Asp Pro Gly Asn Val Ala
            530                 535                 540
Leu Arg Thr Glu Ala Gln Ala Ser Leu Lys Asp His Val Leu Val Leu
545                 550                 555                 560
Asp Glu Ala Ser Met Val Ser Asn Glu Asp Lys Glu Lys Leu Val Arg
                565                 570                 575
Leu Ala Asn Leu Ala Gly Val His Arg Leu Val Leu Ile Gly Asp Arg
            580                 585                 590
Lys Gln Leu Gly Ala Val Asp Ala Gly Lys Pro Phe Ala Leu Leu Gln
            595                 600                 605
Arg Ala Gly Ile Ala Arg Ala Glu Met Ala Thr Asn Leu Arg Ala Arg
            610                 615                 620
Asp Pro Val Val Arg Glu Ala Gln Ala Ser Ala Gln Ala Gly Asp Val
625                 630                 635                 640
Arg Asn Ala Leu Arg His Leu Lys Ser His Thr Val Glu Ala Lys Gly
                645                 650                 655
Asp Gly Ala Gln Val Ala Ala Glu Thr Trp Leu Ala Leu Asp Lys Glu
            660                 665                 670
Thr Arg Ala Arg Thr Ser Ile Tyr Ala Ser Gly Arg Ala Ile Arg Ser
            675                 680                 685
Ala Val Asn Ala Ala Val Gln Gln Gly Leu Leu Ala Asn Arg Glu Ile
            690                 695                 700
Gly Pro Gly Met Met Lys Leu Asp Val Leu Asp Arg Val Asn Ala Thr
705                 710                 715                 720
Arg Glu Glu Leu Arg His Leu Pro Ala Tyr Arg Ala Gly Gln Val Leu
                725                 730                 735
Glu Ile Ser Arg Lys Gln Gln Ala Leu Gly Leu Ser Val Gly Glu Tyr
            740                 745                 750
```

```
Arg Val Leu Gly Gln Asp Arg Lys Gly Arg Leu Val Glu Val Glu Asp
            755                 760                 765

Lys Arg Gly Lys Arg Phe Arg Phe Asp Pro Ala Arg Ile Lys Ala Gly
        770                 775                 780

Lys Gly Asp Glu Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Ala Ile Ala Gly Gly Lys
            820                 825                 830

Ile Thr Phe Glu Thr Ser Gln Gly Asp Gln Val Glu Leu Lys Arg Asp
            835                 840                 845

Asp Pro Met Leu Lys Arg Ile Asp Leu Ala Tyr Ala Leu Asn Ala His
        850                 855                 860

Met Ala Gln Gly Leu Thr Ser Asp Arg Gly Ile Ala Val Met Thr Ser
865                 870                 875                 880

Ser Glu Arg Asn Leu Ser Asn Gln Lys Thr Phe Met Val Thr Val Thr
                885                 890                 895

Arg Leu Arg Asp His Leu Thr Leu Val Val Asp Asn Ala Glu Lys Leu
            900                 905                 910

Gly Ala Ala Val Ala Arg Asn Lys Gly Glu Lys Ala Ser Ala Leu Glu
        915                 920                 925

Val Thr Gly Ser Val Lys Ser Thr Ala Ala Lys Gly Ser Gly Val Asp
        930                 935                 940

Gln Leu Lys Pro Glu Glu Ala Asn Lys Ala Lys Glu Leu Thr Arg
945                 950                 955                 960

<210> SEQ ID NO 74
<211> LENGTH: 966
<212> TYPE: PRT
<213> ORGANISM: Escherichia coli

<400> SEQUENCE: 74

Met Leu Ser His Met Val Leu Thr Arg Gln Asp Ile Gly Arg Ala Ala
1               5                   10                  15

Ser Tyr Tyr Glu Asp Gly Ala Asp Tyr Tyr Ala Lys Asp Gly Asp
            20                  25                  30

Ala Ser Glu Trp Gln Gly Lys Gly Ala Glu Leu Gly Leu Ser Gly
        35                  40                  45

Glu Val Asp Ser Lys Arg Phe Arg Glu Leu Leu Ala Gly Asn Ile Gly
    50                  55                  60

Glu Gly His Arg Ile Met Arg Ser Ala Thr Arg Gln Asp Ser Lys Glu
65                  70                  75                  80

Arg Ile Gly Leu Asp Leu Thr Phe Ser Ala Pro Lys Ser Val Ser Leu
                85                  90                  95

Gln Ala Leu Val Ala Gly Asp Ala Glu Ile Ile Lys Ala His Asp Arg
            100                 105                 110

Ala Val Ala Arg Thr Leu Glu Gln Ala Glu Arg Ala Gln Ala Arg
        115                 120                 125

Gln Lys Ile Gln Gly Lys Thr Arg Ile Glu Thr Gly Asn Leu Val
        130                 135                 140

Ile Gly Lys Phe Arg His Glu Thr Ser Arg Glu Arg Asp Pro Gln Leu
145                 150                 155                 160

His Thr His Ala Val Ile Leu Asn Met Thr Lys Arg Ser Asp Gly Gln
```

```
                165                 170                 175
Trp Arg Ala Leu Lys Asn Asp Glu Ile Val Lys Ala Thr Arg Tyr Leu
            180                 185                 190
Gly Ala Val Tyr Asn Ala Glu Leu Ala His Glu Leu Gln Lys Leu Gly
            195                 200                 205
Tyr Gln Leu Arg Tyr Gly Lys Asp Gly Asn Phe Asp Leu Ala His Ile
    210                 215                 220
Asp Arg Gln Gln Ile Glu Gly Phe Ser Lys Arg Thr Glu Gln Ile Ala
225                 230                 235                 240
Glu Trp Tyr Ala Ala Arg Gly Leu Asp Pro Asn Ser Val Ser Leu Glu
                245                 250                 255
Gln Lys Gln Ala Ala Lys Val Leu Ser Arg Ala Lys Lys Thr Ser Val
            260                 265                 270
Asp Arg Glu Ala Leu Arg Ala Glu Trp Gln Ala Thr Ala Lys Glu Leu
            275                 280                 285
Gly Ile Asp Phe Ser Arg Glu Trp Ser Gly Arg Glu Lys Gly Gly
            290                 295                 300
Ser Glu Lys Gln Ala His Ser Phe Met Pro Ser Asp Glu Ala Ala Lys
305                 310                 315                 320
Arg Ala Val Arg Tyr Ala Ile Asn His Leu Thr Glu Arg Gln Ser Val
                325                 330                 335
Met Asp Glu Arg Glu Leu Val Asp Thr Ala Met Lys His Ala Val Gly
            340                 345                 350
Ala Ala Arg Leu Glu Asp Ile Gln Lys Glu Leu Leu Arg Gln Thr Glu
            355                 360                 365
Thr Gly Tyr Leu Ile Arg Glu Ala Pro Arg Tyr Arg Pro Gly Gly Gln
    370                 375                 380
Thr Gly Pro Thr Asp Glu Pro Gly Lys Thr Arg Ala Glu Trp Val Ala
385                 390                 395                 400
Glu Leu Ala Ala Lys Gly Met Lys Gln Gly Ala Ala Arg Glu Arg Val
                405                 410                 415
Asp Asn Ala Ile Lys Thr Gly Gly Leu Val Pro Ile Glu Pro Arg Tyr
            420                 425                 430
Thr Thr Gln Thr Ala Leu Glu Arg Glu Lys Arg Ile Leu Gln Ile Glu
            435                 440                 445
Arg Asp Gly Arg Gly Ala Val Ala Pro Val Ile Ala Ala Glu Ala Ala
    450                 455                 460
Arg Glu Arg Leu Ala Ser Thr Asn Leu Asn Gln Gly Gln Arg Glu Ala
465                 470                 475                 480
Ala Glu Leu Ile Val Ser Ala Ala Asn Arg Val Gly Val Gln Gly
                485                 490                 495
Phe Ala Gly Thr Gly Lys Ser His Met Leu Asp Thr Ala Lys Gln Met
            500                 505                 510
Ile Glu Gly Glu Gly Tyr His Val Arg Ala Leu Ala Ala Tyr Gly Ser
            515                 520                 525
Gln Val Lys Ala Leu Arg Glu Leu Asn Val Glu Ala Asn Thr Leu Ala
    530                 535                 540
Ser Phe Leu Arg Ala Lys Asp Lys Asn Ile Asp Ser Arg Thr Val Leu
545                 550                 555                 560
Val Ile Asp Glu Ala Gly Val Val Pro Thr Arg Leu Met Glu Gln Thr
                565                 570                 575
Leu Lys Leu Ala Glu Lys Ala Gly Ala Arg Val Val Leu Met Gly Asp
            580                 585                 590
```

Thr Ala Gln Thr Lys Ala Ile Glu Ala Gly Arg Pro Phe Asp Gln Leu
            595                 600                 605

Gln Ala Ala Gly Met Gln Thr Ala His Met Arg Glu Ile Gln Arg Gln
        610                 615                 620

Lys Asn Pro Glu Leu Lys Ile Ala Val Glu Leu Ala Ala Gly Lys
625                 630                 635                 640

Ala Ser Ser Leu Glu Arg Ile Lys Asp Val Thr Glu Ile Lys Asn
            645                 650                 655

His His Glu Arg Arg Ala Ala Val Ala Glu Ala Tyr Ile Ala Leu Lys
        660                 665                 670

Pro Asp Glu Arg Asp Arg Thr Leu Ile Val Ser Gly Thr Asn Glu Ala
            675                 680                 685

Arg Arg Glu Ile Asn Gln Ile Val Arg Glu Gly Leu Gly Thr Ala Gly
        690                 695                 700

Lys Gly Ile Glu Phe Asp Thr Leu Val Arg Val Asp Thr Thr Gln Ala
705                 710                 715                 720

Glu Arg Arg His Ser Lys Asn Tyr Gln Val Gly His Val Ile Gln Pro
            725                 730                 735

Glu Arg Asp Tyr Ala Lys Thr Gly Leu Gln Arg Gly Glu Leu Tyr Arg
        740                 745                 750

Val Val Glu Thr Gly Pro Gly Asn Arg Leu Thr Val Ile Gly Glu His
            755                 760                 765

Asp Gly Gln Arg Ile Gln Phe Ser Pro Met Thr His Thr Lys Ile Ser
770                 775                 780

Val Tyr Gln Pro Glu Arg Ala Glu Leu Ala Val Gly Asp Thr Ile Arg
785                 790                 795                 800

Ile Thr Arg Asn Asp Lys His Leu Asp Leu Ala Asn Gly Asp Arg Met
            805                 810                 815

Lys Val Val Ala Val Glu Asp Arg Lys Val Thr Val Thr Asp Gly Lys
        820                 825                 830

Arg Asn Val Glu Leu Pro Thr Asp Lys Pro Leu His Val Asp His Ala
        835                 840                 845

Tyr Ala Thr Thr Val His Ser Ser Gln Gly Leu Thr Ser Asp Arg Val
        850                 855                 860

Leu Ile Asp Ala His Ala Glu Ser Arg Thr Thr Ala Lys Asp Val Tyr
865                 870                 875                 880

Tyr Val Ala Ile Ser Arg Ala Arg Phe Glu Ala Arg Val Phe Thr Asn
            885                 890                 895

Asp Arg Gly Lys Leu Pro Ala Ala Ile Ala Arg Glu Asn Ile Lys Ser
        900                 905                 910

Ala Ala His Asp Leu Ala Arg Asp Arg Gly Gly Arg Ser Ala Ala Ala
        915                 920                 925

Glu Arg Gln Arg Glu Gln Gln Arg Glu Ala Glu Arg Asn Arg Gln Thr
930                 935                 940

Gln Gln Pro Ala His Asp Arg Gln Lys Ala Ala Arg Glu Ala Glu Arg
945                 950                 955                 960

Gly Met Glu Ala Gly Arg
            965

<210> SEQ ID NO 75
<211> LENGTH: 8
<212> TYPE: PRT
<213> ORGANISM: Artificial sequence
<220> FEATURE:

-continued

<223> OTHER INFORMATION: RecD-like motif I of TrwC Eco

<400> SEQUENCE: 75

Gly Phe Ala Gly Thr Gly Lys Ser
1               5

<210> SEQ ID NO 76
<211> LENGTH: 10
<212> TYPE: PRT
<213> ORGANISM: Artificial sequence
<220> FEATURE:
<223> OTHER INFORMATION: RecD-like motif V of TrwC Eco

<400> SEQUENCE: 76

Tyr Ala Thr Thr Val His Ser Ser Gln Gly
1               5                   10

<210> SEQ ID NO 77
<211> LENGTH: 14
<212> TYPE: PRT
<213> ORGANISM: Artificial sequence
<220> FEATURE:
<223> OTHER INFORMATION: MobF motif III of TrwC Eco

<400> SEQUENCE: 77

His Glu Thr Ser Arg Glu Arg Asp Pro Gln Leu His Thr His
1               5                   10

<210> SEQ ID NO 78
<211> LENGTH: 1101
<212> TYPE: PRT
<213> ORGANISM: Agrobacterium tumefaciens C58

<400> SEQUENCE: 78

Met Ala Ile Ala His Phe Ser Ala Ser Ile Val Ser Arg Gly Asp Gly
1               5                   10                  15

Arg Ser Val Val Leu Ser Ala Ala Tyr Gln His Cys Ala Lys Met Glu
            20                  25                  30

Tyr Glu Arg Glu Ala Arg Thr Ile Asp Tyr Thr Arg Lys Gln Gly Leu
        35                  40                  45

Val His Gln Glu Phe Ile Leu Pro Ala Asp Ala Pro Lys Trp Val Arg
    50                  55                  60

Ala Leu Ile Ala Asp Cys Ser Val Ala Gly Ala Ser Glu Ala Phe Trp
65                  70                  75                  80

Asn Lys Val Glu Ala Phe Glu Lys Arg Ser Asp Ala Gln Leu Ala Arg
                85                  90                  95

Asp Leu Thr Ile Ala Leu Pro Arg Glu Leu Thr Ser Glu Gln Asn Ile
            100                 105                 110

Ala Leu Val Arg Asp Phe Val Glu Lys His Ile Leu Gly Lys Gly Met
        115                 120                 125

Val Ala Asp Trp Val Tyr His Asp Asn Pro Gly Asn Pro His Ile His
    130                 135                 140

Leu Met Thr Thr Leu Arg Pro Leu Thr Glu Asp Gly Phe Gly Ala Lys
145                 150                 155                 160

Lys Val Ala Val Ile Gly Glu Asp Gly Gln Leu Val Arg Thr Lys Ser
                165                 170                 175

Gly Lys Ile Leu Tyr Glu Leu Trp Ala Gly Ser Thr Asp Asp Phe Asn
            180                 185                 190

Val Val Arg Asp Gly Trp Phe Glu Arg Leu Asn His His Leu Thr Leu
        195                 200                 205

```
Gly Gly Ile Asp Leu Lys Ile Asp Gly Arg Ser Tyr Glu Lys Gln Gly
        210                 215                 220

Ile Asp Leu Glu Pro Thr Ile His Leu Gly Val Gly Ala Lys Ala Ile
225                 230                 235                 240

Ser Arg Lys Ala Glu Gln Gln Gly Val Arg Pro Glu Leu Glu Arg Ile
                245                 250                 255

Glu Leu Asn Glu Glu Arg Arg Ser Glu Asn Thr Arg Arg Ile Leu Lys
                260                 265                 270

Asn Pro Ala Ile Val Leu Asp Leu Ile Met Arg Glu Lys Ser Val Phe
            275                 280                 285

Asp Glu Arg Asp Val Ala Lys Val Leu His Arg Tyr Val Asp Asp Pro
290                 295                 300

Ala Val Phe Gln Gln Leu Met Leu Arg Ile Ile Leu Asn Pro Glu Val
305                 310                 315                 320

Leu Arg Leu Gln Arg Asp Thr Ile Glu Phe Ala Thr Gly Glu Lys Val
                325                 330                 335

Pro Ala Arg Tyr Ser Thr Arg Ala Met Ile Arg Leu Glu Ala Thr Met
            340                 345                 350

Ala Arg Gln Ala Met Trp Leu Ser Asp Lys Glu Thr His Ala Val Ser
            355                 360                 365

Thr Ala Val Leu Leu Ala Ala Thr Phe Gly Arg His Gly Arg Leu Ser
370                 375                 380

Glu Glu Gln Lys Ala Ala Ile Glu Cys Ile Ala Gly Pro Ala Arg Ile
385                 390                 395                 400

Ala Ala Val Val Gly Arg Ala Gly Ala Gly Lys Thr Thr Met Met Lys
                405                 410                 415

Ala Ala Arg Glu Ala Trp Glu Leu Ala Gly Tyr Arg Val Val Gly Gly
            420                 425                 430

Ala Leu Ala Gly Lys Ala Ser Glu Gly Leu Asp Lys Glu Ala Gly Ile
            435                 440                 445

Glu Ser Arg Thr Leu Ser Ser Trp Glu Leu Arg Trp Asn Arg Gly Arg
450                 455                 460

Asp Val Leu Asp Asn Lys Thr Val Phe Val Met Asp Glu Ala Gly Met
465                 470                 475                 480

Val Ala Ser Lys Gln Met Ala Gly Phe Val Asp Ala Val Val Arg Ala
                485                 490                 495

Gly Ala Lys Ile Val Leu Val Gly Asp Pro Glu Gln Leu Gln Pro Ile
            500                 505                 510

Glu Ala Gly Ala Ala Phe Arg Ala Ile Val Asp Arg Ile Gly Tyr Ala
            515                 520                 525

Glu Leu Glu Thr Ile Tyr Arg Gln Arg Glu Asp Trp Met Arg Lys Ala
            530                 535                 540

Ser Leu Asp Leu Ala Arg Gly Asn Val Glu Lys Ala Leu Ala Leu Tyr
545                 550                 555                 560

Asn Ala Asn Ala Arg Ile Val Gly Glu Arg Leu Lys Ala Glu Ala Val
                565                 570                 575

Glu Arg Leu Ile Ala Asp Trp Asn Arg Asp Tyr Asp Gln Thr Lys Thr
            580                 585                 590

Thr Leu Ile Leu Ala His Leu Arg Arg Asp Val Arg Met Leu Asn Val
            595                 600                 605

Met Ala Arg Glu Lys Leu Val Glu Arg Gly Ile Val Gly Glu Gly His
610                 615                 620
```

```
Val Phe Arg Thr Ala Asp Gly Glu Arg Arg Phe His Ala Gly Asp Gln
625                 630                 635                 640

Ile Val Phe Leu Lys Asn Glu Thr Leu Leu Gly Val Lys Asn Gly Met
            645                 650                 655

Ile Gly His Val Val Glu Ala Val Pro Asn Arg Ile Val Ala Val Val
            660                 665                 670

Gly Asp Arg Asp His Arg His Val Val Glu Gln Arg Phe Tyr
        675                 680                 685

Ser Asn Leu Asp His Gly Tyr Ala Thr Thr Ile His Lys Ser Gln Gly
    690                 695                 700

Ala Thr Val Asp Arg Val Lys Val Leu Ala Ser Leu Ser Leu Asp Arg
705                 710                 715                 720

His Leu Thr Tyr Val Ala Met Thr Arg His Arg Glu Asp Leu Gln Leu
                725                 730                 735

Tyr Tyr Gly Cys Arg Ser Phe Ala Phe Asn Gly Gly Leu Ala Lys Val
            740                 745                 750

Leu Ser Arg Lys Asn Ala Lys Glu Thr Thr Leu Asp Tyr Glu Arg Gly
        755                 760                 765

Lys Leu Tyr Arg Glu Ala Leu Arg Phe Ala Glu Asn Arg Gly Leu His
770                 775                 780

Ile Met Gln Val Ala Arg Thr Met Leu Arg Asp Arg Leu Asp Trp Thr
785                 790                 795                 800

Leu Arg Gln Lys Thr Lys Val Ser Asp Leu Val His Arg Leu Arg Ala
                805                 810                 815

Leu Gly Glu Arg Leu Gly Leu Asp Gln Ser Pro Lys Thr Gln Thr Met
            820                 825                 830

Lys Glu Ala Ala Pro Met Val Thr Gly Ile Lys Thr Phe Ser Gly Ser
        835                 840                 845

Val Ala Asp Thr Val Gly Asp Lys Leu Gly Ala Asp Pro Thr Leu Lys
    850                 855                 860

Gln Gln Trp Glu Glu Val Ser Ala Arg Phe Arg Tyr Val Phe Ala Asp
865                 870                 875                 880

Pro Glu Thr Ala Phe Arg Ala Val Asn Phe Asp Thr Val Leu Ala Asp
                885                 890                 895

Lys Glu Ala Ala Lys Ala Val Leu Gln Lys Leu Glu Ala Glu Pro Ala
            900                 905                 910

Ser Ile Gly Ala Leu Lys Gly Lys Thr Gly Ile Leu Ala Ser Lys Thr
        915                 920                 925

Glu Arg Glu Ala Arg Arg Val Ala Glu Val Asn Val Pro Ala Leu Lys
930                 935                 940

Arg Asp Leu Glu Gln Tyr Leu Arg Met Arg Glu Thr Ala Thr Leu Arg
945                 950                 955                 960

Ile Val Thr Glu Glu Gln Ala Leu Arg Gln Arg Val Ser Ile Asp Ile
                965                 970                 975

Pro Ala Leu Ser Pro Ala Ala Arg Val Val Leu Glu Arg Val Arg Asp
            980                 985                 990

Ala Ile Asp Arg Asn Asp Leu Pro Ala Ala Leu Gly Tyr Ala Leu Ser
        995                 1000                1005

Asn Arg Glu Thr Lys Leu Glu Ile Asp Gly Phe Asn Gln Ala Val
        1010                1015                1020

Thr Glu Arg Phe Gly Glu Arg Thr Leu Leu Ser Asn Val Ala Arg
        1025                1030                1035

Glu Pro Ser Gly Lys Leu Tyr Glu Lys Leu Ser Asp Gly Met Arg
```

```
                1040                1045                1050

Pro Glu Gln Lys Glu Gln Leu Lys Gln Ala Trp Pro Ile Met Arg
        1055                1060                1065

Thr Ala Gln Gln Leu Ala Ala His Glu Arg Thr Val Gln Ser Leu
    1070                1075                1080

Lys Gln Ala Glu Glu Leu Arg Gln Thr Leu Arg Gln Ala Pro Val
    1085                1090                1095

Leu Lys Gln
    1100

<210> SEQ ID NO 79
<211> LENGTH: 8
<212> TYPE: PRT
<213> ORGANISM: Artificial sequence
<220> FEATURE:
<223> OTHER INFORMATION: RecD-like motif I of TraA Atu

<400> SEQUENCE: 79

Gly Arg Ala Gly Ala Gly Lys Thr
1               5

<210> SEQ ID NO 80
<211> LENGTH: 10
<212> TYPE: PRT
<213> ORGANISM: Artificial sequence
<220> FEATURE:
<223> OTHER INFORMATION: RecD-like motif V of TraA Atu

<400> SEQUENCE: 80

Tyr Ala Thr Thr Ile His Lys Ser Gln Gly
1               5                   10

<210> SEQ ID NO 81
<211> LENGTH: 18
<212> TYPE: PRT
<213> ORGANISM: Artificial sequence
<220> FEATURE:
<223> OTHER INFORMATION: MobQ motif III of TraA Atu

<400> SEQUENCE: 81

Gly Met Val Ala Asp Trp Val Tyr His Asp Asn Pro Gly Asn Pro His
1               5                   10                  15

Ile His

<210> SEQ ID NO 82
<211> LENGTH: 878
<212> TYPE: PRT
<213> ORGANISM: Sulfobacillus acidophilus TPY

<400> SEQUENCE: 82

Met Ser Ala Thr Asp Arg Glu Ile Asp Pro Ser Thr Gly Ala Val Arg
1               5                   10                  15

Tyr Phe Ala Glu Ser Gly Glu Pro Pro Gly Arg Trp Arg Gly His Ala
            20                  25                  30

Ala Ser Leu Gly Arg Pro Gly Gly Asp Ile Val Lys Ala Gly Glu Leu
        35                  40                  45

Glu Arg Leu Leu Asn Gly Gln His Pro Glu Ser Gly Glu Ser Leu Val
    50                  55                  60

Gln Thr Gln Ala Gly Lys Ser His Arg Pro Gly Trp Asp Leu Thr Phe
65                  70                  75                  80

Ser Ser Pro Lys Ser Val Ser Ala Val Trp Ala Ala Ala Asp Pro Glu
```

-continued

```
                85                  90                  95
Leu Arg Ala Ala Ile Glu Arg Ala His Glu Ala Ala Val Gln Ala Ala
                100                 105                 110
Phe Asp Tyr Leu Gln Ala Asn Ala Ala Tyr Thr Arg Arg Gly Lys Gly
                115                 120                 125
Gly Thr Glu Leu Glu Arg Val Gln Leu Ile Gly Ile Glu Tyr Gln His
                130                 135                 140
Ser Thr Ser Arg Ala Gln Asp Pro His Leu His Ser His Leu Leu Ile
145                 150                 155                 160
Ala Asn Val Ala Gln Arg Ser Asp Gly Thr Trp Gly Thr Leu Glu Ser
                165                 170                 175
Arg Pro Met Phe Gln His Arg Met Ala Ala Gly Ser Leu Tyr Gln Ser
                180                 185                 190
Glu Leu Ala Ala Arg Leu Arg Asp Met Gly Phe Glu Ile Val Lys Gly
                195                 200                 205
Arg Gly Gly Thr Phe Glu Ile Asp Gly Val Pro Gly Asp Leu Lys Lys
                210                 215                 220
Leu Trp Ser Gly Arg His Glu Gln Met Glu Ala Asn Gly Ala Thr Gly
225                 230                 235                 240
Gln Ser Arg Glu Ala Glu Arg Ala Phe Leu Glu Gly Arg Pro Glu Lys
                245                 250                 255
Gly Lys Ile His Arg Pro Ser Leu Phe Ala Lys Trp Gly Ala Glu Ala
                260                 265                 270
Ala Ala His Gly Leu Asp Pro Val Lys Ile Arg Thr Glu Leu Met Arg
                275                 280                 285
Gly Arg Ile Gln Ser Ala Glu Pro Leu Glu Trp Ala Gln Ile Arg Glu
                290                 295                 300
Arg Leu Thr Ala Asp Arg Ser Thr Phe Arg Arg Glu Asp Val Ile Arg
305                 310                 315                 320
Gln Val Ala Thr Ala Ser Tyr Gly Gln Tyr Ser Ala Gln Gln Leu Gln
                325                 330                 335
Ala Leu Val Asp Ala Ala Leu Thr Gln Ser Glu Ser Gly Phe Val Arg
                340                 345                 350
Leu Gly Ser Asp Asp Arg Gly Glu Phe Tyr Thr Thr Val Glu His Leu
                355                 360                 365
Glu Arg Glu Lys Arg Met Leu Ser Ala Met Gly Arg Leu Ala Ala Ser
                370                 375                 380
Thr Thr His Ala Ala Asp Val Arg Ala Val Glu Arg Ala Ile Ser Lys
385                 390                 395                 400
Asp Arg Gly Gly Trp Lys Leu Ser Asp Glu Gln Ala Gln Ala Val Arg
                405                 410                 415
Ala Leu Ala Gly Gly Ser Arg Ile Ala Thr Thr Arg Gly Ala Ala Gly
                420                 425                 430
Thr Gly Lys Thr Thr Ser Met Ile Ala Leu Lys Glu Ala Tyr Glu Ser
                435                 440                 445
Ser Gly Tyr Lys Leu Leu Gly Ala Thr Ile Ser Asn Gln Ala Ala Gln
                450                 455                 460
Val Leu Glu Lys Glu Ser Gly Ile Thr Ser Met Ser Val Ala Lys Leu
465                 470                 475                 480
Leu Tyr Glu Leu Ala Ser Ala Glu Glu Lys Ser Glu Thr Met Ala Arg
                485                 490                 495
Met Gln Trp Ala Glu Gln Glu Glu Ala Lys Ala Arg Gln Ala Ala Asp
                500                 505                 510
```

Arg Gly Glu Glu Tyr Glu Pro Lys Pro Phe Pro Gly Met Gly Val Ala
            515                 520                 525

Asp Ala Val Phe Glu Arg Val Phe Pro Ala Lys Ala Lys Lys Asp Ala
            530                 535                 540

Ile Thr Leu Asp Glu Arg Thr Ile Val Ile Val Asp Glu Ala Gly Met
545                 550                 555                 560

Val Asp Thr Pro Gln Leu Ala Gln Leu Ile Glu His Val Glu Arg Ser
            565                 570                 575

Gly Ala Lys Ile Val Leu Ile Gly Asp Glu Arg Gln Ile Gln Ala Val
            580                 585                 590

Gly Ala Gly Gly Phe Gln Ala Ala Arg Gln Ile Thr Arg Gln Val
            595                 600                 605

Gly Gly Asp Ala Glu Leu Thr Glu Val Arg Arg Gln Lys Val Ala Trp
            610                 615                 620

Gln Arg Glu Ala Ala Glu Gln Ile Ser Leu Gly Gln Ala Arg Glu Ala
625                 630                 635                 640

Leu Gln Met Tyr Glu Arg Gly Arg Leu His Thr Ala Asp Gly Pro
            645                 650                 655

Glu Glu Ala Ala Arg Glu Leu Val Gln Asp Trp Ile Arg Asp Arg Leu
            660                 665                 670

Gln Asp Lys Ala Ala Ser Gln Leu Ile Ile Ala Ser Ser His Ala Gln
            675                 680                 685

Gly Ala Val Leu Asn His Leu Ala Gln Glu Thr Leu Arg Ser His Gly
            690                 695                 700

Met Leu Gly Pro Leu Val Ala Glu Gly Leu Ser Thr Ala Arg Gln Gly
705                 710                 715                 720

Lys His Asp Leu Tyr Val Gly Asp Glu Ile Arg Phe Ile Lys Asn Ala
            725                 730                 735

Lys Lys Gln Gly Trp Ile Asn Gly Asp Arg Gly Thr Val Ile Gly Met
            740                 745                 750

Gly Pro Ala Gly Gln Ile Arg Val Arg Leu Glu Glu Ser Gly Gln Val
            755                 760                 765

Val Glu Phe Asp Pro Arg Gln Tyr Arg His Trp Gln Leu Ala Tyr Ala
770                 775                 780

Ser Thr Ala His Lys Ser Gln Gly Ser Thr Val Asp Arg Ala Tyr Tyr
785                 790                 795                 800

Leu Leu Ser Ser Gly Asp His Arg Glu Leu Gly Tyr Val Ala Ala Ser
            805                 810                 815

Arg His Lys Gln Asp Leu Arg Leu Tyr Val Asp Gln Ser Val Tyr Glu
            820                 825                 830

Ala Lys Ser Asp Arg Asp Gln Leu Ile Gln Glu Ile Ala Arg Ser Leu
            835                 840                 845

Ala Lys Ser Asp Arg Lys Glu Ile Ala Leu Ser Leu Ala Ala Lys Ala
            850                 855                 860

Gly Ser Asp Arg Val Gln Asp His Asp Thr Gly His Ser Arg
865                 870                 875

<210> SEQ ID NO 83
<211> LENGTH: 8
<212> TYPE: PRT
<213> ORGANISM: Artificial sequence
<220> FEATURE:
<223> OTHER INFORMATION: RecD-like motif I of TrwC Sac

<400> SEQUENCE: 83

Gly Ala Ala Gly Thr Gly Lys Thr
1               5

<210> SEQ ID NO 84
<211> LENGTH: 10
<212> TYPE: PRT
<213> ORGANISM: Artificial sequence
<220> FEATURE:
<223> OTHER INFORMATION: RecD-like motif V of TrwC Sac

<400> SEQUENCE: 84

Tyr Ala Ser Thr Ala His Lys Ser Gln Gly
1               5                   10

<210> SEQ ID NO 85
<211> LENGTH: 14
<212> TYPE: PRT
<213> ORGANISM: Artificial sequence
<220> FEATURE:
<223> OTHER INFORMATION: MobF motif III of TrwC Sac

<400> SEQUENCE: 85

His Ser Thr Ser Arg Ala Gln Asp Pro His Leu His Ser His
1               5                   10

<210> SEQ ID NO 86
<211> LENGTH: 909
<212> TYPE: PRT
<213> ORGANISM: Acidithiobacillus ferrivorans SS3

<400> SEQUENCE: 86

Met Leu Ser Ile His Ala Lys Lys Gly Ser Thr Ala Glu His Val Ala
1               5                   10                  15

Gln Val Ala Asp Tyr Pro Asp Glu Gln Pro Glu Gln Arg Pro Glu Gln
            20                  25                  30

Gln Ser Arg Pro Ala Asn Gly Thr Gly Ala Ile Glu Asp Tyr Tyr Ser
        35                  40                  45

Gln Ser Asn Gly Gly Thr Pro Ser Ile Trp Val Gly Ala Gly Ala Glu
    50                  55                  60

Ala Ile Gly Leu Ala Gly Gln Ala Val Glu Arg Glu Thr Met Thr Arg
65                  70                  75                  80

Leu Leu Gln Gly Leu His Pro Asp Asp Gly Arg Ala Leu Val Asp Lys
                85                  90                  95

Ala Gly Pro Gln Arg Arg Tyr Gly Tyr Asp Leu Thr Phe Ser Ala Pro
            100                 105                 110

Lys Ser Val Ser Ile Val Trp Ala Val Ala Asp Arg Asp Leu Arg Glu
        115                 120                 125

Ala Ile Ala Thr Ala His Asp Ala Ala Val Ala Gln Ala Leu Arg His
    130                 135                 140

Ile Glu Thr His Leu Pro Val Ala Arg Arg Gly His Ala Gly Glu Glu
145                 150                 155                 160

Arg Glu Leu Ala His Leu Ile Thr Gly Val Tyr Arg His Ala Ser Ser
                165                 170                 175

Arg Glu Gln Asp Pro Gln Ile His Ser His Ala Leu Leu Met Asn Leu
            180                 185                 190

Ala Gln Arg Leu Asp Gly Thr Trp Gly Ala Ile Glu Ser Trp Glu Ile
        195                 200                 205

Tyr Arg His Lys Met Ala Leu Gly Ala Leu Tyr Arg Thr Val Leu Ala
        210                 215                 220

```
Gln Arg Leu Gln Glu Met Gly Phe Gly Ile Glu Arg Asp Gly Asp Ser
225                 230                 235                 240

Phe Arg Ile Leu Gly Val Ser Glu Asp Ala Glu Arg Glu Phe Ser Arg
            245                 250                 255

Arg Arg Gln Gln Ile Glu Thr Leu Leu Leu Glu Arg Gly Arg Ser Asn
            260                 265                 270

Ala Glu Ala Ala Ala Leu Ala Thr Leu Asp Thr Arg Arg Lys Glu
        275                 280                 285

Val Ile Asp Arg Ala Ile Leu Ala Ala Asp Trp Arg Glu Arg Ala Ala
        290                 295                 300

His Tyr Gly Leu Ser Ala Lys Thr Val Gln Ala Leu Arg Gln Gly Leu
305                 310                 315                 320

Leu Ala Ala Ser Tyr Asp Arg Ala Ala Val Leu Arg Asp Leu Thr Ala
                325                 330                 335

His Asp Ser Thr Phe Glu Glu Arg His Ile Trp His Arg Val Ala Val
            340                 345                 350

Ala Ala Gln Ala Cys Gly Met Gly Tyr Asp Glu Ile Arg Ala Glu Val
            355                 360                 365

Ala Gln Leu Arg Arg Asp Thr Glu Ile Val Pro Leu Gln Ala Phe Gly
        370                 375                 380

Pro Ala Arg Phe Thr Thr Arg Glu Met Gln Ser Ile Glu Gln Gln Met
385                 390                 395                 400

Val Thr Asp Ala Gln Ala Leu Ala Ala Val Asp Trp His Leu Val Asp
                405                 410                 415

Gly Ala Thr Val Arg Arg Ala Ile Glu Ala Asp Arg Glu Ala Glu
                420                 425                 430

Gln Lys Gly Phe Ser Leu Ser Glu Glu Gln Arg Arg Ala Ile Trp His
            435                 440                 445

Ile Thr His Arg Ile Gly Ala Leu Gln Met Ile Gln Gly His Ala Gly
        450                 455                 460

Ala Gly Lys Thr Thr Met Leu Asp Ala Ala Arg Arg Ala Trp Glu Ala
465                 470                 475                 480

Ala Gly Phe Arg Val His Gly Ala Ala Ile Ala Lys Lys Ala Ala His
                485                 490                 495

Gly Leu Phe His Gly Ala Asn Ile Asp Ser Gln Ser Leu Ala Ala Leu
            500                 505                 510

Leu Leu Ser Leu Lys Pro Gly Glu Asp Pro Val Thr Gly Glu Pro Ile
        515                 520                 525

Pro Pro Thr Arg Thr Leu Asn Ala Arg Asp Val Ile Val Ile Asp Glu
        530                 535                 540

Ala Gly Met Val Gly Ser Arg Met Met Gln Glu Leu Leu Ala Gln Val
545                 550                 555                 560

Arg Ala Ser Gly Ala Lys Leu Val Leu Val Gly Asp Ile Ala Gln Leu
                565                 570                 575

Gln Ala Ile Asp Ala Gly Gly Ala Phe Arg Ala Leu Gln Lys Thr Gly
            580                 585                 590

Pro Asp Ala Val Ala Tyr Leu Lys Glu Asn Leu Arg Gln Arg Gly Glu
            595                 600                 605

Lys Ala Glu Asp Met Lys Lys Val Val Ala Leu Thr Arg Gln Gly Asp
        610                 615                 620

Ala Ala Lys Ala Leu Glu Ile Leu Asp Arg His Gly Leu Ile Glu Ile
625                 630                 635                 640
```

```
Ala Asp Gly Trp Pro Glu Ala Ala Ala Met Ala Val Gly Arg Trp Val
                645                 650                 655

Asn Leu Tyr Asp Ala Glu Gln Pro Gln Glu Ala Leu Leu Leu Ala Ala
            660                 665                 670

Thr Asn Ala Ala Thr Glu Thr Leu Asn Ala Leu Ala Arg His Ala Leu
        675                 680                 685

Lys Ser Arg Gly Leu Leu Asp Asp Arg Pro Ala Val Thr Ile Thr Val
690                 695                 700

Arg Asp Arg Gln Gly Lys Ser Leu Gly Gln Arg Glu Ile Ala Leu Gly
705                 710                 715                 720

Glu Arg Leu Val Phe Arg Ala Asn Arg Asn His Ala Gly Ile Leu Asn
                725                 730                 735

Asn Glu Ala Gly Thr Val Thr Ala Leu Ser Glu Gly Phe His Gly Pro
            740                 745                 750

Glu Ile Thr Ile Arg Lys Asp Asp Gly Ser Glu Ile Thr Ile Ile Pro
        755                 760                 765

Gly Gln Ser Val Pro Glu Gly Arg Thr Glu Arg Gln Ile Ser Pro Gly
770                 775                 780

Ala Gly Tyr Ala Gln Ile Glu Tyr Ala Tyr Ala Gly Thr Thr His Arg
785                 790                 795                 800

Asn Gln Gly Thr Thr Ala Asp His Val Val Val Phe Ala Asp Gly Ser
                805                 810                 815

Met Glu Ser Arg Glu Lys Ala Tyr Val Asp Leu Ser Arg Met Arg His
            820                 825                 830

Thr Thr Ala Val Val Phe Ala Arg Pro Asp Ile Glu Asn Asp Leu Ala
        835                 840                 845

Glu Leu Gly Met Glu Pro Glu Val Gln Gly Phe Asp Ala Ile Lys Lys
850                 855                 860

Ile Ile Gly Ala Met Ser Arg Ser Gln Gln Lys Asn Thr Ser Leu Asp
865                 870                 875                 880

Tyr Thr Val Thr Gly Lys Pro Glu Pro Glu Thr Gly Thr Thr Glu Ser
                885                 890                 895

Thr Pro Ala Ser Leu Pro His Arg Gly Arg Val Ala Ser
            900                 905

<210> SEQ ID NO 87
<211> LENGTH: 8
<212> TYPE: PRT
<213> ORGANISM: Artificial sequence
<220> FEATURE:
<223> OTHER INFORMATION: RecD-like motif I of TrwC Afe

<400> SEQUENCE: 87

Gly His Ala Gly Ala Gly Lys Thr
1               5

<210> SEQ ID NO 88
<211> LENGTH: 10
<212> TYPE: PRT
<213> ORGANISM: Artificial sequence
<220> FEATURE:
<223> OTHER INFORMATION: RecD-like motif V of TrwC Afe

<400> SEQUENCE: 88

Tyr Ala Gly Thr Thr His Arg Asn Gln Gly
1               5                   10

<210> SEQ ID NO 89
```

<211> LENGTH: 14
<212> TYPE: PRT
<213> ORGANISM: Artificial sequence
<220> FEATURE:
<223> OTHER INFORMATION: MobF motif III of TrwC Afe

<400> SEQUENCE: 89

His Ala Ser Ser Arg Glu Gln Asp Pro Gln Ile His Ser His
1               5                   10

<210> SEQ ID NO 90
<211> LENGTH: 1185
<212> TYPE: PRT
<213> ORGANISM: Terriglobus saanensis SP1PR4

<400> SEQUENCE: 90

Met Leu Thr Ile Ser Lys Ala Ile Ser Val Gln Ala Gln Thr Tyr
1               5                   10                  15

His Lys Leu Glu Tyr Thr Ser Asp Ala Gln Ser Tyr Tyr Lys Gln Glu
                20                  25                  30

Asp Thr Val Arg Gly Glu Trp Gln Gly Lys Leu Ala Ala Ser Ile Gly
            35                  40                  45

Leu Ser Gly Glu Val Ser Pro Leu Glu Phe Ser Arg Leu Thr Glu Gly
        50                  55                  60

Ile His Pro Gln Thr Glu Ala Gln Met Val Arg His Arg Glu Gly Gln
65                  70                  75                  80

Glu Tyr Thr Ser Ala Asp Gly Ser Val Thr Lys Pro Val Glu His Arg
                85                  90                  95

Ala Gly Trp Asp Ala Thr Phe Ser Ala Pro Lys Ser Val Ser Leu Thr
            100                 105                 110

Ala Leu Val Gly Gly Asp Glu Arg Val Thr Glu Ala His Arg Ala Ala
        115                 120                 125

Val Thr Thr Ala Leu Asp Glu Leu Glu Lys Tyr Thr His Ala Arg Ile
130                 135                 140

Gly Gly Asn Asn Pro Ala Glu Met Thr Gly Lys Phe Val Ala Ala Lys
145                 150                 155                 160

Phe Glu His Asp Thr Ala Arg Pro Val Asn Gly Tyr Ala Ala Pro Gln
                165                 170                 175

Leu His Thr His Ala Ile Ile Phe Asn Val Thr Glu Arg Glu Asp Gly
            180                 185                 190

Ser Thr Arg Ala Ile Gln Glu Arg Thr Phe Phe Glu Ser Gln Asn Tyr
        195                 200                 205

Ala Thr Ala Val Tyr Gln Ser Val Leu Thr His Arg Leu Arg Lys Leu
210                 215                 220

Gly Tyr Glu Ile Glu Pro Gly Gln Ser Gly Ala Pro Glu Ile Lys Gly
225                 230                 235                 240

Tyr Ser Gln Ala Tyr Leu Asp Ala Ser Ser Pro Arg Ser Gln Gln Ile
                245                 250                 255

Lys Glu Gln Met Glu Arg Ala Gly Phe Gln Gly Pro Glu Ala Ala Gln
            260                 265                 270

Ile Ala Ala His Ala Thr Arg Asp Arg Lys Gln Thr Leu Thr Pro Ser
        275                 280                 285

Gly Val Leu Ala Ala His Lys Glu Met Ala Ala Glu Tyr Gly Asn Gln
290                 295                 300

Pro Glu Arg Val Ile Gly Ala Arg Glu Arg Val Leu Thr Gln Ala
305                 310                 315                 320

-continued

```
Gln Gly Thr Gly Val Gln Pro Asp Ser Arg Gly Ala Val Ala Phe Ala
                    325                 330                 335

Lys Glu Lys Val Phe Glu Arg Glu Ala Val Ala Asp Glu Arg Val Ile
            340                 345                 350

Met Arg Glu Ala Leu Arg Arg Gly Met Gly Glu Val Ser Phe Ser Glu
        355                 360                 365

Val Gln Ser Glu Phe Gln Arg Arg Glu Glu Gly Glu Phe Arg Ser
370                 375                 380

Val Gln Gly Gln Lys Tyr Ser Ser Gly Arg Ser Phe Thr Thr Pro Glu
385                 390                 395                 400

Thr Ile Ala Asp Glu Arg Ala Asn Val Arg His Val Leu Asp Gly Leu
                405                 410                 415

Gly Ala Ala Ala Pro Met Leu Ser Thr Ala Ala Asp Gln Gln Ala
            420                 425                 430

Lys Ser Arg Asp Phe Leu Asn Glu Ala Gln Gln Thr Ala Ile Arg Glu
            435                 440                 445

Val Leu Thr Ser Thr Asp Arg Val His Gly Phe Gln Gly Leu Ala Gly
        450                 455                 460

Thr Gly Lys Thr Ser Thr Leu Ala Ala Ile Arg Glu Gly Ala Glu Gln
465                 470                 475                 480

Gly Gly Tyr Lys Val Glu Gly Phe Ala Pro Thr Ser Lys Ala Thr Gly
                485                 490                 495

Gln Leu Arg Glu Ser Gly Ile Glu Ala Asn Thr Leu Gln Ser Phe Leu
            500                 505                 510

Ala Gln Gln Lys Asn Ala Asp Ser Ala Ser Lys His Leu Tyr Met Leu
        515                 520                 525

Asp Glu Ser Ser Leu Ala Ser Thr Arg Gln Met Arg Ala Phe Leu Glu
530                 535                 540

Lys Ile His Gln Glu Asp Arg Val Leu Val Ile Gly Asp Thr Arg Gln
545                 550                 555                 560

His Gln Gly Val Asp Ala Gly Arg Pro Phe Gln Gln Met Gln Glu Ala
                565                 570                 575

Gly Met Gln Thr Ser Lys Leu Asp Thr Ile Met Arg Gln Lys Asp Pro
            580                 585                 590

Glu Leu Leu Arg Ala Val Gln Tyr Leu Ala Thr Asn Glu Thr Glu Lys
        595                 600                 605

Gly Ile Ala Leu Leu Ser Gln Gln Gly Arg Val Thr Glu Leu Ala Arg
        610                 615                 620

Ala Ser Glu Arg Ile Val Ala Ile Ala Arg Asp Tyr Ala Ala Arg Pro
625                 630                 635                 640

Glu Asn Thr Leu Ile Val Ser Pro Asp Asn Arg Ser Arg Gln Gln Ile
                645                 650                 655

Asn Glu Ala Val Arg Gly Glu Leu Leu Lys Asp Gly Thr Leu Ala Gln
            660                 665                 670

Asp Gly Arg Gln Phe Leu Thr Leu Ser His Arg Ser Asp Met Thr Gly
        675                 680                 685

Pro Asp Arg Thr Trp Ala Ala Met Tyr Arg Pro Gly Asp Val Val Gln
690                 695                 700

Tyr Glu Arg Gly Ser Lys Ala Glu Gly Ile Gly Arg Gly Ser Phe Gly
705                 710                 715                 720

Val Val Gln Ser Ser Asp Ala Ala Ser Asn Arg Leu Thr Val Glu Phe
                725                 730                 735

Ser Asn Gly Ser Ser Val Glu Tyr Asp Pro Lys Arg Val Tyr Gly Val
```

```
                740              745            750
Asn Val Tyr Arg Glu Thr Ser Arg Glu Phe Ala Thr Gly Asp Arg Leu
            755              760            765
Gln Phe Ser Ala Ile His Lys Asp Leu Gly Ile Ser Asn Arg Asp Met
            770              775            780
Gly Thr Ile Thr Lys Met Glu Pro Asp Arg Leu Thr Val Leu Met Asp
785             790              795            800
Gly Lys Glu Gln Arg Ser Val Ser Phe Asn Pro Ala Asp Phe Arg Gln
            805              810            815
Phe Asp His Gly Tyr Ala Val Thr Ser His Ser Ser Gln Gly Leu Thr
            820              825            830
Thr Asp Arg Val Ile Ala Asn Ile Asp Thr Asp Ser Ser Arg Ser Leu
            835              840            845
Ile Asn Asn Arg Leu Ala Tyr Val Ala Ile Ser Arg Ala Ser Glu Asp
            850              855            860
Ala Arg Ile Tyr Thr Asn Asp Ala Ala Thr Leu Gly Gln Arg Leu Ser
865             870              875            880
Thr Asp Val Thr Lys Thr Ala Ala Leu Asp Phe Thr Ala Arg Pro Glu
            885              890            895
His Ser Ala Ala Gln Glu Val Ser Lys Ala Arg Thr Val Val Val His
            900              905            910
Glu Tyr Asn Asn Pro Asp Ser Arg Leu Ala Ser Val Thr Arg Glu Tyr
            915              920            925
Val Ile Arg Pro Glu Arg Ser Ile Ile Phe Ala Pro Asp Arg Ala Glu
            930              935            940
Arg Glu Lys Leu Thr Gln Ile Ile Arg Ala Asp Leu Tyr Ala Asn Gly
945             950              955            960
Lys Leu Gly His Asp Ala Gln Ala Met Ser Val Leu Ile Glu Lys Glu
            965              970            975
Thr Gly Ser Lys Met Arg Val Glu Ser Tyr Gln Pro Gly Asp Lys Ile
            980              985            990
Gln Tyr Lys Thr Gly Ser Pro Gly Leu Asp Gly Ile Pro His Asp Ser
            995              1000           1005
His Ala Thr Val Val Ser Thr Thr Pro Arg Ser Asn Leu Leu Ser
            1010             1015           1020
Val Arg Phe Asp Ala Thr Arg Glu Glu Val Ser Tyr Asn Pro Ala
            1025             1030           1035
Gln Phe Arg Thr Gln Thr Arg Glu Ser Arg Val Tyr Gln Glu Glu
            1040             1045           1050
Thr Arg Glu Val Ala Gln Gly Glu Arg Val Arg Phe Thr Thr Tyr
            1055             1060           1065
Asp Lys Glu Ile Gly Val Arg Ser Gly Asp Leu Gly Thr Val Thr
            1070             1075           1080
Arg Ile Gly Gln Asp His Ser Met Thr Val Lys Met Asp Ser Gly
            1085             1090           1095
Arg Thr Ala Glu Val Ser Pro Glu Lys Ala Leu His Ile Asp Tyr
            1100             1105           1110
Gly Tyr Ala Val Asp Ser Leu Lys Asn Val Arg Ala Glu Arg Val
            1115             1120           1125
Ile Ala Thr Gly Asp Arg Leu Thr His Gln Ser Phe Gln Gly Thr
            1130             1135           1140
Ser Ser Lys Ala Gly Leu Ser Leu Tyr Thr Asn Ala Pro Gln Gln
            1145             1150           1155
```

-continued

```
Asp Ser Ser Pro Thr Lys Glu Ile Ala Ser Pro Glu Leu Ala Gln
    1160            1165                1170

Pro Ala Lys Gln Gln His Asp Phe Gly Ile Gly Phe
    1175            1180                1185

<210> SEQ ID NO 91
<211> LENGTH: 8
<212> TYPE: PRT
<213> ORGANISM: Artificial sequence
<220> FEATURE:
<223> OTHER INFORMATION: RecD-like motif I of TrwC Tsa

<400> SEQUENCE: 91

Gly Leu Ala Gly Thr Gly Lys Thr
1               5

<210> SEQ ID NO 92
<211> LENGTH: 10
<212> TYPE: PRT
<213> ORGANISM: Artificial sequence
<220> FEATURE:
<223> OTHER INFORMATION: RecD-like motif V of TrwC Tsa

<400> SEQUENCE: 92

Tyr Ala Val Thr Ser His Ser Ser Gln Gly
1               5                   10

<210> SEQ ID NO 93
<211> LENGTH: 18
<212> TYPE: PRT
<213> ORGANISM: Artificial sequence
<220> FEATURE:
<223> OTHER INFORMATION: MobF motif III of TrwC Tsa

<400> SEQUENCE: 93

His Asp Thr Ala Arg Pro Val Asn Gly Tyr Ala Ala Pro Gln Leu His
1               5                   10                  15

Thr His

<210> SEQ ID NO 94
<211> LENGTH: 1186
<212> TYPE: PRT
<213> ORGANISM: Microlunatus phosphovorus NM-1

<400> SEQUENCE: 94

Met Thr Val Ser Met Arg Val Met Thr Ala Gly Asp Gly Tyr Lys Tyr
1               5                   10                  15

Leu Leu Arg Ser Val Ala Ala Gly Asp Gly Asp Arg Ser Leu Ser Thr
                20                  25                  30

Pro Leu Thr Arg Tyr Tyr Ala Glu Ala Gly Asn Pro Gly Phe Trp
            35                  40                  45

Ile Gly Gln Gly Leu Ala Ala Leu Gly His Gly Glu Leu Thr Thr Gly
        50                  55                  60

Ser Glu Val Ser Glu Ala Gln Leu Glu Leu Leu Ile Gly Ser Gly Arg
65                  70                  75                  80

Asp Pro Ile Thr Gly Asp Pro Leu Gly Lys Ala Tyr Pro Thr Phe Ala
                85                  90                  95

Pro Val Ala Asp Arg Ile Glu Arg Arg Ile Lys Ala Leu Asp Ala Glu
            100                 105                 110

Leu Gly Pro Ala Ala Arg Ala Val Glu Thr Ala Arg Ile Glu Ala Glu
        115                 120                 125
```

```
Glu Ile Glu Arg Gly Thr Arg Arg Ala Val Ala Gly Phe Asp Phe Thr
    130                 135                 140

Phe Ser Val Pro Lys Ser Val Ser Ala Leu Trp Ala Val Ala Asp Ala
145                 150                 155                 160

Gly Thr Gln Ala Leu Ile Ala Asp Ala His His Ala Ala Val Ala Glu
                165                 170                 175

Leu Val Ala Phe Ile Glu Gly Glu Val Ala Val Thr Arg Thr Gly Ala
                180                 185                 190

Asp Gly Pro Glu Gly Thr Val Ala His Val Asp Val Leu Gly Val Ala
            195                 200                 205

Ala Thr Ala Phe Asp His Tyr Asp Ser Arg Ala Gly Asp Pro Gln Leu
210                 215                 220

His Thr His Val Val Ile Ser Asn Lys Val Lys Thr Ala Gln Asp Gly
225                 230                 235                 240

Lys Trp Arg Ala Leu Ala Gly Arg Pro Met His Ala Ala Val Val Ala
                245                 250                 255

Val Ser Glu Leu Tyr Asn Ala Ala Leu Ala Asp Gln Leu Thr Arg Thr
                260                 265                 270

Leu Gly Ile Glu Trp Glu Ser Arg Asp Arg Gly Arg Asp Arg Asn Pro
            275                 280                 285

Ala Trp Glu Leu Val Gly Val Thr Glu Glu Leu Ile Gly Glu Phe Ser
290                 295                 300

Thr Arg Ser His His Ile Glu Ala Glu Lys Glu Arg Leu Ile Ala Glu
305                 310                 315                 320

Tyr Val Ala Thr His Gly Arg Gln Pro Ser Ala Arg Ile Val Leu Lys
                325                 330                 335

Leu Arg Ala Gln Ala Thr Leu Ala Thr Arg Pro Glu Lys His Ile His
                340                 345                 350

Ser Leu Ala Asp Leu Thr Arg Gln Trp Arg Glu Arg Ala Gly Arg Val
            355                 360                 365

Leu Gly Gln Asp Ala Thr Gly Trp Ala Arg Thr Leu Thr Arg Gln Ala
    370                 375                 380

Ala Asp Ala Pro Ala Arg Val Leu Arg Ala Asp Val Pro Leu Asp
385                 390                 395                 400

Val Val Arg Glu Val Gly Leu Ser Val Met Ala Val Val Ser Glu Lys
                405                 410                 415

Arg Ser Thr Trp Met Arg Trp Asn Leu His Ala Glu Ala Ser Arg Gln
                420                 425                 430

Met Met Gly Trp Arg Phe Gly Thr Met Leu Asp Arg Glu Ala Ile Thr
            435                 440                 445

Gly Leu Val Val Asp Ala Ala Glu Gln Ala Ser Leu Arg Leu Thr Pro
    450                 455                 460

Pro Glu Leu Ala Ser Ser Pro Val Gln Phe Arg Arg Ser Asp Gly Thr
465                 470                 475                 480

Ser Arg Phe Arg Pro His Ala Ser Val Leu Phe Ser Ser Glu Ala Leu
                485                 490                 495

Leu Ala Ala Glu Asp Arg Leu Leu Ala Arg Ala Asp Thr Leu Ala Gly
            500                 505                 510

Pro Val Val Gly Leu Glu Thr Val Glu Gln Ile Thr Ser Arg Pro Asp
    515                 520                 525

Pro Arg Gly Arg Met Leu Gly Glu Asp Gln Ala Ala Ala Leu Ala Ala
    530                 535                 540
```

```
Ile Ala Val Ser Gly Arg Thr Leu Asp Val Leu Val Gly Pro Ala Gly
545                 550                 555                 560

Ala Gly Lys Thr Thr Ala Met Asn Ala Leu Arg Arg Ala Trp Glu Lys
                565                 570                 575

Glu His Gly Pro Gly Ser Val Val Gly Leu Ala Pro Ser Ala Val Ala
            580                 585                 590

Ala Gln Val Leu Ala Asp Asp Leu Gly Val Val Thr Glu Asn Thr Ala
        595                 600                 605

Lys Trp Trp Gln Asn His Leu Met His Gly Thr Thr Phe Glu Ala Gly
    610                 615                 620

Gln Leu Ile Ile Ile Asp Glu Ala Ser Leu Ala Gly Thr Ala Ser Leu
625                 630                 635                 640

Asp Arg Ile Thr Ala Glu Ala Glu Gln Ala Gly Ala Lys Thr Leu Leu
                645                 650                 655

Val Gly Asp Trp Gly Gln Leu Gln Ser Val Asp Ala Gly Gly Ala Phe
            660                 665                 670

Ser Met Leu Val His Ala Arg Asp Asp Thr Pro Glu Leu Leu Asp Ile
        675                 680                 685

His Arg Phe Thr His Arg Trp Glu Lys Thr Thr Ser Leu Gln Leu Arg
    690                 695                 700

His Gly Arg Pro Glu Ala Ile Asp Thr Leu Ile Asp His Asp Arg Ile
705                 710                 715                 720

Thr Gly Gly Glu Gln Glu Ala Met Ile Asp Ala Ala Tyr Gly Ala Trp
                725                 730                 735

Arg His Asp Leu Ala Ala Gly Arg Ala Ser Ile Leu Val Ala Glu Thr
            740                 745                 750

His Glu Thr Val Thr Ala Leu Asn Ala Arg Ala Arg Ala Asp Arg Ile
        755                 760                 765

Ile Asp Gly Thr Val His Gly Thr Arg Glu Val Gly Leu His Asp Gly
    770                 775                 780

Thr Ala Val Ser Glu Gly Asp Leu Val Ile Thr Arg His Asn Asp Arg
785                 790                 795                 800

Arg Leu Arg Asn Gly Arg Ser Trp Val Arg Asn Gly Asp Arg Trp Thr
                805                 810                 815

Val Ala Gly Val His Ala Asp Gly Ser Val Ser Ile Arg Pro Val Gly
            820                 825                 830

Arg Arg Arg Arg Gly Gly Ile Val Leu Pro Ala Asp Tyr Val Ala Glu
        835                 840                 845

His Leu Asp Leu Gly Tyr Ala Ile Thr Ala His Arg Ala Gln Gly Val
    850                 855                 860

Thr Thr Asp Thr Ala His Val Ile Ala Thr Thr Thr Arg Glu
865                 870                 875                 880

Asn Phe Tyr Val Ala Met Thr Arg Gly Ala Asp Gly Asn Tyr Ala Tyr
                885                 890                 895

Val Val Leu Asp Arg Pro Asp Ser His Gly Val Pro His Pro Ser
            900                 905                 910

Asp Asn Pro Asp Ala Thr Ala Arg Ser Val Leu Tyr Gly Val Ile Gln
        915                 920                 925

His Ile Gly Ala Glu Leu Ser Ala His Glu Thr Ile Thr Ala Glu His
    930                 935                 940

Glu Arg Trp Ser Asn Ile Gly Gln Leu Ala Ala Glu Tyr Glu Thr Ile
945                 950                 955                 960

Ala Gln Ala Ala Gln His Asp Arg Trp Gly Ala Leu Leu Ala Ala Ala
```

-continued

```
                          965                 970                 975
    Gly Leu Ala Ser Ala Gln Val Asp Ala Val Leu Asp Ser Asp Ala Tyr
                    980                 985                 990

Pro Ala Leu Ser Ala Glu Leu Arg  His Ala Glu Ala Asn  His His Asp
            995                1000                1005

Leu Asp  Thr Leu Leu Pro Arg  Leu Ile Ala Ala Arg  Gly Leu Gly
        1010                1015                1020

Asp Ala  Asp Asp Ile Ala Ser  Val Ile His Ala Arg  Val Ala Arg
        1025                1030                1035

Ala Thr  Ala Arg Pro Ala Gly  Ser Gly Arg Thr Arg  Lys Pro Pro
        1040                1045                1050

Arg Leu  Ile Ala Gly Leu Ile  Pro Tyr Ala His Gly  Pro Met Ala
        1055                1060                1065

Asp Asp  Met Arg Gln Ala Leu  Asp Glu Arg His Glu  Leu Ile Glu
        1070                1075                1080

Ala Arg  Ala Asp Ala Val Leu  Thr Gly Ala Leu Thr  Asp Lys Ala
        1085                1090                1095

Leu Trp  Thr Ala Gln Leu Gly  Pro Ala Pro Lys Asp  Ala Lys Gln
        1100                1105                1110

Arg Arg  Ala Trp Arg Arg Ala  Ala Val Ile Val Ala  Ala Tyr Arg
        1115                1120                1125

Asp Arg  Tyr Gln Ile Thr Asp  Asp Arg Ser Pro Leu  Gly Pro Ala
        1130                1135                1140

Pro Gln  Ser Thr Arg Gln Lys  Ile Asp Ala Ala Arg  Ala Arg Ala
        1145                1150                1155

Ala Leu  Asp Arg Ala Arg Ala  Ile Thr Asp Glu Thr  Gln Pro Glu
        1160                1165                1170

Pro Ala  Arg Ser Ala Thr Thr  Arg Pro Ala Arg Thr  Leu
        1175                1180                1185

<210> SEQ ID NO 95
<211> LENGTH: 8
<212> TYPE: PRT
<213> ORGANISM: Artificial sequence
<220> FEATURE:
<223> OTHER INFORMATION: RecD-like motif I of TrwC Mph

<400> SEQUENCE: 95

Gly Pro Ala Gly Ala Gly Lys Thr
1               5

<210> SEQ ID NO 96
<211> LENGTH: 10
<212> TYPE: PRT
<213> ORGANISM: Artificial sequence
<220> FEATURE:
<223> OTHER INFORMATION: RecD-like motif V of TrwC Mph

<400> SEQUENCE: 96

Tyr Ala Ile Thr Ala His Arg Ala Gln Gly
1               5                   10

<210> SEQ ID NO 97
<211> LENGTH: 14
<212> TYPE: PRT
<213> ORGANISM: Artificial sequence
<220> FEATURE:
<223> OTHER INFORMATION: MobF motif III of TrwC Mph

<400> SEQUENCE: 97
```

His Tyr Asp Ser Arg Ala Gly Asp Pro Gln Leu His Thr His
1               5                   10

<210> SEQ ID NO 98
<211> LENGTH: 1843
<212> TYPE: PRT
<213> ORGANISM: Thermodesulfovibrio yellowstonii DSM 11347

<400> SEQUENCE: 98

Met Val Asn Phe Leu Glu Lys Glu Gly Tyr Ile Gln Tyr Arg Glu Thr
1               5                   10                  15

Val Asn Gly Glu Thr Ile Ser Lys Ser Asp Asn Ala Thr Val Leu
            20                  25                  30

Val Asn Thr His Leu Cys Gly Arg Leu Asp Pro Gln Ile His Asn His
            35                  40                  45

Ile Ser Phe Phe Asn Phe Thr Arg Thr Glu Asn Gly Asp Trp Lys Ala
50                  55                  60

Ile Asn Ser Asp Ala Ile Tyr Ser Asn Lys Tyr Met Phe Glu Ala Tyr
65                  70                  75                  80

Leu Glu Asn Gln Leu Ala Tyr Gln Leu Lys Gln Gln Gly Ile Asn Thr
                85                  90                  95

Glu Leu Val Lys Glu Gly Asn Ser Lys Glu Tyr Val Thr Lys Ile Ala
            100                 105                 110

Gly Leu Asn Glu Glu His Trp Lys Gly Ile Ala Arg Thr Ser Glu Leu
        115                 120                 125

Ile Asp Lys Tyr Leu Glu Gln His Lys Glu Glu Leu Leu Gln Lys Tyr
130                 135                 140

Pro Asn Ala Thr Glu Ser Gln Leu Arg Glu Tyr Ala Tyr Leu Glu Ile
145                 150                 155                 160

Arg Gln Ser Lys Gln Ser Lys Thr Ile Gly Glu Leu Phe Lys Gln Val
                165                 170                 175

Glu Asp Ser Leu Lys Glu Gln Gly Leu Thr Gln Gln Asp Ile Ile Lys
            180                 185                 190

Leu Val Ser Glu Lys Arg Glu Asn Leu Thr Gln Glu Leu Asn Gln Ala
        195                 200                 205

Asn Lys Glu Glu Leu Ala Lys Glu Ile Ile Asn Lys Ala Ile Asp Glu
210                 215                 220

Val Ile Asp Arg Asn Ser Thr Phe Ser Gln Ser Asp Leu Phe Lys Ala
225                 230                 235                 240

Ala Phe Gln Ile Ser Ala Gly Arg Val Asp Ser Asp Thr Leu Val Gln
                245                 250                 255

Ala Val Lys Glu Asn Glu Arg Leu Ile Glu Met Gly Tyr Val Gln Asp
            260                 265                 270

Lys Gln His Asn Arg Ala Asn Ala Thr Tyr Gln Glu Lys Tyr Phe Thr
        275                 280                 285

Ser Gln Glu Val Ile Ala Trp Glu His Asn Ile Leu Lys Ser Ile Glu
290                 295                 300

Glu Gly Lys Gly Ser Val Glu Lys Ile Thr Glu Gln Arg Tyr Glu Asn
305                 310                 315                 320

Glu Lys Leu Thr Lys Ser Gln Leu Glu Ala Ile Asn His Ile Leu Gln
                325                 330                 335

Ser Thr Asp Arg Tyr Thr Ala Val Val Gly Trp Ala Gly Val Gly Lys
            340                 345                 350

Thr Thr Phe Val Gly Glu Met Ser Lys Glu Leu Gly Lys Ile Asn Glu

```
                355                 360                 365
Ile Ala Lys Glu Ala Gly Tyr Arg Leu Ile Gly Val Ser Asn Thr Asn
        370                 375                 380
Thr Ala Val Asn Glu Leu Lys Glu Val Gly Ile Glu Ala Met Thr Thr
385                 390                 395                 400
Ala Lys Phe Leu Asn Ser Ala Lys Ala Leu Gln Ser Leu Asp Ser Lys
                405                 410                 415
Thr Ile Leu Ile Val Asp Glu Ala Ser Phe Leu Ser Thr Lys Asp Met
        420                 425                 430
Ser Thr Ile Leu Asp Lys Thr Arg Glu Ser Gly Cys Arg Ile Val Phe
                435                 440                 445
Ile Gly Asp Asp Arg Gln Leu Pro Gly Val Gln Ala Gly Ser Pro Phe
        450                 455                 460
Ala Ala Leu Ile Arg Glu Asn Lys Ile Asn His Val Lys Met Thr Asp
465                 470                 475                 480
Ile Val Arg Gln Arg Asn Glu Glu Leu Lys Ser Ala Val Tyr Asp Ile
                485                 490                 495
Tyr His Lys Asn Ile Glu Ser Ala Leu Asn Lys Ile Thr Phe Lys Thr
        500                 505                 510
Ile Glu Arg Asp Ser Ala Leu Glu Ile Ala Thr His Ala Leu Lys Ser
                515                 520                 525
Asp Lys Pro Ile Asn Ile Val Asp Arg Glu Ile Phe Glu Lys Val Lys
        530                 535                 540
Glu Met Phe Glu Gly Gln Gly Ser Ala Thr Gln Tyr Val Gln Gln Phe
545                 550                 555                 560
Lys Ser Ala Pro Phe Glu Arg Glu Ile Ile Glu Lys Leu Gly Ile Glu
                565                 570                 575
Asp Ala Gly Gln Arg Glu Ala Phe Phe Phe Tyr Lys Asp Phe Gly Phe
        580                 585                 590
His Glu Gly Glu Asn Pro His Gly Ile Lys Glu Asp Gln Ala Lys Lys
                595                 600                 605
Ser Ile Arg Gln Met Ile Lys Met Gly Trp Val Val Ala Thr Glu Val
        610                 615                 620
Glu Val Asn Gly Lys Lys Tyr Gly Ala Tyr Gln Lys Thr Gly Leu Phe
625                 630                 635                 640
Gly Val Asp Pro Ser Arg Ile Arg Glu Val Leu Gly Glu Lys Tyr Glu
                645                 650                 655
Glu Tyr Gln Lys Gln Ile Glu Gln Gln Lys Glu Ile Leu Arg Glu
        660                 665                 670
Ile Ala Lys Glu Tyr Ile Ser Gln Gly Tyr Lys Asn Ser Ala Ile Ser
                675                 680                 685
Val Ala Thr Asn Gln Asp Ala Lys Ile Leu Asn Ser Leu Ile Ser Glu
        690                 695                 700
Glu Leu Arg Asn Gly Glu Leu Lys Gly Ala Lys Ser Ile Glu Val Asn
705                 710                 715                 720
Val Trp Val Asn Lys Asn Leu Asp Asn Val Glu Arg Leu Lys Ala Ser
                725                 730                 735
Ser Tyr Asn Val Gly Asp Lys Leu Leu Val Met Ser Ser Gly Gly Gly
        740                 745                 750
Val Ser Val Gly Lys Glu Leu Phe Val Lys Glu Val Asp Ile Val Lys
                755                 760                 765
Asn Thr Leu Lys Val Glu Tyr Thr Thr Lys Lys Gly Glu Val Lys Glu
        770                 775                 780
```

-continued

```
Arg Val Phe Asn Ile Glu Lys Leu Gly Asp Lys Val Gln Ala Phe Gln
785                 790                 795                 800

Asn Glu Ser Ile Gln Ile Ala Glu Gly Glu Lys Leu Ile Phe Asn Asn
            805                 810                 815

Thr Tyr Arg Asn Lys Asn Phe Ala Asn Ser Glu Phe Ala Tyr Val Lys
        820                 825                 830

Ser Ile Asn Asn Glu Asp Gly Ser Ile Thr Ile Val Ser Lys Leu Asp
    835                 840                 845

Ser Asp Lys Ala Lys Thr Thr Thr Phe Thr Lys Glu Glu Leu Ala Gln
850                 855                 860

Gly Val His Phe Gln His Gly Tyr Ala Val Thr Ala Asp His Met Gln
865                 870                 875                 880

Gly Lys Thr Thr Gln Asn Val Ile Ala Phe Glu Thr Arg Asn Tyr Glu
            885                 890                 895

Asn Phe Leu Val Ser Ile Thr Arg Ala Lys Gln Asn Ala Thr Ile Tyr
        900                 905                 910

Ser Thr Met Ser Lys Glu Arg Phe Ile Glu Lys Ala Ser Glu Glu Ala
    915                 920                 925

Thr Lys Glu Arg Ile Glu Arg Met Ala Tyr Lys Phe Asn Glu Glu Val
930                 935                 940

Phe Asn Thr Val Lys Glu Gln Ile Tyr Lys Asn Phe Lys Gln Gln
945                 950                 955                 960

Glu Gln Val Lys Glu Gln Gly Phe Glu Asn Glu Arg Glu Gly Gln Phe
            965                 970                 975

Gln Lys Gln Glu Ser Lys Glu Gln Ser Glu Arg Tyr Gln Glu Ser Val
        980                 985                 990

Phe Trp Ala Ser Glu Ala Ile Lys  Asn Tyr Glu Lys Ser  Glu Tyr Gln
        995                 1000                1005

Lys Trp  Ala Lys Asn Phe Ser  Glu Lys Asp Phe Lys  Ala Val Gln
    1010                1015                1020

Lys Pro  Gln Lys Pro Asn Ile  Val Lys Lys Ile Ala  Asn Ala Met
    1025                1030                1035

Val Asp  Ser Asn Tyr Val Asp  Arg Lys Phe Lys Asp  Trp Leu Asn
    1040                1045                1050

Gly Lys  Thr Arg Asp Lys Phe  Glu Lys Trp Thr Leu  Lys Asp Gln
    1055                1060                1065

Ile Lys  Thr Trp Trp Lys Asn  Asn Leu Asn Arg Asp  Leu Glu Lys
    1070                1075                1080

Leu Thr  Gly Gln Lys Arg Arg  Asp Tyr Trp Lys Thr  Tyr Glu Val
    1085                1090                1095

Tyr Thr  Lys Asp Gln Asn Gly  Gln Trp His Lys Gly  Ile Gln Lys
    1100                1105                1110

Leu His  Val Arg Val Arg Gly  Asp Lys Thr Thr Ile  Glu Gly Tyr
    1115                1120                1125

Thr Leu  Thr Lys Asp Gly Ile  His Tyr Phe Lys Ile  Glu Lys Gln
    1130                1135                1140

Lys Gly  Leu Phe Gly Ile Glu  Lys Val Leu Asp Gln  Ser Met Glu
    1145                1150                1155

Phe Ala  Pro His Gln Leu Ser  Pro Val Gln Gln Ile  Ala Ala Val
    1160                1165                1170

Gly Ala  Gln Lys Pro Val Ile  Gln His Val Glu Pro  Pro Lys Leu
    1175                1180                1185
```

-continued

| | | | | | | | | | | | | |
|---|---|---|---|---|---|---|---|---|---|---|---|---|
| Glu | Lys | Tyr | Phe | Thr | Pro | Ala | Gln | Met | Lys | Asn | Ile | Gln | Asp | Met |
| | 1190 | | | | 1195 | | | | 1200 | | | |

Ala Arg Glu Ile Val Gln Lys Gln Gln Glu Lys Gln Gln Lys Ile
    1205                    1210                  1215

Ser Glu Val Arg Glu Tyr Glu Gln Lys Ser His Glu His Ile Arg
    1220                    1225                  1230

Glu Pro Ile Gln Lys Trp Gln Glu Met Val Gln Ala Gly Asp Arg
    1235                    1240                  1245

Phe Asn Glu Val Leu Ala Asn Thr Trp Gln Lys Trp Gln Ser Gln
    1250                    1255                  1260

Ala Gln Asn Val Arg Glu Phe Ile Ile Gln Lys Asp Arg Thr Thr
    1265                    1270                  1275

Asn Lys Glu Ile Phe Gln Trp Ser Lys Glu Asn Gln Ile Gly Lys
    1280                    1285                  1290

Glu Val Val Leu Ala Thr Thr Arg Glu Met Gln Asp Lys Gly Leu
    1295                    1300                  1305

Ile Cys Val Glu Ser Tyr Asp Glu Lys Thr Arg Thr Ile Thr Phe
    1310                    1315                  1320

Ile Ser Ala Ser Lys Leu Ser Glu Gln Gln Lys Ala Ile Ser Lys
    1325                    1330                  1335

Ala Val Glu Ser Ile Tyr Arg Asn Ser Ser Lys Trp Ser Phe Ser
    1340                    1345                  1350

Leu Lys Asp Ile Lys Ala Glu Leu Lys Arg Ser Gly Val Asp Ala
    1355                    1360                  1365

Ala Asp Arg Thr Ile Tyr Lys His Leu Ser Ser Met Gly Tyr Lys
    1370                    1375                  1380

Lys Asp Asp Lys Gly Arg Phe His Phe Leu Asn Asp Ser Ile His
    1385                    1390                  1395

Val Arg Gln Asp Arg Glu Ile Ile Ser Val Phe Ala Glu Lys Thr
    1400                    1405                  1410

Ser Gly Lys Gly Tyr Phe Thr Ala Ser Glu Leu His Lys Asn Ile
    1415                    1420                  1425

Ser His Ile His His Ile His Pro Gln Arg Leu Glu Lys Tyr Leu
    1430                    1435                  1440

His Glu Glu Lys Thr Leu Lys Leu Ile Gly Phe Gln Lys Asn Ser
    1445                    1450                  1455

Asp Gly Lys Leu Glu Ala Ile Phe Cys His Lys Gln Asp Tyr Glu
    1460                    1465                  1470

Asn Ser Lys Gln His Trp Leu Asn Ser Ile Ala Ser Ile Pro Gln
    1475                    1480                  1485

Lys Ala Asp Glu Gln Leu Val Arg Phe Tyr Ile Glu Lys Glu Gly
    1490                    1495                  1500

Ile Ser Pro Trp Lys Asn Leu Thr Lys Asp Gln Leu Gln Lys Leu
    1505                    1510                  1515

Gln Ser Glu Phe Lys Asn Ala Gly Val Asn Glu Lys Lys Gly Tyr
    1520                    1525                  1530

Phe Phe Ser Cys Val Glu Arg Val Gln His Gln Met Arg Glu Thr
    1535                    1540                  1545

Glu Ile Gln Arg Val Met Gln Thr Ile Arg Phe Met Thr Glu Arg
    1550                    1555                  1560

Met Gln Gln Ser Gln Gln Gln Gln Glu His Ser Leu Ala Gln Gln
    1565                    1570                  1575

Asn Val Gln Ile Asp Arg Glu Val Leu Lys Met His Ser Met Leu

```
                    1580                1585                1590

Asn Arg Asn Ile Gln Tyr Asp Ile Thr His Glu Glu Phe Gln Arg
    1595                1600                1605

Val Lys Glu Tyr Met Asp Thr His Asn Gly Ser Val Val Ala Met
    1610                1615                1620

Gln Asn Pro Pro Gln Asn Glu Lys Tyr Ser Ser Val Leu Tyr Thr
    1625                1630                1635

Thr Lys Lys Asp Ile Tyr Met Glu Lys Ala Met Ala Glu Lys Ile
    1640                1645                1650

Gly Val Lys Tyr Gln Asn Glu Ser Thr Ala Tyr Phe Ser Ser Lys
    1655                1660                1665

Asp Leu Val Ser Asn Thr Gly Leu Gly Lys Asp Lys Ile Asp Gln
    1670                1675                1680

Ala Met His Lys Met Phe Arg Ser Gly Trp Val Ile Pro Val Thr
    1685                1690                1695

Val Ser Thr Asp Lys Lys Leu Tyr Gly Ala Trp Gln Lys Thr Ser
    1700                1705                1710

Leu Tyr Gly Val Asp Thr Glu Arg Val Lys Glu Ala Tyr Gly Lys
    1715                1720                1725

Glu Lys Glu Lys Val Val Gln Gln Leu Lys Glu Glu Trp Lys Lys
    1730                1735                1740

Ile Lys Ala Gln Glu Gln Gly Asn Lys Lys Glu Lys Asp Tyr Ile
    1745                1750                1755

Ser Lys Thr Asp Ile Arg Asn Glu Leu Asn Asn Glu Val His Thr
    1760                1765                1770

Lys Ala Ile Ser Glu Gly Ile Lys Arg Ser Leu Asp Gly Asn Ile
    1775                1780                1785

Ile Ser Glu His Lys Ile Thr Ile Lys Thr Lys Glu Ser Asp Ser
    1790                1795                1800

Lys Glu Val Thr Val Tyr Lys Pro Ala Gln Ser Ile Glu Lys Ser
    1805                1810                1815

Gln Ser Gln Ser His Glu Lys Ser Thr Asn Pro Ser Gln Asp Lys
    1820                1825                1830

Thr Ala Ser Val Ser Met Glu Arg Gly Arg
    1835                1840

<210> SEQ ID NO 99
<211> LENGTH: 8
<212> TYPE: PRT
<213> ORGANISM: Artificial sequence
<220> FEATURE:
<223> OTHER INFORMATION: RecD-like motif I of TrwC Tye

<400> SEQUENCE: 99

Gly Trp Ala Gly Val Gly Lys Thr
1               5

<210> SEQ ID NO 100
<211> LENGTH: 10
<212> TYPE: PRT
<213> ORGANISM: Artificial sequence
<220> FEATURE:
<223> OTHER INFORMATION: RecD-like motif V of TrwC Tye

<400> SEQUENCE: 100

Tyr Ala Val Thr Ala Asp His Met Gln Gly
1               5                   10
```

<210> SEQ ID NO 101
<211> LENGTH: 13
<212> TYPE: PRT
<213> ORGANISM: Artificial sequence
<220> FEATURE:
<223> OTHER INFORMATION: MobF motif III of TrwC Tye

<400> SEQUENCE: 101

His Leu Cys Gly Arg Leu Asp Pro Gln Ile His Asn His
1               5                   10

<210> SEQ ID NO 102
<211> LENGTH: 942
<212> TYPE: PRT
<213> ORGANISM: Rhodothermus marinus SG0.5JP17-172

<400> SEQUENCE: 102

Met Ile Arg Gly Val Leu Ile Ser Arg Ala Ser Val Gln Arg Gln Leu
1               5                   10                  15

Asp His Met Ala Ala Val Pro Gly Arg Gln Asp Val Val Trp His Gly
                20                  25                  30

Ile Ala Leu Ser His Asp Gly Leu Gln Gly Ile Ala Arg Glu Gly Lys
            35                  40                  45

Leu Ser Val Ala Gly Thr Gly Ala Arg Leu Leu Gln Leu Pro Ala Gln
        50                  55                  60

Val Ser Thr Lys Gln Ala Thr Ala Leu Ile Leu Gly His Gln Trp Asp
65                  70                  75                  80

Gly Val Asp Ile Gly Gly Arg Gln Val Cys Arg Pro Met Tyr Gly Ile
                85                  90                  95

Val Trp Gly Ala Asp Lys Thr Ile Ser Gln Leu Leu Ala His Glu Gln
            100                 105                 110

Leu Arg Pro Leu Val Leu Glu Ala Met His Glu Ala Val Gln Lys Ala
        115                 120                 125

Leu Ala Glu Thr Glu Arg Leu Leu Trp Thr Arg Ala Gly Lys Gly Gly
    130                 135                 140

Arg Glu Ala Val Pro Val Arg Gly Val Leu Ala Leu Tyr Ser Ile His
145                 150                 155                 160

Met Thr Ser Gly Asp Gly Ser Pro His Leu His Val His Ile Gly Leu
                165                 170                 175

Arg Ala Thr Ala Pro Ser Val Asp Gly Arg Trp Arg Thr Leu Asp Pro
            180                 185                 190

Arg Ala Val Phe Gly Leu Trp Lys Arg Thr Leu Asp Gly Ala Ile Gly
        195                 200                 205

Arg His Leu Tyr Gln Ala Leu Gln Gln Arg Gly Ile His Val Asp Glu
    210                 215                 220

His Val Leu Val Gly Ser Thr Trp Thr Pro Ala Ile Arg Ser Leu Thr
225                 230                 235                 240

Pro His Ser Glu Arg Leu Ser Arg Arg Gln Gln Val Leu Glu Ala
                245                 250                 255

Leu Ala Thr Leu Ala Asp Asp Pro Thr Trp Arg Gln Asn Leu Val Ala
            260                 265                 270

Trp Arg Ile Thr Arg Arg Asp Val Ala Leu Glu Ala Val Glu His Gly
        275                 280                 285

Leu Asp Arg Met Leu Arg Asp Pro Glu Gln Ala Arg Arg Val Ala Ala
    290                 295                 300

Val Trp Gly Ile Pro Glu Gly Glu Ile Glu Lys Ala Leu Gly Arg Thr

```
                305                 310                 315                 320
Leu Pro Glu Ala Pro Leu Lys Lys Ala Leu Phe Arg Tyr Ala Glu
                325                 330                 335
Ala Val Arg Met Arg Asp Ala Gln Val Arg Leu Gln Thr Ala Arg Gln
            340                 345                 350
Ile Phe Gly Glu Leu Gln Gly His Ile Arg Arg Trp Cys Val Gly Asp
            355                 360                 365
Ile Thr Ala Ala Leu Ala Tyr His Thr Asp Ala Ser Ala Thr Ala
            370                 375                 380
Leu Thr Tyr Trp Leu Leu Arg Asp Trp Gln His Leu Gly Leu Ile Gln
385                 390                 395                 400
Thr Arg Gln Ser Leu Ser Ala Ala Val Phe Ser Arg Leu Leu Lys Gly
                405                 410                 415
Glu Ile Thr Ser Thr Thr Glu Leu Arg Ala Val Phe Gly Pro His Ala
            420                 425                 430
Tyr Val Val Thr Thr Arg Gln Leu Glu Glu Gln Ala Leu Tyr Glu
            435                 440                 445
Lys Ala Leu Gly Leu Ala Arg Ala Arg Gln Pro Ile Leu Thr Asn
450                 455                 460
Ala Pro Ala His Phe Thr Pro Glu Gln Arg Ala Ala Leu Asp Val Leu
465                 470                 475                 480
Arg Arg Gly Arg Ala Leu Ser Val Val Gln Gly Val Ala Gly Ala Gly
                485                 490                 495
Lys Thr Thr Leu Leu His Pro Leu Val Glu Ala Gln Gln Gly
                500                 505                 510
Leu Arg Val Gln Val Leu Ala Arg Asn Ala Ile Ile Ala Arg Glu Leu
            515                 520                 525
Gly Glu Glu Leu Gly Val Pro Ser Ser Thr Leu Glu Thr Ala Thr Arg
            530                 535                 540
Gln Gly Leu Arg Pro Arg Gln Pro Thr Leu Leu Ile Val Asp Glu Gly
545                 550                 555                 560
Gly Val Val Asp Leu His His Met Gln Ala Leu Leu Glu Ala Ala Ser
                565                 570                 575
Gln Pro His Met Gln Leu Val Leu Leu Gly Asp Arg Gln Gln Thr Gln
            580                 585                 590
Pro Ile Asp Gln Arg Ala Ala Phe Ala Ile Val Ala Ala Ala Ala
            595                 600                 605
Arg Ala Gly Gln Leu Arg Gln Leu Arg Thr Ser Phe Arg Thr Gln Ala
            610                 615                 620
Trp Gln Ala Glu His Glu Ala Leu Arg Arg Ala Leu Ser Pro Gln His
625                 630                 635                 640
Ala Gln Lys Ala Val Ala Met Ala Gly Ala Asp Gly Arg Ile Tyr Gly
                645                 650                 655
Ser Thr Asp Leu Thr Thr Ala Ile Arg Gln Ala Val Asp Trp Trp Gln
            660                 665                 670
Ala Leu Ser Arg Arg Glu Ser Thr Val Ile Leu Ser Pro Thr Asn Glu
            675                 680                 685
Leu Ala Ala Ala Ala Thr Glu Ala Gln Ser Arg Leu Gly Ile Thr
            690                 695                 700
Ile Asp Pro Arg Thr Arg Leu Arg Trp Gly Gln Arg Cys Gly Ile Gly
705                 710                 715                 720
Asp Thr Val Arg Ile Arg Phe Asn Arg His Asp Leu Gly Leu Leu Asn
                725                 730                 735
```

```
Gly Thr Thr Ala Arg Val Val Asp Ile Asp Gln Asp Gly Ile Thr Ile
            740                 745                 750

Glu His Arg Gly Arg Leu Tyr Leu Asp His Gly Trp Thr Ala Glu
        755                 760                 765

His Val Glu Leu Ala Tyr Ala Leu Thr Ile Asp Ser Ala Gln Gly Leu
    770                 775                 780

Thr Val Asp Arg Ala Ile Val Leu Ala Thr Glu Thr Gly His Ser Arg
785                 790                 795                 800

Leu Tyr Thr Ala Ala Thr Arg Gly Arg Gln Ala Pro Val Trp Val Val
                805                 810                 815

Val His Asp Glu Glu Thr Pro Asp Gln Ala Leu Glu Arg Arg Leu
    820                 825                 830

Gln Arg Asp Asp Ile Ala Arg Thr Gly His Glu His Val Gly Gln Arg
            835                 840                 845

Ile Gly Lys Ser Thr Ser Pro Glu Lys Glu Arg Leu Leu Ala Ile Leu
850                 855                 860

Gln Arg Leu Glu Glu His Asp Leu Ile Asp Pro Asp Leu Ala Arg Leu
865                 870                 875                 880

Tyr Arg Ala Arg Ile Leu Asn Asp Ala Thr Arg Pro Arg Ala Lys Arg
                885                 890                 895

Phe Ile Glu Leu His Val Gln Leu Ile Gln Gln Ala Gln Gly Arg Arg
            900                 905                 910

Asp Val Leu Arg Leu Val Arg Thr Ala Arg Tyr Glu Glu Ala Gln Arg
            915                 920                 925

Leu Leu Glu Arg Gly Arg Asn Arg Asp Asp Gly Leu Glu Leu
        930                 935                 940

<210> SEQ ID NO 103
<211> LENGTH: 8
<212> TYPE: PRT
<213> ORGANISM: Artificial sequence
<220> FEATURE:
<223> OTHER INFORMATION: RecD-like motif I of TrwC Rma

<400> SEQUENCE: 103

Gly Val Ala Gly Ala Gly Lys Thr
1               5

<210> SEQ ID NO 104
<211> LENGTH: 10
<212> TYPE: PRT
<213> ORGANISM: Artificial sequence
<220> FEATURE:
<223> OTHER INFORMATION: RecD-like motif V of TrwC Rma

<400> SEQUENCE: 104

Tyr Ala Leu Thr Ile Asp Ser Ala Gln Gly
1               5                   10

<210> SEQ ID NO 105
<211> LENGTH: 14
<212> TYPE: PRT
<213> ORGANISM: Artificial sequence
<220> FEATURE:
<223> OTHER INFORMATION: MobF motif III of TrwC Rma

<400> SEQUENCE: 105

His Met Thr Ser Gly Asp Gly Ser Pro His Leu His Val His
1               5                   10
```

<210> SEQ ID NO 106
<211> LENGTH: 961
<212> TYPE: PRT
<213> ORGANISM: Oceanicaulis alexandrii HTCC2633

<400> SEQUENCE: 106

```
Met Ala Ile Phe His Phe Ser Ala Lys Val Ile Gly Arg Ser Ser Gly
1               5                   10                  15

Arg Ser Ala Val Ala Ala Ala Tyr Arg Ala Gly Glu Gln Leu His
            20                  25                  30

Asp Gln Arg Ile Asp Arg Thr His Asp Phe Thr Asn Lys Ala Gly Val
            35                  40                  45

Leu His Ser Glu Val Met Leu Pro Lys Gly Ala Pro Glu Ala Phe Ala
        50                  55                  60

Asp Arg Ala Thr Leu Trp Asn Ala Val Glu Ala Glu Lys Arg Lys
65                  70                  75                  80

Asp Ala Gln Leu Ala Arg Glu Val Glu Phe Ala Leu Pro Arg Glu Leu
                85                  90                  95

Ser Lys Lys Asp Asn Ile Lys Leu Thr Arg Glu Phe Val Lys Ala Glu
            100                 105                 110

Phe Val Glu Lys Gly Met Ile Ala Asp Leu Asn Val His Trp Asp Ile
        115                 120                 125

Gly Glu Asp Gly Lys Ala Lys Pro His Ala His Ala Met Leu Thr Met
130                 135                 140

Arg Glu Val Thr Lys Asp Gly Phe Gly Ala Lys Val Arg Asp Trp Asn
145                 150                 155                 160

Arg Thr Ala Leu Ile Glu Gln Trp Arg Glu Arg Trp Ala Asp His Val
                165                 170                 175

Asn Arg Ala Leu Ala Glu Arg Asp Ile Asp Ala Arg Ile Asp His Arg
            180                 185                 190

Ser Leu Glu Ala Gln Gly Ile Ala Leu Glu Pro Gln Asp Lys Ile Gly
        195                 200                 205

Pro Ala Ala Ser Arg Ile Gly Gly Arg Gly Leu Glu Ala Glu Arg Ile
    210                 215                 220

Glu Glu His Arg Ala Ile Ala Gln Arg Asn Gly Glu Arg Ile Ile Ala
225                 230                 235                 240

Asn Pro Ala Leu Ala Leu Asp Ala Ile Thr His Gln Gln Ala Thr Phe
                245                 250                 255

Thr Arg Arg Asp Leu Ala Ala Phe Val His Arg His Ser Asp Gly Lys
            260                 265                 270

Glu Gln Phe Asp Ala Ala Tyr Asn Ala Val Arg Ser Ser Ala Asp Met
        275                 280                 285

Ile Ala Leu Gly Thr Asp Gly Arg Gly Gln Asp Arg Phe Thr Ser Arg
    290                 295                 300

Ala Met Ile Glu Ala Glu Gln Arg Leu His Arg Ala Ala Asp Thr Met
305                 310                 315                 320

Ala Glu Arg Lys Gly His Ala Val Asn Asp Val Gln Arg Asn Ala Ala
                325                 330                 335

Phe Ala Asn Ala Ala Lys Arg Gly Leu Val Leu Ser Gly Glu Gln Lys
            340                 345                 350

Ser Ala Phe Glu His Val Thr Asn Ser Lys Gly Leu Thr Ile Val Val
        355                 360                 365

Gly Tyr Ala Gly Thr Gly Lys Ser Ala Met Leu Gly Val Ala Arg Glu
    370                 375                 380
```

Ala Trp Glu Gly Ala Gly Asn Thr Val Arg Gly Ala Ala Leu Ser Gly
385                 390                 395                 400

Ile Ala Ala Glu Gly Met Glu Asn Gly Ser Gly Ile Ala Ser Arg Thr
            405                 410                 415

Ile Ala Ser Leu Glu His Gln Trp Gly Lys Gly Arg Glu Gln Leu Thr
            420                 425                 430

Ser Arg Asp Val Leu Val Ile Asp Glu Ala Gly Met Val Gly Thr Arg
            435                 440                 445

Gln Met Glu Arg Val Leu Ser His Ala Ala Lys Ala Gly Ala Asn Val
        450                 455                 460

Val Leu Val Gly Asp Gln Gln Leu Gln Ala Ile Glu Ala Gly Ala
465                 470                 475                 480

Ala Phe Arg Ala Ile His Glu Arg His Gly Val Glu Ile Ser Glu
                485                 490                 495

Val Arg Arg Gln Leu Ser Ala Trp Gln Gln Asp Ala Thr Arg His Leu
            500                 505                 510

Ala Thr Gly Arg Thr Gly Glu Ala Ile Ser Thr Tyr Glu Glu Arg Gly
            515                 520                 525

Met Val His Ala Ala Asp Thr Arg Glu Thr Ala Arg Ala Asp Leu Ile
    530                 535                 540

Leu Arg Trp Asn Gln Glu Arg Gln Asp Ser Pro Gly Asp Ser Arg Ile
545                 550                 555                 560

Ile Leu Thr His Thr Asn Asp Glu Val Arg Glu Leu Asn Arg Met Ala
                565                 570                 575

Arg Glu Lys Met Arg Lys Ala Gly Ala Leu Gly Ala Asp Ala Thr Ile
            580                 585                 590

Lys Ala Ala Arg Gly Glu Arg Gln Phe Ala Ser Gly Asp Arg Ile Ile
            595                 600                 605

Phe Leu Arg Asn Glu Arg Gly Leu Gly Val Lys Asn Gly Thr Leu Gly
    610                 615                 620

Thr Val Ala Met Ala Asn Asp Gln Ser Met Ala Val Arg Thr Asp Asp
625                 630                 635                 640

Gly Arg Glu Val Ala Phe Asp Thr Lys Asp Tyr Ala His Ile Asp His
                645                 650                 655

Gly Tyr Ala Ala Thr Ile His Lys Ala Gln Gly Met Thr Val Asp Arg
            660                 665                 670

Ala His Val Leu Ala Thr Pro Gly Leu Asp Ser His Ser Ala Tyr Val
        675                 680                 685

Ala Met Ser Arg His Arg Glu Gly Leu Ala Leu His Tyr Gly Arg Asn
    690                 695                 700

Asp Phe Ala Asp Gln Ser Lys Leu Val Arg Leu Leu Ser Arg Glu Arg
705                 710                 715                 720

Gly Lys Asp Leu Ala Gly Asp Tyr Lys Pro Glu Gln Ala Phe Ala Glu
                725                 730                 735

Leu Arg Gly Ile Ser Phe Arg Glu Ile Ile Glu Val Val Arg Gln
            740                 745                 750

Val Pro Glu Arg Ala Lys Ser Ile Phe Gly Asn Phe Arg Pro Gln Ala
        755                 760                 765

Arg Gln Leu Glu Pro Ile Pro Ala Leu Ala Asn Met Gln Asp Asp Gln
    770                 775                 780

Arg Arg Ala Val Glu Arg Tyr Ala Arg Ala Leu Gly Asp Ile Ala Thr
785                 790                 795                 800

Met Gln Thr Lys Gly Leu Pro Val Leu Pro His Gln Lys Ala Ala Leu
                805                 810                 815

Glu Lys Ala Gly Lys Ala Leu Asp Ala Ile Arg Pro His Ala Ala Thr
            820                 825                 830

Asp Leu Ala Lys Ala Leu Asp Arg Arg Pro Glu Leu Ile Ala Glu Ala
        835                 840                 845

Ala Gly Gly Arg Ser Gln Glu Ala Met Arg Ala Met Gln His Glu Ala
    850                 855                 860

Ala Val Arg Thr Asp Pro Ala Leu Arg Thr Glu Arg Phe Val Ser Asp
865                 870                 875                 880

Trp Gln Gly Leu Ser Thr Ala Arg Lys Gln Leu Glu Gln Gln Gly Asp
                885                 890                 895

Arg Ala Gly Ala Ala Arg Val Ser Ala Lys Gln Asn Glu Leu Ala Lys
            900                 905                 910

Ser Leu Glu Arg Asp Pro Gln Val Glu Gly Leu Leu Arg Gly Lys Ser
        915                 920                 925

Arg Glu Leu Gly Ile Asp Pro Lys Pro Glu Arg Ser Ile Ala Asn Glu
    930                 935                 940

Leu Ser Thr Thr Leu Thr Arg Glu Arg Thr Arg Ser Phe Asp Met Gly
945                 950                 955                 960

Ile

<210> SEQ ID NO 107
<211> LENGTH: 8
<212> TYPE: PRT
<213> ORGANISM: Artificial sequence
<220> FEATURE:
<223> OTHER INFORMATION: RecD-like motif I of TrwC Oma

<400> SEQUENCE: 107

Gly Tyr Ala Gly Thr Gly Lys Ser
1               5

<210> SEQ ID NO 108
<211> LENGTH: 10
<212> TYPE: PRT
<213> ORGANISM: Artificial sequence
<220> FEATURE:
<223> OTHER INFORMATION: RecD-like motif V of TrwC Oma

<400> SEQUENCE: 108

Tyr Ala Ala Thr Ile His Lys Ala Gln Gly
1               5                   10

<210> SEQ ID NO 109
<211> LENGTH: 24
<212> TYPE: PRT
<213> ORGANISM: Artificial sequence
<220> FEATURE:
<223> OTHER INFORMATION: MobQ motif III of TrwC Oma

<400> SEQUENCE: 109

Gly Met Ile Ala Asp Leu Val Asn Val His Trp Asp Ile Gly Glu Asp
1               5                   10                  15

Gly Lys Ala Lys Pro His Ala His
            20

<210> SEQ ID NO 110
<211> LENGTH: 970
<212> TYPE: PRT
<213> ORGANISM: Citromicrobium sp. JLT1363

<400> SEQUENCE: 110

Met Leu Ser Val Ala Asn Val Arg Ser Pro Ser Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Val Gly Glu Gly Ala Lys Arg Leu Gly Leu Asn Gly Lys Val
            35                  40                  45

Glu Ala Gln Thr Phe Asp Ala Leu Leu Arg Gly Glu Leu Pro Asp Gly
50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Leu Glu Ala Leu
                100                 105                 110

His Trp Ala Glu Lys Asn Ala Ala Glu Thr Arg Met Val Glu Lys Gly
            115                 120                 125

Lys Thr Val Thr Gln Ala Thr Gly Asn Leu Ala Ile Gly Leu Phe Gln
130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Thr Leu Lys His Gly Asn Phe Glu Ala Arg Gly Ile Thr Arg Glu Gln
210                 215                 220

Val Met Ala Phe Ser Ser Arg Arg Gln Glu Val Leu Asp Ala Arg Arg
225                 230                 235                 240

Gly Ser Gly Leu Glu Ala Gly Arg Ile Ala Ala Leu Asp Thr Arg Ala
                245                 250                 255

Ser Lys Asp Gly Ile Glu Asp Arg Glu Ala Leu Gly Met Gln Trp Ser
            260                 265                 270

Asp Thr Ala Lys Ser Ile Gly Leu Asp Leu Ala Pro Leu Val Glu Arg
        275                 280                 285

Ala Gln Thr Arg Ser Leu Lys Gln Ser Ile Glu Thr Gly Arg Phe Gly
290                 295                 300

Ser Leu Val Glu Arg Gly Arg Ala Trp Leu Gly Arg Phe Val Ala His
305                 310                 315                 320

Val Arg Gly Asp Pro Ala Asp Pro Leu Val Pro Lys Ser Val Leu Arg
                325                 330                 335

Gln Asp Arg Glu Thr Ile Ala Ala Gln Ala Val Ala Ser Ala Val
            340                 345                 350

Arg His Leu Ser Gln Arg Glu Ala Ala Phe Glu Arg Thr Ala Leu Tyr
        355                 360                 365

Lys Ala Ala Leu Asp Phe Gly Leu Pro Ala Thr Ile Ala Asp Ile Glu
            370                 375                 380

Lys Arg Thr Arg Ala Leu Val Arg Ser Gly Asp Leu Ile Ala Gly Met
385                 390                 395                 400

Gly Glu His Lys Asp Trp Leu Ala Ser Arg Asp Glu Val Leu Thr Glu

```
                    405                 410                 415
Gln Arg Ile Val Ser Glu Val Ala Ala Gly Lys Gly Ala Ser Ser Ser
                420                 425                 430

Ala Val Glu Pro Glu Ser Ala Thr Asp Arg Val Gln Ala Ala Ala Met
                435                 440                 445

Thr Gly Gln Gly Phe Arg Leu Asn Glu Gly Gln Leu Gly Ala Ala Lys
                450                 455                 460

Leu Ile Leu Thr Ser Glu Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Ser Val Ile Gly Leu Ala Ile Gln Asn Thr Leu Val
                500                 505                 510

Gln Met Leu Glu Arg Asp Thr Gly Ile Gly Ser Gln Thr Leu Ala Arg
                515                 520                 525

Phe Leu Gly Gly Trp Lys Lys Leu Leu Asp Asp Pro Gly Asn Ala Ala
                530                 535                 540

Leu Arg Ala Glu Ala Lys Ala Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Asp Val His Arg Leu Val Leu Met Gly Asp Arg
                580                 585                 590

Lys Gln Leu Gly Ala Val Asp Ala Gly Lys Pro Phe Ala Leu Leu Gln
                595                 600                 605

Arg Thr Gly Met Ala Arg Ala Glu Met Ala Thr Asn Leu Arg Ala Arg
                610                 615                 620

Asp Pro Val Val Arg Glu Ala Gln Ala Ala Gln Ala Gly Asp Val
625                 630                 635                 640

Arg Thr Ala Leu Arg His Leu Gln Pro His Thr Leu Glu Ala Arg Gly
                645                 650                 655

Asp Gly Ala Leu Val Ala Ala Asn Thr Trp Leu Ala Leu Asp Lys Asp
                660                 665                 670

Thr Arg Ser Arg Thr Ser Ile Tyr Ala Ser Gly Arg Ala Ile Arg Ser
                675                 680                 685

Ala Val Asn Ala Ala Val Gln Gln Gly Leu Leu Ala Asn Gly Glu Ile
                690                 695                 700

Gly Pro Gly Lys Ala Glu Leu Gly Val Leu Asp Arg Val Asn Thr Thr
705                 710                 715                 720

Arg Glu Glu Leu Arg His Leu Ser Ala Tyr Gln Pro Gly Arg Val Leu
                725                 730                 735

Glu Val Ser Arg Lys Gln Ala Leu Gly Leu Ser Ala Gly Glu Tyr
                740                 745                 750

Arg Val Leu Gly Gln Asp Arg Lys Gly Arg Gln Val Glu Val Ala Asp
                755                 760                 765

Lys Arg Gly Lys Arg Phe Arg Phe Asp Pro Ala Arg Ile Arg Ala Gly
                770                 775                 780

Lys Gly Asp Gln Asn Leu Thr Leu His Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Ala Val Val Gly Gly Lys
                820                 825                 830
```

```
Val Thr Phe Glu Thr Ser Lys Gly Asp Gln Val Glu Leu Lys Lys Asp
        835                 840                 845

Asp Pro Met Leu Lys Arg Ile Asp Leu Ala Tyr Ala Leu Asn Ala His
        850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Ile Thr
                885                 890                 895

Arg Leu Arg Asp His Leu Thr Leu Val Val Asp Ser Ser Asp Arg Leu
                900                 905                 910

Gly Ala Ala Val Ala Arg Asn Lys Gly Glu Lys Ala Ser Ala Leu Glu
                915                 920                 925

Val Thr Ala Gln Val Ala Pro Thr Glu Lys Lys Asn Gly Glu Leu Asp
                930                 935                 940

Gln Leu Lys Pro Glu Glu Ala Asn Lys Ala Glu Lys Glu Ile Ala Arg
945                 950                 955                 960

Ser Lys Ser Lys Thr Leu Asp Phe Gly Ile
                965                 970

<210> SEQ ID NO 111
<211> LENGTH: 14
<212> TYPE: PRT
<213> ORGANISM: Artificial sequence
<220> FEATURE:
<223> OTHER INFORMATION: MobF motif III of TrwC Cjlt

<400> SEQUENCE: 111

His Asp Thr Asn Arg Asn Gln Glu Pro Asn Leu His Phe His
1               5                   10

<210> SEQ ID NO 112
<211> LENGTH: 974
<212> TYPE: PRT
<213> ORGANISM: Erythrobacter sp. SD-21

<400> SEQUENCE: 112

Met Leu Ser Val Ala Asn Val Arg Ser Pro Ser Ala Ala Ala Ser Tyr
1               5                   10                  15

Phe Ala Ala Asp Asn Tyr Tyr Thr Gly Ala Asp Ala Asp Arg Ser Gly
                20                  25                  30

Thr Trp Val Gly Lys Gly Ala Glu Arg Leu Gly Leu Glu Gly Arg Val
            35                  40                  45

Asn Ala Glu Gln Phe Asp Ala Leu Leu Arg Gly Glu Leu Pro Gly Gly
        50                  55                  60

Ile Gln Val Gly Asn Ala Gly Gln Ala His Arg Pro Gly Thr Asp Leu
65                  70                  75                  80

Thr Phe Ser Leu Pro Lys Ser Trp Ser Leu Leu Ala Leu Val Gly Gly
                85                  90                  95

Asp Gln Arg Ile Ile Asp Ala Tyr Arg Glu Ala Val Ile Glu Thr Leu
                100                 105                 110

Arg Trp Ala Glu Lys Asn Ala Ala Gln Thr Arg Met Gly Ser Gln Ala
            115                 120                 125

Gly Tyr Gly Lys Val Ala Thr Asp Asn Leu Thr Ile Gly Leu Phe Gln
        130                 135                 140

His Asp Thr Asn Arg Asn Gln Glu Pro Asn Leu His Phe His Ala Val
145                 150                 155                 160
```

Val Ala Asn Val Thr Gln Gly Ser Asp Gly Lys Trp Arg Ala Leu Arg
            165                 170                 175

Asn Asp Lys Leu Trp Ser Phe Asn Thr Leu Leu Asn Ser Met Thr Met
        180                 185                 190

Ala Arg Phe Arg Leu Ala Val Glu Lys Met Gly Tyr Glu Ala Gly Pro
        195                 200                 205

Val Gly Lys His Gly Asn Phe Glu Ala Ala Gly Ile Ala Arg Glu Gln
    210                 215                 220

Val Met Ala Phe Ser Thr Arg Arg Glu Glu Val Leu Asp Ala Val Arg
225                 230                 235                 240

Gln Leu Gly Glu Asn Thr Pro Lys Thr Arg Asp Ile Ala Val Leu Asp
            245                 250                 255

Thr Arg Lys Ser Lys Ala Pro Val Arg Asp Arg Asp Gly Leu Leu Asp
            260                 265                 270

Ala Trp Arg Gln Lys Ala Gln Glu Val Gly Ile Asp Leu Ala Gly Leu
        275                 280                 285

Ile Asp Ala Ser Gln Met Arg Ala Ala Lys Val Ala Gly Gly Ser
    290                 295                 300

Lys Glu Gln Ser Leu Leu Gln Arg Gly Ile Thr Lys Leu Arg Glu Phe
305                 310                 315                 320

Ala Gln Arg Ile Lys Gly Asp Pro Ala Asp Pro Leu Ile Pro Ala His
            325                 330                 335

Val Leu Lys Gln Asp Ala Pro Thr Ile Ala Ala Ala Gln Ala Val Ala
            340                 345                 350

Ser Ala Val Arg His Leu Ser Gln Arg Glu Ala Ala Phe Pro Arg Glu
        355                 360                 365

Gly Leu Leu Lys Ala Ala Leu Asp Phe Gly Leu Pro Thr Thr Val Asp
    370                 375                 380

His Val Glu Thr Arg Val Asn Ala Leu Val Arg Ser Gly Ala Leu Glu
385                 390                 395                 400

Pro Gly Lys Gly Asp His Lys Gly Trp Leu Ala Ser Arg Glu Ala Leu
            405                 410                 415

Asp Leu Glu Ser Thr Ile Leu Ala Asn Val Asp Gln Gly Arg Gly Ala
            420                 425                 430

Val Leu Pro Ile Leu Asp Arg Lys Asp Ala Ala Glu Arg Val Gln Ala
        435                 440                 445

Val Ala Ala Ile Asn His Gly Ile Ser Leu Asn Glu Gly Gln Glu Asp
450                 455                 460

Ala Ala Gly Leu Val Leu Ser Ser Arg Asp Arg Ile Val Ala Ile Gln
465                 470                 475                 480

Gly Ile Ala Gly Ala Gly Lys Ser Ser Val Met Lys Pro Val Ala Gln
            485                 490                 495

Leu Leu Gly Glu Glu Gly Lys Gln Val Leu Gly Leu Ala Val Gln Asn
            500                 505                 510

Thr Leu Val Gln Met Leu Glu Arg Asp Thr Gly Ile Arg Ser Met Thr
        515                 520                 525

Ile Ala Arg Phe Leu Ala Gln Trp Gly Arg Leu Leu His Glu Pro Gly
    530                 535                 540

Asn Ala Thr Leu Leu Ser Glu Ala Arg Gly Ala Leu Gly Asp His Val
545                 550                 555                 560

Leu Val Leu Asp Glu Ala Ser Met Val Ser Asn Glu Asp Lys Ala Lys
            565                 570                 575

Leu Val Arg Leu Ala Asn Leu Ala Glu Val His Arg Leu Val Leu Val

```
                580             585             590
Gly Asp Lys Arg Gln Leu Gly Ala Val Asp Ala Gly Lys Pro Phe Asp
            595                 600             605
Leu Val Gln Gln Ala Gly Ile Glu Arg Ala Asp Met Asp Val Asn Leu
        610                 615                 620
Arg Gly Arg Asp Pro Val Leu Arg Ala Gln Ala Ala Ala Gln Glu
625                 630                 635                 640
Gly Arg Ile Asp Asp Ala Leu Gln Ala Leu Ala Pro Ser Thr Ile Glu
                645                 650                 655
Ala Arg Gly Asp Ser Ala Ile Val Ala Ala Glu Lys Trp Leu Ser Leu
            660                 665                 670
Ser Pro Ala Asp Arg Asp Arg Thr Ser Ile Tyr Ala Ser Gly Arg Ala
        675                 680                 685
Leu Arg Ser Ala Val Asn Glu Ala Val Gln Arg Gly Leu Lys Ala Asn
    690                 695                 700
Gly Glu Leu Gly Leu Arg Ser Gly Arg Leu Thr Val His Ser Arg Val
705                 710                 715                 720
Asn Val Thr Asn Glu Glu Leu Arg Tyr Leu Arg Thr Tyr Gln Pro Gly
                725                 730                 735
Met Val Leu Asn Phe Arg Ser Arg Asp Ser Thr Gln Lys Leu Ser Lys
            740                 745                 750
Gly Asp Tyr Thr Val Lys Thr Ile Asp His Ala Arg Lys Gln Leu Val
        755                 760                 765
Leu Glu Asp Arg Lys Gly Arg Leu Arg Lys Phe Asn Pro Ala Arg Leu
    770                 775                 780
Arg Pro Gly Ala Val Glu Ser Arg Leu Ser Leu Phe Glu Arg Lys Ser
785                 790                 795                 800
Leu Ser Ile Ile Glu Gly Asp Lys Ile Arg Trp Thr Asn Asp His
                805                 810                 815
Lys Arg Gly Leu Phe Asn Ala Asp Gln Ala Arg Ile Val Ala Ile Asp
            820                 825                 830
Thr Lys Gly Val Leu Val Glu Thr Ser Gly Gly Gln Glu Leu Arg Leu
        835                 840                 845
Ser Arg Gly Asp Pro Met Leu Lys Arg Val Asp Leu Ala Tyr Ala Leu
    850                 855                 860
Asn Ala His Met Ala Gln Gly Leu Thr Ser Asp Arg Gly Ile Ala Val
865                 870                 875                 880
Met Asp Ser His Glu Arg Asn Leu Ala Asn Arg Gln Thr Phe Leu Val
                885                 890                 895
Ser Val Thr Arg Leu Arg Asp Gly Leu Thr Leu Ile Ala Asp Asn Ala
            900                 905                 910
Glu Lys Leu Gly Arg Ala Ile Lys Ser Asn Ser Gly Val Lys Ala Ser
        915                 920                 925
Ala Leu Glu Val Thr Gln Arg Leu Lys Ala Ala Ala Lys Gly Leu
    930                 935                 940
Ser Gln Asp Arg Asp Val Gly Ser Ala Ser Pro Ala Ser Asp Lys Pro
945                 950                 955                 960
Glu Leu Thr Lys Glu Arg Val Lys Pro Phe Glu Ile Gly Ile
                965                 970

<210> SEQ ID NO 113
<211> LENGTH: 970
<212> TYPE: PRT
<213> ORGANISM: Erythrobacter sp. NAP1
```

<400> SEQUENCE: 113

```
Met Leu Ser Val Ala Asn Val Arg Ser Pro Ser Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Ile Gly Asp Gly Ala Lys Arg Leu Gly Leu Glu Gly Lys Val
            35                  40                  45

Glu Ala Gln Ala Phe Asp Ala Leu Leu Arg Gly Leu Pro Asp Gly
50                  55                  60

Ser Ser Val Gly Asn Pro Gly Gln Thr His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Leu Glu Ala Leu
                100                 105                 110

His Trp Ala Glu Lys Asn Ala Ala Glu Thr Arg Met Val Glu Lys Gly
            115                 120                 125

Lys Thr Val Thr Gln Thr Thr Gly Asn Leu Ala Ile Gly Leu Phe Gln
130                 135                 140

His Asp Thr Asn Arg Asn Gln Glu Pro Asn Leu His Phe His Ala Val
145                 150                 155                 160

Ile Ala Asn Val Thr Arg Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Thr Leu Lys His Gly Asn Phe Glu Ala Arg Gly Ile Thr Arg Glu Gln
210                 215                 220

Val Met Ala Phe Ser Ser Arg Gln Glu Val Leu Asp Ala Arg Arg
225                 230                 235                 240

Gly Pro Gly Leu Glu Ala Gly Arg Ile Ala Ala Leu Asp Thr Arg Ala
                245                 250                 255

Ser Lys Asp Gly Ile Glu Asp Arg Glu Ala Leu Gly Met Gln Trp Ser
            260                 265                 270

Asp Thr Ala Lys Ser Ile Gly Leu Asp Leu Ala Pro Leu Val Glu Arg
        275                 280                 285

Ala Arg Thr Arg Thr Leu Arg Gln Ser Ile Glu Thr Gly Arg Phe Gly
290                 295                 300

Ser Leu Val Glu Arg Gly Arg Ala Trp Leu Gly Arg Phe Ala Ala His
305                 310                 315                 320

Val Arg Gly Asp Pro Ala Asp Pro Leu Val Pro Lys Ser Val Leu Arg
                325                 330                 335

Gln Asp Arg Glu Thr Ile Ala Ala Gln Ala Val Ala Ser Ala Val
            340                 345                 350

Arg His Leu Ser Gln Arg Glu Ala Ala Phe Glu Arg Thr Ala Leu Tyr
        355                 360                 365

Lys Ala Ala Leu Asp Phe Gly Leu Pro Thr Thr Ile Ala Asp Ile Glu
        370                 375                 380

Lys Arg Thr Arg Ala Leu Val Arg Ser Gly Asp Leu Ile Ala Gly Lys
385                 390                 395                 400

Gly Asp His Arg Gly Trp Leu Ala Ser Arg Asp Ala Val Leu Thr Glu
```

-continued

```
                405                 410                 415
Gln Gln Ile Val Ser Glu Val Ala Ala Gly Arg Gly Ala Ser Ser Pro
            420                 425                 430
Ala Ile Glu Arg Gly Ser Ala Thr Asp Arg Val Gln Thr Ala Ala Met
            435                 440                 445
Ala Gly Gln Gly Phe Arg Leu Asn Glu Gly Gln Leu Gly Ala Ala Lys
        450                 455                 460
Leu Ile Leu Thr Ser Glu Asp Arg Thr Ile Ala Val Gln Gly Ile Ala
465                 470                 475                 480
Gly Ala Gly Lys Ser Ser Val Leu Lys Pro Val Thr Glu Val Leu Arg
                485                 490                 495
Asp Glu Gly Arg Pro Val Ile Gly Leu Ala Ile Gln Asn Thr Leu Val
                500                 505                 510
Gln Met Leu Glu Arg Asp Thr Gly Ile Gly Ser Gln Thr Leu Ala Arg
            515                 520                 525
Phe Leu Gly Gly Trp Lys Lys Leu Leu Asp Asp Pro Gly Asn Ala Ala
        530                 535                 540
Leu Arg Leu Glu Ala Lys Ala Ala Leu Lys Asp His Val Leu Val Leu
545                 550                 555                 560
Asp Glu Ala Ser Met Val Ser Asn Glu Asp Lys Glu Lys Leu Val Arg
                565                 570                 575
Leu Ala Asn Leu Ala Gly Val His Arg Leu Val Leu Met Gly Asp Arg
                580                 585                 590
Lys Gln Leu Gly Ala Val Asp Ala Gly Lys Pro Phe Ala Leu Leu Gln
            595                 600                 605
Arg Thr Gly Thr Ala Ser Ala Glu Met Ala Thr Asn Leu Arg Ala Arg
            610                 615                 620
Asp Pro Val Val Arg Glu Ala Gln Ala Ala Gln Ala Gly Glu Val
625                 630                 635                 640
Arg Lys Ala Leu Arg His Leu Gln Pro His Thr Val Glu Ala Lys Gly
                645                 650                 655
Asp Gly Ala Leu Val Ala Ala Asp Thr Trp Leu Ala Leu Asp Lys Asp
                660                 665                 670
Asp Arg Ala Arg Thr Ser Ile Tyr Ala Ser Gly Arg Ala Ile Arg Ser
            675                 680                 685
Ala Val Asn Ala Ala Ile Gln Gln Gly Leu Leu Ala Asn Gly Glu Ile
        690                 695                 700
Gly Pro Gly Lys Ala Glu Leu Gly Val Leu Asp Arg Val Asn Thr Thr
705                 710                 715                 720
Arg Glu Glu Leu Arg His Leu Ser Ala Tyr Gln Pro Gly Arg Val Leu
                725                 730                 735
Glu Val Ser Arg Lys Gln Ala Leu Gly Leu Ser Ala Gly Glu Tyr
                740                 745                 750
Arg Val Leu Gly Gln Asp Arg Lys Gly Arg Gln Val Glu Val Ala Asp
            755                 760                 765
Lys Arg Gly Lys Arg Phe Arg Phe Asp Pro Ala Arg Ile Arg Ala Gly
            770                 775                 780
Lys Gly Asp Gln Asn Leu Thr Leu His Glu Pro Arg Lys Leu Glu Ile
785                 790                 795                 800
His Glu Gly Asp Arg Ile Arg Trp Thr Arg Asn Asp His Arg Arg Gly
                805                 810                 815
Leu Phe Asn Ala Asp Gln Ala Arg Val Val Ala Val Val Gly Gly Lys
            820                 825                 830
```

```
Val Thr Phe Glu Thr Ser Lys Gly Asp Gln Val Glu Leu Lys Lys Asp
            835                 840                 845

Asp Pro Met Leu Lys Arg Ile Asp Leu Ala Tyr Ala Leu Asn Ala His
    850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Ile Thr
                885                 890                 895

Arg Leu Arg Asp His Leu Thr Leu Val Val Asp Ser Ser Asp Arg Leu
                900                 905                 910

Gly Ala Val Ala Arg Asn Lys Gly Lys Ala Ser Ala Leu Glu
                915                 920                 925

Val Thr Ala Gln Leu Thr Pro Thr Glu Lys Lys Asn Gly Glu Leu Asp
            930                 935                 940

Gln Leu Lys Pro Glu Glu Ala Asn Lys Ala Glu Lys Glu Leu Ala Arg
945                 950                 955                 960

Ser Lys Ser Lys Thr Leu Asp Phe Gly Ile
                965                 970

<210> SEQ ID NO 114
<211> LENGTH: 978
<212> TYPE: PRT
<213> ORGANISM: Novosphingobium pentaromativorans US6-1

<400> SEQUENCE: 114

Met Leu Ser Val Ala Asn Val Arg Thr Ala Gly Gly Ala Ala Asn Tyr
1               5                   10                  15

Phe Ala Ala Asp Asn Tyr Tyr Thr Arg Ala Asp Ala Glu Arg Ser Gly
            20                  25                  30

Gln Trp Leu Gly Arg Gly Ala Glu Thr Leu Gly Leu Arg Gly Val Ile
        35                  40                  45

Glu Ala Ser Gln Phe Glu Ala Val Leu Lys Gly Met Leu Pro Asp Gly
    50                  55                  60

Ser Arg Val Gly Ser Asp Asn Arg Ala His Arg Ala Gly Thr Asp Leu
65                  70                  75                  80

Thr Phe Ser Met Pro Lys Ser Trp Ser Ile Leu Ala Leu Val Gly Gly
                85                  90                  95

Asp Arg Arg Ile Leu Asp Ala Tyr Gly Ala Ala Val Arg Glu Thr Leu
            100                 105                 110

Ala Trp Ala Glu Lys Asn Leu Ala Glu Thr Arg Met Glu Val Arg Gly
        115                 120                 125

Lys Glu Arg Val Val Ala Thr Arg Asn Leu Val Ile Gly Leu Phe Gln
    130                 135                 140

His Asp Thr Asn Arg Asn Gln Glu Pro Asn Ala His Phe His Ala Val
145                 150                 155                 160

Val Ala Asn Val Thr Gln Gly Pro Asp Gly Lys Trp Arg Ala Leu Arg
                165                 170                 175

Asn Asp Lys Ile Trp Glu His Asn Thr Leu Leu Asn Ala Met Thr Met
            180                 185                 190

Ala Arg Phe Arg Leu Ala Val Glu Lys Leu Gly Tyr Gln Val Gly Glu
        195                 200                 205

Tyr Gly Lys His Gly Asn Phe Glu Ala Val Gly Val Pro Lys Pro Val
    210                 215                 220

Arg Asp Ala Phe Ser Ser Arg Arg Ala Glu Ile Leu Asp Lys Leu Ser
```

```
            225                 230                 235                 240
        Thr Met Glu Gly Lys Gly Leu Ala Ala Arg Asn Ala Ala Asn Leu Met
                        245                 250                 255
        Thr Arg Ala Asp Lys Gly Pro Val Ala Asp Arg Gln Ala Leu Val Asp
                        260                 265                 270
        Gln Trp Arg Glu Ala Ala Ala Gln Leu Gly Val Asp Pro Arg Leu Val
                        275                 280                 285
        Ile Ser Lys Ala Asn Ala Arg Ala Thr Thr Asp Ile Gly Ser Val Ser
        290                 295                 300
        Gly Ile Gly Asn Ser Val Arg Ser Ile Gly Gln Arg Ala Arg Leu Leu
        305                 310                 315                 320
        Ala Ala Thr Phe Ala Glu His Leu Gly Leu Arg Gln Gly Asp Pro Leu
                        325                 330                 335
        Val Pro Arg Asp Met Glu Arg Arg Thr Pro Glu Gln Ile Ala Ala Val
                        340                 345                 350
        His Ala Val Ala Ser Ala Ile Arg His Leu Gly Glu Arg Glu Ala Ala
                        355                 360                 365
        Phe Ser Arg Thr Glu Ile Tyr Arg Ser Ala Leu Gly Phe Ala Leu Pro
                        370                 375                 380
        Thr Thr Leu Pro Asp Ile Glu His Arg Val Asp Gln Leu Leu Arg Gln
        385                 390                 395                 400
        Gly His Leu Gln Lys Gly Lys Gly Ala Asp Arg Asn Leu Val Thr Thr
                        405                 410                 415
        Arg Asp Ala Ile Gly Leu Glu Gln Arg Ile Ala Ala Val Glu Thr
                        420                 425                 430
        Gly Arg Gly His Gly Ser Ala Val Val Glu Ala Asp Val Ala Gly Glu
                        435                 440                 445
        Arg Leu Gln Ala Leu Ser Gln Leu Lys Tyr Gly Leu Thr Leu Asn Pro
                        450                 455                 460
        Gly Gln Glu Gly Ala Gly Arg Leu Leu Leu Ala Ser His Asn Arg Ile
        465                 470                 475                 480
        Val Ala Ile Gln Gly Val Ala Gly Ala Gly Lys Ser Thr Val Leu Lys
                        485                 490                 495
        Pro Val Ala Asp Ile Leu Arg Glu Glu Gly Arg Ser Val Leu Gly Leu
                        500                 505                 510
        Ala Val Gln Asn Thr Leu Val Gln Met Leu Glu Arg Asp Thr Gly Ile
                        515                 520                 525
        Pro Ser Met Thr Val Ala Arg Phe Leu Arg Gln His Gln Gly Leu Leu
                        530                 535                 540
        Glu Gly Ala Asp Gln Ala Arg Leu Ala Glu Ala Arg Ala Ser Leu Arg
        545                 550                 555                 560
        Gly Thr Thr Val Leu Leu Asp Glu Ala Ser Met Val Gly Asn Ala Asp
                        565                 570                 575
        Lys Glu Lys Leu Val Arg Leu Ala Asn Leu Leu Gln Leu Asp Arg Phe
                        580                 585                 590
        Ala Ser Ile Gly Asp Arg Lys Gln Leu Gly Ala Val Asp Ala Gly Lys
                        595                 600                 605
        Pro Phe Asp Val Met Gln Lys Ala Gly Val Glu Thr Ala Thr Met Asn
                        610                 615                 620
        Thr Asn Leu Arg Ala Arg Asp Lys Ala Leu Arg Asp Ala Gln Tyr Ala
        625                 630                 635                 640
        Ala Gln Gly Gly Asn Ile Asp Glu Ala Leu Arg His Leu Gly Pro His
                        645                 650                 655
```

```
Val Val Ala Ser Gly Asn Thr Ala Val Asp Ala Ala Ala Trp
            660                 665                 670

Leu Ser Leu Ser Pro Ala Glu Arg Glu Val Thr Ala Ile Tyr Ala Ser
        675                 680                 685

Gly Arg Asn Leu Arg Gly Gln Val Asn Glu Ala Val Gln Ile Gly Leu
    690                 695                 700

Lys Ala Asn Gly Glu Leu Gly Pro Gly Ser Leu Gly Leu Thr Val Leu
705                 710                 715                 720

Ser Arg Val Asn Leu Thr Arg Glu Glu Met Arg Tyr Ser Arg Ser Tyr
                725                 730                 735

Ala Ala Gly Met Val Leu Glu Val Asp Arg Arg Gln Arg Gly Gln Gly
            740                 745                 750

Leu Gln Lys Gly Arg Tyr Glu Val Val Glu Thr Asp Pro Thr Arg Glu
        755                 760                 765

His Val Met Leu Gln Asn Glu Arg Gly Lys Arg Phe Glu Phe Arg Pro
    770                 775                 780

Gly Gln Met Arg Pro Gln Gly Glu Gln Asp Pro Leu Arg Leu Phe Glu
785                 790                 795                 800

Val Arg Pro Leu Glu Ile His Asp Gly Asp Arg Ile Arg Trp Thr Ala
                805                 810                 815

Thr Asp His Lys Arg Gly Leu Leu Asn Ala Asp Gln Ala Arg Ile Val
            820                 825                 830

Ala Val Asp Ala Lys Gly Val Thr Val Lys Thr Ser Leu Gly Ala Glu
        835                 840                 845

His Arg Leu Gly Leu Ser Asp Pro Met Leu Glu Arg Leu Asp Leu Ala
    850                 855                 860

Tyr Ala Leu Asn Ala His Met Ala Gln Gly Leu Thr Ser Asn Arg Gly
865                 870                 875                 880

Ile Ala Val Met Asp Ser Arg Glu Arg Asn Leu Ala Asn Gln Gln Thr
                885                 890                 895

Phe Leu Val Thr Ile Thr Arg Leu Arg Asp Gly Leu Thr Leu Phe Val
            900                 905                 910

Asp Asn Ala Gly Lys Leu Glu Ala Ala Val Glu Arg Asn Pro Gly Met
        915                 920                 925

Lys Arg Ser Ala Leu Glu Thr Val Asn Gln Leu Arg Asp Ala Ala Ala
    930                 935                 940

Met Gly Gln Ala Lys Gly Lys Ala Ser Asp Arg Ser Gln Glu Pro Ala
945                 950                 955                 960

Arg Glu Pro Pro Glu Leu Asp Arg Ser Ile Thr Lys Pro Phe Glu Ile
                965                 970                 975

Gly Ile

<210> SEQ ID NO 115
<211> LENGTH: 8
<212> TYPE: PRT
<213> ORGANISM: Artificial sequence
<220> FEATURE:
<223> OTHER INFORMATION: RecD-like motif I of TrwC Npe

<400> SEQUENCE: 115

Gly Val Ala Gly Ala Gly Lys Ser
1               5

<210> SEQ ID NO 116
<211> LENGTH: 14
```

```
<212> TYPE: PRT
<213> ORGANISM: Artificial sequence
<220> FEATURE:
<223> OTHER INFORMATION: MobF motif III of TrwC Npe

<400> SEQUENCE: 116

His Asp Thr Asn Arg Asn Gln Glu Pro Asn Ala His Phe His
1               5                   10

<210> SEQ ID NO 117
<211> LENGTH: 981
<212> TYPE: PRT
<213> ORGANISM: Novosphingobium nitrogenifigens DSM 19370

<400> SEQUENCE: 117

Met Ile Ser Phe Lys Ala Leu Pro Ser Ala Ser Thr Ala Glu Tyr
1               5                   10                  15

Phe Ser Lys Asp Asn Tyr Tyr Thr Leu Gly Gln Ala Gln Glu Leu Ser
                20                  25                  30

Ala Trp Thr Gly Arg Ala Ala Glu Asp Leu Gly Leu Ala Gly Arg Val
            35                  40                  45

Asp Glu Lys Val Phe Ala Leu Leu Glu Gly Lys Leu Pro Asn Gly
50                  55                  60

Val Gln Ile Ala Ala Ser Gln Gly Lys His Arg Ala Gly Val Asp Ile
65                  70                  75                  80

Thr Phe Ala Ala Ser Lys Ser Val Ser Leu Ala Leu Ile Gly Gly
                85                  90                  95

Asp Glu Arg Ile Val Val Ala Met Gln Glu Ser Val Gln Ala Ala Leu
            100                 105                 110

Thr Trp Val Glu Lys Asn Val Met Glu Ala Arg Ile Trp Asp Pro Val
        115                 120                 125

Leu Gly Glu Gln Val Pro Glu Lys Thr Gly Asn Leu Val Ala Ala Thr
130                 135                 140

Phe Leu His Asp Val Ser Arg Asn Asn Asp Pro Gln Leu His Val His
145                 150                 155                 160

Ser Ile Val Ala Asn Ala Thr Arg Ala Ser Asp Gly Lys Trp Arg Ala
                165                 170                 175

Met Thr Asn Lys Ala Phe Tyr Glu Ala Gln His Ile Ile Ser Ala Val
            180                 185                 190

Gln Asn Ala Glu Leu Arg Thr Arg Ile Glu Ala Leu Gly Tyr Glu Thr
        195                 200                 205

Thr Pro Ala Lys Asn Pro Ile Asp Gly Ala Phe Glu Val Gln Gly Val
    210                 215                 220

Ser Arg Glu Val Val Glu Ala Phe Ser Ser Arg Arg Leu Glu Ile Leu
225                 230                 235                 240

Ala Ala Leu Ala Lys Ser Gly Arg Gly Ser Ala Ala Glu Arg Gln Ile
                245                 250                 255

Val Thr Leu Asn Thr Arg Lys Asp Lys Asp Leu Thr Leu Asp Pro Glu
            260                 265                 270

Gln Arg Asn Leu Gly Trp His Glu Thr Ala Arg Ser Leu Gly Phe Asp
        275                 280                 285

Pro Ala Pro Leu Ile Asn Gln Ala Arg Glu Arg Ala Gly Arg Asp Gln
    290                 295                 300

Thr Val Trp Thr Arg Ile Val Asp Gly Ile Arg Gly Ile Gly Ala Lys
305                 310                 315                 320

Gly Met Ala Ile Ala Ala Ala Met Gly Ile Thr Pro Gly Asp Gly Asp
```

```
                    325                 330                 335
Pro Leu Val Pro Glu Arg Leu Gly Arg Leu Asp Pro Val Ser Tyr Ala
                340                 345                 350
Ala Ala Gln Ala Val Ala Ser Ala Ala Arg Glu Leu Gly Glu Asn Glu
                355                 360                 365
Ala Ala Phe Ser Arg His Asp Leu Ile Arg Thr Ala Leu Glu Arg Gln
            370                 375                 380
Gly Pro Phe Thr Val Ser His Ile Glu Ala Arg Ile Asp Gln Leu Thr
385                 390                 395                 400
Arg Gly Gly Gln Leu Ile Gly Arg Glu Gln Met Leu Thr Ser Glu Gln
                405                 410                 415
Ala Leu Ala Met Glu Ser Arg Val Ile Asp Leu Ala Glu Ala Gly Lys
                420                 425                 430
Gly Ala Ile Glu Pro Ile Ala Thr Gly Val Gln Val Gly Ala Arg Leu
                435                 440                 445
Gln Ala Ala Ala Arg Glu Leu Gly Leu Arg Arg Leu Asn Pro Gly Gln
            450                 455                 460
Glu Arg Ala Gly Val Ala Ile Leu Thr Ser Arg Asp Arg Val His Leu
465                 470                 475                 480
Ile Gln Gly Gly Ala Gly Val Gly Lys Ser Ala Ala Leu Ala Pro Val
                485                 490                 495
Ala Ala Ile Ala Arg Ala Glu Gly His Gln Val Ile Ala Leu Ala His
                500                 505                 510
Val Gly Arg Met Ala Arg Glu Phe Gly Ala Lys Val Asn Ala Pro Ala
                515                 520                 525
Ser Thr Val Asp Gly Phe Leu Arg Lys Tyr Glu Arg Val Ile Asp Gly
                530                 535                 540
Thr Ala Tyr Pro Val Lys Met Glu Ala Ala Arg Gln Ala Leu Ser Gly
545                 550                 555                 560
Thr Leu Ile Met Val Asp Glu Ala Ser Gln Ile Gly Thr Asp Arg Phe
                565                 570                 575
Ala Arg Leu Ile Glu Leu Ala Asn Lys Met Glu Val Ala Gly Leu Val
                580                 585                 590
Phe Ala Gly Asp Lys Gly Gln Leu Pro Ala Ile Glu Arg Gly Arg Pro
            595                 600                 605
Phe Ala Asp Leu Gln Arg Glu Asp Val Ala Arg Ser Ala Ile Thr Glu
            610                 615                 620
Asn Leu Arg Ala Lys Thr Pro Gln Met Gln Ala Ile Asn Lys Ala Ile
625                 630                 635                 640
Glu Glu Gly Asp Ile Ala Gly Ala Phe Glu Ala Leu Arg Pro Thr Thr
                645                 650                 655
Ser Thr Val Pro Leu Gly Lys Ala Ala Glu Thr Ala Ala Thr Met Trp
                660                 665                 670
Ala Asn Leu Pro Arg Asp Glu Arg Gln Thr Val Leu Leu Ala Ser
            675                 680                 685
Gly Arg Ala Met Arg Thr Ala Gly Asn Ala Ala Thr Gln Arg Ala Leu
            690                 695                 700
Leu Ala Lys Gly Glu Leu Gly Val Ala Lys Ala Ser Leu Lys Val Leu
705                 710                 715                 720
Asp Arg Ile Thr Ile Thr Lys Glu Gly Ala Arg Gln Leu Lys Gly Tyr
                725                 730                 735
Gln Asp Gly Arg Leu Val Glu Phe Thr Thr Asn Leu Pro Lys Ala Gly
                740                 745                 750
```

```
Phe Ala Arg Gly Glu Ile Gly Glu Val Val Asn Val Ala Asp Gly Lys
            755                 760                 765

Val Glu Leu Val Met Glu Gly Glu Val Arg Ser Phe Asp Pro Ser
770                 775                 780

Arg Leu Pro Arg Asn Leu Lys His Asp Ala Val Thr Ile Tyr Glu Gln
785                 790                 795                 800

Lys Gln Ile Thr Ile His Glu Gly Asp Arg Ile Arg Trp Thr Ala Lys
                805                 810                 815

Asp Glu Ala Arg Glu Leu Phe Asn Gly Asp Met Ala His Val Lys Arg
            820                 825                 830

Ile Asp Gly Asp Ser Ile Ile Val Arg Thr Ala Asn Gly Asp Glu His
            835                 840                 845

Gln Leu Phe Gly Lys Asp Pro Met Arg Asp Arg Phe Asp Leu Ala Tyr
850                 855                 860

Ala Ile Asn Val His Ile Ala Gln Gly Ile Thr Ala Lys Ala Gly Ile
865                 870                 875                 880

Val Met Met Ser Ser Leu Glu Arg Leu Leu Asn Ser Ser Arg Ala Phe
                885                 890                 895

Val Val Ala Ala Thr Arg Ile Ala Glu Thr Ile His Leu Val Val Asp
            900                 905                 910

Asp Pro Asn Lys Val Glu Lys Gln Val Glu Arg Asn Pro Gly Asp Lys
            915                 920                 925

Thr Ser Ala Arg Glu Val Ala Lys Pro Thr Ser Glu Thr Asp Lys Lys
            930                 935                 940

Ala Glu Lys Lys Asp Phe Glu Lys Glu Arg Asp Tyr Ala Lys Glu Leu
945                 950                 955                 960

Lys Lys His Leu Gly Ile Asp Lys Met Thr Glu Ala Arg Ser Arg Asp
                965                 970                 975

Trp Asp Met Gly Leu
            980

<210> SEQ ID NO 118
<211> LENGTH: 8
<212> TYPE: PRT
<213> ORGANISM: Artificial sequence
<220> FEATURE:
<223> OTHER INFORMATION: RecD-like motif I of TrwC Nni

<400> SEQUENCE: 118

Gly Gly Ala Gly Val Gly Lys Ser
1               5

<210> SEQ ID NO 119
<211> LENGTH: 10
<212> TYPE: PRT
<213> ORGANISM: Artificial sequence
<220> FEATURE:
<223> OTHER INFORMATION: RecD-like motif V of TrwC Nni

<400> SEQUENCE: 119

Tyr Ala Ile Asn Val His Ile Ala Gln Gly
1               5                   10

<210> SEQ ID NO 120
<211> LENGTH: 14
<212> TYPE: PRT
<213> ORGANISM: Artificial sequence
<220> FEATURE:
<223> OTHER INFORMATION: MobF motif III of TrwC Nni
```

<400> SEQUENCE: 120

His Asp Val Ser Arg Asn Asn Asp Pro Gln Leu His Val His
1               5                   10

<210> SEQ ID NO 121
<211> LENGTH: 1010
<212> TYPE: PRT
<213> ORGANISM: Sphingomonas wittichii RW1

<400> SEQUENCE: 121

Met Leu Ser Val Ala Ser Val Arg Ser Ala Ser Gly Ala Ala Asn Tyr
1               5                   10                  15

Phe Ala Lys Asp Asp Tyr Tyr Thr Val Glu Gly Ser Ser Glu Ile Ser
                20                  25                  30

Ala Trp Gly Gly Glu Gly Ala Gly Ala Leu Gly Leu Ser Gly Glu Val
            35                  40                  45

Gly Lys Asp Ala Phe Glu Gly Met Leu Asn Gly Ile Leu Pro Ser Gly
        50                  55                  60

Glu Gly Val Ala Gln Val Glu Asn Arg Arg Ala Gly Leu Asp Leu Thr
65                  70                  75                  80

Phe Ser Met Pro Lys Ser Ala Ser Ile Leu Ala Tyr Val Ala Gly Asp
                85                  90                  95

Lys Arg Ile Leu Ala Ala Asn Met Ala Ala Val Gln Lys Thr Met Ala
            100                 105                 110

Trp Val Glu Lys Asn Leu Ala Glu Gly Arg Lys Asp Ile Gly Gly Arg
        115                 120                 125

Thr Val Pro Val Ala Thr Gly Asn Leu Val Tyr Ala Leu Phe Gln His
    130                 135                 140

Asp Thr Ser Arg Ala Leu Asp Pro Gln Gly His Ile His Ala Val Ile
145                 150                 155                 160

Ala Asn Leu Thr Arg Leu Pro Asp Gly Lys Trp Gln Ala Leu His Ala
                165                 170                 175

Asp Lys Ile Trp Ser His Asn Thr Val Ile Gly Ser Ile Tyr His Ala
            180                 185                 190

Tyr Leu Arg Glu Gly Ile Glu Gln Leu Gly Phe Arg Ile Glu Ala Leu
        195                 200                 205

Gly Lys His Gly Thr Phe Glu Ile Ala Gly Val Pro Arg Lys Val Ile
    210                 215                 220

Asp Ala Tyr Ser Gln Arg Arg Glu Ala Ile Leu Glu Lys Ala Ala Ala
225                 230                 235                 240

Leu Gly Ile Val Ser His Lys Gly Arg Asp Gln Ile Thr Thr Asn Thr
                245                 250                 255

Arg Asp Pro Lys Leu Asn Val Lys Asp Arg Asp Ala Leu Lys Gln Glu
            260                 265                 270

Trp Ile Asp Lys Ala Ala Ser Leu Gly Phe Asp Gly Lys Ala Leu Val
        275                 280                 285

Glu Gly Ala Leu Ala Arg Ser Asp Arg His Gly Ala Leu Gly Pro Leu
    290                 295                 300

Glu Arg Gly Tyr Lys Ala Val Thr Glu Ala Ile Ala Ala Gly Arg Glu
305                 310                 315                 320

Lys Leu Gly Asp Leu Val Arg Pro Ala Asp Pro Leu Val Asp Arg Gly
                325                 330                 335

Leu Ala Arg Val Thr Gln Ser Pro Ala Ile Ala Arg Ala Gln Leu Ala
            340                 345                 350

```
Val Ala Ser Ala Val Arg Ile His Ser Glu Arg Glu Ala Ala Phe Pro
            355                 360                 365

Ile His Arg Leu Ala Lys Thr Ala Leu Asp Leu Gly Leu Lys Asp Val
    370                 375                 380

Thr Ile Asp Arg Ile Glu Gln Arg Ile Gln Gln Leu Val Ala Arg Gly
385                 390                 395                 400

Thr Leu Leu Arg Gly Gln Glu Arg Ala Ala Asp Phe Val Thr Thr Arg
                405                 410                 415

Gln Ala Leu Ala Thr Glu Thr Gln Ile Leu Thr Gln Val Glu Ala Gly
            420                 425                 430

Arg Gly Gln Ala Asn Pro Ile Ile Asp Ala Ser Glu Ala Pro Gly Arg
            435                 440                 445

Leu Gln Ala Ala Ala Thr Gln Pro Leu Asn Thr Gly Gln Leu Ala Ala
        450                 455                 460

Ala Thr Leu Ile Leu Gly Ser Ala Asp Arg Thr Val Ser Ile Gln Gly
465                 470                 475                 480

Ile Ala Gly Ala Gly Lys Ser Thr Met Leu Gln Ala Val Ala Arg Val
                485                 490                 495

Ala Glu Ala Glu Gly Arg Ala Ile Thr Gly Leu Ala Phe Gln Asn Lys
            500                 505                 510

Met Val Ala Asp Leu Ala Glu Gly Ala Gly Val Pro Ala Gln Thr Ile
        515                 520                 525

Ala Ser Phe Val Leu Ala His Glu Arg Tyr Val Ala Glu Pro Gln Gly
        530                 535                 540

Pro Gly Tyr Asp Ala Ala Arg Ala Ala His Ala Gly Ser Met Leu Val
545                 550                 555                 560

Val Asp Glu Thr Ser Met Val Ser Ser Asn Asp Met Leu Lys Leu His
                565                 570                 575

Ala Ile Val Glu Thr Leu Gly Val Asp Lys Leu Val Leu Val Gly Asp
            580                 585                 590

Arg Gln Gln Leu Ser Ser Ile Asp Ala Gly Lys Ser Phe Ala Met Ile
        595                 600                 605

Gln Ala Ala Gly Gly Thr Leu Ala Arg Met Asp Glu Asn Ile Arg Gln
    610                 615                 620

Arg Thr Asp Val Leu Arg Thr Val Ala Ala Leu Ala Asn Ile Gly Lys
625                 630                 635                 640

Ala Ser Glu Ala Met Arg Val Leu Gly Asp Lys Val Ile Glu Ala Ser
                645                 650                 655

Gln Pro Ala Glu His Ala Ala Asp Leu Trp Leu Ala Leu Asp Pro Ala
            660                 665                 670

Glu Arg Gln Ala Thr Ala Val Phe Ala Ser Gly Arg Glu Ala Arg Ala
        675                 680                 685

Ala Ile Asn Glu Arg Ile Gln Ala Gly Leu Ala Ala Glu Gly Ser Leu
    690                 695                 700

Glu Gly Glu Gly Ile His Leu Thr Val Tyr Glu Arg Val Asn Thr Thr
705                 710                 715                 720

Arg Glu Glu Leu Arg Tyr Ala Ala Thr Tyr Arg Ala Gly Met Thr Leu
                725                 730                 735

Glu Val Gly Arg Gly Gly Gly Gln Asp Ile Gly Leu Arg Ala Gly Arg
            740                 745                 750

Tyr Asp Val Leu Ala Val His Ala Asn Gly Lys Val Glu Leu Gly Glu
        755                 760                 765
```

-continued

```
Gly Arg Arg Arg Ile Arg Phe Asp Pro Leu Lys Leu Ser Pro Thr Glu
        770                 775                 780

Thr Arg Asp Arg Leu Gln Leu Thr Glu Lys Lys Asp Leu His Leu Arg
785                 790                 795                 800

Ala Gly Asp Arg Ile Arg Trp Thr Ala Asn Asp Lys Pro Arg Gly Leu
                805                 810                 815

Thr Asn Ala Ser Leu Ala Arg Val Val Ala Val Asp Arg Asp Ser Val
            820                 825                 830

Thr Val Glu Thr Ala Gly Arg Asp Arg Leu Val Leu Ala Phe Gly Asp
        835                 840                 845

Pro Met Leu Ser Arg Val Asp Leu Ala Tyr Ala Leu Asn Met His Met
850                 855                 860

Ala Gln Gly Ile Thr Thr Asp Lys Ala Ile Thr Val Met Asp Ser His
865                 870                 875                 880

Glu Arg Asn Leu Ser Asn Gln Arg Leu Phe Asn Val Gly Val Thr Arg
                885                 890                 895

Val Arg Asp Asp Leu Thr Met Val Val Asp Asp Lys Ala Lys Leu Glu
            900                 905                 910

Arg Gln Leu Asp His Asn Pro Gly Asn Lys Thr Ser Ala Leu Glu Thr
        915                 920                 925

Leu Gly Arg Leu Glu Ile Asp Gly Pro Gly Arg Ala Gln Ala Ser Gly
930                 935                 940

Pro Phe Asp Pro Gly Pro Val Glu Gly Gly Pro Gly Pro Lys Ala Ala
945                 950                 955                 960

Glu Gly Leu Asp Gly Phe Pro Pro Val Pro Pro Ala Glu Gly Gln Val
                965                 970                 975

Ala Ala Arg Ala Lys Ser Asp Asp Leu Ser Ala Pro Arg Leu Lys Pro
            980                 985                 990

Glu Gln Ala Asp Leu Leu Pro Pro  Leu Pro Glu Arg Ser  Leu Gly Leu
        995                 1000                1005

Asp Leu
    1010

<210> SEQ ID NO 122
<211> LENGTH: 10
<212> TYPE: PRT
<213> ORGANISM: Artificial sequence
<220> FEATURE:
<223> OTHER INFORMATION: RecD-like motif V of TrwC Swi

<400> SEQUENCE: 122

Tyr Ala Leu Asn Met His Met Ala Gln Gly
1               5                   10

<210> SEQ ID NO 123
<211> LENGTH: 14
<212> TYPE: PRT
<213> ORGANISM: Artificial sequence
<220> FEATURE:
<223> OTHER INFORMATION: MobF motif III of TrwC Nni

<400> SEQUENCE: 123

His Asp Thr Ser Arg Ala Leu Asp Pro Gln Gly His Ile His
1               5                   10

<210> SEQ ID NO 124
<211> LENGTH: 1014
<212> TYPE: PRT
<213> ORGANISM: Sphingomonas sp. KA1
```

<400> SEQUENCE: 124

Met His Ser Ile Ala Ala Val Arg Ser Ser Gly Gly Ala Ala Asp Tyr
1               5                   10                  15

Phe Ala Asn Asp Asn Tyr Tyr Thr Ala Gln Glu Ser Ala Gln Ala Gly
            20                  25                  30

Val Trp Ala Gly Glu Gly Ala Arg Ala Leu Gly Leu Glu Gly Thr Val
        35                  40                  45

Gly Arg Asp Ala Phe Glu Ala Ile Leu Asn Gly His Leu Pro Asp Gly
    50                  55                  60

Asp Lys Val Gly Gln Val Glu Gly Arg Arg Leu Gly Leu Asp Leu Thr
65                  70                  75                  80

Phe Ser Met Pro Lys Ser Ala Ser Ile Leu Ala Leu Val Ser Gly Asp
                85                  90                  95

Arg Arg Ile Leu Asp Ala His Met Ala Ala Val Arg Ser Thr Met Ser
                100                 105                 110

Gln Leu Val Glu Lys Gln Leu Ala Glu Gly Arg Asn Tyr Glu Arg Ser
            115                 120                 125

Arg Ser Gly Glu Pro Glu Lys Thr Gly Asn Leu Val Tyr Ala Leu Phe
    130                 135                 140

Ala His Asp Thr Ser Arg Ala Leu Asp Pro Gln Gly His Ile His Ala
145                 150                 155                 160

Val Val Ala Asn Leu Thr Arg Asp Leu Lys Gly Asn Trp Lys Ala Leu
                165                 170                 175

Trp Asn Gly Glu Ile Trp Lys Asn Asn Thr Thr Ile Gly Gln Phe Tyr
            180                 185                 190

His Ala Ala Phe Arg Ala Gln Leu Gln Lys Leu Gly Tyr Glu Thr Glu
        195                 200                 205

Ala Ser Gly Lys His Gly Ala Phe Glu Ile Lys Gly Val Pro Thr Ala
    210                 215                 220

Val Ile Lys Ala Phe Ser Thr Arg Ala Asn Glu Ile Glu Ala Lys Ile
225                 230                 235                 240

Ala Glu Thr Gly Ala Thr Arg Leu Ala Thr Lys Lys Gln Ile Thr Leu
                245                 250                 255

Tyr Thr Arg Asp Pro Lys Leu Ala Val Glu Asp Arg Ala Ala Leu Ala
                260                 265                 270

Glu Gly Trp Lys Thr Arg Ala Ala Glu Leu Gly Phe Asp Gly Lys Pro
            275                 280                 285

Leu Ile Ala Glu Ala Met Ala Arg Ala His Gln Val Arg Pro Thr
290                 295                 300

Leu Arg Glu Thr Ala Ser Gln Ala Phe Ala Glu Val Ala Glu Arg Ile
305                 310                 315                 320

Ser Ala Ala Met Arg Pro Pro Ser Ala Leu Ala Val Ser Gly Pro Ala
                325                 330                 335

Ala Leu Phe Leu Ser Ala Glu Thr Ile Lys Ala Gln His Ala Thr Ala
                340                 345                 350

Ser Ala Ile Arg His Leu Ser Glu Arg Glu Ala Phe Ser Pro Gln
            355                 360                 365

Ala Ile Leu Ser Ala Ala Leu Gly Phe Gln Ile Lys Gly Leu Glu Gly
        370                 375                 380

Gly Ala Val Ala Leu Arg Ile Gly Glu Leu Val Arg Glu Gly His Leu
385                 390                 395                 400

Ile Pro Gly Lys Ser Asp Arg Leu Asp Gly His Tyr Asp Leu Val Thr

-continued

```
                405                 410                 415
Thr Pro Ala Ala Leu Gly Arg Glu Gln Gln Ile Leu Asp Arg Ile Asp
            420                 425                 430
Ala Gly Ala Gly Lys Gly Arg Val Phe Met Ala Pro Glu Val Ala Met
            435                 440                 445
Val Arg Leu Gln Ala Ala Arg Glu Leu Gly Ile Glu Arg Ala Gly
450                 455                 460
Ser Asp Gly Trp Gln Leu Asn Ala Gly Gln Leu Ala Ala Gly Val Ala
465                 470                 475                 480
Val Leu Ser Gly Lys Asp Arg Phe Leu Asn Ile Gln Gly Val Ala Gly
                485                 490                 495
Ala Gly Lys Ser Thr Leu Leu Gly Ala Leu Asp Lys Val Leu Ser Ala
            500                 505                 510
Glu Gly Val Lys Leu Val Gly Leu Ala Phe Gln Asn Lys Met Val Ala
            515                 520                 525
Asp Leu Arg Gly Gly Gly Ser Gly Met Met Thr Ala Glu Gln Met Arg
            530                 535                 540
Glu Ala Gly Ile Glu Ala Trp Thr Ile Ala Ser Phe Val Asn Arg Tyr
545                 550                 555                 560
Ala Gly Pro Ala Ala Gln Gly Gln Gly Glu Arg Phe Glu Thr Ala Arg
                565                 570                 575
Thr Ala Leu Gln Asn Thr Val Ile Ile Thr Asp Glu Ser Ser Met Val
            580                 585                 590
Ser Ser Arg Asp Met Ala Ser Leu Thr Met Ile Ala Glu Arg Leu Asp
            595                 600                 605
Leu Ala Lys Ala Pro Phe Ile Gly Asp Arg Gln Gln Leu Ser Ala Ile
            610                 615                 620
Glu Gln Gly Lys Met Phe Ala Val Ser Gln Ala Ala Gly Gln Ala Thr
625                 630                 635                 640
Val Arg Met Asp Glu Asn Ile Arg Gln Lys Gly Ser Pro Leu Leu Leu
                645                 650                 655
Ala Val Ala Gly Leu Ser Asn Glu Gly His Ala Gly Leu Ala Leu Asp
            660                 665                 670
Leu Leu Ala Ala His Gly Arg Val Ile Glu Asp Lys Ala Asp His Ile
            675                 680                 685
Ala Ala Ala Ala Asp Leu Trp Leu Ser Leu Ala Pro Glu Glu Arg Ala
            690                 695                 700
Arg Thr Ala Ile Phe Thr Ala Gly Arg Asp Asp Arg Thr Arg Ile Asn
705                 710                 715                 720
Gly Leu Val Gln Gln Gly Leu Leu Lys Glu Gly Ser Leu Ala Gly Pro
                725                 730                 735
Gly Val Pro Phe Ser Thr Leu Gln Ser Ala Asn Ala Thr Arg Glu Glu
            740                 745                 750
Met Arg Phe Ala Ser Thr Tyr Arg Pro Gly Gln Val Leu Glu Ala Arg
            755                 760                 765
Met Asp Val Arg Glu Leu Gly Leu Arg Arg Gly Glu Tyr Asp Val Val
            770                 775                 780
Ala Ile Gly Arg Asp Gly Lys Val Thr Leu Glu Arg Asp Gly Lys Arg
785                 790                 795                 800
Lys Val Ile Asp Pro Asp Arg Ile Asp Pro Gln His Arg Phe Asp Arg
                805                 810                 815
Ile Gly Leu Tyr Asp Arg Lys Asp Ile Thr Leu His Gly Gly Glu Thr
            820                 825                 830
```

```
Val Phe Trp Arg Glu Lys Asp Gly Pro Arg Asp Ile Ala Lys Ser Thr
            835                 840                 845

Tyr Ala Lys Val Val Ser Ala Thr Gly Gln Ala Val Thr Leu Glu Leu
    850                 855                 860

Ala Asp Lys Arg Gln Ile Thr Leu Pro Ser Ser Asp Pro Met Leu Arg
865                 870                 875                 880

Arg Leu Asp Leu Gly Tyr Ala Leu Asn Ala His Met Ala Gln Gly Met
                885                 890                 895

Thr Gln Ala Gln Ala Ile Glu Val Ile Ser Ser Arg Gln Arg Asn Leu
            900                 905                 910

Ala Thr Gln Arg Thr Gln Asn Val Leu Asn Thr Arg Ala Thr Asp Asp
            915                 920                 925

Met Arg Val Val Thr Asn Asp Leu Glu Ala Leu Lys Phe Gln Leu Asp
    930                 935                 940

Arg Thr Pro Gly Asn Lys Thr Ser Ala Leu Glu Thr Val Gly Arg Leu
945                 950                 955                 960

Glu Val Asp Ala Arg Pro Ala Asn Pro Ile Glu Pro Arg Gln Leu Pro
                965                 970                 975

Glu Leu Arg Met Ser Pro Glu Leu Lys Ala Lys Leu Asp Ala Ala Leu
            980                 985                 990

Gly Pro Val Ala Ala Pro Ala Val Arg Gln Leu Pro Val Pro Glu Lys
            995                 1000                1005

Ser Leu Gly Leu Asp Leu
    1010

<210> SEQ ID NO 125
<211> LENGTH: 1018
<212> TYPE: PRT
<213> ORGANISM: Candidatus Puniceispirillum marinum IMCC1322

<400> SEQUENCE: 125

Met Val Ala Ser Phe Ser Ser Leu Gly Ser Ala Ser Ala Thr Thr Gly
1               5                   10                  15

Tyr Phe Glu Lys Asp Gly Tyr Tyr Ala Arg Asp Pro Glu His Arg
            20                  25                  30

Gln Ala Ser Phe Trp Tyr Gly Arg Gly Ala Glu Glu Leu Gly Leu Ala
        35                  40                  45

Ala Pro Arg Asp Asp Pro Asp Ala Arg Ala Arg His Ile Asp Ala Glu
    50                  55                  60

Asp Phe Arg Ser Ile Leu Glu Gly Tyr Val Pro Asp Thr Asp Ile Arg
65                  70                  75                  80

Leu Gly His Lys Arg Asp Gly Glu His Lys His Arg Pro Gly Phe Asp
                85                  90                  95

Leu Thr Leu Ser Ala Pro Lys Ser Val Ser Leu Ala Ala Leu Leu His
            100                 105                 110

Gly Asp Lys Arg Val Ile Ala Ala His Asp Ala Ala Val Lys Ala Thr
        115                 120                 125

Leu Asp His Val Glu Gln Asn Tyr Leu Gln Val Arg Ile His Asp Pro
    130                 135                 140

Ala Thr Gly Arg Lys Pro Arg Phe Asn Ala Pro His Leu Ile Ala Gly
145                 150                 155                 160

Val Phe Arg His Glu Ala Ser Arg Asn Leu Asp Pro Gln Leu His Ser
                165                 170                 175

His Ala Val Ile Ala Asn Met Val Arg Asp Asn Glu Gly Lys Trp Arg
```

```
                180                 185                 190
Ser Val Glu Pro Thr Glu Ile Phe Gln Asn Lys Lys Leu Leu Gly Ala
            195                 200                 205
Phe Tyr Arg Asn Glu Leu Ala Gly Asn Leu Ile Glu Leu Gly Tyr Lys
        210                 215                 220
Leu Asp Pro Leu Gln Leu Gly Thr Met Gln Ser Phe Glu Ile Ser Gly
225                 230                 235                 240
Tyr Asp Lys Ala Leu Arg Asp Ala Phe Ser Thr Arg Arg Gln Asp Ile
                245                 250                 255
Leu Lys Tyr Met Asp Glu Arg Gly Trp Glu Lys Asn Glu Lys Met Ala
            260                 265                 270
Gln Arg Ala Ala Leu Ile Thr Arg Gly Arg Lys Asn Glu Pro Asp Arg
        275                 280                 285
Ala Leu Met His Ala Gln Trp Gly Glu Arg Leu Ala Glu Leu Gln Arg
    290                 295                 300
Asp Gly Ile Gly Leu Gly Ile Thr Thr Pro Arg Arg Thr Ala Ala Leu
305                 310                 315                 320
Ala Glu Arg Val Ala Ala Met Asn Thr Pro Asp Met Arg Asn Glu Ile
                325                 330                 335
Ala Gln Gly Ala Leu Ala Trp Ala Leu Ala His Leu Glu Glu Arg Lys
            340                 345                 350
Thr Val Phe Thr His Pro Glu Leu Val Ala Thr Ala Leu Ser Gln Thr
        355                 360                 365
Pro Gly Lys Thr Gly Leu Asp Glu Ile Glu Thr Gly Leu Thr Gly Leu
    370                 375                 380
Lys Asn Ser Gly Arg Val Ile Asp Ala Val Ile Pro Asp Arg Arg Ser
385                 390                 395                 400
Asp Arg Ala Met Ala Val Leu Thr Thr Asp Arg Ala Ile Glu Thr Glu
                405                 410                 415
Arg Asp Ile Leu Gln Arg Leu Glu His Gly Arg Gly Gly Gly Gly Ser
            420                 425                 430
Val Pro Val Thr Arg Asp Leu Glu Gln Thr Leu Thr Ser Gly Gln Leu
        435                 440                 445
Thr Ser Gly Gln Gln Asp Ala Ile Arg Thr Ile Leu Gln Ser Asp Asp
    450                 455                 460
Lys Ile Ile Gly Ile Gln Gly Arg Ala Gly Thr Gly Lys Thr His Met
465                 470                 475                 480
Leu Asn Thr Val Val Asp Leu Ala Glu Asp Ala Lys Ile Phe Gly Leu
                485                 490                 495
Ala Pro Thr Ala Ser Ala Ala Arg Thr Leu Glu Ala Glu Ala Gln Ile
            500                 505                 510
Pro Ala Gly Thr Leu Gln Gly Phe Leu Met Arg Asn Ala Gly Leu Ala
        515                 520                 525
Asp Gly Ser Met Asp Pro Ala Arg Val Ala Thr Ile Lys Ala Arg Leu
    530                 535                 540
Asp Gly Ala Ile Ile Val Asp Glu Ala Ser Leu Ala Ser Ala Val
545                 550                 555                 560
Glu Met Arg Asp Leu Leu Gln Ile Thr Asp Lys Leu Asp Leu Gln Arg
                565                 570                 575
Leu Val Leu Val Gly Asp Thr Arg Gln Leu Asn Gly Val Gly Ala Gly
            580                 585                 590
Ala Pro Phe Arg Leu Met Gln Gln Ala Gly Met Glu Thr Ala Ser Met
        595                 600                 605
```

-continued

Arg Asp Ile Val Arg Gln Arg Asp Pro Leu Leu Lys Asp Ala Val His
610                 615                 620

Glu Ala Ser Leu Gly Arg Gly Glu Ala Ala Leu Glu Met Leu Lys Glu
625                 630                 635                 640

Ser Val Ile Glu Thr Asp Lys Gln Ser Leu Ser Ile Glu Ala Ala Glu
                645                 650                 655

Gln Trp Leu Glu Leu Gly Asp Asp Glu Arg Ala Ala Thr Leu Leu Val
            660                 665                 670

Ala Pro Met Arg His Gln Arg Asp Glu Ile Asn Glu His Ile Arg Glu
        675                 680                 685

Ala Leu Val Asp Asp Gly Thr Ile His Gly Asp Val Met Glu Ile Thr
690                 695                 700

Arg Leu Asp Ser Tyr Cys Met Thr Arg Ala Gln Lys Gln Asp Pro Ala
705                 710                 715                 720

Asn Tyr Gln Ala Gly Asp Lys Val Val Phe Ala Val Asp Ser Asn Arg
                725                 730                 735

Thr Gly Leu Lys Ala Asn Glu Ile Tyr Thr Val Ala Asp His Asp Glu
            740                 745                 750

Arg Phe Val Thr Leu Val Asp Gly Asp Gly Glu Met Arg Cys Phe Asp
        755                 760                 765

Pro Gly Gly Ile Val Thr Arg Arg Asp Ile Ala Ser Arg Leu Asp
770                 775                 780

Val Phe Glu Pro Val Glu Met Ser Leu Gln Ala Gly Asp His Ile Arg
785                 790                 795                 800

Trp Thr Arg Asn Asp Asn Ala Arg Gly Leu Ile Asn Ala Arg Gln Ala
                805                 810                 815

Glu Val Thr Asp Ile Thr Ser Glu Gln Gly Ile Gln Ser Val His Met
            820                 825                 830

Arg Thr Asn Asp Gly Arg Thr Leu Ser Leu Asp His Asp Pro Gln
        835                 840                 845

Leu Gly His Cys Asp Tyr Ala Phe Ala Ser Thr Ala His Gly Ala Gln
850                 855                 860

Gly Gln Thr Met Asp Arg Val Ile Ala Val Met Asp Ser Asp His Val
865                 870                 875                 880

Ala Leu Ser Asn Gln Lys Thr Phe Tyr Val Glu Ile Ser Arg Ala Arg
                885                 890                 895

Asp Glu Val Thr Ile Val Thr Asp Asp Arg Leu Gln Leu Ala Asp Thr
            900                 905                 910

Leu Ala Ser Asn Ser Gly Glu Met Ala Ser Ala Leu Glu Ala Ile Gly
        915                 920                 925

Glu Val Thr Thr Arg Glu Ala Pro Ala Ala Pro Ala Leu Asp Val Asn
930                 935                 940

His Asp Arg Val Thr Asp Ile Ala Thr Ala Glu Met Thr Pro Thr Glu
945                 950                 955                 960

Pro Met Leu Glu Arg Tyr Asp Glu Pro Pro Pro Thr His Glu Ala
                965                 970                 975

Glu Tyr Gly Glu Thr Val Arg His Glu Pro Thr Ser Glu Asp Gly Ser
            980                 985                 990

Ile Val Thr Arg Glu Arg Glu Pro Glu Pro Thr Glu Glu Lys Thr Lys
        995                 1000                1005

Glu Arg Asp Ile Gly Met Glu Met Gly Leu
    1010                1015

<210> SEQ ID NO 126
<211> LENGTH: 8
<212> TYPE: PRT
<213> ORGANISM: Artificial sequence
<220> FEATURE:
<223> OTHER INFORMATION: RecD-like motif I of TrwC Pma

<400> SEQUENCE: 126

Gly Arg Ala Gly Thr Gly Lys Thr
1               5

<210> SEQ ID NO 127
<211> LENGTH: 10
<212> TYPE: PRT
<213> ORGANISM: Artificial sequence
<220> FEATURE:
<223> OTHER INFORMATION: RecD-like motif V of TrwC Pma

<400> SEQUENCE: 127

Phe Ala Ser Thr Ala His Gly Ala Gln Gly
1               5                   10

<210> SEQ ID NO 128
<211> LENGTH: 14
<212> TYPE: PRT
<213> ORGANISM: Artificial sequence
<220> FEATURE:
<223> OTHER INFORMATION: MobF motif III of TrwC Pma

<400> SEQUENCE: 128

His Glu Ala Ser Arg Asn Leu Asp Pro Gln Leu His Ser His
1               5                   10

<210> SEQ ID NO 129
<211> LENGTH: 994
<212> TYPE: PRT
<213> ORGANISM: Parvularcula bermudensis HTCC2503

<400> SEQUENCE: 129

Met Val Ala Ser Ile Ala Ala Val Ser Ser Ala Ser Ala Gly Ala Ala
1               5                   10                  15

Tyr Tyr Gly Lys Asp Asn Tyr Ala Lys Gly Gly Asp Ala Pro Glu
                20                  25                  30

Pro Ser Ser Trp Phe Gly Lys Gly Ala Ala Ser Leu Gly Leu Lys Gly
            35                  40                  45

Gly Val Glu Thr Glu Thr Phe Glu Arg Val Leu Asn Gly Glu Thr Leu
        50                  55                  60

Asp Gly Arg Arg Val Gly Gln Arg Glu Gly Glu Thr Ala Glu Gln Ala
65                  70                  75                  80

Gln Ala Arg Ala His Arg Pro Gly Ile Asp Leu Thr Phe Ser Pro Pro
                85                  90                  95

Lys Asp Val Ser Leu Leu Leu Tyr Ile Gly Gly Asp Lys Arg Ile Leu
            100                 105                 110

Gly Ala His Arg Ala Ala Val Asp Gln Thr Leu Lys Trp Ala Glu Arg
        115                 120                 125

Asn Leu Ala Gly Thr Arg Ile Arg Thr Gly Pro Ser Ala Thr Pro Ala
    130                 135                 140

Val Lys Thr Gly Asn Leu Val Ile Ala Arg Phe Glu His Asp Ile Ser
145                 150                 155                 160

Arg Asp Lys Asp Pro Gln Leu His Thr His Ala Val Ile Ala Asn Ile
                165                 170                 175

-continued

```
Thr Lys Thr Asp Asp Gly Arg Trp Arg Ala Leu His Asn Asp Pro Phe
            180                 185                 190
Phe Ala His Arg Lys Thr Leu Ser Leu Ala Tyr Asp Ala Thr Leu Arg
        195                 200                 205
Asn Ala Leu Arg Glu Leu Gly Tyr Arg Val Lys Leu Glu Asp Gly Lys
    210                 215                 220
Ser Gly Arg Tyr Ser Val Asp Gly Val Pro Asp Gly Ala Arg Ala Glu
225                 230                 235                 240
Phe Ser Lys Gly Lys Asp Arg Ile Asp Ser Ala Val Gly Leu Lys
                245                 250                 255
His Pro Thr Pro Ser Ala Arg Asp Lys Leu Ala Val Lys Thr Arg Pro
            260                 265                 270
Ala Lys Asp Glu Leu Arg Gln Glu Arg Val Ala Leu Arg Glu Thr
        275                 280                 285
Arg Gly Ala Pro Trp Lys Ala Thr Leu Glu His Thr Val Ala Val Ser
    290                 295                 300
Val Glu Arg Gln Ala Gln Gly His Leu Gln Arg Pro Leu Asp Asp Arg
305                 310                 315                 320
Ala Val Gly Arg Val Gly Met Glu Gly Leu Ala Arg Arg Met Ala Gln
                325                 330                 335
Asn Leu Phe Arg Pro Thr Lys Thr Leu Arg Leu Ser Glu Asn Asp Pro
            340                 345                 350
Tyr Lys Leu Glu Arg Ala Ala Ser Glu Lys Gly Tyr Ser Ala Arg Ala
        355                 360                 365
Ala Val Ser Phe Gly Leu Arg His His Glu Glu Arg Glu Ala Ala Phe
    370                 375                 380
Ser Leu His His Val Arg Arg Thr Ala Leu Glu His Ala Ala Asp Gly
385                 390                 395                 400
Val Thr Leu Arg Asp Ile Asp Arg Glu Leu Arg Phe Leu Arg Ala Asn
                405                 410                 415
Arg Lys Leu Leu Val Asn Ala Lys Asp Pro Asn Ala Glu Ser Thr Thr
            420                 425                 430
Lys Arg Ser Leu Thr His Glu Glu Arg Thr Leu Ser Leu Leu Gln Asp
        435                 440                 445
Ala Gly Arg Thr Gly Pro Leu Val Pro Glu Gln Thr Leu Arg Ser Ala
    450                 455                 460
Leu Glu Ser Thr His Leu Thr Gly Gly Gln Lys Ala Ala Ile Gly Leu
465                 470                 475                 480
Ile Leu Gly Gly Pro Asn Arg Leu Val Gly Val Gln Gly Tyr Ala Gly
                485                 490                 495
Thr Gly Lys Thr Thr Met Met Arg Gln Thr Ala Ala Leu Ala Arg Asp
            500                 505                 510
Leu Ala Pro Leu Ala Lys Lys Asp Gly Tyr Lys Val Leu Gly Leu Ala
        515                 520                 525
Pro Thr His Ser Ala Arg Lys Thr Leu Glu Glu Ser Gly Gly Phe Asp
    530                 535                 540
Ser Arg Thr Val Ser Ala Phe Leu Arg Glu Ala Gly Gly Thr Leu
545                 550                 555                 560
Pro Pro Asp Ile Lys Asn Thr Ile Val Leu Ile Asp Glu Ala Ser Phe
                565                 570                 575
Leu Ser Thr Arg Asn Met Asn Ala Leu Leu Glu Arg Leu Ile Ala Leu
            580                 585                 590
```

Lys Pro Ala Lys Ile Val Leu Ser Gly Asp Arg Arg Gln His Gly Ala
            595                 600                 605

Val Glu Ala Gly Arg Pro Phe Asp Ile Ala Gln Arg Ala Gly Leu Pro
610                 615                 620

Thr Ala Ile Met Lys Asp Ile Val Arg Leu Pro Lys Asp Glu Gly His
625                 630                 635                 640

Arg Asp Gln Arg Ala Ala Val Glu Ala Ala Gln Gly Lys Val Ala
                645                 650                 655

Val Ala Met Lys Arg Leu Gly Ala Asn Ile Val Glu Arg Pro Gly Asn
            660                 665                 670

Leu Ala Gly Gly Ala Val Glu Ala Trp Arg Ala Leu Pro Lys Asp Lys
            675                 680                 685

Gln Asp Lys Ala Leu Leu Val Ala Pro Ser His Arg Leu Arg Glu Ala
            690                 695                 700

Ile Asn Gln Gly Ile Arg Ser Glu Leu Ile Ala Asn Gly Arg Leu Ser
705                 710                 715                 720

Ala Glu Thr Met Thr Ile Ser Val Leu Arg Ser Lys Asn Leu Thr Arg
                725                 730                 735

Ala Glu Ala Met Ser Pro Arg Ser Tyr Ala Ala Gly Asp Ile Leu Gln
            740                 745                 750

Phe His Ala Arg Leu Asp Ala Ile Asn Ala Lys Lys Asn Thr Arg Arg
            755                 760                 765

Leu Val Thr Ala Val Asp Glu Glu Arg Gly Arg Leu Thr Leu Arg Asn
770                 775                 780

Ala Arg Gly Lys Asp Gln Thr Val Pro Leu Ser Arg Leu Gln Gly Arg
785                 790                 795                 800

Tyr Glu Asn Thr Pro Tyr Ser Leu His Arg Glu Glu Pro Leu Glu Leu
                805                 810                 815

Arg Arg Gly Asp Ser Val Met Phe Thr Arg Ser Asn Pro Asp Ala Gly
            820                 825                 830

Leu Ser Ala Met Asp Ala Ala Lys Val Val Gly Trp Asp Gln Glu Arg
            835                 840                 845

Val Ser Leu Asn Val Ser Gly Thr Gln Arg Gln Phe Gly Arg Asp Asp
850                 855                 860

Pro Ala Leu Arg Ser Leu Thr His Gly Tyr Ala Met Thr Ser His Ala
865                 870                 875                 880

Ala Gln Gly Arg Thr Ala Lys Asp Val Val Ala Val Met Asp Ser Lys
                885                 890                 895

Glu Arg Ala Leu Thr Ser Gln Val Gly Phe Tyr Val Ser Ile Ser Arg
            900                 905                 910

Ser Ala Asp Thr Leu Ala Leu Ile Val Asn Asp Lys Glu Arg Val Leu
            915                 920                 925

Asn Thr Met Gln Arg Gln Thr Gly Leu Lys Thr Ser Ala Met Glu Thr
930                 935                 940

Glu Gly Arg Ile Gly Asp Leu Thr Asp Leu Gly Thr His Gln Gly Thr
945                 950                 955                 960

Gly Thr Thr Ser Ser Leu Ser Val Pro Ala Leu Ala Ala Asp Gln Arg
                965                 970                 975

Asn Glu Ala Thr Gly Asn Glu Gln Asp Ser Ser Leu Asp Gln Gly Leu
            980                 985                 990

Ser Leu

<210> SEQ ID NO 130

```
<211> LENGTH: 8
<212> TYPE: PRT
<213> ORGANISM: Artificial sequence
<220> FEATURE:
<223> OTHER INFORMATION: RecD-like motif I of TrwC Pbe

<400> SEQUENCE: 130

Gly Tyr Ala Gly Thr Gly Lys Thr
1               5

<210> SEQ ID NO 131
<211> LENGTH: 10
<212> TYPE: PRT
<213> ORGANISM: Artificial sequence
<220> FEATURE:
<223> OTHER INFORMATION: RecD-like motif V of TrwC Pbe

<400> SEQUENCE: 131

Tyr Ala Met Thr Ser His Ala Ala Gln Gly
1               5                   10

<210> SEQ ID NO 132
<211> LENGTH: 14
<212> TYPE: PRT
<213> ORGANISM: Artificial sequence
<220> FEATURE:
<223> OTHER INFORMATION: MobF motif III of TrwC Pbe

<400> SEQUENCE: 132

His Asp Ile Ser Arg Asp Lys Asp Pro Gln Leu His Thr His
1               5                   10

<210> SEQ ID NO 133
<211> LENGTH: 961
<212> TYPE: PRT
<213> ORGANISM: Acidovorax sp. JS42

<400> SEQUENCE: 133

Met Ile Ser Met Asn Asn Val Gly Ser Ala Gly Gln Ala Leu His Tyr
1               5                   10                  15

Phe Ser Ala Asp Asn Tyr Tyr Thr Gln Asp Glu Gly Leu Glu His Ser
                20                  25                  30

Glu Trp Phe Gly Lys Gly Ala Glu His Leu Gly Leu Ser Gly Lys Ile
        35                  40                  45

Asp Arg Gln Ala Phe Phe Glu Val Leu Asn Gly Lys Val Asp Gly Gln
    50                  55                  60

Glu Leu Gly Lys Trp Val Lys Asn Glu Glu Thr Gly Glu Lys Glu Arg
65                  70                  75                  80

Glu His Arg Pro Gly Thr Asp Met Thr Phe Ser Ala Pro Lys Ser Val
                85                  90                  95

Ser Leu Met Ala Glu Val Tyr Gly Lys Arg Asp Val Arg Glu Ala His
                100                 105                 110

Glu Ala Ala Val Lys Lys Ala Leu Ser His Ile Glu Thr Glu Leu Ala
        115                 120                 125

Arg Thr Arg Gln Thr Val Asp Gly Lys Thr Glu Ala Val Gln Thr Gly
    130                 135                 140

Asn Val Thr Val Ala Met Phe Arg His Asn Thr Ser Arg Asp Leu Asp
145                 150                 155                 160

Pro Gln Thr His Thr His Ala Val Ile Met Asn Ala Thr Lys Arg Glu
                165                 170                 175

Asp Gly Gln Trp Arg Ser Leu Thr Asn Glu Glu Ile Tyr Asn Ala Gln
```

```
                180             185             190
Arg Val Ile Gly Ala Ile Tyr Thr Ser Glu Leu Ala Asp Arg Leu Gln
            195             200             205
Ala Leu Gly Tyr Asp Ile Arg Arg Thr Asp Glu Lys Gly Asn Phe Glu
            210             215             220
Ile Ala Gly Ile Thr Arg Glu Gln Ile Glu His Phe Ser Gln Arg Arg
225             230             235             240
Ala Glu Ile Glu Ala Ala Leu Lys Ala Lys Gly Val Asp Ile Asp Asp
            245             250             255
Ala Ser Ala Gln Gln Lys Glu Asp Ala Thr Leu Lys Thr Arg Ala Arg
            260             265             270
Lys Val Asp Val Asp His Glu Ala Leu Ile Gly Ser Trp Lys Glu Arg
            275             280             285
Ala Lys Asp Ile Gly Ile Asp Phe Asp Ala Ile Gln Ala Lys Ala Asp
            290             295             300
Ala Gln Arg Ala Gln Gly Gly Val Val Arg Ala Asp Lys Leu Thr Gly
305             310             315             320
Arg Glu Ala Met Ser Phe Ala Ala Ala His Leu Ile Glu Arg Glu Ala
            325             330             335
Val Val Ser Lys Asn Asp Leu Met Ala Ala Ile Glu His Gly Ala
            340             345             350
Gly Arg Val Ser Ala Ser Glu Val Lys Arg Ala Phe Asp Lys Leu Glu
            355             360             365
Lys Asp Gly Asp Leu Val Ala Leu Pro Asp Gly Asn Tyr Thr Thr Lys
            370             375             380
Lys Met Leu Gly Ser Glu Met Trp Ala Leu Asp Gln Val Arg Ala Gln
385             390             395             400
Lys Gly Gln Thr Pro Lys Met Met Glu Pro Glu Ala Val Ala Ala Arg
            405             410             415
Ile Ala Gln Ala Glu Gly Arg Gln Gly Phe Lys Tyr Ser Glu Gly Gln
            420             425             430
Lys Glu Ala Ile Ser Lys Val Leu Thr Thr Glu Asp Arg Tyr Val Ala
            435             440             445
Val Gln Gly Leu Ala Gly Thr Gly Lys Thr Thr Met Leu Lys Gly Val
            450             455             460
Arg Glu Met Ala Gln Glu Gln Gly Tyr Thr Val Arg Gly Met Ala Pro
465             470             475             480
Thr Gly Ala Ala Ser Lys Val Leu Ala Arg Glu Thr Gly Ile Ala Thr
            485             490             495
Asp Thr Val Ser Met Phe Gln Ile Lys Glu Arg Gln Leu Gln Lys Asp
            500             505             510
Ile Glu Phe Ala Lys Gln Tyr Ala Pro Asp Phe Gln Lys Ala Glu
            515             520             525
Val Trp Ile Val Asp Glu Ser Ser Phe Leu Ser Gln Arg Gln Lys Ala
            530             535             540
Gln Leu Asp His Met Ala Glu Lys Ala Gly Ala Lys Val Val Tyr Leu
545             550             555             560
Gly Asp Thr Leu Gln Leu Gln Gly Val Glu Ala Gly Lys Pro Phe Glu
            565             570             575
Leu Ala Gln Arg Asp Gly Met Glu Thr Ala Tyr Met Thr Glu Ile Asn
            580             585             590
Arg Gln Lys Thr Ala Asp Leu Lys Gln Ala Val Asp Ile Ile Thr Gly
            595             600             605
```

Arg Asp Asn Leu Gly Asp Gly Gln Arg Leu Thr Gln Val Glu Leu Ala
610                 615                 620

Asn Asn Ala Arg Ala Phe Glu Tyr Met Asp Lys Ala Gly Met Ile Arg
625                 630                 635                 640

Glu Ile Pro Glu Lys Ser Glu Asp Lys Gly Arg Leu Val Ala Ala
                645                 650                 655

Val Val Gln Asp Ile Leu Lys Leu Asp Lys Ala Glu Arg Glu Arg Thr
                660                 665                 670

Ile Val Ile Thr Ala Tyr Asn Glu Asp Arg Arg Ala Ile Asn Ala Gly
            675                 680                 685

Val Arg Glu Gly Leu Lys Glu Gln Gly Glu Leu Ser Arg Ser Glu Asp
690                 695                 700

Thr Arg Glu Ile Tyr Thr Ser Lys Gly Trp Thr Arg Ala Met Gln Lys
705                 710                 715                 720

Glu Ala Gln Tyr Tyr Lys Ala Gly Asp Val Val Arg Phe Gly Arg Asp
                725                 730                 735

Tyr Gln Gln Ile Asp Ala Lys Lys Gly Glu Tyr Met Arg Val Ser Ala
            740                 745                 750

Val Asp Ala Pro Asn Gly Thr Val Val Leu Gln Lys Glu Asp Gly Ser
            755                 760                 765

Val Ile Ala Trp Gln Pro Lys Lys His Asn Lys Ile Glu Val Tyr Asp
770                 775                 780

Arg Asp Thr Arg Glu Leu Ala Lys Gly Asp Leu Ile Arg Ile Thr Arg
785                 790                 795                 800

Asn Glu Gly Glu Phe Lys Asn Gly Glu Val Ala Arg Val Thr Ala Val
                805                 810                 815

Ala Gly Asp Lys Val Thr Leu Glu Leu Lys Gln Gly Lys Asp Val Ser
            820                 825                 830

Leu His Gln Val Asp Leu Ser Arg Asn Lys His Trp Asp His Ala Tyr
    835                 840                 845

Ala Gln Thr Val His Ala Ser Gln Gly Ala Thr Gln His Arg Ala Ile
850                 855                 860

Phe His Ile Arg Ala Pro Gln Thr Glu Ser Glu Lys Lys Gln Glu Arg
865                 870                 875                 880

Ala Leu Glu Asn Met Ala Lys Val Phe Gly Asp Arg Ser Phe Tyr Val
                885                 890                 895

Gly Ala Thr Arg Ala Ser His Glu Leu Arg Ile Tyr Thr Asn Asp Lys
            900                 905                 910

Ala Val Ala Ala Lys Ala Val Ala Lys Gln Asp Lys Thr Ser Ala
            915                 920                 925

Val Glu Thr Leu Arg Gln His Glu Arg Ala Thr Ala Ile Thr Ala Asp
930                 935                 940

Lys Ala Gly Gln Arg Pro Val Ser Pro Gln Arg Asn Gly Asp Val Gln
945                 950                 955                 960

Arg

<210> SEQ ID NO 134
<211> LENGTH: 10
<212> TYPE: PRT
<213> ORGANISM: Artificial sequence
<220> FEATURE:
<223> OTHER INFORMATION: RecD-like motif V of TrwC Ajs

<400> SEQUENCE: 134

```
Tyr Ala Gln Thr Val His Ala Ser Gln Gly
1               5                   10
```

<210> SEQ ID NO 135
<211> LENGTH: 14
<212> TYPE: PRT
<213> ORGANISM: Artificial sequence
<220> FEATURE:
<223> OTHER INFORMATION: MobF motif III of TrwC Ajs

<400> SEQUENCE: 135

```
His Asn Thr Ser Arg Asp Leu Asp Pro Gln Thr His Thr His
1               5                   10
```

<210> SEQ ID NO 136
<211> LENGTH: 936
<212> TYPE: PRT
<213> ORGANISM: Caulobacter crescentus NA1000

<400> SEQUENCE: 136

```
Met Gly Arg Arg Gln Ile Pro Gly Cys Arg Ala Arg Val Gln Leu Glu
1               5                   10                  15

Arg Arg Arg Thr Gly Leu Met Val Ala Ser Leu Ser Ser Leu Ser Ser
                20                  25                  30

Ser Ala Gln Ala Ser Ser Tyr Tyr Glu Ala Asp Asp Tyr His Ala Glu
            35                  40                  45

Gly Ala Ala Pro Ser Arg Trp Gln Gly Ser Gly Ala Ala Ala Leu
        50                  55                  60

Gly Leu Glu Gly Glu Val Asp Pro Glu Arg Phe Arg Gln Leu Leu Asp
65                  70                  75                  80

Gly Val Leu Ser Asp His Val Ala Leu Gly Ala Arg Arg Asp Glu Gly
                85                  90                  95

Arg Gln His Arg Pro Gly Trp Asp Leu Thr Leu Ser Ala Pro Lys Ser
                100                 105                 110

Ile Ser Ile Met Ala Leu Val Ala Gly Asp Arg Arg Leu His Ala Ala
            115                 120                 125

His Ala Ala Ala Val Glu Ala Ala Leu Ala Phe Thr Glu Arg His Ala
        130                 135                 140

Gly Gly Thr Arg Ile Arg Asp Gly Glu Arg Val Ala His Val Arg Thr
145                 150                 155                 160

Gly Ala Leu Ala Met Ala Thr Phe Gln His Glu Thr Ser Arg Ala Gln
                165                 170                 175

Asp Pro Gln Leu His Thr His Ala Val Ile Leu Asn Met Thr Arg Asp
                180                 185                 190

Leu Glu Gly Thr Trp Arg Ser Leu Asp Ser Arg Ala Leu Tyr Gln Leu
            195                 200                 205

Gln Lys Thr Ile Gly Glu Val Tyr Arg Gln Glu Leu Ala Gly Ala Val
        210                 215                 220

Arg Ala Leu Gly Tyr Ala Ile Glu Val Gly Lys Glu Ser Met Phe Glu
225                 230                 235                 240

Ile Ser Asp Val Pro Ala Ser Val Arg Glu Ala Phe Ser Glu Arg Ala
                245                 250                 255

Arg Gln Val Glu Ala His Leu Ala Thr Lys Gly Leu Thr Arg Ala Thr
                260                 265                 270

Ala Thr Ala Glu Glu Lys Gln Ala Ala Thr Leu Tyr Thr Arg Ala Ser
            275                 280                 285

Lys Lys Ala Ala Asp Arg Ala Glu Leu Ser Arg Ala Trp Arg Val Glu
```

```
            290             295             300
Ala Asp Gly Leu Gly Phe Ser Ser Glu Ala Arg Arg Ser Leu Leu Thr
305                 310                 315                 320

Glu Ala Leu Asp Arg Ala Glu Ala Ser Lys Ala Ile Arg Asp Arg Gly
                325                 330                 335

Ala Val Leu Ala Gln Asp Ala Val Arg Phe Ala Ala Glu Lys Leu Gly
                340                 345                 350

Glu Arg Gln Ala Ile Phe Ser Arg Ala Glu Leu Glu Arg Glu Ala Gly
                355                 360                 365

Arg Lys Ala Ile Gly Leu Ala Thr Arg Thr Glu Ile Met Ala Ala Val
        370                 375                 380

Asp Lys Arg Gln Gln Ser His Gln Leu Glu Ala Arg Ala Leu Arg Ser
385                 390                 395                 400

Pro Ile Gly Leu Asp Leu Glu Gly Phe Thr Thr Asp Arg Ala Ile Ala
                405                 410                 415

His Glu Lys Arg Leu Leu Glu Ile Glu Arg Glu Gly Arg Asn Ala Leu
                420                 425                 430

Ala Pro Ile Val Pro Ile Glu Ala Ser Arg Ile Ile Asn Ala Ala
        435                 440                 445

Ser Leu Ala Ala Ser Glu Arg Gly Leu Ala Trp Ser Asp Asp Gln Arg
        450                 455                 460

Arg Ala Thr Lys Ala Val Leu Thr Ser Arg Ser Ala Val Val Gly Val
465                 470                 475                 480

Gln Gly Phe Ala Gly Thr Ala Lys Thr Thr Val Leu Ala Thr Leu
                485                 490                 495

Ala Lys Ala Ala Ala Glu Gln Gly Tyr Gln Val Lys Ala Leu Ala Pro
                500                 505                 510

Ser Ala Ser Ala Ala Ile Thr Leu Gly Glu Ala Leu Asp Leu Glu Gly
        515                 520                 525

Arg Thr Ile Ala Arg His Leu Val Glu Arg Pro Asn Ala Arg Pro Ser
        530                 535                 540

Ala Arg Glu Leu Trp Ile Val Asp Glu Ala Ser Leu Val Ser Ala Arg
545                 550                 555                 560

Asp Met Ala Arg Leu Leu Asp Glu Ala Gln Arg Arg Gly Ala Arg Thr
                565                 570                 575

Leu Leu Val Gly Asp Ala His Gln Leu Gly Ser Val Gly Ala Gly Ala
                580                 585                 590

Ala Phe Arg Gln Leu Gln Asp Ala Gly Leu Glu Thr Ala His Leu Thr
        595                 600                 605

Lys Ile Val Arg Gln Ser Asn Thr Leu Thr Leu Glu Ala Val Glu Ala
610                 615                 620

Thr Leu Ala Gly His Ala Arg Arg Ala Phe Asp Ala Leu Asp Arg Gly
625                 630                 635                 640

Gly Gly Gln Ile Ile Glu Ala Gln Ser Val Glu Asp Arg Gln Ala Leu
                645                 650                 655

Ile Ala Ala His Phe Ala Gln Leu Asp Ser Ala Gln Arg Arg Arg Thr
                660                 665                 670

Leu Ile Ile Asp Pro Ser Arg Glu Gly Arg Glu Gln Leu Thr Ala Arg
                675                 680                 685

Ile Arg Ala Glu Leu Ile Ala Ala Gly His Leu Gly Lys Ala Ala Val
        690                 695                 700

Thr Val Thr Ser Leu Val Ala Lys Asp Leu Thr Gln Ala Glu Arg Lys
705                 710                 715                 720
```

Glu Ala Gly Ser Tyr Ala Pro Gly Asp Ile Val Thr Phe Ala Arg Thr
            725                 730                 735

Leu Thr Gly Lys Ala Val Ala Lys Asp Thr Ala Tyr Glu Val Gln Ala
        740                 745                 750

Val Asp Ala Arg Arg Thr Val Thr Leu Ser Asp Gly Arg Asp Ala
    755                 760                 765

Arg Ile Asp Trp Ala Pro His Arg Trp Gly Ser Ala Glu Ala Phe Glu
770                 775                 780

Pro Val Asp Arg Glu Leu Arg Gln Gly Asp Arg Ile Glu Phe Thr Arg
785                 790                 795                 800

Asn Asn Met Arg Leu His Gln Val Asn Gly Leu Gln Gly Glu Ile Val
                805                 810                 815

Ser Leu Asp Val Glu Ala Arg Lys Ala Gln Val Arg Thr Asp Arg Gly
            820                 825                 830

His Ile Arg Thr Leu Asp Leu Asn Ala Leu Gln Asp Arg His Phe Arg
        835                 840                 845

His Ala Tyr Val Gln Thr Ala Phe Ala Ala Gln Gly Arg Thr Thr Asp
    850                 855                 860

His Val Leu Phe His Ala Glu Ser Gln Arg Ser Asn Leu Ile Asp Gln
865                 870                 875                 880

Ala Thr Leu Tyr Val Ala Ile Ser Arg Ala Arg His Gly Ala Thr Ile
                885                 890                 895

Val Thr Asp Asp Arg Ala Lys Val Ile Arg Gly Val Glu Ala Arg Ser
            900                 905                 910

Gly Arg Arg Leu Thr Ala Leu Gly Ala Glu Gly Ser Gly Arg Glu Ala
        915                 920                 925

Gly Leu Asp Gln Asp Ala Gly Leu
    930                 935

<210> SEQ ID NO 137
<211> LENGTH: 8
<212> TYPE: PRT
<213> ORGANISM: Artificial sequence
<220> FEATURE:
<223> OTHER INFORMATION: RecD-like motif I of TrwC Ccr

<400> SEQUENCE: 137

Gly Phe Ala Gly Thr Ala Lys Thr
1               5

<210> SEQ ID NO 138
<211> LENGTH: 10
<212> TYPE: PRT
<213> ORGANISM: Artificial sequence
<220> FEATURE:
<223> OTHER INFORMATION: RecD-like motif V of TrwC Ccr

<400> SEQUENCE: 138

Tyr Val Gln Thr Ala Phe Ala Ala Gln Gly
1               5                   10

<210> SEQ ID NO 139
<211> LENGTH: 14
<212> TYPE: PRT
<213> ORGANISM: Artificial sequence
<220> FEATURE:
<223> OTHER INFORMATION: MobF motif III of TrwC Ccr

<400> SEQUENCE: 139

His Glu Thr Ser Arg Ala Gln Asp Pro Gln Leu His Thr His
1               5                   10

<210> SEQ ID NO 140
<211> LENGTH: 936
<212> TYPE: PRT
<213> ORGANISM: Sphingopyxis alaskensis RB2256

<400> SEQUENCE: 140

Met Val Ala Ser Val Ser Ala Leu Thr Ser Ser Ala Gln Ala Ser Ser
1               5                   10                  15

Tyr Tyr Glu Ala Asp Asp Tyr Tyr Ala Glu Gly Gly Leu Ser Pro Ser
                20                  25                  30

Glu Trp Gln Gly Lys Gly Ala Glu Leu Gly Leu Ser Gly Asp Val
            35                  40                  45

Asp Arg Asp Gln Phe Arg Glu Leu Leu Asp Gly Lys Val Ala Gly Gln
    50                  55                  60

Gln Leu Gly Thr Val Arg Asp Gly Gln Leu Glu His Arg Pro Gly Trp
65                  70                  75                  80

Asp Val Thr Leu Ser Ala Pro Lys Ser Val Ser Ile Met Ala Glu Val
                85                  90                  95

Ala Gly Asp Arg Arg Leu Ile Glu Ala His Gly Gln Ala Val Lys Thr
                100                 105                 110

Thr Leu Ala His Ile Glu Ala His Met Ala Ala Thr Arg Val Arg His
            115                 120                 125

Gly Gly Ser Val Thr Arg Glu Ala Thr Gly Asn Leu Val Val Ala Gly
        130                 135                 140

Phe Gln His Gly Thr Ser Arg Ala Gln Asp Pro Gln Leu His Thr His
145                 150                 155                 160

Asn Val Ile Met Asn Ala Thr Gln Gly Glu Asp Gly Ser Trp Arg Ser
                165                 170                 175

Leu Glu Pro Arg Ala Ile Tyr Gln Leu Gln Lys Gln Ile Gly Ala Ile
            180                 185                 190

Tyr Arg Gln Glu Leu Ala Leu Lys Val Gly Glu Leu Gly Tyr Glu Ile
        195                 200                 205

Ala Pro Gly Lys Glu Ser Met Phe Glu Ile Lys Gly Val Ser Glu Ala
    210                 215                 220

Ala Met Ala Ala Phe Ser Thr Arg Ser Ala Glu Ile Glu Ala Ala Leu
225                 230                 235                 240

Gly Glu Arg Gly Thr Ser Arg Glu Glu Ala Ser Ala Ala Glu Lys Gln
                245                 250                 255

Val Ala Ala Leu Asp Thr Arg Gln Ala Lys Val Val Ala Asp His Gly
            260                 265                 270

Ala Leu Val Ala Asp Trp Arg Glu Thr Ala Asp Arg Ala Gly Phe Asp
        275                 280                 285

Ala Glu Ala Arg Leu Ala Leu Val Arg Glu Ala Glu Ala Arg Ala Ala
    290                 295                 300

Asn Gly Val Gln Leu Pro Asp Pro Ser Val Ala Asp Arg Ala Val Ala
305                 310                 315                 320

His Ala Ala Asp Lys Leu Gly Glu Arg Gln Ser Val Phe Ala Val Ala
                325                 330                 335

Ala Leu His Glu Glu Ala Gly Arg Val Gly Leu Gly Lys Val Gly Tyr
            340                 345                 350

Ser Glu Ile Gly Glu Ala Ile Gly Arg Ala Thr Lys Glu Gly Glu Leu
        355                 360                 365

-continued

Val Glu Arg Thr Phe Leu Asp Arg Arg Gly Ala Ala Phe Ala Gly Phe
    370                 375                 380

Thr Thr Ser Gln Asn Ile Ala Ala Glu Lys Thr Leu Leu Arg Ile Glu
385                 390                 395                 400

Ala Arg Gly Arg Gly Ala Leu Ala Pro Ile Ala Ser Pro Leu Ala Ala
                405                 410                 415

Ala Lys Ala Val Ala Gly Ala Ala Ala Gln Ala Glu Arg Ser Gly Phe
            420                 425                 430

Gly Trp Asn Pro Asp Gln Lys Ala Ala Thr Glu Gln Leu Leu Thr Ser
        435                 440                 445

Arg Asn Arg Val Thr Ala Val Gln Gly Tyr Ala Gly Thr Ala Lys Thr
    450                 455                 460

Thr Thr Val Leu Ala Thr Phe Ala Arg Glu Ala Glu Ala Arg Gly Val
465                 470                 475                 480

Ser Val Val Ala Leu Ala Pro Thr Ala Ser Ala Ala Met Thr Leu Gly
                485                 490                 495

Glu Ala Leu Gly Thr Arg Gly Asp Thr Val Ala Arg His Leu Leu Ala
            500                 505                 510

Pro Glu Asp Ser Ala Pro Gly Gln Pro Val Ala Trp Ile Val Asp Glu
        515                 520                 525

Ala Ser Leu Leu Ser Ala Arg Asp Thr Ala Arg Leu Phe Glu Leu Ala
    530                 535                 540

Glu Gln His Asp Ala Arg Ile Ile Leu Val Gly Asp Val Lys Gln Leu
545                 550                 555                 560

Gly Ser Val Glu Ala Gly Ala Ala Phe Ala Gln Leu Gln Gly Val Gly
                565                 570                 575

Met Glu Thr Ala Lys Leu Gly Glu Ile Val Arg Gln Ser Asn Ala Ala
            580                 585                 590

Thr Lys Glu Ala Val Leu Ala Ser Ile Glu Gly Asp Ala Lys Lys Ala
        595                 600                 605

Leu Ala Ala Leu Asp Arg Gly Gly Gln Ile Val Glu His Ala Asp
    610                 615                 620

Arg Ser Gly Arg Phe Ala Ala Ile Ala Asp Arg Tyr Ala Gly Leu Asp
625                 630                 635                 640

Lys Ala Ala Arg Thr Arg Thr Leu Val Ile Glu Pro Ser Arg Glu Gly
                645                 650                 655

Arg Asp Ala Leu Thr Gly Ile Arg Thr Ala Leu Val Asn Ser Gly
            660                 665                 670

Ala Leu Ser Gly Pro Ala Val Thr Met Glu Ser Leu Val Asn Lys Gly
        675                 680                 685

Leu Thr Arg Ala Glu Ala Arg Asp Pro Leu Ser Tyr Asp Arg Gly Asp
    690                 695                 700

Val Val Arg Phe Thr Arg Asp Tyr Ala Asp Lys Gly Val Ala Arg Gly
705                 710                 715                 720

Asp Ala Tyr Arg Val Glu Ala Val Asn Pro Ala Lys Ala Ala Ile Ala
                725                 730                 735

Leu Arg Ser Glu Asp Gly Arg Glu Val Asp Trp Arg Leu Arg Gln Trp
            740                 745                 750

Gly Ala Gly Lys Val Gln Val Phe Ala Pro Gln Asn Ile Asp Leu Arg
        755                 760                 765

Thr Gly Asp Ser Ile Arg Phe Thr Arg Asn Asp Arg Asp Ala Gly Arg
    770                 775                 780

```
Ile Asn Gly Ala Arg Gly Glu Val Ile Ala Val Asp Glu Gln Ala Arg
785                 790                 795                 800

Thr Ala Thr Val Leu Gly Ala Arg Gly Gln Val Gln Thr Leu Asp Leu
            805                 810                 815

Asp Ala Val Arg Asp Arg His Ile Ala His Ala Tyr Val Asp Thr Ala
        820                 825                 830

Phe Ala Ala Gln Gly Arg Thr Ala Asp His Val Ile Ile His Ala Asp
    835                 840                 845

Ser Lys Ala Thr Asn Leu Val Asp Gln Lys Ser Phe Tyr Val Gly Ile
850                 855                 860

Ser Arg Ala Lys Glu Ser Ala Thr Ile Val Thr Asp Asp Arg Ala Lys
865                 870                 875                 880

Leu Thr Ser Ala Ile Asn Glu Arg Ala Gly Ala Val Gln Thr Ala Leu
            885                 890                 895

Ser Gln Ala Pro Ala Ala Gly Ala Gly Met Val Gln Ser Ala Ile Ala
        900                 905                 910

Ala Pro Ala Ala Asp Lys Ala Ile Ser Ala Ala Val Ser Gln Ala Ala
    915                 920                 925

Thr Ser Leu Pro Gly Met Gly Leu
930                 935
```

<210> SEQ ID NO 141
<211> LENGTH: 8
<212> TYPE: PRT
<213> ORGANISM: Artificial sequence
<220> FEATURE:
<223> OTHER INFORMATION: RecD-like motif I of TrwC Sal

<400> SEQUENCE: 141

```
Gly Tyr Ala Gly Thr Ala Lys Thr
1               5
```

<210> SEQ ID NO 142
<211> LENGTH: 10
<212> TYPE: PRT
<213> ORGANISM: Artificial sequence
<220> FEATURE:
<223> OTHER INFORMATION: RecD-like motif V of TrwC Sal

<400> SEQUENCE: 142

```
Tyr Val Asp Thr Ala Phe Ala Ala Gln Gly
1               5                   10
```

<210> SEQ ID NO 143
<211> LENGTH: 14
<212> TYPE: PRT
<213> ORGANISM: Artificial sequence
<220> FEATURE:
<223> OTHER INFORMATION: MobF motif III of TrwC Sal

<400> SEQUENCE: 143

```
His Gly Thr Ser Arg Ala Gln Asp Pro Gln Leu His Thr His
1               5                   10
```

<210> SEQ ID NO 144
<211> LENGTH: 927
<212> TYPE: PRT
<213> ORGANISM: Acetobacter tropicalis NBRC 101654

<400> SEQUENCE: 144

```
Met Val Ala Thr Val Ser Gly Leu Thr Asn Ala Ala Gln Ala Ser Ala
1               5                   10                  15
```

```
Tyr Tyr Glu Ala Glu Asp Tyr Tyr Ser Glu Asp Gly Asn Ala Pro Ser
             20                  25                  30

Val Trp Leu Gly Lys Gly Ala Ala Glu Leu Gly Leu Phe Gly Glu Ile
         35                  40                  45

Asp Gln Glu Ala Phe Thr Arg Leu Leu His Gly Glu Ile Thr Glu Asp
     50                  55                  60

His Arg Leu Gly Thr Ser Arg Asp Gly Glu Trp Ser His Arg Pro Gly
 65                  70                  75                  80

Trp Asp Leu Thr Phe Ser Ala Pro Lys Ser Val Ser Val Met Ala Glu
                 85                  90                  95

Val Ala Gly Asp Arg Arg Leu Ile Glu Ala His Glu Ala Ala Val Gln
            100                 105                 110

Arg Thr Leu Ser Leu Ala Glu Gln His Leu Ala Ala Thr Arg Ile Arg
        115                 120                 125

Glu Asp Gly Glu Val Arg Glu Val Thr Gln Asn Leu Val Ile Ala
    130                 135                 140

Ser Phe Arg His Gly Thr Ser Arg Ala Leu Asp Pro Gln Leu His Ser
145                 150                 155                 160

His Asn Val Ile Leu Asn Met Thr Gln Asp His Asp Gly Gln Trp Arg
                165                 170                 175

Ser Leu Glu Pro Arg Ala Leu Tyr Gln Leu Gln Lys Gln Leu Gly Ala
            180                 185                 190

Leu Tyr Arg Gln Glu Leu Ala His Glu Val Thr Glu Leu Gly Tyr Glu
        195                 200                 205

Ile Thr Lys Gly Lys Asp Ser Ser Phe Glu Ile Ala Gly Leu Ser Pro
    210                 215                 220

Glu Ser Leu Glu Ala Phe Ser Gln Arg Ala Gln Ala Ile Glu Ala Gln
225                 230                 235                 240

Leu Ala Glu Arg Gly Lys Ser Arg Ala Gln Ala Ser Ala Ala Glu Lys
                245                 250                 255

Gln Thr Ile Ala Leu Asp Thr Arg Gln Ala Lys Glu Ala Val Pro Gln
            260                 265                 270

Ala Glu Leu Val Gln Ala Trp Arg Glu Ala Ala Asp Ser Ala Gly Leu
        275                 280                 285

Thr Glu Glu Lys Arg Arg Gln Leu Val Ala Glu Ala Gln Gly Arg Leu
    290                 295                 300

Ala Ala Gln Ser Ala Gln Lys Ser Ser Asn Ala Phe Gly Arg Glu Leu
305                 310                 315                 320

Leu Ala Asp Gln Ala Val Ala Gln Gly Ala Met Leu Gly Glu Arg
                325                 330                 335

Asn Ser Val Phe Ala Thr Thr Ala Leu His Glu Ala Gly Arg Phe
            340                 345                 350

Ala Ile Gly Ala Val Ser Gln Ala Glu Ile Ala Glu Ala Ile Thr Arg
        355                 360                 365

Ala Glu Thr Ala Gly Gly Leu Glu Lys Arg Thr Tyr Leu Asp Tyr Arg
    370                 375                 380

Gly Ala Ser Phe Glu Gly Met Thr Thr Ala Ala Asn Ile Ala His Glu
385                 390                 395                 400

Met Thr Leu Leu Arg Leu Glu Glu Asp Gly Arg His Gln Ala Ala Pro
                405                 410                 415

Ile Leu Ser Pro Leu Glu Ala Gly Lys Ala Val Ala Glu Val Glu Gln
            420                 425                 430
```

Arg Ser Ala Leu Lys Gly His Thr Trp Asn Glu Glu Gln Arg Ala Ala
            435                 440                 445

Thr Thr Gln Ile Leu Thr Ser Asn Asn Gln Ile Val Gly Leu Gln Gly
    450                 455                 460

Tyr Ala Gly Thr Ala Lys Thr Ser Thr Val Leu Ala Thr Val Ala Lys
465                 470                 475                 480

Ser Ala Glu Ala Gln Gly Tyr Arg Val Thr Ala Leu Ala Pro Thr Ala
                485                 490                 495

Ser Ala Ala Gln Val Leu Gly Asp Ala Leu Asp Ser Arg Ala Asp Thr
                500                 505                 510

Leu Ala Arg His Leu Leu Ala Pro Gly Arg Pro Ser Ser Gln Pro Gln
        515                 520                 525

Leu Trp Ile Val Asp Glu Ala Ser Leu Val Ser Ala Lys Asp Met Ala
        530                 535                 540

Lys Leu Leu Ser Thr Ala Gln Ser His Arg Ala Arg Val Leu Leu Val
545                 550                 555                 560

Gly Asp Ile Lys Gln Leu Gly Ser Ile Glu Ala Gly Ala Ala Phe Glu
                565                 570                 575

Gln Leu Gln Glu Ala Gly Met Glu Thr Ala Arg Leu Thr Ser Ile Leu
                580                 585                 590

Arg Gln Thr Asn Glu His Thr Lys Ala Ala Val Glu Ala Ser Leu Glu
            595                 600                 605

Gly Asn Ala Lys Lys Ala Leu Glu Ala Leu Asp Arg Gly Gly Gly Arg
        610                 615                 620

Val Val Ala Ile Ala Asp Arg Glu Gly Arg Phe Ala Gln Ile Ala Glu
625                 630                 635                 640

Asp Tyr Ala Ala Leu Ser Pro Glu Glu Arg Gln Lys Thr Leu Val Ile
                645                 650                 655

Glu Pro Ser Arg Glu Gly Arg Asp Ala Leu Thr Gln Asp Ile Arg Asn
            660                 665                 670

Lys Leu Ile Glu Arg Gly Gln Leu Gly Ala Glu Val Leu Lys Ala Thr
        675                 680                 685

Lys Phe Val Ser Lys Asp Leu Thr Lys Ala Glu Ala Lys Arg Ala Glu
    690                 695                 700

Ser Tyr Glu Leu Gly Asp Ile Val Arg Phe Ala Lys Asp Tyr Ala Asp
705                 710                 715                 720

Lys Gly Val Ser Arg His Gly Ala Tyr Arg Val Ile Gln Ala Asp Glu
                725                 730                 735

Ala Lys Asn Val Leu Thr Leu Gln Asp Glu Arg Gly Arg Glu Leu Ala
            740                 745                 750

Trp His Pro Arg Gln Trp Gly Ala Gln Ala Gln Val Tyr Arg Glu
        755                 760                 765

Glu Ala Leu Glu Leu Arg Val Gly Asp Arg Val Gln Phe Thr Arg Asn
770                 775                 780

Asp Lys Ala Ala Lys Arg Val Asn Gly Gln Leu Gly Glu Val Ile Thr
785                 790                 795                 800

Ile Asp Pro Asp Arg Gly Leu Ala Arg Val Lys Leu Gln Gly Asn Arg
                805                 810                 815

Ile Glu Thr Leu Asn Leu Glu Ser Ala Arg Asp Arg His Phe Ser His
            820                 825                 830

Ala Tyr Ala Ser Thr Ala Phe Ala Ala Gln Gly Arg Thr Ala Glu Arg
        835                 840                 845

Val Phe Ala Asn Ala Glu Ser Ser Ala Thr His Leu Leu Glu Gln Lys

```
                850                 855                 860

Ser Phe Tyr Val Ala Leu Ser Arg Ala Lys Val Glu Ser Val Leu Tyr
865                 870                 875                 880

Thr Asp Asp Arg Ser Lys Met Gln Val Gly Leu Gln Glu Arg Ala Gly
                885                 890                 895

Ile Ala Thr Arg Ala Leu Lys Glu Arg Gly Ala Asp Met Gln Asp Gly
                900                 905                 910

Lys Gln Lys Ala Gln Glu Lys Ala Gln Ala Ala Ser Leu Ala Leu
        915                 920                 925

<210> SEQ ID NO 145
<211> LENGTH: 10
<212> TYPE: PRT
<213> ORGANISM: Artificial sequence
<220> FEATURE:
<223> OTHER INFORMATION: RecD-like motif V of TrwC Atr

<400> SEQUENCE: 145

Tyr Ala Ser Thr Ala Phe Ala Ala Gln Gly
1               5                   10

<210> SEQ ID NO 146
<211> LENGTH: 14
<212> TYPE: PRT
<213> ORGANISM: Artificial sequence
<220> FEATURE:
<223> OTHER INFORMATION: MobF motif III of TrwC Atr

<400> SEQUENCE: 146

His Gly Thr Ser Arg Ala Leu Asp Pro Gln Leu His Ser His
1               5                   10

<210> SEQ ID NO 147
<211> LENGTH: 917
<212> TYPE: PRT
<213> ORGANISM: Acidobacterium capsulatum

<400> SEQUENCE: 147

Met Leu Thr Ile Ser Lys Pro Leu Ser Ser Thr Gln Ala Gln Thr Tyr
1               5                   10                  15

His Ala Lys Glu Phe Thr Ala Ala Glu Gln Asn Tyr Trp Lys Gln Glu
            20                  25                  30

Asp Ile Ile Gln Gly Glu Trp Arg Gly Gln Leu Ala Glu Lys Phe Glu
        35                  40                  45

Leu Ser Gly Ala Val Gly Gly Gln Glu Phe Ala Arg Leu Ala Glu Gly
    50                  55                  60

Gln His Pro Gln Thr Gly Glu Gln Leu Val Arg His Arg Ala Val His
65                  70                  75                  80

Glu Tyr Lys Thr Glu Asp Gly Arg Thr Val Thr Pro Val Glu His Arg
                85                  90                  95

Ala Gly Trp Asp Ala Thr Phe Ser Ala Pro Lys Ser Val Ser Leu Thr
            100                 105                 110

Ala Leu Val Gly Gly Asp Ser Glu Val Arg Glu Ala His Arg Lys Ala
        115                 120                 125

Val Ala Phe Ala Leu Ala Glu Leu Glu Arg Tyr Thr Gln Val Arg Ile
    130                 135                 140

Gly Gly Asn Asn Pro Pro Glu Thr Thr Gly Arg Phe Val Ala Ala Thr
145                 150                 155                 160

Phe Glu His Asp Thr Ala Arg Pro Val Gly Gly Tyr Ala Ala Pro Gln
```

-continued

```
            165                 170                 175
Leu His Thr His Ala Val Val Phe Asn Met Thr Glu Cys Glu Asp Gly
            180                 185                 190

Thr Ile Arg Ala Leu Gln Pro Arg Ser Leu Phe Glu Thr Gln Gln Phe
            195                 200                 205

Ala Thr Ala Val Tyr Gln Ser His Leu Thr Tyr Gln Leu Arg Ser Leu
    210                 215                 220

Gly Tyr Glu Ile Glu Pro Gly Arg Ser Ala Pro Glu Ile Lys Gly
225                 230                 235                 240

Tyr Ser Gln Glu Tyr Leu Asp Ala Ser Pro Arg Arg Gln Gln Ile
            245                 250                 255

Val Glu Ala Val Ala Arg Ser Gly Phe Ser Gly Pro Glu Ala Ala Gln
            260                 265                 270

Ile Ala Ala His Asn Thr Arg Asp Gly Lys Gln Ile Leu Ser Pro Arg
            275                 280                 285

Glu Val Val Ala Ala His Arg Gln Ile Ala Ala Glu Phe Gly Asn Gln
            290                 295                 300

Ala Asp Thr Val Ile Ala Glu Ala Arg Ser Arg Gln Glu Gln Ala
305                 310                 315                 320

Arg Glu Asn Pro Pro Asp Glu Arg Lys Gln Gln Val Asn Ser Ala Val
                    325                 330                 335

Thr Phe Ala Arg Asp Lys Gly Phe Glu Arg Glu Ala Val Leu Asp Glu
            340                 345                 350

Arg Ala Ile Leu Val Asp Ala Met Arg Lys Gly Met Gly Glu Met Thr
            355                 360                 365

Tyr Pro Glu Val Arg Ala Gly Phe Glu Ala Arg Val Arg Ser Gly Glu
370                 375                 380

Phe Arg Glu Val Ser His Asp Gly Lys Ala Ala Ala Arg Ser Phe Thr
385                 390                 395                 400

Thr Ala Gly Thr Ile Gln Ala Glu Lys Glu Ile Ile Ala Ser Val Arg
            405                 410                 415

Glu Gly Gln His Arg Ser Pro Gln Leu Met Ser Val Gln Asp Ala Ile
            420                 425                 430

Pro Leu Thr Glu Ala Arg Gln Gln Leu Asn Gln Thr Gln Arg Lys Ala
            435                 440                 445

Ile Glu Gln Ile Leu Thr Ser Arg Asp Gln Ile Gln Gly Leu Gln Gly
            450                 455                 460

Ser Ala Gly Ser Gly Lys Thr Ser Thr Leu Ser Ala Ile Arg Leu Gly
465                 470                 475                 480

Ala Glu Gln Asn Gly Tyr Val Val Glu Gly Phe Ala Pro Thr Ser Arg
                    485                 490                 495

Ala Ala His Gln Leu Arg Asp Ala Gly Ile Ser Ala Asp Thr Leu Gln
            500                 505                 510

Gly Phe Leu Ala Arg Ala Arg Val Gln Asp Ala Pro Gly Arg Arg His
            515                 520                 525

Leu Tyr Met Val Asp Glu Ser Ser Leu Ala Ser Thr Glu Gln Met Arg
            530                 535                 540

Asp Phe Leu Arg Arg Ile Ser Lys Glu Asp Lys Val Leu Leu Ile Gly
545                 550                 555                 560

Asp Val Arg Gln His Gln Gly Val Asp Ala Gly Lys Pro Phe Glu Gln
            565                 570                 575

Leu Gln Gln Ser Gly Met Gln Thr Ala Ile Leu Asp Arg Ile Val Arg
            580                 585                 590
```

```
Gln Lys Asp Pro Glu Leu Leu Arg Ala Val Glu His Leu Ser Lys Asn
            595                 600                 605

Gln Thr Glu Ala Gly Leu Gln Met Leu Gln Gln Gly Arg Val Thr
            610                 615                 620

Glu Ile Val Asp Pro Glu Gln Arg Ile Ser Ala Ile Ala Lys Ala Tyr
625                 630                 635                 640

Ala Met His Pro Glu Lys Thr Ile Ile Val Ser Pro Asp Asn Ala Ser
            645                 650                 655

Arg Arg Ala Ile Asn Gln Ala Val Arg Gln Thr Leu Gln Ser Leu Gly
            660                 665                 670

Arg Leu Asp Ala Glu Asp Arg Ser Ile Asn Val Leu Thr Pro Arg Ser
            675                 680                 685

Asp Met Thr Gly Ala Asp Arg Ala Trp Ala Ala Arg Tyr Gln Pro Gly
            690                 695                 700

Asp Val Leu His Tyr Ile Arg Gly Ser Lys Glu Leu Gly Ile Glu Gly
705                 710                 715                 720

Gly Ser Tyr Ala Glu Val Ile Ala Ala Thr Pro Lys Asp Asn Leu Val
            725                 730                 735

Thr Ile Arg Lys Ser Asp Gly Glu Leu Val Thr Tyr Asp Pro Ser Arg
            740                 745                 750

Leu His Gly Ile Ser Ala Tyr Lys Glu Ile Glu Arg Glu Phe Ala Ile
            755                 760                 765

Gly Asp Arg Val Gln Leu Thr Ala Pro Asn Arg Asp Leu Gln Val Ala
            770                 775                 780

Asn Arg Asp Leu Gly Thr Leu Lys Ser Phe Asp Ala Gly Arg Ile
785                 790                 795                 800

Thr Leu Arg Met Asp Ser Gly Lys Asp Val Ser Phe Asp Pro Arg Asp
            805                 810                 815

Met Arg His Phe Asp His Gly Tyr Ala Val Thr Ser Tyr Ser Ala Gln
            820                 825                 830

Gly Leu Thr Ser Glu Arg Val Leu Val Asn Met Asp Ile Glu Val His
            835                 840                 845

Pro Glu Leu Ile Asn Gly Arg Phe Ala Tyr Val Ser Val Ser Arg Ala
            850                 855                 860

Ser Gln Glu Ala Gln Ile Phe Thr Asn Asp Ala Ser Asn Leu Ala Glu
865                 870                 875                 880

Ser Leu Ser Arg Asp Val Ser Lys Thr Ser Ala Ile Pro Ala Pro Arg
            885                 890                 895

Pro Glu Leu Ile Gln Asp Arg Ala Glu Thr Arg Ser Ile Gly Leu Gly
            900                 905                 910

His Ala Leu Ser His
        915

<210> SEQ ID NO 148
<211> LENGTH: 8
<212> TYPE: PRT
<213> ORGANISM: Artificial sequence
<220> FEATURE:
<223> OTHER INFORMATION: RecD-like motif I of TrwC Aca

<400> SEQUENCE: 148

Gly Ser Ala Gly Ser Gly Lys Thr
1               5

<210> SEQ ID NO 149
```

```
<211> LENGTH: 10
<212> TYPE: PRT
<213> ORGANISM: Artificial sequence
<220> FEATURE:
<223> OTHER INFORMATION: RecD-like motif V of TrwC Aca

<400> SEQUENCE: 149

Tyr Ala Val Thr Ser Tyr Ser Ala Gln Gly
1               5                   10

<210> SEQ ID NO 150
<211> LENGTH: 18
<212> TYPE: PRT
<213> ORGANISM: Artificial sequence
<220> FEATURE:
<223> OTHER INFORMATION: MobF motif III of TrwC Aca

<400> SEQUENCE: 150

His Asp Thr Ala Arg Pro Val Gly Gly Tyr Ala Ala Pro Gln Leu His
1               5                   10                  15

Thr His

<210> SEQ ID NO 151
<211> LENGTH: 1184
<212> TYPE: PRT
<213> ORGANISM: Granulicella tundricola

<400> SEQUENCE: 151

Met Leu Thr Ile Ser Lys Ala Ile Ser Ser Ala Gln Ala Gln Thr Tyr
1               5                   10                  15

His Lys Leu Glu Tyr Thr Ser Asp Ala Gln Ser Tyr Tyr Lys Gln Asp
                20                  25                  30

Glu Thr Val Lys Gly Glu Trp Gln Gly Lys Leu Ala Ala Ser Leu Gly
            35                  40                  45

Leu Ser Gly Glu Val Ala Pro Leu Glu Phe Ser Arg Leu Thr Glu Gly
        50                  55                  60

Ile His Pro Gln Thr Glu Ala Gln Met Val Arg His Arg Glu Gly Gln
65                  70                  75                  80

Glu Tyr Thr Asn Ala Asp Gly Ser Val Thr Lys Pro Val Gln His Arg
                85                  90                  95

Ala Gly Trp Asp Ala Thr Phe Ser Ala Pro Lys Ser Val Ser Leu Thr
            100                 105                 110

Ala Leu Val Gly Gly Asp Glu Arg Val Thr Glu Ala His Arg Ala Ala
        115                 120                 125

Val Thr Thr Ala Leu Glu Glu Leu Glu Lys Tyr Thr His Ala Arg Ile
    130                 135                 140

Gly Gly Asn Asn Pro Ala Glu Val Thr Gly Lys Phe Val Ala Ala Lys
145                 150                 155                 160

Phe Glu His Asp Thr Ala Arg Pro Val Asn Gly Tyr Ala Ala Pro Gln
                165                 170                 175

Leu His Thr His Ala Ile Ile Phe Asn Val Thr Gln Arg Glu Asp Gly
            180                 185                 190

Ser Thr Arg Ala Ile Gln Glu Arg Thr Phe Phe Glu Ser Gln Asn Tyr
        195                 200                 205

Ala Thr Ala Val Tyr Gln Ser Val Leu Thr His Gln Leu Arg Lys Leu
    210                 215                 220

Gly Tyr Glu Ile Glu Pro Gly Gln Ser Gly Ala Pro Gln Ile Leu Gly
225                 230                 235                 240
```

```
Phe Thr Gln Ala Tyr Leu Asp Ala Ser Ser Pro Arg Ser Arg Gln Ile
                245                 250                 255

Lys Glu Gln Met Glu Arg Val Gly Phe Gln Gly Pro Glu Ala Ala Gln
            260                 265                 270

Ile Ala Ala His Ala Thr Arg Asp Arg Lys Gln Thr Leu Thr Pro Ala
        275                 280                 285

Glu Val Leu Ala Ala His Lys Glu Met Ala Lys Asp Phe Gly Asp Gln
    290                 295                 300

Pro Glu Arg Val Val Ala Asp Ala Arg Glu Arg Ala Leu Thr Gln Ala
305                 310                 315                 320

Gln Glu Ile Ser Val Gln Pro Asp Ser Arg Gly Ala Val Ala Phe Ala
                325                 330                 335

Lys Glu Lys Val Phe Glu Arg Glu Ala Val Ala Asp Glu Arg Leu Ile
            340                 345                 350

Met Arg Glu Ala Leu Arg Arg Gly Met Gly Glu Val Ser Phe Ser Asp
        355                 360                 365

Val Gln Ser Glu Phe Gln Arg Arg Gln Ala Glu Gly Glu Phe Arg Ser
    370                 375                 380

Val Gln Gly Gln Lys Tyr Ala Ser Gly Arg Ser Phe Thr Thr Pro Glu
385                 390                 395                 400

Thr Ile Ala Asp Glu Arg Ala Asn Val Gln His Val Leu Asn Gly Gln
                405                 410                 415

Gly Ala Ser Ala Pro Met Leu Ser Thr Ala Ala Ala Glu Arg Gln Ala
            420                 425                 430

Thr Ser Arg Asp Phe Leu Asn Glu Ala Gln Gln Thr Ala Ile Arg Glu
        435                 440                 445

Val Leu Thr Ser Thr Asp Arg Ile His Gly Phe Gln Gly Leu Ala Gly
    450                 455                 460

Thr Gly Lys Thr Ser Thr Leu Ala Ala Ile Arg Glu Gly Ala Glu Gln
465                 470                 475                 480

Gly Asn Tyr Lys Val Glu Gly Phe Ala Pro Thr Ser Lys Ala Ala Gly
                485                 490                 495

Gln Leu Arg Glu Ala Gly Ile Glu Ala Asn Thr Leu Gln Ser Phe Leu
            500                 505                 510

Ala Arg Gln Lys Ala Pro Asp Ser Ser Arg His Leu Tyr Met Leu Asp
        515                 520                 525

Glu Ser Ser Leu Ala Ser Thr Lys Gln Met Arg Ala Phe Leu Glu Lys
    530                 535                 540

Ile His Pro Gln Asp Arg Val Leu Val Ile Gly Asp Thr Arg Gln His
545                 550                 555                 560

Gln Gly Val Asp Ala Gly Arg Pro Phe Gln Gln Met Gln Glu Ala Gly
                565                 570                 575

Met Gln Thr Ser Lys Leu Asp Thr Ile Met Arg Gln Lys Asp Pro Glu
            580                 585                 590

Leu Leu Arg Ala Val Gln His Leu Ala Thr Asn Glu Thr Glu Met Gly
        595                 600                 605

Ile Ala Leu Leu Thr Gln Gln Gly Arg Val Thr Glu Leu Ala Asn Ala
    610                 615                 620

Ser Glu Arg Ile Ala Ala Ile Ala Arg Asp Tyr Ala Ala Lys Pro Glu
625                 630                 635                 640

Asn Thr Leu Ile Val Ser Pro Asp Asn Arg Ser Arg Gln Gln Ile Asn
                645                 650                 655

Glu Ala Val Arg Gly Glu Leu Leu Lys Ala Gly Lys Leu Ala Glu Asp
```

```
              660                 665                 670
Gly Arg Gln Phe Leu Thr Leu Ser His Arg Ser Asp Met Thr Gly Pro
            675                 680                 685

Asp Arg Thr Trp Ala Ala Met Tyr Arg Pro Gly Asp Val Val Gln Tyr
    690                 695                 700

Glu Arg Gly Ser Lys Ala Glu Gly Ile Glu Arg Gly Ser Phe Gly Val
705                 710                 715                 720

Val Arg Ser Ser Asp Ala Ala Thr Asn Arg Leu Thr Val Glu Leu Pro
                725                 730                 735

Asn Gly Val Asn Val Glu Tyr Asp Pro Lys Arg Val Tyr Gly Val Asn
            740                 745                 750

Val Tyr Arg Glu Thr Ser Arg Glu Phe Ala Thr Gly Asp Arg Leu Gln
        755                 760                 765

Phe Ser Ala Ile Tyr Lys Asp Leu Gly Ile Ser Asn Arg Asp Met Gly
    770                 775                 780

Thr Ile Thr Arg Met Glu Pro Asp Arg Leu Thr Val Leu Met Asp Gly
785                 790                 795                 800

Lys Glu Gln Arg Ser Val Ser Phe Asn Pro Ile Glu Phe Arg Gln Phe
                805                 810                 815

Asp His Gly Tyr Ala Val Thr Ser His Ser Ser Gln Gly Leu Thr Thr
            820                 825                 830

Asp Arg Val Ile Ala Asn Ile Asp Thr Glu Ser Ser Arg Ser Leu Ile
        835                 840                 845

Asn Asn Arg Leu Ala Tyr Val Ala Ile Ser Arg Ala Ser Glu Asp Ala
    850                 855                 860

Arg Ile Tyr Thr Asn Asp Ala Ala Thr Leu Gly Gln Arg Leu Ala Thr
865                 870                 875                 880

Asp Val Thr Lys Thr Ala Ala Leu Asp Phe Thr Ala Lys Pro Glu Pro
                885                 890                 895

Arg Ala Thr Gln Glu Ala Ser Lys Ala Arg Thr Val Ala Val His Glu
            900                 905                 910

Tyr Lys Asn Ser Asp Ser Arg Leu Ala Ala Val Ala Thr Glu Tyr Val
        915                 920                 925

Ser Arg Pro Glu Arg Ser Val Ile Val Ala Leu Asp Arg Ala Glu Arg
    930                 935                 940

Glu Gln Leu Thr Gln Leu Val Arg Ala Asp Leu Tyr Ala Gln Gly Lys
945                 950                 955                 960

Leu Gly Arg Asp Ala Gln Ala Ile Ser Val Leu Ile Glu Lys Ala Thr
                965                 970                 975

Gly Asn Lys Met Arg Val Asp Ser Tyr Gln Pro Gly Glu Lys Ile Gln
            980                 985                 990

Tyr Lys Thr Gly Ser Pro Gly Leu Asn Gly Ile Pro His Glu Ser Gln
        995                 1000                1005

Ala Thr Val Val Ser Thr Thr Ser Arg Gly Asn Leu Leu Ser Ile
    1010                1015                1020

Arg Phe Asp Ala Thr Arg Glu Glu Val Ser Tyr Asn Pro Gly Gln
    1025                1030                1035

Leu Arg Thr Ala Thr Arg Glu Ser Arg Val Tyr Gln Glu Ala Thr
    1040                1045                1050

Arg Glu Val Ala Glu Gly Glu Arg Val Arg Phe Thr Arg Tyr Asp
    1055                1060                1065

Lys Asp Met Gly Val Arg Ser Gly Asp Leu Gly Thr Val Thr Arg
    1070                1075                1080
```

```
Ile Gly  Glu Asp His Ala Met  Arg Val Lys Met Asp  Ser Gly Lys
    1085                1090                1095

Ile Ala  Glu Val Pro Pro Glu  Lys Ala Gln His Ile  Asp Tyr Gly
    1100                1105                1110

Tyr Val  Val Asp Ser Leu Lys  Asp Val Arg Ala Glu  Arg Val Ile
    1115                1120                1125

Ala Thr  Gly Asp Gly Leu Thr  Gln Gln Ala Phe Gln  Ala Ala Ser
    1130                1135                1140

Ser Lys  Ala Asp Leu Ala Leu  Tyr Thr Ser Pro Pro  Gln Gln Glu
    1145                1150                1155

Phe Ala  Ser Ser Lys Glu Ile  Ala Val Thr Glu Phe  Ala Gln Pro
    1160                1165                1170

Thr Lys  Gln Gln Asn Asp Phe  Gly Ile Gly Phe
    1175                1180

<210> SEQ ID NO 152
<211> LENGTH: 1156
<212> TYPE: PRT
<213> ORGANISM: Burkholderia multivorans ATCC 17616

<400> SEQUENCE: 152

Met Ile Ser Lys Glu Pro Ile Arg Ser Val Ala Asp Ala Ala Arg Tyr
1               5                   10                  15

His Asp Lys Ser Phe Asn Lys Asp Ala Gly Lys Lys Ala Asp Asn Tyr
            20                  25                  30

Tyr Val Asn Glu Lys Ala Thr Ala His Trp Gln Gly Arg Gly Ala Asp
        35                  40                  45

Phe Leu Gly Ile Arg Gly Lys Ala Val Thr Lys Glu Glu Phe Ile Gln
    50                  55                  60

Phe Leu Ser Gly Arg Met Pro His Pro Asp Thr Gly Lys Ile Gln Asn
65                  70                  75                  80

Leu Ala Asn Asn Ser Lys Gly Asp Lys Arg Arg Ala Gly Ile Asp Phe
                85                  90                  95

Thr Ile Ala Pro Pro Lys Ser Val Ser Ile Ala Ala Leu Val Gly Lys
            100                 105                 110

Asp Asp Arg Val Ile Ala Ala His Leu Ala Ala Asn Ala Arg Thr Met
        115                 120                 125

Glu Trp Phe Glu Lys His Ala Ser Leu Ile Arg Val Lys Asp Glu Lys
    130                 135                 140

Gly Arg Asn Arg Pro Glu Val Ala Gly Asn Leu Leu Tyr Ala Thr Val
145                 150                 155                 160

Leu His Glu Thr Asn Arg Glu Asn Glu Pro Gln Leu His Asn His Asn
                165                 170                 175

Val Ile Val Ser Ala Val Tyr Asp Gly Ala Arg His Ser Trp Arg Ser
            180                 185                 190

Leu Thr Asn Asp Leu Leu Tyr Thr Leu Arg Ala Arg Gly Asp Ile Ile
        195                 200                 205

Tyr Lys Ala Glu Leu Ala Ala Ala Leu Arg His Leu Gly Tyr Gln Leu
    210                 215                 220

Val Tyr Ala Glu Asn Gly Ile Asp Phe Glu Leu Lys Gly Phe Ser Arg
225                 230                 235                 240

Asp His Val Asp Thr Phe Ser Thr Arg Ala Val Gln Val Arg Glu Ala
                245                 250                 255

Leu Leu Lys His Gly Ile Asp Pro Gly Glu Ala Ser Phe Asp Ala Arg
```

-continued

```
                260                 265                 270
Arg Val Ala Lys Leu Asp Ser Arg Ala Ala Lys Gln Glu His Pro Arg
            275                 280                 285
Glu Ile Leu Gln Ser Val Trp Glu Glu Thr Ala Lys Glu Ala Asn Leu
        290                 295                 300
Asp Val Ala Ser Ile Val Glu Arg Ala Arg Glu Ala Phe Ala Asp Arg
305                 310                 315                 320
Gln Val Pro Arg Gly Val Glu Arg Thr Val Glu His Gly Ala Ala
                325                 330                 335
Met Gly Gln Asp Ser Gly Pro Ser Arg Gly Ala Ala Val Ser Val Ser
            340                 345                 350
Asn Asp Ala Arg Ala Asn Ala Leu Arg Ala Val Ser Trp Ala Ile Glu
        355                 360                 365
His Leu Thr Glu Arg Glu Gln Ala Phe Thr Leu Val Asp Leu Glu Val
    370                 375                 380
Thr Ala Leu Lys Phe Ser Arg Gly Ser Ile Ser Glu Ile Glu Trp Ala
385                 390                 395                 400
Ile Asp Gln His Val Arg Asn His Met Leu Val Asp Arg Gly Ile Thr
                405                 410                 415
Val Gly Gly Gln Ile Gln Tyr Thr Thr His Lys Ala Ile Asp Asn Glu
            420                 425                 430
Leu Lys Leu Ala Glu His Ile Leu Ala Gly Arg Gly Gln Gly Asn Val
        435                 440                 445
Val Leu Asp Ala Glu Asp Gln Phe Asp Ala Val Ala Ala Phe Glu
    450                 455                 460
Ala Lys Lys Thr Ala Glu Ile Gly Glu Gln Phe Lys Leu Ser Gly Glu
465                 470                 475                 480
Gln Ile Gln Ala Ala Arg Asn Val Leu Met His Glu Asp Ser Ile Gln
                485                 490                 495
Gly Ile Gln Gly Glu Ala Gly Thr Gly Lys Thr Ala Ala Leu Ala Met
            500                 505                 510
Val Lys Asp Val Ala Gln Ala Met Gly Trp Glu Val Ile Gly Val Ala
        515                 520                 525
Thr Ser Ala Ala Ala Lys Glu Leu Glu Ala Ser Ser Gly Ile Gln
    530                 535                 540
Ser Asp Thr Val Ala Gly Tyr Phe Ala Lys Arg Asp Ser Ala Ile Arg
545                 550                 555                 560
Ala Val Glu Leu Arg Leu Gln Asp Leu Arg Lys Ser Ile Ser Glu Arg
                565                 570                 575
Ala Thr Leu Arg Gly Leu Asp Asp Gln Arg Ile Glu Ala Arg Thr Leu
            580                 585                 590
Ala Val Lys Ser Glu Asp Ile Asp Tyr Gly Thr His Arg Tyr Thr Phe
        595                 600                 605
Asp His Gln Arg Gly Glu Val Phe Arg Ser Pro Glu Asn Leu Arg Asn
    610                 615                 620
Ala Ile Gly Ala Ala Leu Ser Glu Ile Ala Ala Arg His Arg Glu Ala
625                 630                 635                 640
Ala Gly Thr Glu Gln Gly His Pro Val Thr Leu Gly Glu Gln Ala Arg
                645                 650                 655
Glu Thr Val Arg Ala Ala Ala Asn Val Ala Ala Ser Leu Gly Arg
            660                 665                 670
Arg Leu Met Thr Phe Glu Gln Ile Gly Thr Ala Glu Ala Val Ala Ala
        675                 680                 685
```

Arg Asn Thr Leu Tyr Leu Glu Arg Gln Gly Ser Ala Thr Glu Leu Asp
690                 695                 700

Ala Glu Tyr Ala Arg Thr Gln Ala Lys Leu Glu Asn Leu Arg Arg Tyr
705                 710                 715                 720

Gly Asn Val Asp Gly Lys Lys Thr Leu Ile Val Met Asp Glu Ser Ser
                725                 730                 735

Leu Thr Gly Val Asp Asp Thr Glu Lys Leu Leu Arg Phe Ala Arg Glu
            740                 745                 750

Ile Gly Ala Arg Thr Val Leu Gln Gly Asp Val Lys Gln His Gly Ser
                755                 760                 765

Val Ala Ala Gly Arg Ala Phe Glu Gln Ala Gln Ile Ala Gly Met Asn
770                 775                 780

Val Ser Ile Leu Glu Glu Thr Arg Arg Phe Arg Asp Ala Thr Ala Gln
785                 790                 795                 800

Thr Arg Gln Ala Leu Ala Asp Met Lys Ala Gly Asn Tyr Ala Gln Ala
                805                 810                 815

Ile Ala Arg Leu Asp Thr Leu Arg Val Ala Glu Ser Asp Leu Ala Lys
                820                 825                 830

Thr Val Ala Glu Arg Tyr Leu Glu Asn Leu Gln Glu Leu Thr Ala Lys
                835                 840                 845

Gly Val Asp Ala Pro Lys Val Gly Val Ala Ile Thr Asn Ser Asp
850                 855                 860

Arg Lys Leu Ile Asn Ala Ala Val His Gln Ala Leu Thr Asp Val Gly
865                 870                 875                 880

Ile Ile Ser Gly Pro His Phe Glu Lys Pro His Leu Asp Pro Lys
                885                 890                 895

Met Thr Gly Ala Glu Gln Arg Tyr Ala Ser Met Leu Ser Arg Asn Arg
                900                 905                 910

Val Asp Ala Leu Ile Tyr Arg Lys Ser Tyr Arg Glu Ile Gly Val Glu
                915                 920                 925

Lys Gly Asp Val Leu Thr Val Thr Gly Tyr Asp Val Gln Lys Asn Arg
930                 935                 940

Ile Tyr Ala Leu Asn Ala Lys Gly Lys Ser Val Glu Ile Asn Pro Gln
945                 950                 955                 960

Arg Gln Asp Tyr Phe Ser Pro Ala Ile Gln Glu Ser Arg Val Phe Ala
                965                 970                 975

Val Gly Asp Arg Val Glu Thr Arg Ala Ile Ile Arg Leu Pro Gly Gln
                980                 985                 990

Glu Leu Asn Arg Leu Asp Asn Gly Thr Gln Gly Val Ile Val Ala Ile
                995                 1000                1005

Asp Ser Leu Gly Ala Lys Ile Arg Trp Tyr Arg Asp Gly Lys Glu
1010                1015                1020

Ser Asp Leu Lys Asn Asp Asp Leu Arg Phe Val Asp His Ala Tyr
1025                1030                1035

Ala His Thr Ser Tyr Lys Glu Gln Gly Ala Thr Asn His Arg Glu
1040                1045                1050

Ile Val Ala Val Ser Lys Ile Gly Ala Arg Val Phe Asn Arg Glu
1055                1060                1065

Ala Ala Tyr Val Ala Ala Ser Arg Ala Lys Asp Asn Thr Glu Ile
1070                1075                1080

Ile Thr Ser Asp Leu Asp Thr Leu Leu Arg Asn Ala Gly Arg Glu
1085                1090                1095

```
Val Gly Lys Thr Thr Ala Val Glu Phe Glu Arg Ala Glu Ser Ser
    1100                1105                1110

Leu Asp Gln Ser Ala Asp Gln Gly Ala Lys His Gly Ala Thr Arg
    1115                1120                1125

Ser Ile Glu Val Ala Pro Thr Arg Ser Val Glu Thr Glu Arg Thr
    1130                1135                1140

Leu Glu Arg Ser Pro Asp Pro Gly Asn Leu Leu Gly Phe
    1145                1150                1155
```

<210> SEQ ID NO 153
<211> LENGTH: 8
<212> TYPE: PRT
<213> ORGANISM: Artificial sequence
<220> FEATURE:
<223> OTHER INFORMATION: RecD-like motif I of TrwC Bmu

<400> SEQUENCE: 153

```
Gly Glu Ala Gly Thr Gly Lys Thr
1               5
```

<210> SEQ ID NO 154
<211> LENGTH: 10
<212> TYPE: PRT
<213> ORGANISM: Artificial sequence
<220> FEATURE:
<223> OTHER INFORMATION: RecD-like motif V of TrwC Bmu

<400> SEQUENCE: 154

```
Tyr Ala His Thr Ser Tyr Lys Glu Gln Gly
1               5                   10
```

<210> SEQ ID NO 155
<211> LENGTH: 14
<212> TYPE: PRT
<213> ORGANISM: Artificial sequence
<220> FEATURE:
<223> OTHER INFORMATION: MobF motif III of TrwC Aca

<400> SEQUENCE: 155

```
His Glu Thr Asn Arg Glu Asn Glu Pro Gln Leu His Asn His
1               5                   10
```

<210> SEQ ID NO 156
<211> LENGTH: 986
<212> TYPE: PRT
<213> ORGANISM: Legionella longbeachae NSW150

<400> SEQUENCE: 156

```
Met Leu Ser Ile Gln Pro Leu Lys Ser Ala Lys Gly Ala Ala Asp Tyr
1               5                   10                  15

Tyr Ala Ala Thr Phe Asn Tyr Ala Gly Asp Ala Gln Ala Met Arg
                20                  25                  30

Trp Leu Gly Gln Ala Ser Gln Lys Met Gln Leu Thr Gly Ile Val Gln
            35                  40                  45

Lys Glu Gln Met Leu Ala Leu Leu Glu Gly Gln Leu Pro Asn Gly Gln
        50                  55                  60

Ser Leu His Asn Leu Gln Gly Glu His Arg Pro Gly Phe Asp Met Thr
65                  70                  75                  80

Phe Ser Ala Pro Lys Ser Val Ser Leu Leu Val Gly Leu Gly Val Ala
                    85                  90                  95

Pro Glu Leu Val Arg Tyr His Asp Glu Ala Val Ala Tyr Ala Ile Asp
                100                 105                 110
```

```
Gln Ile Glu Lys Glu Phe Ala Glu Ala Arg Val Ser Arg Asn Gly Ala
        115                 120                 125

Ile Phe Tyr Glu Lys Thr Glu Asn Leu Ala Val Ala Ala Phe Arg Gln
130                 135                 140

Pro Ser Ser Arg Ala Asn Asp Pro Ala Leu His Thr His Cys Val Thr
145                 150                 155                 160

Met Asn Leu Thr Phe His Glu Gly Lys Ala Arg Ser Leu Ala Ser Asp
                165                 170                 175

Ile Ser Arg Ser Asn Gly Val Ile Glu Gln Ile Gln Asn Asn Ala His
                180                 185                 190

Tyr Cys Gly Leu Met Tyr Arg Gln His Leu Ala Asn Arg Leu Lys Glu
                195                 200                 205

Ala Asp Phe Pro Leu Arg Leu Ser Gly Asp Gly Leu Phe Glu Ile Asp
        210                 215                 220

Gly Ile Pro Glu Lys Val Leu Gln Gly Phe Ser Arg Arg Glu Asp
225                 230                 235                 240

Ile Glu Arg His Met Glu Glu Lys Gly Trp Ser Gly Ala Lys Ser Ala
                245                 250                 255

Ser Ala Ala Thr Leu Leu Thr Arg Gln Asn Lys Glu Glu His Asp Ile
        260                 265                 270

Thr Leu Leu Glu Gln Asp Trp Lys Glu Arg Ala Lys Asp Leu Gly Phe
        275                 280                 285

Asp Ala Gln Ala Phe Met Gln Asn Arg Asn Gln Val Gln Ser Leu Ser
        290                 295                 300

Trp Phe Ser Ala Ile Lys Asp Lys Leu Met Ala Leu Val Gly Lys Gln
305                 310                 315                 320

Ser Lys Asp Lys Ser Pro Ser Glu Met Asp Ala Ala Ile Ala Cys Val
                325                 330                 335

His Val Ala Thr Glu Thr Leu Ser Gln Arg Thr Ser Met Phe Ser Ala
                340                 345                 350

Arg Gly Leu Ala Phe Glu Ala Met Lys His Ser Leu Val Tyr Pro Lys
        355                 360                 365

Ala Val Ser Lys Glu Ser Ile Asn Asp Ala Ile Gln His Glu Ile Lys
        370                 375                 380

Asn Gln Ser Leu Tyr Glu Ala Arg Cys Pro Glu Thr Gly Gln Arg Phe
385                 390                 395                 400

Leu Thr Thr Pro Trp Leu Leu Thr Thr Glu Thr Glu Thr Leu Ala Arg
                405                 410                 415

Ile Glu His Asn Lys Gly Val Val Pro Ala Ile Ala Thr Lys Glu Thr
                420                 425                 430

Val Lys Ala Phe Gln Lys Gln Arg His Pro Leu Leu Pro Tyr Pro Leu
        435                 440                 445

Thr His Ser Gln Lys Glu Ala Met Thr Val Leu Leu Thr Ser Lys Asp
        450                 455                 460

Arg Tyr Leu Ala Ile Gln Gly Tyr Ala Gly Val Ala Lys Thr Ser Met
465                 470                 475                 480

Leu Ser Glu Ala Lys Leu Leu Ile Glu Ala Gln Gly Tyr Ala Leu Arg
                485                 490                 495

Gly Ile Thr Val Ala Ser Ser Ala Ala Tyr Glu Leu Gln Glu Lys Ala
                500                 505                 510

Gly Ile Lys Thr Asp Val Phe Pro Leu Val His Gln Glu Leu Lys Asn
                515                 520                 525
```

```
Ala Pro Thr Ala Ser Leu Ser Lys Thr Leu Phe Ile Val Asp Glu Ala
    530                 535                 540

Ser Met Leu Ser Ser His Gln Gly His Glu Leu Met Lys Gln Ile Glu
545                 550                 555                 560

Arg Thr His Ala Arg Leu Val Leu Val Gly Asp Lys Ala Gln Leu Pro
                565                 570                 575

Ser Val Asn Ala Gly Arg Ile Phe Gly Leu Thr Gln Glu Tyr Gly Ile
            580                 585                 590

Glu His Ser Ile Met Asp Glu Ile Val Arg Gln Lys Asn Thr Val Leu
        595                 600                 605

Lys Glu Ala Val Ile Ala Ala Thr Lys Gly Asn Val Lys Glu Ala Leu
    610                 615                 620

Asp Lys Leu Asp Val Lys Glu Cys Val Thr His Glu Glu Arg Ile Ala
625                 630                 635                 640

Trp Ile Ala Asn His Trp Leu Ser Leu Ser Gln Lys Gly Arg Asp Asp
                645                 650                 655

Thr Leu Leu Phe Ala Pro Thr His Ala His Arg Glu Glu Ile Thr Lys
            660                 665                 670

Leu Ile Arg Asn Gly Leu Lys Gly Glu Gly Ile Leu Glu Asn Glu Gly
        675                 680                 685

Leu Cys Gln Thr Val Leu Lys Ala Lys Lys Met Glu Pro Ile Gln Ser
    690                 695                 700

Arg Phe Ile Ala Tyr Tyr Gln Lys Gly Asp Lys Val Arg Phe Asn Gln
705                 710                 715                 720

Glu Phe Lys Thr Asn Asn Ile Gln Ala Gly Ala Tyr Tyr Thr Val Gly
                725                 730                 735

Glu Ile Ser Lys Lys Asn Arg Gln Asp Asn Val Leu Pro Leu Ile Asn
            740                 745                 750

Glu Gln Gly Lys Gln Ile Gln Phe Lys Leu Asn Asn Leu Pro Lys Tyr
        755                 760                 765

Lys Thr His Asn Ala Ala Phe Glu Arg Ile Ile Glu Leu Tyr Gln Pro
    770                 775                 780

Lys Lys Leu Glu Leu Leu Val Gly Asp Lys Val Met Trp Thr Arg Asn
785                 790                 795                 800

Phe Lys Ala Asn Asn Leu Arg Asn Gly Gln Cys Ala Thr Leu His Glu
                805                 810                 815

Ile Lys Glu Asn Val Phe Thr Phe Ile Thr Lys Glu Gly Arg Gln Leu
            820                 825                 830

Thr Leu Glu Lys Asp His Pro Ala Leu Lys His Leu Asp Tyr Ser Tyr
        835                 840                 845

Val Leu Thr Asn Tyr Lys Val Gln Gly Lys Asp Ala Pro Phe Gly Ile
    850                 855                 860

Gly Leu Met Glu Ser Tyr His Arg Phe Gly Thr Thr Leu Asn Asn Phe
865                 870                 875                 880

Tyr Val Gln Ile Ser Arg Ala Ile His Gly Met Ile Leu Val Thr Asp
                885                 890                 895

Asn Lys Glu Glu Leu Val His Ala Ile Arg Arg Asn Thr Glu Glu Lys
            900                 905                 910

Pro Val Ala Leu Asp Arg Ile Ser Ser Glu Gln Leu Val Arg His Glu
        915                 920                 925

Glu Arg Phe Val Gln Ser Asn Lys Phe Ser Met Gln Ala Val Ile Thr
    930                 935                 940

Lys Lys Gln Ala Phe Glu Ser Gln Lys Ser Pro Gln Ser Arg His Gln
```

```
                945                 950                 955                 960
Lys Ile Thr Met Asp Glu Leu Leu Val Pro His Lys Lys Thr Glu Ile
                    965                 970                 975

Asn Arg Pro Leu Ile Lys Glu Leu Glu Leu
            980                 985

<210> SEQ ID NO 157
<211> LENGTH: 8
<212> TYPE: PRT
<213> ORGANISM: Artificial sequence
<220> FEATURE:
<223> OTHER INFORMATION: RecD-like motif I of TrwC Llo

<400> SEQUENCE: 157

Gly Tyr Ala Gly Val Ala Lys Thr
1               5

<210> SEQ ID NO 158
<211> LENGTH: 10
<212> TYPE: PRT
<213> ORGANISM: Artificial sequence
<220> FEATURE:
<223> OTHER INFORMATION: RecD-like motif V of TrwC Llo

<400> SEQUENCE: 158

Tyr Val Leu Thr Asn Tyr Lys Val Gln Gly
1               5                   10

<210> SEQ ID NO 159
<211> LENGTH: 14
<212> TYPE: PRT
<213> ORGANISM: Artificial sequence
<220> FEATURE:
<223> OTHER INFORMATION: MobF motif III of TrwC Llo

<400> SEQUENCE: 159

Gln Pro Ser Ser Arg Ala Asn Asp Pro Ala Leu His Thr His
1               5                   10

<210> SEQ ID NO 160
<211> LENGTH: 1047
<212> TYPE: PRT
<213> ORGANISM: Asticcacaulis excentricus CB 48

<400> SEQUENCE: 160

Met Leu Lys Ile Thr Arg Leu Lys Ser Ala Ser Arg Ser Gly Asp Tyr
1               5                   10                  15

Tyr Gly Lys Asp Asp Tyr Tyr Val Thr Gly Glu Ala Asn Thr Pro Asn
            20                  25                  30

Leu Arg Trp Gly Gly Glu Gly Ala Ala Gln Leu Gly Leu Val Gly Glu
        35                  40                  45

Ala Asn Ser Leu Asp Phe Lys Lys Leu Leu Lys Gly Ile Asn Pro Asp
    50                  55                  60

Pro Asp Gly Ser Ala Leu Ser Lys Ala Asp Glu Ala Leu Arg Glu Gln
65                  70                  75                  80

Ala Gly Ala Ser Gly Glu Thr Asp Pro Glu Arg Thr Ile Pro Lys His
                85                  90                  95

Ala Pro Gly Trp Asp Met Thr Phe Ser Ala Thr Lys Ser Ala Ser Ile
            100                 105                 110

Met Ala Leu Val Ala Gly Asp Asp Arg Ile Gln Ala Ala Phe Asn Arg
        115                 120                 125
```

```
Ser Val Gln Ser Thr Met Asp Tyr Ala Glu Lys His Phe Ala Ile Thr
    130                 135                 140
Arg Gln Arg Thr Asp Gly Gly Ala Pro Lys Gln Ile Leu Thr Gly Asn
145                 150                 155                 160
Leu Thr Tyr Ala Thr Thr Ser His Ser Met Ser Arg Ala Gly Asp Pro
                165                 170                 175
Glu Met His Asn His Val Val Leu Ala Asn Ala Thr Arg Met Glu Asp
            180                 185                 190
Gly Thr Trp Arg Ala Leu Glu Thr Ala Pro Leu Tyr Lys His Gln Gln
        195                 200                 205
Phe Leu Gly Asn Val Gln Lys Ala Glu Phe Ala His Glu Leu Lys Lys
    210                 215                 220
Leu Gly Tyr Asn Leu Val Gln Gly Lys Thr Gln Gly Thr Trp Glu Ile
225                 230                 235                 240
Ala Glu Phe Ser Ala Ala Tyr Arg Gly Glu Asn Asp Lys Ala Gly Ile
                245                 250                 255
Gly Pro Ala Asp Leu Leu Ile Asp Thr Phe Ser Lys Arg His Val Glu
            260                 265                 270
Ile Met Gly Lys Ile Ala Ala Glu Ala Asp Lys Gly Arg Glu Leu
        275                 280                 285
Ser Lys Gly Glu Arg Gln Thr Leu Ile Leu Lys Asp Arg Pro Gln Lys
    290                 295                 300
Leu Leu Thr Asp Arg Asp Val Gln Gln Ala Leu Trp Lys Glu Val Ala
305                 310                 315                 320
Arg Asp Ala Gly Val Asp Leu Asp Gln Ile Val Ser Ala Ala Lys Thr
                325                 330                 335
Arg Glu Val Gly Gln Asp Leu Thr Pro Gln Arg Lys Gly Asp Ile Gly
            340                 345                 350
Leu Ala Gly Lys Val Met Ala Tyr Ile Asp Glu Lys Val Leu Gly Arg
        355                 360                 365
Thr Arg Asp Leu Ser Ala Glu Ala Ser Leu Ala Leu Gly Leu Arg Ser
    370                 375                 380
Gln Glu Arg Gln Ser Thr Ile Phe Thr Pro Tyr Ala Val Ile Phe Asp
385                 390                 395                 400
Ala Met Leu Ala Asn Gly Asn Arg His Arg Ile Gln Asp Tyr Gln Ala
                405                 410                 415
Thr Gly Phe Leu Gln Arg Pro Glu Ile Val Lys Ala Asp Arg Glu Lys
            420                 425                 430
Leu Ala His Ile Thr Thr Gln Arg Ala Ile Thr Met Glu Asp Ala Ile
        435                 440                 445
Val Glu Arg Val Ile Arg Ser Gln Ala Arg Ser Lys Ala Phe Thr Pro
    450                 455                 460
Asp Val Ser Asp Arg Ala Met Tyr Gly Ile Val Ala Asp Gly Lys Ala
465                 470                 475                 480
Leu Ala Pro Asn Thr Gln Gln Ala Val Val Gln His Val Leu Thr
                485                 490                 495
Asp Gly Ala Arg Tyr Ser Val Ile His Gly Ser Ala Gly Thr Gly Lys
            500                 505                 510
Thr Thr Thr Phe Asp Leu Val Arg Gln Thr Leu Asp Arg Leu Ser Ala
        515                 520                 525
Gly Gln Ile Glu Ile Val Ala Leu Ala Pro Thr His Lys Ala Lys Gly
    530                 535                 540
Glu Leu Ala Asp Arg Ala Gly Ile Ala Thr Glu Thr Val Gln Met Phe
```

```
        545                 550                 555                 560
Leu Leu Gln Gln Gln Lys Gly Ser Thr Gln Thr Ala Pro Ser Ser Gln
                565                 570                 575
Met Ala Asn Leu Lys Gly Lys Trp Leu Leu Val Asp Glu Gly Ser Met
                580                 585                 590
Leu Ser Asn Val Gln Met Asp Arg Ile Ile Asp Val Ala Glu Arg Ser
                595                 600                 605
Gly Val Asp Lys Val Ile Phe Ser Phe Asp Glu Arg Gln Leu Ala Ala
                610                 615                 620
Met Glu Ala Gly Ala Pro Thr Arg Leu Ala Met His Ala Gly Ala Ser
625                 630                 635                 640
Thr Val Tyr Leu Lys Asp Asn Val Arg Gln Ala Gln Met Pro Val Leu
                645                 650                 655
Arg Ala Gly Ile Met Lys Met Ala Asp Gly Lys Pro Trp Glu Ala Leu
                660                 665                 670
Pro Ser Ile Arg Pro Tyr Val Thr Glu Thr Arg Ser Asn Asp Asp Gln
                675                 680                 685
Ile Leu Ala Arg Ala Ala Val Ala Lys Trp Arg Glu Met Gly Pro Asp
                690                 695                 700
Thr Lys Val Val Val Gly Thr Asn Lys Met Arg Gly Leu Ala Asn Ala
705                 710                 715                 720
Met Ile Arg Thr Glu Leu Gln Gly Met Gly Leu Val Gly Arg Glu Asp
                725                 730                 735
Val Ala His Lys Thr Tyr Val Ser Glu Asn Arg Ser Pro Glu Gln Leu
                740                 745                 750
Gly Met Ile Thr Ala Tyr Ala Leu Gly Gln Arg Ile Ile Phe His Lys
                755                 760                 765
Ala Asp Glu Ala Asn Arg Ile Gly Arg His Thr Val His Ser Val Val
                770                 775                 780
Gly Ile Asp Met Arg Thr Asn Arg Leu Thr Leu Gln Ser Thr Glu Tyr
785                 790                 795                 800
Gly Lys Arg Ser Tyr Asn Leu Ala Gly Leu Thr Ser Gly Arg Asp Glu
                805                 810                 815
Pro Thr Phe Gly Val Tyr Arg Glu Gln Thr Ile Lys Leu Ser Val Gly
                820                 825                 830
Asp Gln Leu Ala Trp Asn Ile Thr Asp Lys Lys Ala Gly Val Thr Asn
                835                 840                 845
Asn Asp Ala Phe Thr Val Ala Ala Ile Lys Gly Ser Lys Leu Ala Thr
                850                 855                 860
Gln Arg Glu Val Glu Ile Asp Gly Val Arg Thr Leu Lys Thr Gln Val
865                 870                 875                 880
Phe Asp Leu Glu Asn Asp Pro Val Ala Arg Phe Met Ser His Gly Tyr
                885                 890                 895
Ser Leu Thr Ala Asn Arg Ala Gln Gly Ala Ser Phe Gly Lys Val Val
                900                 905                 910
Ala Val Leu Gly Ser Tyr Met Gly Glu Phe Ala Asn Gln Ala Arg Gly
                915                 920                 925
Tyr Val Met Ala Ser Arg Pro Arg Gln Glu Phe Gln Trp Val Thr Asp
                930                 935                 940
Asp Leu Lys Ser Leu Phe Arg Arg Leu Ala Glu Asn Asp Gly Ile Asn
945                 950                 955                 960
Pro Ser Ala Leu Asn His Ile Asp Arg Ala Met Asp Leu Ala Asp Lys
                965                 970                 975
```

Ala Asp Arg Val Lys Pro Ala Pro Gln Pro Asp Lys Ala Pro Glu Ile
            980                 985                 990

Pro Lys Pro Glu Pro Val Thr Ala Lys Ala Lys Glu Thr Glu Lys Glu
        995                 1000                1005

Lys Ser Glu Val Ala Asn Pro Gly Gly His His Ile Thr Glu Asp
    1010                1015                1020

Gln Lys Ser Ser Ser Lys Glu Lys Asp Ile Gly Glu Lys His Ile
    1025                1030                1035

Ala Gln Asn Asp Ile Leu Phe Arg Ile
    1040                1045

<210> SEQ ID NO 161
<211> LENGTH: 8
<212> TYPE: PRT
<213> ORGANISM: Artificial sequence
<220> FEATURE:
<223> OTHER INFORMATION: RecD-like motif I of TrwC Aex

<400> SEQUENCE: 161

Gly Ser Ala Gly Thr Gly Lys Thr
1               5

<210> SEQ ID NO 162
<211> LENGTH: 10
<212> TYPE: PRT
<213> ORGANISM: Artificial sequence
<220> FEATURE:
<223> OTHER INFORMATION: RecD-like motif V of TrwC Aex

<400> SEQUENCE: 162

Tyr Ser Leu Thr Ala Asn Arg Ala Gln Gly
1               5                   10

<210> SEQ ID NO 163
<211> LENGTH: 14
<212> TYPE: PRT
<213> ORGANISM: Artificial sequence
<220> FEATURE:
<223> OTHER INFORMATION: MobF motif III of TrwC Aex

<400> SEQUENCE: 163

His Ser Met Ser Arg Ala Gly Asp Pro Glu Met His Asn His
1               5                   10

<210> SEQ ID NO 164
<211> LENGTH: 981
<212> TYPE: PRT
<213> ORGANISM: Methylobacterium radiotolerans JCM 2831

<400> SEQUENCE: 164

Met Thr Ala Ser Leu His Arg Leu Gly Ala Gly Ala Pro Ala Ala
1               5                   10                  15

Tyr Tyr Thr Gln Asp Ser Gln Arg Glu Ala Arg Pro Asp Lys Arg Asp
            20                  25                  30

Glu Tyr Tyr Leu Ser Asp Gly Gly Val Trp Trp Ser Ser Gly Gly
        35                  40                  45

Thr Ile Val Arg His Gly Ala Ala Ile Asp Ala Ala Ser Phe Arg Asp
    50                  55                  60

Leu Cys Ala Gly Leu His Pro Gly Thr Gly Lys Pro Leu Val Arg Gly
65                  70                  75                  80

Ala Gly Pro Gly His Trp Ala Gly Val Asp Cys Thr Met Thr Pro Gly

-continued

```
                85                  90                  95
Lys Ser Val Ser Val Leu Trp Met Ala Gly Thr Pro Glu Gln Arg Ala
            100                 105                 110
Ala Ile Glu Ala Ala His Arg Ala Ala Val Glu Arg Ala Leu Ser Phe
            115                 120                 125
Val Thr Ala Glu Gly Leu Val Thr Val Arg Thr Gly Ala Gly Gly Thr
            130                 135                 140
Glu Gln His Arg Pro Arg Asp Leu Ile Val Gly Arg Phe Asp His Tyr
145                 150                 155                 160
Thr Thr Arg Glu Gly Asp Pro Asn Ile His Thr His Cys Val Phe Ile
            165                 170                 175
Asn Val Ala Gly Ala Pro Glu Asn Ala Gly Ala Gly Arg Tyr Lys Ser
            180                 185                 190
Arg Thr His Leu Thr Ile Glu Pro Glu Arg Leu Tyr Ala Ala Gln Leu
            195                 200                 205
Gly Val Gly Ala Ala Tyr Arg Ala Ala Leu Ala Glu Gly Leu Arg Glu
            210                 215                 220
Gln Phe Gly Leu Gln Tyr Arg Glu Ala Gly Arg Gly Gln Trp Glu Val
225                 230                 235                 240
Ala Cys Val Pro Glu Ala Leu Leu Ala Ala Phe Ser Lys Arg Ser Glu
            245                 250                 255
Gln Ile Leu Ala Tyr Ala Gly Gly Ala Ser Ser Ala Gln Arg Glu
            260                 265                 270
Ile Ala Ala Leu Ala Thr Arg Arg Gly Lys Glu Glu Leu Pro Thr Gly
            275                 280                 285
Pro Glu Leu Glu Ala Arg Trp Arg Lys Glu Leu Ala Ala Cys Ala Ile
            290                 295                 300
Asp Pro Trp Leu Ala Ala Arg His Pro Glu Arg Asp Pro Ala Phe Val
305                 310                 315                 320
Met Ala Ala Glu Arg Asp Arg Glu Arg Glu Ala Pro Phe Asp Pro Pro
            325                 330                 335
Glu Ile Pro Gly Asp Ser Pro Met Ala Arg Ala Ala Ser Ala Leu Phe
            340                 345                 350
Arg His Glu Ser Val Val Ala Arg Lys Asp Leu Leu Gln Arg Ala Leu
            355                 360                 365
Glu Val Ala Gly Val Ala Gly Ile Gly Val Asp Ala Val Glu Ala Glu
            370                 375                 380
Leu Ala Gln Phe Glu Arg Asp Gly Ala Leu Leu Leu Ala Asp Ala
385                 390                 395                 400
Glu Leu Val Pro Gly Ala Ser Ala Cys Trp Thr Ser Pro Gly Ile Ala
            405                 410                 415
Ala Cys Glu Ala Ala Met Leu Arg Ala Ala Asp Arg Pro Leu Glu Arg
            420                 425                 430
Thr Trp Ile Thr Pro Glu Ala Val Glu Ala Ala Leu Ala Asp Ala Pro
            435                 440                 445
His Leu Ser Pro Glu Gln Gly Glu Ala Val Arg His Ala Ala Gly Arg
            450                 455                 460
Asp Gly Val Ala Leu Leu Gln Ala Gly Ala Gly Thr Gly Lys Thr Thr
465                 470                 475                 480
Thr Ala Ala Ala Leu Val Ala Ala Ala Arg Gly Ser Gly Leu Arg Val
            485                 490                 495
Ile Gly Leu Ala Pro Ser Trp Val Ala Ala Asp Glu Leu Gly Arg Ser
            500                 505                 510
```

```
Thr Gly Ile Pro Ala Gln Ala Ile Ala Arg Trp Arg Gln Asp Gln Thr
        515                 520                 525

Gln Ala Ala Gly Pro Asp Ala Ile His His Pro Asp Arg Ser Ala Val
    530                 535                 540

Leu Asp Ala Asp Thr Leu Val Met Val Asp Glu Ala Gly Met Val Ala
545                 550                 555                 560

Thr Arg Asp Met Glu Ala Val Leu Ser Ala Arg Ser Val Gly Ala
                565                 570                 575

Lys Val Val Leu Ile Gly Asp Arg Arg Gln Leu Ala Ser Val Gly Gly
                580                 585                 590

Ala Ser Ala Leu Arg Ala Val Ala Asp Val Val Gly Arg Ser Ala Val
        595                 600                 605

Leu Glu Gln Val Arg Arg Gln Thr Val Glu Trp Gln Arg Ala Ala Ser
    610                 615                 620

Val Leu Met Ala Arg Gly Glu Val Glu Ala Ala Leu Arg Ala Tyr Ala
625                 630                 635                 640

Ala Arg Asp Arg Ile Glu Leu Val Ala Gly Ala Glu Ala Ala Gln Val
                645                 650                 655

Arg Ala Leu Ala Val Trp Ser Glu Gln Arg Ala Ala His Gly Glu Asp
        660                 665                 670

Val Leu Ile Val Thr Arg Arg Asn Ala Asp Ala Ala Leu Asn Val
    675                 680                 685

Gln Ala Arg Ala Val Leu Arg Gly Glu Gly Arg Leu Gly Pro Asp Leu
    690                 695                 700

Ile Thr Leu Pro Ala Arg Asp Arg Asp Arg Pro Val Pro Leu Ala
705                 710                 715                 720

Leu Ala Val Gly Asp Ala Leu Arg Phe Gly Glu Ser Leu Pro His Leu
                725                 730                 735

Gly Leu Arg Asn Gly Asn Arg Ala Arg Val Glu Ala Ile Thr Ala Glu
                740                 745                 750

Pro Glu Arg Gly Val Arg Leu Arg Leu Ala Leu Glu Asp Gly Arg Ala
        755                 760                 765

Leu Glu Val Ala Trp Ser Asp Leu Ala Gln Gln Pro Arg Phe Gly Arg
    770                 775                 780

Lys Trp Pro Gln Pro Arg Ile Val His Ala Tyr Ala Gly Thr Val Tyr
785                 790                 795                 800

Ala Ala Gln Gly Arg Thr Ser Ser Ala Ala Val Met Tyr Val Gly Ala
                805                 810                 815

Ala Thr Asp Ala Arg Glu Leu Tyr Val Gly Leu Thr Arg His Arg His
        820                 825                 830

Glu Ala Arg Val Val Glu Arg Asp Arg Leu Asp Ala Leu Cys Arg
    835                 840                 845

Gln Arg Gln Ala Asp Ala Arg Met Pro Ala Thr Asp Ala Met Val Leu
    850                 855                 860

Glu Arg Leu Phe Arg Glu Ala Arg Thr Tyr Ser Glu Lys Val Asn Val
865                 870                 875                 880

Val Asp His Ala Ala Asp Arg Val Ala Phe Val Arg Asp Gly Ser Leu
                885                 890                 895

Gly Thr Arg Glu Leu Val Gly Gln Gly Ile Asp Val Arg Arg Met Met
                900                 905                 910

Cys Ala Ala Arg Leu Leu Arg Glu Ala Met Ala Trp Leu Gly Val Glu
        915                 920                 925
```

```
Gln Leu Ile Val Pro Thr Trp Arg Leu Val Asp Ala Tyr Gly Arg Arg
            930                 935                 940

Leu Thr Gln Ala Pro Ala Arg Val Thr Arg Ala Leu Val Gly Glu Leu
945                 950                 955                 960

Ala Ser Arg Leu Gly Arg Pro Asp Ala Leu Ser Gly His Glu Arg Gly
                965                 970                 975

His His Ile Glu Arg
            980

<210> SEQ ID NO 165
<211> LENGTH: 8
<212> TYPE: PRT
<213> ORGANISM: Artificial sequence
<220> FEATURE:
<223> OTHER INFORMATION: RecD-like motif I of TrwC Mra

<400> SEQUENCE: 165

Ala Gly Ala Gly Thr Gly Lys Thr
1               5

<210> SEQ ID NO 166
<211> LENGTH: 10
<212> TYPE: PRT
<213> ORGANISM: Artificial sequence
<220> FEATURE:
<223> OTHER INFORMATION: RecD-like motif V of TrwC Mra

<400> SEQUENCE: 166

Tyr Ala Gly Thr Val Tyr Ala Ala Gln Gly
1               5                   10

<210> SEQ ID NO 167
<211> LENGTH: 14
<212> TYPE: PRT
<213> ORGANISM: Artificial sequence
<220> FEATURE:
<223> OTHER INFORMATION: MobF motif III of TrwC Mra

<400> SEQUENCE: 167

His Tyr Thr Thr Arg Glu Gly Asp Pro Asn Ile His Thr His
1               5                   10

<210> SEQ ID NO 168
<211> LENGTH: 949
<212> TYPE: PRT
<213> ORGANISM: Mycobacterium parascrofulaceum ATCC BAA-614

<400> SEQUENCE: 168

Met Ala Arg Val Leu Thr Ile Ala Lys Leu Ser Arg Trp Ser Val Asn
1               5                   10                  15

Tyr Tyr Asn Asp Thr Ala Arg Ala Ala Gly Gln Ala Ala Lys Asp Leu
            20                  25                  30

Gln Cys Ala Asn Gly Gly Leu Gly Glu Tyr Tyr Gly Glu His Asp Thr
        35                  40                  45

Arg Thr Pro Val Trp Val Cys Ala Gly Asp Ala His Arg Ala Ala Glu
    50                  55                  60

Leu Val Gly Leu Ser Asp Ala Glu Arg Ala Gly Gly Asp Ala Asp Pro
65                  70                  75                  80

Gly Val Val Ala Arg Trp Leu Asp Glu Gly Ile Ala Pro Asn Gly Ala
                85                  90                  95

Cys Gly Arg Ala Phe Gly Lys Gly Ser Val His Gly Phe Asp Leu Thr
                100                 105                 110
```

-continued

Phe Cys Ala Pro Lys Ser Val Ser Leu Val Arg Ala Leu Arg Ala Asn
            115                 120                 125

Glu Val Ala Asp Lys Ala Val Leu Ala Ala His Thr Thr Ala Ile Ala
130                 135                 140

Glu Ala Leu Lys Tyr Leu Ala Val His Ala Gly Tyr Thr Arg Val His
145                 150                 155                 160

Asn Pro Thr Thr Gly Asp Lys Asp Leu Val Arg Leu Pro Gly Leu Val
            165                 170                 175

Ala Val Ala Tyr Gln His Glu Thr Ser Arg Ala Gly Asp Pro His Leu
            180                 185                 190

His Thr His Val Leu Val Pro Asn Arg Gln Ala Arg Ala Asp Gly Arg
            195                 200                 205

Leu Val Ser Leu Asp Gly Thr Ser Leu Phe His Glu Ala Lys Ala Ala
210                 215                 220

Gly Val Ile Tyr Gln Ala Thr Leu Arg Arg Glu Leu His Arg Ser Leu
225                 230                 235                 240

Gly Val Glu Trp Ala Ala Val Asp Pro Arg Thr Gly Met Ala Glu Val
            245                 250                 255

Ala Gly Ile Asp Pro Asn Ser Val Ser Ala Trp Ser Gln Arg Ala Ser
            260                 265                 270

Gln Leu Arg Glu Trp Ala Ala His Asn Leu Val Val Gly Ser Gly
            275                 280                 285

Ala Gly Pro Ser Ala Ala Gln Leu Ala Ala Gln Lys Ala Thr Arg
            290                 295                 300

Pro Ala Lys Pro Glu Gln Leu Pro Trp Val Gln Leu Val Ala Glu Trp
305                 310                 315                 320

Arg Ala Asp Ala Arg Gly Leu Lys Val Asp Arg Ala Ala Phe Leu Gln
            325                 330                 335

Ala Arg Gln Ala Arg Arg Ala Ala Ala Ala Pro Phe His Arg Ala
            340                 345                 350

Arg Leu Ala Ala Ala Ala Lys Ile Glu Lys Ala Ala Phe Thr Arg
            355                 360                 365

Ala Asp Leu Val Glu Val Ile Gly Ala Gln Leu Pro Val Asp Ile Asp
370                 375                 380

Gly Glu Thr Arg Thr Pro Arg Glu Leu Ile Glu Ala Ser Val Asp Ala
385                 390                 395                 400

Val Gly Met Arg Leu Thr Ala Pro Arg Ala Ala His Gln Arg Glu Gly
            405                 410                 415

His Glu Arg Tyr Thr Leu Asp Arg Ile Leu Ala Glu Ala Leu Leu
            420                 425                 430

Leu Asp Ala Val Gly Ala Arg Glu Glu Arg Ser Gln Leu Phe Gly Leu
            435                 440                 445

His Glu Phe Asp Leu Glu Gly Leu Ser Gly Asp Gln Gln Arg Ala Val
450                 455                 460

Arg Thr Ile Ala Trp Leu Pro Trp Leu Val Cys Pro Leu Ser Ala Pro
465                 470                 475                 480

Ala Gly Ala Gly Lys Thr Thr Ser Met Arg Ala Leu Arg Ala Ala Ala
            485                 490                 495

Asn His Ser Gly Lys Arg Val Leu Val Ala Pro Thr Gly Lys Ala
            500                 505                 510

Val Asp Val Ala Val Arg Glu Gly Ala Gly Asp Thr Gly Val Thr Val
515                 520                 525

-continued

```
Ala Ala Ala Leu Arg Ser Leu Arg Glu Asn Thr Leu Thr Leu Thr Pro
        530                 535                 540

Arg Thr Leu Val Val Asp Glu Ala Gly Met Val Gly Thr Asp Ala
545                 550                 555                 560

Leu Arg Glu Leu Leu Ala Ala Thr Ala Ala Gly Val Lys Thr Val
                565                 570                 575

Leu Val Gly Asp Ala Tyr Gln Leu Ala Pro Val Lys Ala Arg Gly Gly
            580                 585                 590

Met Phe Ala Gln Leu Cys Thr Asp Leu Pro Trp Thr Gln Thr Leu Ser
        595                 600                 605

Glu Val Trp Arg Met Gln Asp Pro Ala Glu Arg Ala Ala Ser Leu Ala
610                 615                 620

Leu Arg Asp Gly Gly Pro Ala Pro Val Arg Arg Ala Val Ala Trp Tyr
625                 630                 635                 640

Arg Ala Gln Asp Arg Leu His Ala Gly Asp Pro Ile Ala Met Ala Ala
                645                 650                 655

Asp Ala Leu Ala Ala Tyr Lys Thr Asp Val Ala Ala Gly Lys Asp Ala
            660                 665                 670

Leu Leu Ile Ala Asp Thr Thr Glu Met Val Asp Ala Leu Asn Arg Arg
        675                 680                 685

Leu His Asp Glu Arg Ile Asp Pro Gln Ala Pro Thr Val Ala Ala Ala
690                 695                 700

Arg Gly Gln Arg Leu Ala Val Gly Asp Val Ile Val Ser Arg Arg Asn
705                 710                 715                 720

Glu Pro Ala Ile Pro Val Phe Glu Ala Arg Arg Ala Val Pro Asp Pro
                725                 730                 735

Ser Ala Asp Pro Val Arg Asn Gly Gln Arg Trp Gln Val Leu Ala Val
            740                 745                 750

Asp Arg Glu His Asp Arg Ile Ala Ala Arg Leu Glu Asp Gly Ala
        755                 760                 765

Arg Val Val Leu Ser Gly Asp Tyr Leu Arg Glu His Val Ser Tyr Gly
770                 775                 780

Tyr Ala Val Thr Val His Ala Ala Gln Gly Val Thr Ala Asp Thr Ala
785                 790                 795                 800

His Ala Val Leu Gly Glu Ser Thr Arg Arg Asn Leu Leu Tyr Val Ala
                805                 810                 815

Met Thr Arg Gly Arg Glu Thr Asn His Ala Tyr Leu Tyr Glu Arg Leu
            820                 825                 830

Gly Gly Glu Thr Glu His Glu His Pro Glu Pro Gln Ser Gly Met His
        835                 840                 845

Val Ala Arg Arg Gly Thr Gly His Gln Ala Ala Gln Leu Val Arg Gly
850                 855                 860

Ile Ile Gly His Arg Asn Glu Gln Pro Arg Thr Ala His Asp Val Ala
865                 870                 875                 880

Ala Gln Thr Glu Asp His Ala Gln Leu Pro Ala Arg Val Gln Ser Leu
                885                 890                 895

Leu Ala Arg Arg Ala Ala Gly Val Ala Arg Arg Ala Ala Tyr Gln
            900                 905                 910

Gln Trp Arg Asp Asp Arg Leu Asp Arg Leu Leu Asp Gln Gln Trp
        915                 920                 925

Ile Asp His Gln Arg His Arg Ser Arg Gly Arg Gly Gln Ser Arg Asp
930                 935                 940

Tyr Gly Leu Glu Leu
```

<210> SEQ ID NO 169
<211> LENGTH: 8
<212> TYPE: PRT
<213> ORGANISM: Artificial sequence
<220> FEATURE:
<223> OTHER INFORMATION: RecD-like motif I of TrwC Mpa

<400> SEQUENCE: 169

Ala Pro Ala Gly Ala Gly Lys Thr
1               5

<210> SEQ ID NO 170
<211> LENGTH: 10
<212> TYPE: PRT
<213> ORGANISM: Artificial sequence
<220> FEATURE:
<223> OTHER INFORMATION: RecD-like motif V of TrwC Mpa

<400> SEQUENCE: 170

Tyr Ala Val Thr Val His Ala Ala Gln Gly
1               5                   10

<210> SEQ ID NO 171
<211> LENGTH: 14
<212> TYPE: PRT
<213> ORGANISM: Artificial sequence
<220> FEATURE:
<223> OTHER INFORMATION: MobF motif III of TrwC Mpa

<400> SEQUENCE: 171

His Glu Thr Ser Arg Ala Gly Asp Pro His Leu His Thr His
1               5                   10

<210> SEQ ID NO 172
<211> LENGTH: 526
<212> TYPE: DNA
<213> ORGANISM: Artificial sequence
<220> FEATURE:
<223> OTHER INFORMATION: Polynucleotide used in the Examples
<220> FEATURE:
<221> NAME/KEY: misc_feature
<222> LOCATION: (1)..(4)
<223> OTHER INFORMATION: 2'-O-Methyl-Uracil

<400> SEQUENCE: 172
nnnntttttt tttttttttt tttttttttt tttttttttg ccatcagatt      60
gtgtttgtta gtcgctggtt gtttctgttg gtgctgatat tgcttttgat gccgacccta     120 aatttttgc ctgtttggtt cgctttgagt cttcttcggt tccgactacc ctcccgactg     180
cctatgatgt ttatcctttg gatggtcgcc atgatggtgg ttattatacc gtcaaggact    240
gtgtgactat tgacgtcctt ccccgtacgc cgggcaataa tgtttatgtt ggtttcatgg    300
tttggtctaa ctttaccgct actaaatgcc gcggattggt ttcgctgaat caggttatta    360
aagagattat ttgtctccag ccacttaagt gaggtgattt atgtttggtg ctattgctgg    420
cggtattgct tctgctcttg ctggtggcgc catgtctaaa ttgtttggag gcggtctttt    480
tccccctttt tccccctttt tccccctttt tccccctttt tccccc               526

<210> SEQ ID NO 173
<211> LENGTH: 28
<212> TYPE: DNA
<213> ORGANISM: Artificial sequence
<220> FEATURE:

<223> OTHER INFORMATION: Polynucleotide used in the Examples

<400> SEQUENCE: 173
tgaccgcctc caaacaattt agacatgg                                              28

<210> SEQ ID NO 174
<211> LENGTH: 57
<212> TYPE: DNA
<213> ORGANISM: Artificial sequence
<220> FEATURE:
<223> OTHER INFORMATION: Polynucleotide used in the Examples

<400> SEQUENCE: 174
agcgactaac aaacacaatc tgatggcttt tttttttttt tttttttttt ttttttt           57

<210> SEQ ID NO 175
<211> LENGTH: 80
<212> TYPE: DNA
<213> ORGANISM: Artificial sequence
<220> FEATURE:
<223> OTHER INFORMATION: Polynucleotide used in the Examples

<400> SEQUENCE: 175 cccccccccca cccccccca cccccccca cccccccccc ctattctgtt tatgtttctt         60
gtttgttagc cctattctgt                                                       80

<210> SEQ ID NO 176
<211> LENGTH: 40
<212> TYPE: DNA
<213> ORGANISM: Artificial sequence
<220> FEATURE:
<223> OTHER INFORMATION: Polynucleotide used in the Examples

<400> SEQUENCE: 176
acagaatagg gctaacaaac aagaaacata aacagaatag                                 40

<210> SEQ ID NO 177
<211> LENGTH: 40
<212> TYPE: DNA
<213> ORGANISM: Artificial sequence
<220> FEATURE:
<223> OTHER INFORMATION: Polynucleotide used in the Examples

<400> SEQUENCE: 177
ctattctgtt tatgtttctt gtttgttagc cctattctgt                                 40

<210> SEQ ID NO 178
<211> LENGTH: 163
<212> TYPE: DNA
<213> ORGANISM: Artificial sequence
<220> FEATURE:
<223> OTHER INFORMATION: Polynucleotide used in the Examples

<400> SEQUENCE: 178
tttttttttt tttttttttt tttttttttt tttttttttt tttttttttt gcgttaaatt         60
caattacgtc acattagaaa cgtcagaaac ttcagaaggg cgggcggtcc atgcaacgtc       120
gcattaggaa cgttaattac ttaattcgcc ttacgtgaaa ttc                         163

<210> SEQ ID NO 179
<211> LENGTH: 27
<212> TYPE: DNA
<213> ORGANISM: Artificial sequence
<220> FEATURE:
<223> OTHER INFORMATION: Polynucleotide used in the Examples

<400> SEQUENCE: 179
taatgtgacg taattgaatt taacgct                                         27

<210> SEQ ID NO 180
<211> LENGTH: 83
<212> TYPE: DNA
<213> ORGANISM: Artificial sequence
<220> FEATURE:
<223> OTHER INFORMATION: Polynucleotide used in the Examples

<400> SEQUENCE: 180
ttcacgtaag gcgaattaag taattaacgt tcctaatgcg acgttgcatg gaccgcccgc     60
ccttctgaag tttctgacgt ttc                                             83

<210> SEQ ID NO 181
<211> LENGTH: 5358
<212> TYPE: DNA
<213> ORGANISM: Artificial sequence
<220> FEATURE:
<223> OTHER INFORMATION: Polynucleotide used in the Examples

<400> SEQUENCE: 181
tttttttttt tttttttttt tttttttttt tttttttttt tttttttttt ggttgtttct     60
gttggtgctg atattgcccg gtggtaccgt ctccagccac ttaagtgagg tgatttatgt    120
ttggtgctat tgctggcggt attgcttctg ctcttgctgg tggcgccatg tctaaattgt    180
ttggaggcgg tcaaaaagcc gcctccggtg gcattcaagg tgatgtgctt gctaccgata    240
acaatactgt aggcatgggt gatgctggta ttaaatctgc cattcaaggc tctaatgttc    300
ctaaccctga tgaggccgcc ctagttttg tttctggtgc tatggctaaa gctggtaaag    360
gacttcttga aggtacgttg caggctggca cttctgccgt ttctgataag ttgcttgatt    420
tggttggact tggtggcaag tctgccgctg ataaaggaaa ggatactcgt gattatcttg    480
ctgctgcatt tcctgagctt aatgcttggg agcgtgctgg tgctgatgct tcctctgctg    540
gtatggttga cgccggattt gagaatcaaa aagagcttac taaatgcaa ctggacaatc    600 agaaagagat tgccgagatg caaaatgaga ctcaaaaaga gattgctggc attcagtcgg    660
cgacttcacg ccagaatacg aaagaccagg tatatgcaca aatgagatg cttgcttatc    720 aacagaagga gtctactgct cgcgttgcgt ctattatgga aaacaccaat cttttccaagc    780 aacagcaggt ttccgagatt atgcgccaaa tgcttactca agctcaaacg gctggtcagt    840
attttaccaa tgaccaaatc aaagaaatga ctcgcaaggt tagtgctgag gttgacttag    900
ttcatcagca aacgcagaat cagcggtatg gctcttctca tattggcgct actgcaaagg    960
atatttctaa tgtcgtcact gatgctgctt ctggtgtggt tgatatttt catggtattg   1020 ataaagctgt tgccgatact tggaacaatt tctggaaaga cggtaaagct gatggtattg   1080
gctctaattt gtctaggaaa taaccgtcag gattgacacc ctcccaattg tatgtttca   1140 tgcctccaaa tcttggaggc ttttttatgg ttcgttctta ttacccttct gaatgtcacg   1200
ctgattattt tgactttgag cgtatcgagg ctcttaaacc tgctattgag gcttgtggca   1260
tttctactct ttctcaatcc ccaatgcttg gcttccataa gcagtggat aaccgcatca   1320 agctcttgga agagattctg tcttttcgta tgcagggcgt tgagttcgat aatggtgata   1380
tgtatgttga cggccataag gctgcttctg acgttcgtga tgagtttgta tctgttactg   1440
agaagttaat ggatgaattg gcacaatgct acaatgtgct ccccccaactt gatattaata   1500

```
acactataga ccaccgcccc gaaggggacg aaaaatggtt tttagagaac gagaagacgg    1560
ttacgcagtt ttgccgcaag ctggctgctg aacgccctct taaggatatt cgcgatgagt    1620
ataattaccc caaaaagaaa ggtattaagg atgagtgttc aagattgctg gaggcctcca    1680
ctatgaaatc gcgtagaggc tttgctattc agcgtttgat gaatgcaatg cgacaggctc    1740
atgctgatgg ttggtttatc gttttttgaca ctctcacgtt ggctgacgac cgattagagg    1800
cgttttatga taatcccaat gctttgcgtg actattttcg tgatattggt cgtatggttc    1860
ttgctgccga gggtcgcaag gctaatgatt cacacgccga ctgctatcag tattttttgtg    1920
tgcctgagta tggtacagct aatggccgtc ttcatttcca tgcggtgcac tttatgcgga    1980
cacttcctac aggtagcgtt gaccctaatt ttggtcgtcg ggtacgcaat cgccgccagt    2040
taaatagctt gcaaaatacg tggccttatg gttacagtat gcccatcgca gttcgctaca    2100
cgcaggacgc ttttttcacgt tctggttggt tgtggcctgt tgatgctaaa ggtgagccgc    2160
ttaaagctac cagttatatg gctgttggtt tctatgtggc taaatacgtt aacaaaaagt    2220
cagatatgga ccttgctgct aaaggtctag gagctaaaga atggaacaac tcactaaaaa    2280
ccaagctgtc gctacttccc aagaagctgt tcagaatcag aatgagccgc aacttcggga    2340
tgaaaatgct cacaatgaca aatctgtcca cggagtgctt aatccaactt accaagctgg    2400
gttacgacgc gacgccgttc aaccagatat tgaagcagaa cgcaaaaaga gagatgagat    2460
tgaggctggg aaaagttact gtagccgacg tttttggcggc gcaacctgtg acgacaaatc    2520
tgctcaaatt tatgcgcgct tcgataaaaa tgattggcgt atccaacctg cagagtttta    2580
tcgcttccat gacgcagaag ttaacacttt cggatatttc tgatgagtcg aaaaattatc    2640
ttgataaagc aggaattact actgcttgtt tacgaattaa atcgaagtgg actgctggcg    2700
gaaaatgaga aaattcgacc tatccttgcg cagctcgaga agctcttact ttgcgacctt    2760
tcgccatcaa ctaacgattc tgtcaaaaac tgacgcgttg gatgaggaga agtggcttaa    2820
tatgcttggc acgttcgtca aggactggtt tagatatgag tcacattttg ttcatggtag    2880
agattctctt gttgacattt taaagagcg tggattacta tctgagtccg atgctgttca    2940
accactaata ggtaagaaat catgagtcaa gttactgaac aatccgtacg tttccagacc    3000
gctttggcct ctattaagct cattcaggct tctgccgttt tggatttaac cgaagatgat    3060
ttcgattttc tgacgagtaa caaagtttgg attgctactg accgctctcg tgctcgtcgc    3120
tgcgttgagg cttgcgttta tggtacgctg gactttgtgg gataccctcg ctttcctgct    3180
cctgttgagt ttattgctgc cgtcattgct tattatgttc atcccgtcaa cattcaaacg    3240
gcctgtctca tcatggaagg cgctgaattt acggaaaaca ttattaatgg cgtcgagcgt    3300
ccggttaaag ccgctgaatt gttcgcgttt accttgcgtg tacgcgcagg aaacactgac    3360
gttcttactg acgcagaaga aaacgtgcgt caaaaattac gtgcggaagg agtgatgtaa    3420
tgtctaaagg taaaaaacgt tctggcgctc gccctggtcg tccgcagccg ttgcgaggta    3480
ctaaaggcaa gcgtaaaggc gctcgtcttt ggtatgtagg tggtcaacaa ttttaattgc    3540
aggggcttcg gccccttact tgaggataaa ttatgtctaa tattcaaact ggcgccgagc    3600
gtatgccgca tgacctttcc catcttggct tccttgctgg tcagattggt cgtcttatta    3660
ccatttcaac tactccggtt atcgctggcg actccttcga tggacgcc gttggcgctc    3720
tccgtctttc tccattgcgt cgtggccttg ctattgactc tactgtagac atttttactt    3780
tttatgtccc tcatcgtcac gtttatgtg aacagtggat taagttcatg aaggatggtg    3840
ttaatgccac tcctctcccg actgttaaca ctactggtta tattgaccat gccgcttttc    3900
```

```
ttggcacgat taaccctgat accaataaaa tccctaagca tttgtttcag ggttatttga    3960
atatctataa caactatttt aaagcgccgt ggatgcctga ccgtaccgag gctaaccctg    4020
atgagcttaa tcaagatgat gctcgttatg gtttccgttg ctgccatctc aaaaacattt    4080
ggactgctcc gcttcctcct gagactgagc tttctcgcca aatgacgact tctaccacat    4140
ctattgacat tatgggtctg caagctgctt atgctaattt gcatactgac caagaacgtg    4200
attacttcat gcagcgttac catgatgtta tttcttcatt tggaggtaaa acctcttatg    4260
acgctgacaa ccgtccttta cttgtcatgc gctctaatct ctgggcatct ggctatgatg    4320
ttgatggaac tgaccaaacg tcgttaggcc agttttctgg tcgtgttcaa cagacctata    4380
aacattctgt gccgcgtttc tttgttcctg agcatggcac tatgtttact cttgcgcttg    4440
ttcgttttcc gcctactgcg actaaagaga ttcagtacct taacgctaaa ggtgctttga    4500
cttataccga tattgctggc gaccctgttt tgtatggcaa cttgccgccg cgtgaaattt    4560
ctatgaagga tgttttccgt tctggtgatt cgtctaagaa gtttaagatt gctgagggtc    4620
agtggtatcg ttatgcgcct tcgtatgttt ctcctgctta tcaccttctt gaaggcttcc    4680
cattcattca ggaaccgcct tctggtgatt tgcaagaacg cgtacttatt cgccaccatg    4740
attatgacca gtgtttccag tccgttcagt tgttgcagtg gaatagtcag gttaaattta    4800
atgtgaccgt ttatcgcaat ctgccgacca ctcgcgattc aatcatgact tcgtgataaa    4860
agattgagtg tgaggttata acgccgaagc ggtaaaaatt ttaatttttg ccgctgaggg    4920
gttgaccaag cgaagcgcgg taggttttct gcttaggagt ttaatcatgt ttcagactt     4980 tatttctcgc cataattcaa acttttttc tgataagctg gttctcactt ctgttactcc    5040
agcttcttcg gcacctgttt tacagacacc taaagctaca tcgtcaacgt tatattttga    5100
tagtttgacg gttaatgctg gtaatggtgg ttttcttcat tgcattcaga tggatacatc    5160
tgtcaacgcc gctaatcagg ttgtttctgt tggtgctgat attgcttttg atgccgaccc    5220 taaattttt gcctgtttgg ttcgctttga gtcttcttcg gttccgacta ccctcccgac    5280
tgcctatgat gtttatcctt tgaatggtcg ccatgatggt ggttattata ccgtcaagga    5340
ctgtgtgact attgacgt                                                 5358

<210> SEQ ID NO 182
<211> LENGTH: 57
<212> TYPE: DNA
<213> ORGANISM: Artificial sequence
<220> FEATURE:
<223> OTHER INFORMATION: Polynucleotide used in the Examples

<400> SEQUENCE: 182
gcaatatcag caccaacaga aacaaccttt ttttttttt ttttttttt ttttttt       57
```

ENZYME METHOD

CROSS-REFERENCE TO RELATED APPLICATIONS

This application is a 35 U.S.C. 371 national stage filing of International Application No. PCT/GB2012/053274, filed on Dec. 28, 2012, which claims priority to and benefit of U.S. Provisional Application No. 61/581,332, filed Dec. 29, 2011, the entire contents of each of which are hereby incorporated by reference herein.

FIELD OF THE INVENTION

The invention relates to a new method of characterising a target polynucleotide. The method uses a pore and a RecD helicase. The helicase controls the movement of the target polynucleotide through the pore.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the "Strand Sequencing" method, a single polynucleotide strand is passed through the pore and the identity of the nucleotides are derived. Strand Sequencing can involve the use of a nucleotide handling protein to control the movement of the polynucleotide through the pore.

SUMMARY OF THE INVENTION

The inventors have demonstrated that a RecD helicase can control the movement of a polynucleotide through a pore especially when a potential, such as a voltage, is applied. The helicase is capable of moving a target polynucleotide in a controlled and stepwise fashion against or with the field resulting from the applied voltage. Surprisingly, the helicase is capable of functioning at a high salt concentration which is advantageous for characterising the polynucleotide and, in particular, for determining its sequence using Strand Sequencing. This is discussed in more detail below.

Accordingly, the invention provides a method of characterising a target polynucleotide, comprising:

(a) contacting the target polynucleotide with a transmembrane pore and a RecD helicase such that the target polynucleotide moves through the pore and the RecD helicase controls the movement of the target polynucleotide through the pore; and (b) taking one or more measurements as the polynucleotide moves with respect to the pore wherein the measurements are indicative of one or more characteristics of the target polynucleotide and thereby characterising the target polynucleotide.

The invention also provides:

a method of forming a sensor for characterising a target polynucleotide, comprising forming a complex between a pore and a RecD helicase and thereby forming a sensor for characterising the target polynucleotide;

use of a RecD helicase to control the movement of a target polynucleotide through a pore;

a kit for characterising a target polynucleotide comprising (a) a pore and (b) a RecD helicase; and an analysis apparatus for characterising target polynucleotides in a sample, comprising a plurality of pores and a plurality of a RecD helicase;

a method of characterising a target polynucleotide, comprising:

(a) contacting the target polynucleotide with a RecD helicase such that the RecD helicase controls the movement of the target polynucleotide; and (b) taking one or more measurements as the RecD helicase controls the movement of the polynucleotide wherein the measurements are indicative of one or more characteristics of the target polynucleotide and thereby characterising the target polynucleotide;

use of a RecD helicase to control the movement of a target polynucleotide during characterisation of the polynucleotide;

use of a RecD helicase to control the movement of a target polynucleotide during sequencing of part or all of the polynucleotide;

an analysis apparatus for characterising target polynucleotides in a sample, characterised in that it comprises a RecD helicase; and a kit for characterising a target polynucleotide comprising (a) an analysis apparatus for characterising target polynucleotides and (b) a RecD helicase.

DESCRIPTION OF THE FIGURES

FIG. 1A. Example schematic of use of a helicase to control DNA movement through a nanopore. A ssDNA substrate with an annealed primer containing a cholesterol-tag is added to the cis side of the bilayer. The cholesterol tag binds to the bilayer, enriching the substrate at the bilayer surface. Helicase added to the cis compartment binds to the DNA. In the presence of divalent metal ions and NTP substrate, the helicase moves along the DNA. Under an applied voltage, the DNA substrate is captured by the nanopore. The DNA is pulled through the pore under the force of the applied potential until a helicase, bound to the DNA, contacts the top of the pore, preventing further uncontrolled DNA translocation. After this the helicase proceeds to move the DNA through the nanopore in a controlled fashion.

The schematic shows two possible methods of introducing the DNA to the nanopore: in one mode (top section) the helicase moves the captured DNA into the nanopore in the direction of the applied field, and in the other mode (lower section) the helicase pulls the captured DNA out of the nanopore against the direction of the applied field. When moved with the applied field the DNA is moved to the trans side of the membrane. In both upper and lower sections the arrows on the trans side indicate the direction of motion of the DNA and the arrows on the cis side indicate direction of motion of the helicase with respect to the DNA. When moved against the field, the DNA is moved back to the cis side of the membrane, and the DNA may translocate completely to the cis side if the helicase does not dissociate.

Through substrate design, such as use of suitable leaders, one or both methods can be used at a time. The RecD family of helicases move in the 5'-3' direction along the DNA. Therefore, moving the DNA with the field requires 5' down capture of the DNA, and moving the DNA against the field requires 3' down DNA capture. FIG. 1B. The DNA substrate design used in the Example.

Figure 2:
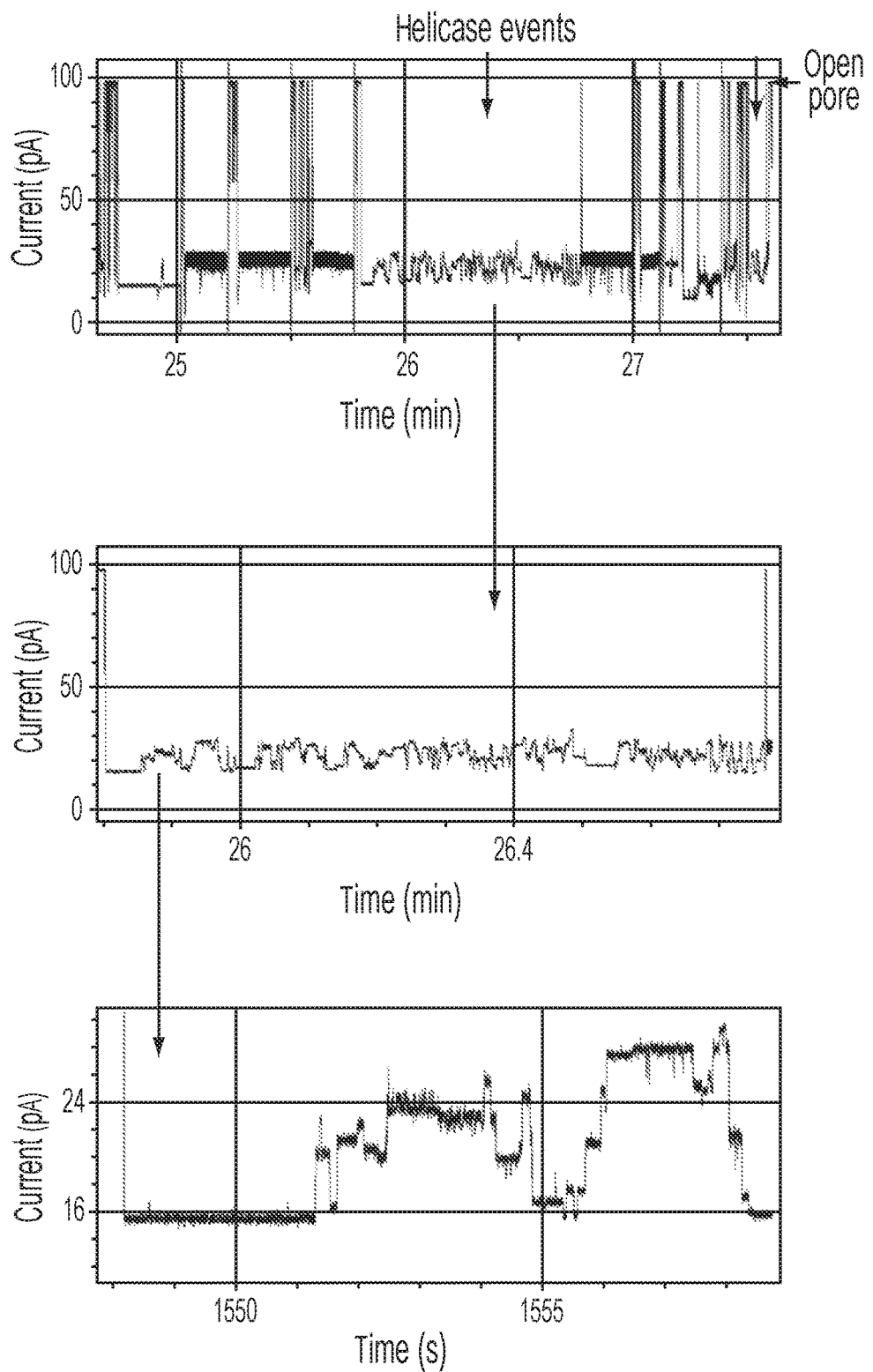

FIG. 2. Helicase is able to move DNA through a nanopore in a controlled fashion, producing stepwise changes in current as the DNA moves through the nanopore (MspA-(B2)8). Example helicase-DNA events (140 mV, 400 mM NaCl, 10 mM Hepes, pH 8.0, 0.60 nM 400 mer DNA (SEQ ID NO: 172, 173 and 174), 100 nM Tra1 Eco (SEQ ID NO: 61), 1 mM DTT, 1 mM ATP, 1 mM $MgCl_2$). Top) Section of current vs. time acquisition of Tra1 400mer DNA events. The open-pore current is ~100 pA. DNA is captured by the nanopore under the force of the applied potential (+140 mV). DNA with enzyme attached results in a long block (at ~25 pA in this condition) that shows stepwise changes in current as the enzyme moves the DNA through the pore. Middle) An enlargement of one of the helicase-controlled DNA events, showing DNA-enzyme capture, and stepwise current changes as the DNA is pulled through the pore. Bottom) Further enlargement of the stepwise changes in current as DNA is moved through the nanopore.

Figures 3A, 3B:
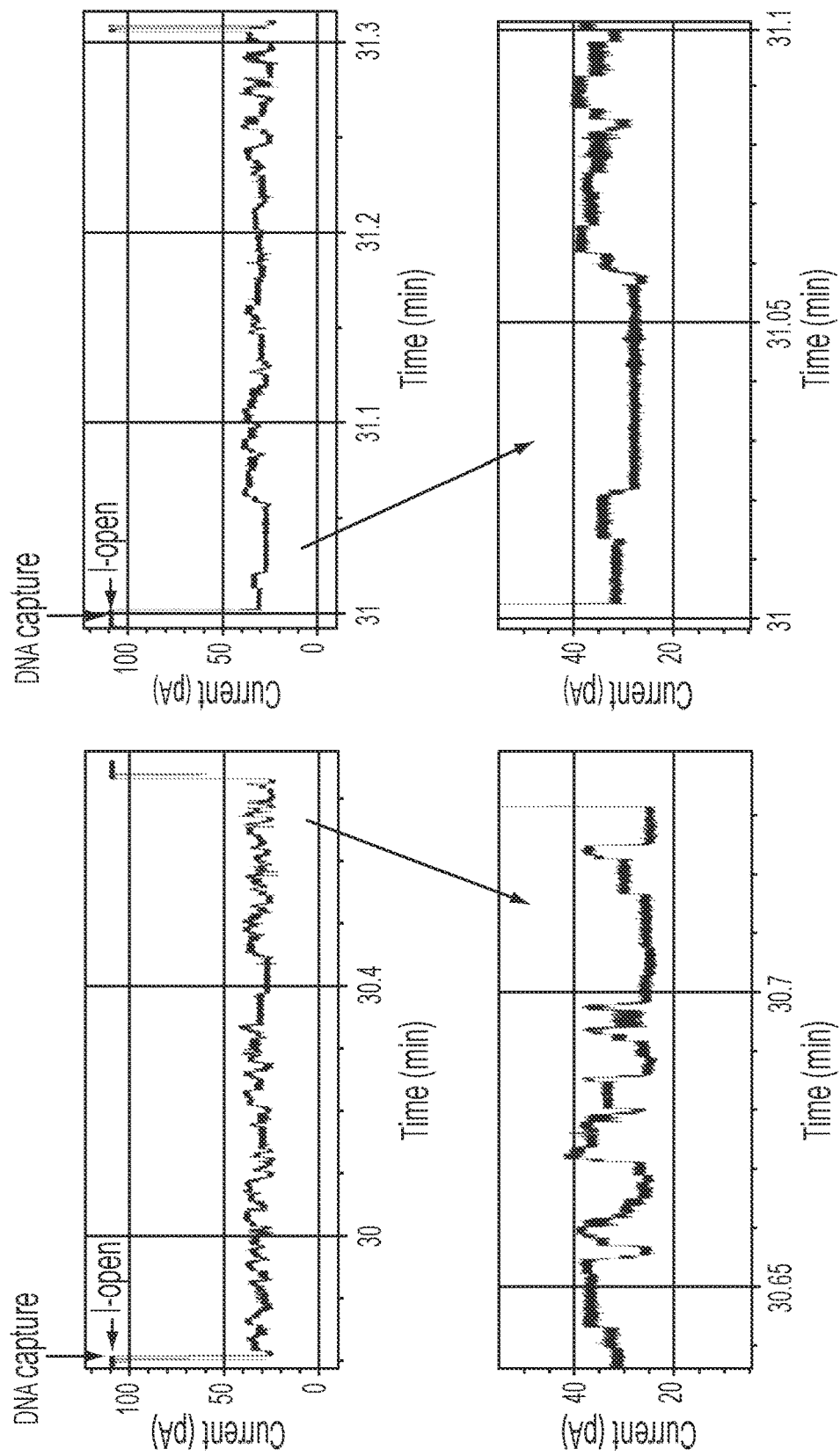

FIGS. 3A and 3B. Further examples of TraI Eco (SEQ ID 61) helicase controlled 400mer DNA (400mer DNA SEQ ID NOs: 172, 173 and 174) movement events through an MspA-B2(8) nanopore. Bottom) An enlargement of a section of the event showing the stepwise changes in current from the different sections of DNA as the strand moves through the nanopore.

Figure 4A:
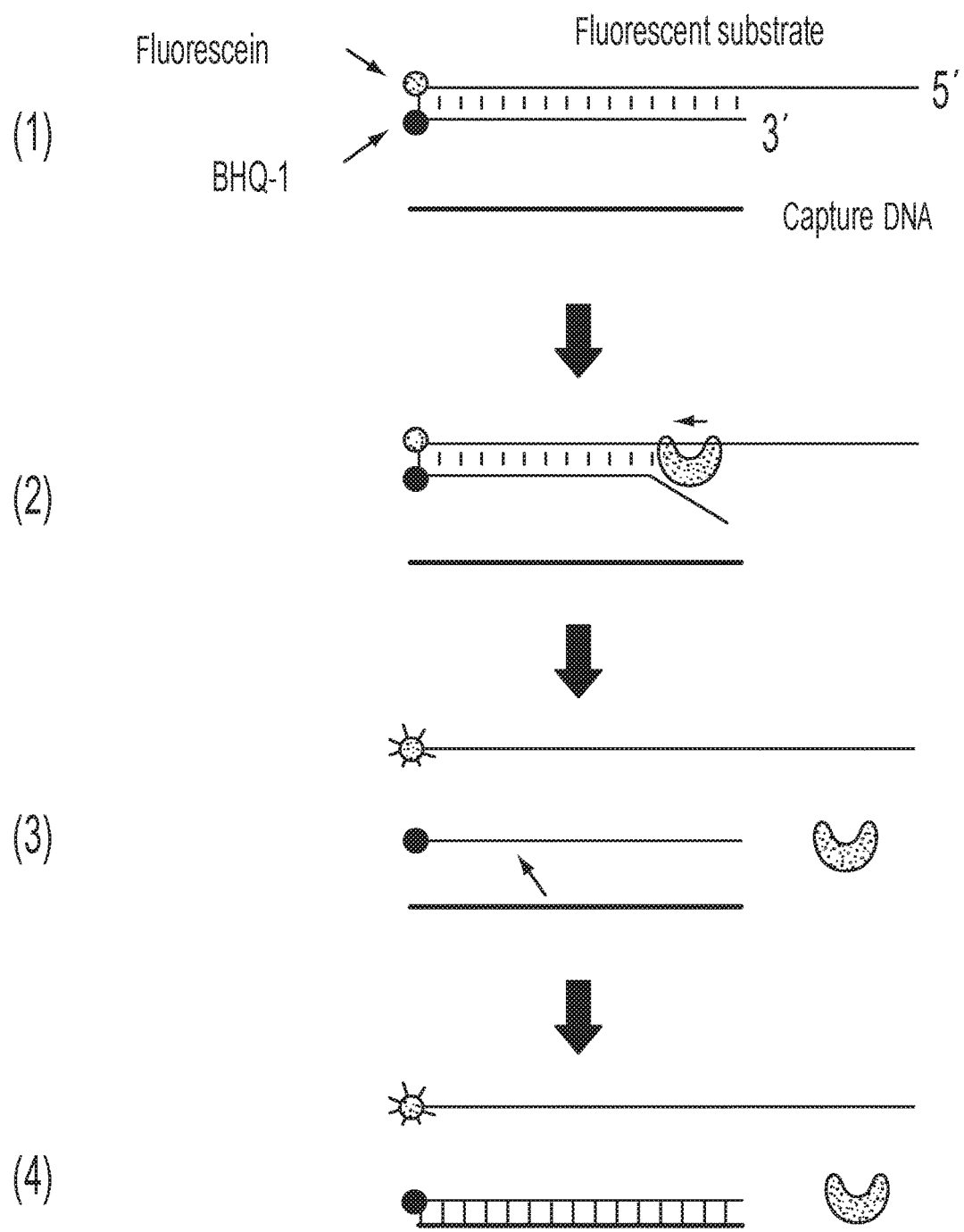
Figure 4B:
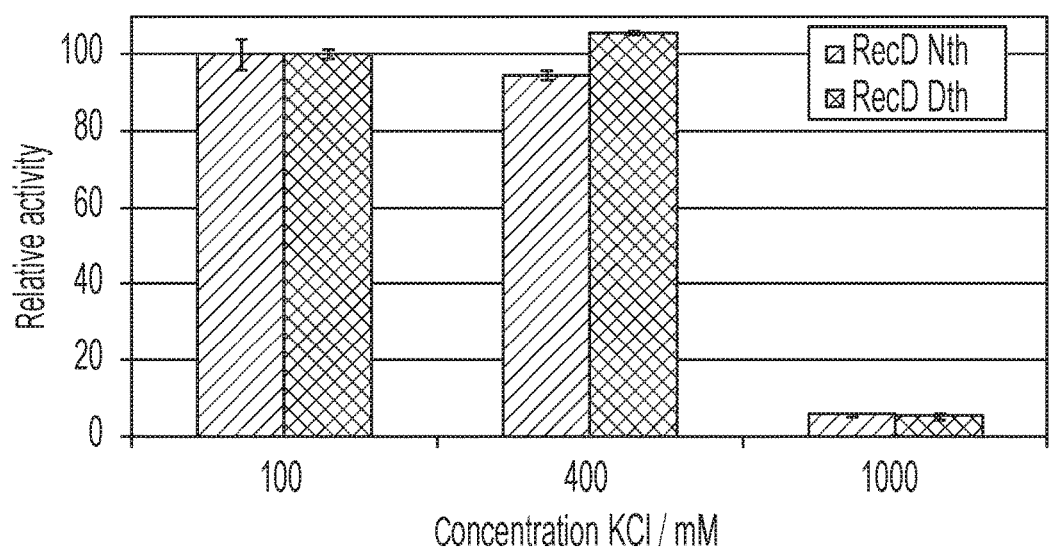

FIGS. 4A and 4B. Fluorescence assay for testing enzyme activity. FIG. 4A. A custom fluorescent substrate was used to assay the ability of the helicase to displace hybridised dsDNA. 1) The fluorescent substrate strand (50 nM final) has a 5' ssDNA overhang, and a 40 base section of hybridised dsDNA. The major upper strand has a carboxyfluorescein base at the 3' end, and the hybridised complement has a black-hole quencher (BHQ-1) base at the 5' end. When hybridised the fluorescence from the fluorescein is quenched by the local BHQ-1, and the substrate is essentially non-fluorescent. 1 μM of a capture strand that is complementary to the shorter strand of the fluorescent substrate is included in the assay. 2) In the presence of ATP (1 mM) and $MgCl_2$ (10 mM), helicase (100 nM) added to the substrate binds to the 5' tail of the fluorescent substrate, moves along the major strand, and displaces the complementary strand as shown. 3) Once the complementary strand with BHQ-1 is fully displaced the fluorescein on the major strand fluoresces. 4) Excess of capture strand preferentially anneals to the complementary DNA to prevent re-annealing of initial substrate and loss of fluorescence. FIG. 4B. Graph of the initial rate of RecD helicase activity in buffer solutions (RecD Nth and Dth SEQ IDs 28 and 35, 100 mM Hepes pH 8.0, 1 mM ATP, 10 mM $MgCl_2$, 50 nM fluorescent substrate DNA, 1 μM capture DNA) containing different concentrations of KCl from 100 mM to 1 M.

FIGS. 5A and 5B. Examples of helicase controlled DNA events using a different Tra1 helicase, TrwC Cba (+140 mV, 10 mM Hepes, pH 8.0, 0.6 nM, 400mer DNA SEQ ID NOs: 172, 172 and 173, 100 nM TrwC Cba SEQ ID 65, 1 mM DTT, 1 mM ATP, 1 mM $MgCl_2$). Top) Section of current vs. time acquisition of TrwC Cba 400mer DNA events. The open-pore current is ~100 pA. DNA is captured by the nanopore under the force of the applied potential (+140 mV). DNA with enzyme attached results in a long block (at ~25 pA in this condition) that shows stepwise changes in current as the enzyme moves the DNA through the pore. Bottom) The bottom traces show enlarged sections of the DNA events, showing the stepwise sequence dependent current changes as the DNA is pulled through the pore.

Figure 6:
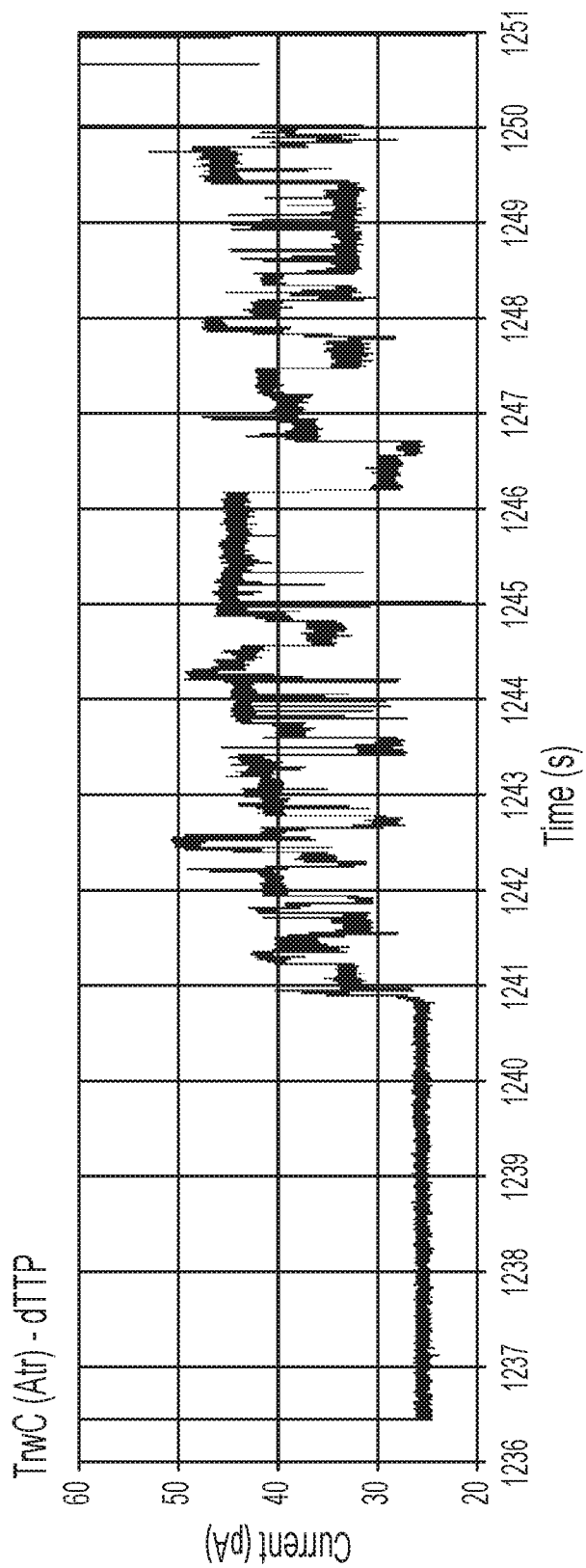

FIG. 6. Example of current trace showing helicase controlled DNA movement using a TrwC (Atr) (SEQ ID NO: 144) helicase.

Figure 7:
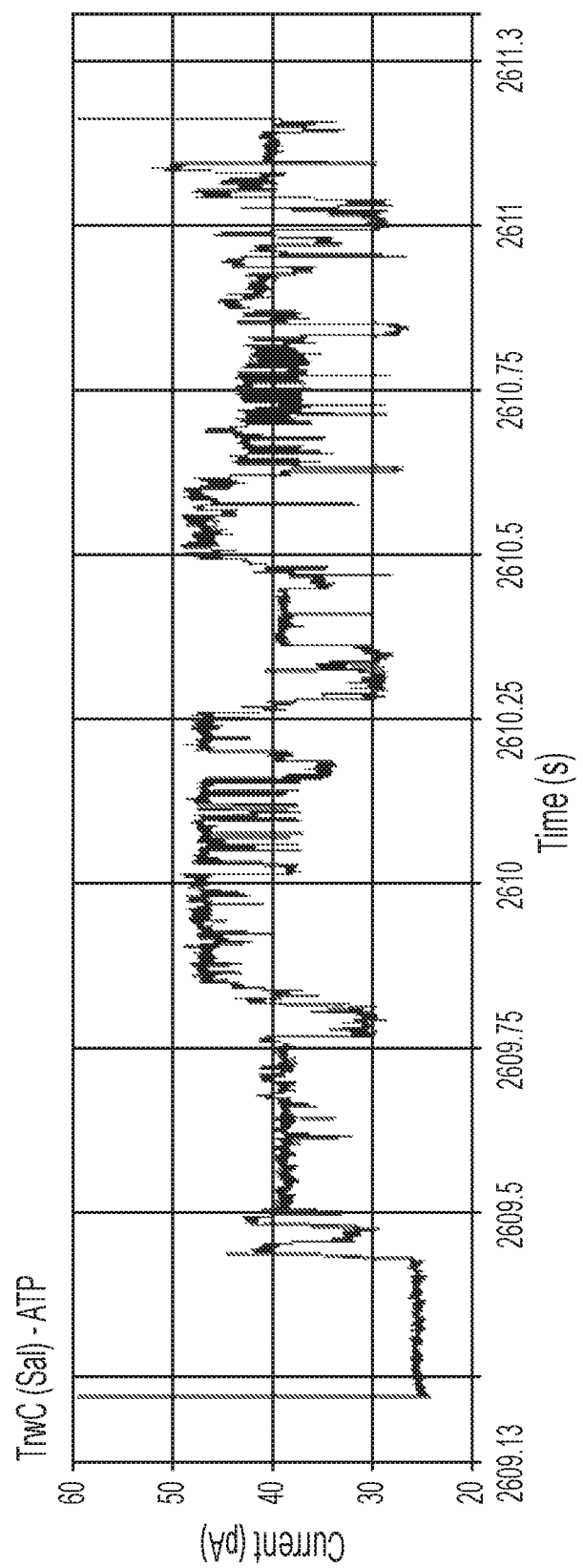

FIG. 7. Example of current trace showing helicase controlled DNA movement using a TrwC (Sal) (SEQ ID NO: 140) helicase.

Figure 8:
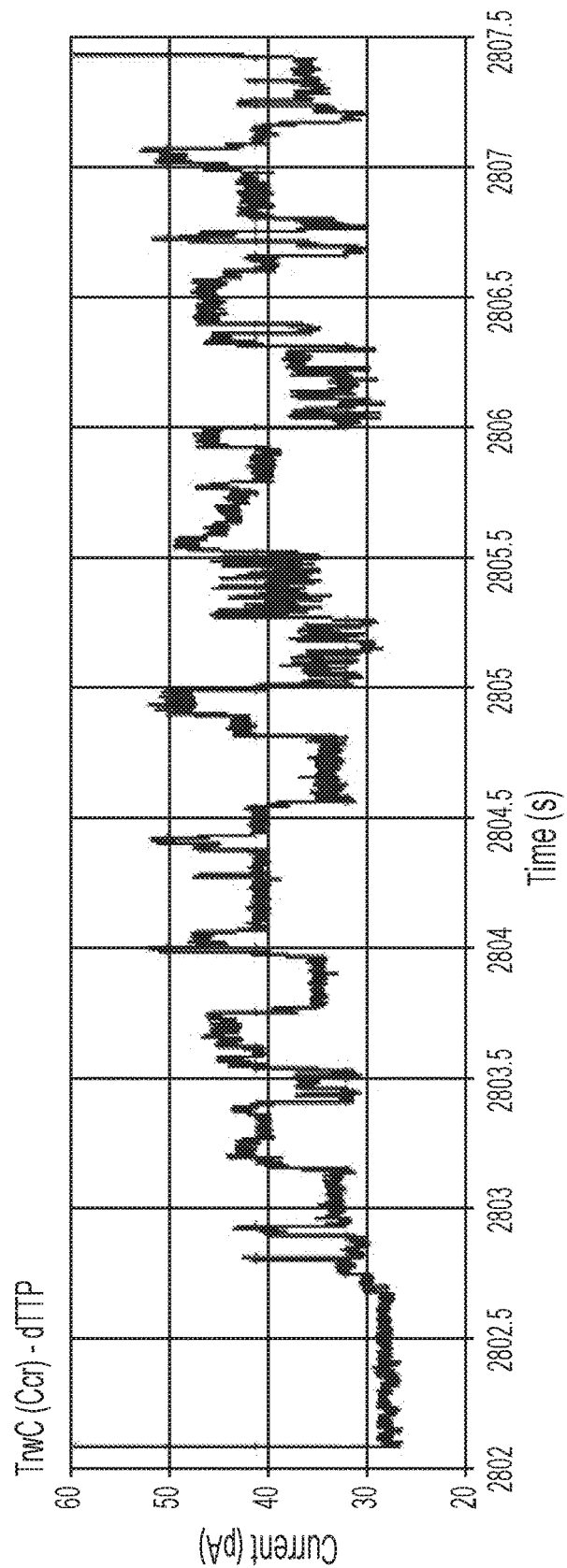

FIG. 8. Example of current trace showing helicase controlled DNA movement using a TrwC (Ccr) (SEQ ID NO: 136) helicase.

Figure 9:
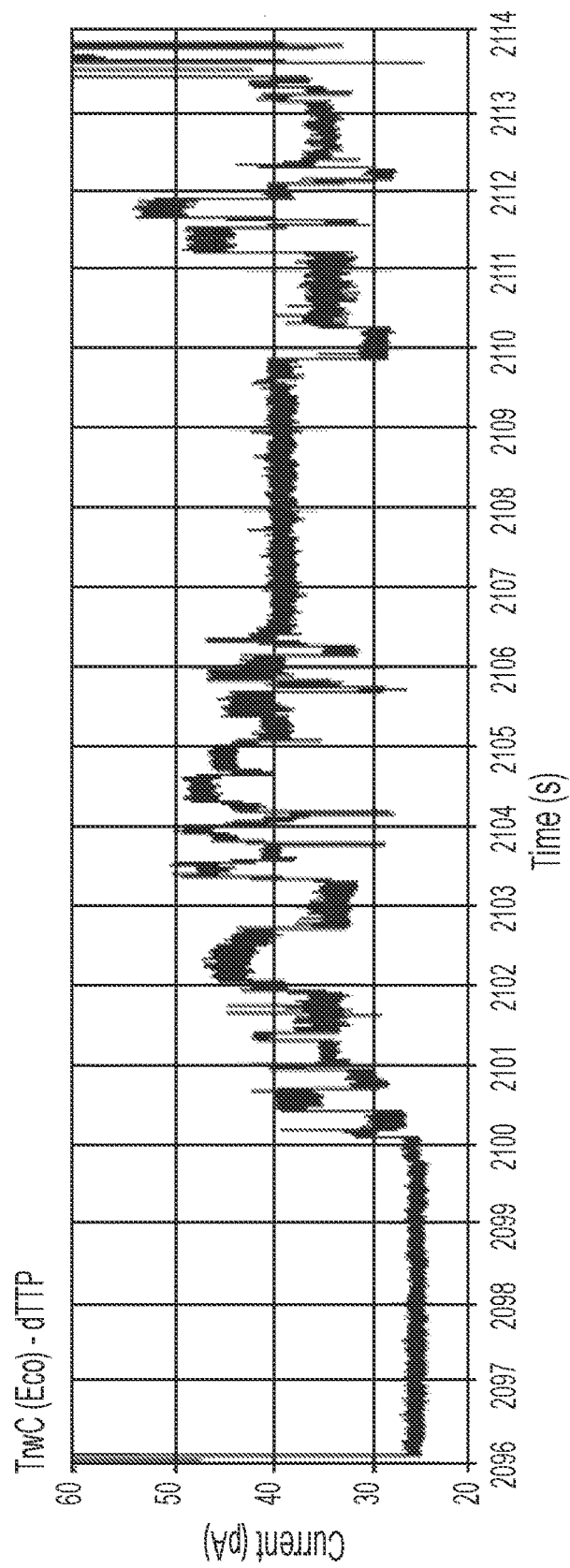

FIG. 9. Example of current trace showing helicase controlled DNA movement using a TrwC (Eco) (SEQ ID NO: 74) helicase.

Figure 10:
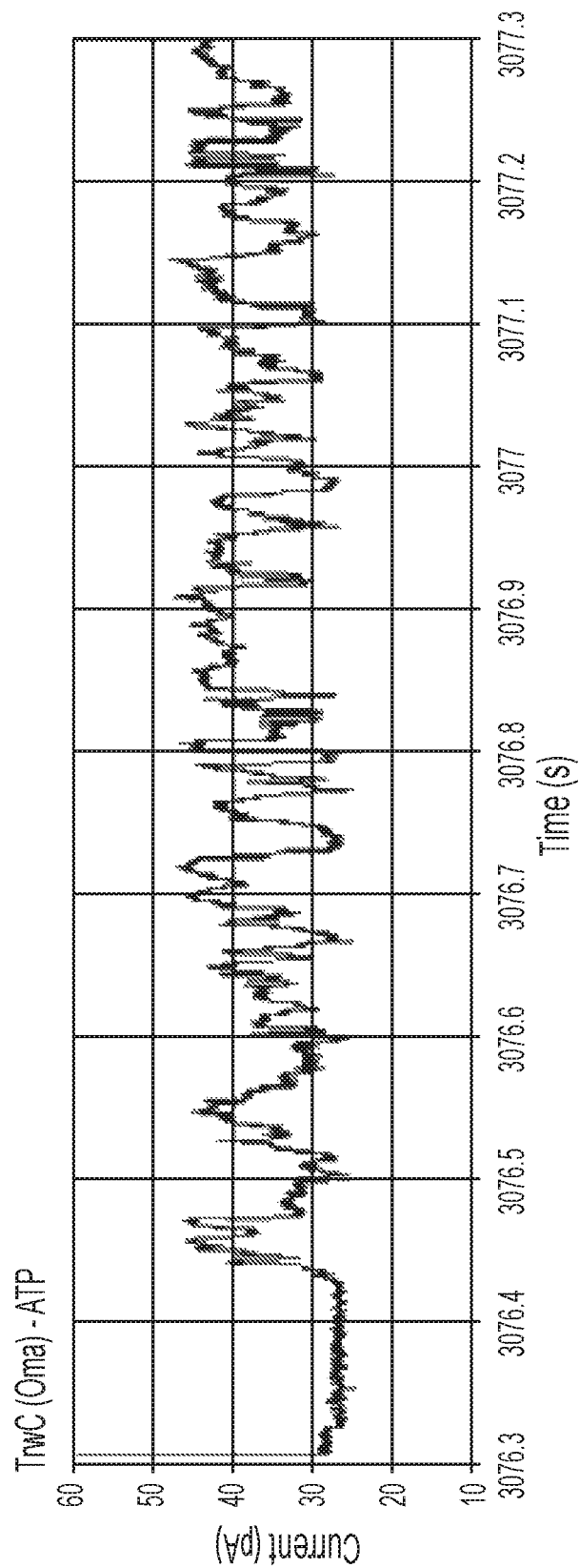

FIG. 10. Example of current trace showing helicase controlled DNA movement using a TrwC (Oma) (SEQ ID NO: 106) helicase.

Figure 11:
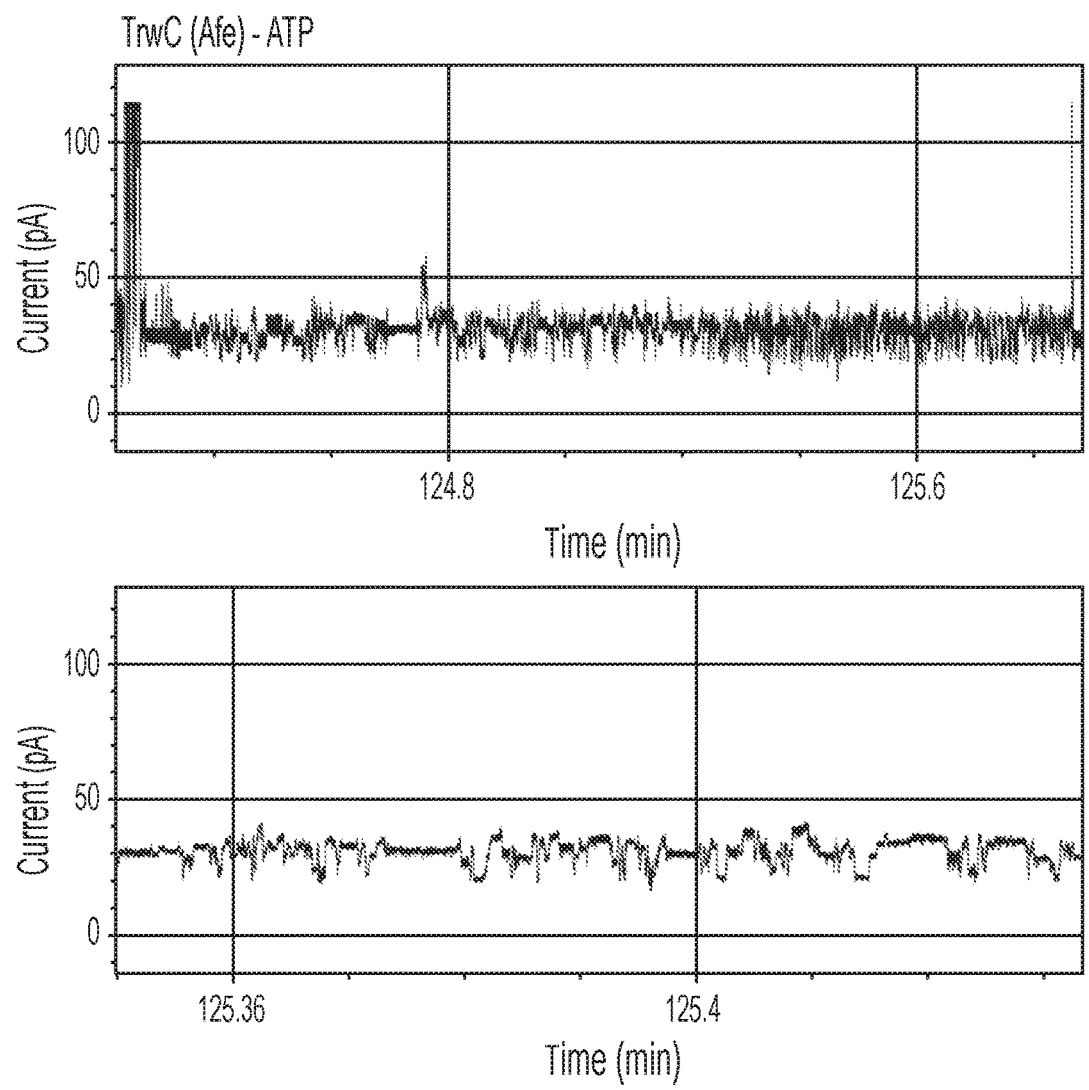

FIG. 11. Example of current trace showing helicase controlled DNA movement using a TrwC (Afe) (SEQ ID NO: 86) helicase. The lower trace shows an expanded region of the helicase controlled DNA movement.

Figure 12:
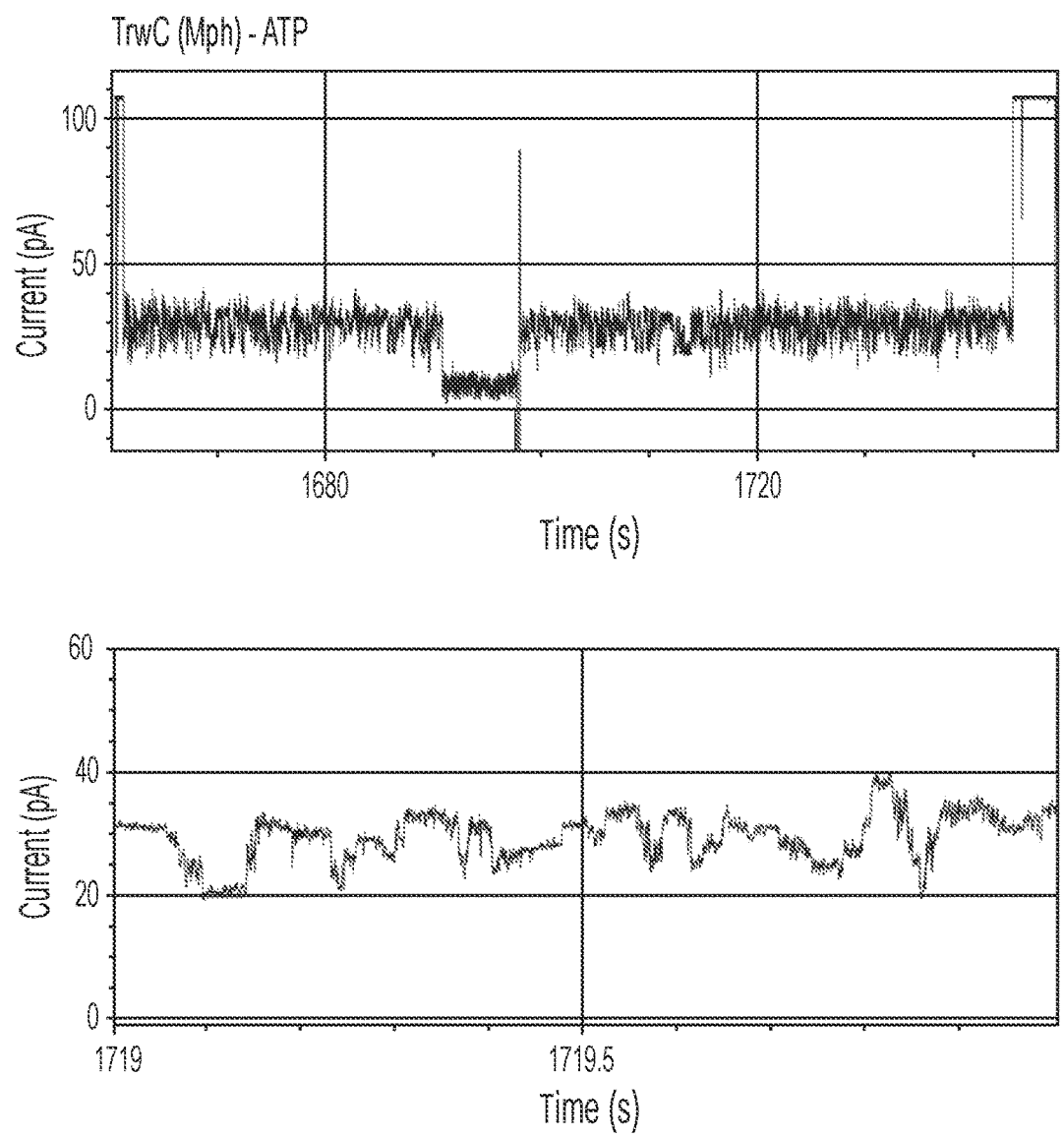

FIG. 12. Example of current trace showing helicase controlled DNA movement using a TrwC (Mph) (SEQ ID NO: 94) helicase. The lower trace shows an expanded region of the helicase controlled DNA movement.

DESCRIPTION OF THE SEQUENCE LISTING

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one subunit of α-hemolysin-E111N/K147N (α-HL-NN; Stoddart et al., PNAS, 2009; 106(19): 7702-7707).

SEQ ID NO: 4 shows the amino acid sequence of one subunit of α-HL-NN.

SEQ ID NOs: 5 to 7 shows the amino acid sequences of MspB, C and D.

SEQ ID NO: 8 shows the sequence of the RecD-like motif I.

SEQ ID NOs: 9, 10 and 11 show the sequences of the extended RecD-like motif I.

SEQ ID NO: 12 shows the sequence of the RecD motif I.

SEQ ID NOs: 13, 14 and 15 show the sequences of the extended RecD motif I.

SEQ ID NO: 16 shows the sequence of the RecD-like motif V.

SEQ ID NO: 17 shows the sequence of the RecD motif V.

SEQ ID NOs: 18 to 45 show the amino acid sequences of the RecD helicases in Table 5.

SEQ ID NOs: 46 to 53 show the sequences of the MobF motif III.

SEQ ID NOs: 54 to 60 show the sequences of the MobQ motif III.

SEQ ID NOs: 61 to 171 show the amino acid sequences of the TraI helicase and TraI subgroup helicases shown in Table 7.

SEQ ID NOs: 172 to 182 show the sequences used in the Examples.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a pore" includes two or more such pores, reference to "a helicase" includes two or more such helicases, reference to "a polynucleotide" includes two or more such polynucleotides, and the like.

All publications, patents and patent applications cited herein, whether supra or infra, are hereby incorporated by reference in their entirety.

Methods of the Invention

The invention provides a method of characterising a target polynucleotide. The method comprises contacting the target polynucleotide with a transmembrane pore and a RecD helicase such that the target polynucleotide moves through the pore and the RecD helicase controls the movement of the target polynucleotide through the pore. One or more characteristics of the target polynucleotide are then measured as the polynucleotide moves with respect to the pore using standard methods known in the art. One or more characteristics of the target polynucleotide are preferably measured as the polynucleotide moves through the pore. Steps (a) and (b) are preferably carried out with a potential applied across the pore. As discussed in more detail below, the applied potential typically results in the formation of a complex between the pore and the helicase. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

In some instances, the current passing through the pore as the polynucleotide moves with respect to the pore is used to determine the sequence of the target polynucleotide. This is Strand Sequencing.

The method has several advantages. First, the inventors have surprisingly shown that RecD helicases have a surprisingly high salt tolerance and so the method of the invention may be carried out at high salt concentrations. In the context of Strand Sequencing, a charge carrier, such as a salt, is necessary to create a conductive solution for applying a voltage offset to capture and translocate the target polynucleotide and to measure the resulting sequence-dependent current changes as the polynucleotide moves with respect to the pore. Since the measurement signal is dependent on the concentration of the salt, it is advantageous to use high salt concentrations to increase the magnitude of the acquired signal. High salt concentrations provide a high signal to noise ratio and allow for currents indicative of the presence of a nucleotide to be identified against the background of normal current fluctuations. For Strand Sequencing, salt concentrations in excess of 100 mM are ideal, for example salt concentrations in excess of 400 mM, 600 mM or 800 mM. The inventors have surprisingly shown that RecD helicases will function effectively at very high salt concentrations such as, for example, 1 M. The invention encompasses helicases which function effectively at salt concentrations in excess of 1M, for example 2M.

Second, when a voltage is applied, RecD helicases can surprisingly move the target polynucleotide in two directions, namely with or against the field resulting from the applied voltage. Hence, the method of the invention may be carried out in one of two preferred modes. Different signals are obtained depending on the direction the target polynucleotide moves with respect to the pore, ie in the direction of or against the field. This is discussed in more detail below.

Third, RecD helicases typically move the target polynucleotide through the pore one nucleotide at a time. RecD helicases can therefore function like a single-base ratchet. This is of course advantageous when sequencing a target polynucleotide because substantially all, if not all, of the nucleotides in the target polynucleotide may be identified using the pore.

Fourth, RecD helicases are capable of controlling the movement of single stranded polynucleotides and double stranded polynucleotides. This means that a variety of different target polynucleotides can be characterised in accordance with the invention.

Fifth, RecD helicases appear very resistant to the field resulting from applied voltages. The inventors have seen very little movement of the polynucleotide under an "unzipping" condition. Unzipping conditions will typically be in the absence of nucleotides, for example the absence of ATP. When the helicase is operating in unzipping mode it acts like a brake preventing the target sequence from moving through the pore too quickly under the influence of the applied voltage. This is important because it means that there are no complications from unwanted "backwards" movements when moving polynucleotides against the field resulting from an applied voltage.

Sixth, RecD helicases are easy to produce and easy to handle. Their use therefore contributed to a straightforward and less expensive method of sequencing.

The method of the invention is for characterising a target polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. One or more nucleotides in the target polynucleotide may be modified, for instance with a label or a tag. The target polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP or dCMP.

A nucleotide may be abasic (i.e. lack a nucleobase).

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

A transmembrane pore is a structure that crosses the membrane to some degree. It permits ions, such as hydrated ions, driven by an applied potential to flow across or within the membrane. The transmembrane pore typically crosses the entire membrane so that ions may flow from one side of the membrane to the other side of the membrane. However, the transmembrane pore does not have to cross the membrane. It may be closed at one end. For instance, the pore may be a well in the membrane along which or into which ions may flow.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and $SiO$, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The polynucleotide may be coupled to the membrane. This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The polynucleotide may be coupled directly to the membrane. The polynucleotide is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the helicase. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the helicase's active site. If the coupling is transient, then when the coupled end randomly becomes free of the bilayer, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the polynucleotide is coupled to an amphiphilic layer. Coupling of polynucleotides to synthetic lipid bilayers has been carried out previously with various different tethering strategies. These are summarised in Table 1 below.

cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer a reactive group attached to it.

A common technique for the amplification of sections of genomic DNA is using polymerase chain reaction (PCR). Here, using two synthetic oligonucleotide primers, a number

TABLE 1

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholestrol | Transient | Pfeiffer, I. and F. Hook (2004). "Bivalent cholesterol-based coupling of oligonucletides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Polynucleotides may be functionalized using a modified phosphoramidite in the synthesis reaction, which is easily compatible for the addition of reactive groups, such as thiol, of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the target DNA amplified will contain a reactive group for coupling.

The transmembrane pore is preferably a transmembrane protein pore. A transmembrane protein pore is a protein structure that crosses the membrane to some degree. It permits ions driven by an applied potential to flow across or within the membrane. A transmembrane protein pore is typically a polypeptide or a collection of polypeptides that permits ions, such as analyte, to flow from one side of a membrane to the other side of the membrane. However, the transmembrane protein pore does not have to cross the membrane. It may be closed at one end. For instance, the transmembrane pore may form a well in the membrane along which or into which ions may flow. The transmembrane protein pore preferably permits analytes, such as nucleotides, to flow across or within the membrane. The transmembrane protein pore allows a polynucleotide, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F el al (1990) J Mol Biol 215:403-10. Software for performing BLAST analyses is publicly available through the National Center for Biotechnology Information (www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, DI3G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. The variant of SEQ ID NO: 2 has the mutation L88N in addition to all the mutations of MS-B1 and is called MS-B2. The pore used in the invention is preferably MS-(B2)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 3

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July, 4(7):497-505).

The monomer derived from Msp may be labelled with a revealing label. The revealing label may be any suitable label which allows the pore to be detected. Suitable labels include, but are not limited to fluorescent molecules, radio-isotopes, e.g. $^{125}$I, $^{35}$S, enzymes, antibodies, antigens, polynucleotides and ligands such as biotin.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with NaBH$_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homoheptamer) or different (heteroheptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the helicase. The variant preferably comprises one or more reactive cysteine residues that facilitate attachment to the helicase. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a Staphylococcus bacterium. Alternatively, the variant may be expressed in vitro or recombinantly by a bacterium such as Escherichia coli. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135, 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive S⁻ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

Any RecD helicase may be used in accordance with the invention. The structures of RecD helicases are known in the art (FEBS J. 2008 April; 275(8): 1835-51. Epub 2008 Mar. 9. ATPase activity of RecD is essential for growth of the Antarctic *Pseudomonas syringae* Lz4W at low temperature. Satapathy A K, Pavankumar T L, Bhattacharjya S, Sankaranarayanan R, Ray M K; EMS Microbiol Rev. 2009 May; 33(3):657-87. The diversity of conjugative relaxases and its application in plasmid classification. Garcilln-Barcia M P, Francia M V, de la Cruz F; J Biol Chem. 2011 Apr. 8; 286(14):12670-82. Epub 2011 Feb. 2. Functional characterization of the multidomain F plasmid TraI relaxase-helicase. Cheng Y, McNamara D E, Miley M J, Nash R P, Redinbo M R).

The RecD helicase typically comprises the amino acid motif X1-X2-X3-G-X4-X5-X6-X7 (hereinafter called the RecD-like motif I; SEQ ID NO: 8), wherein X1 is G, S or A, X2 is any amino acid. X3 is P, A, S or G, X4 is T, A, V, S or C, X5 is G or A, X6 is K or R and X7 is T or S. X1 is preferably G. X2 is preferably G, I, Y or A. X2 is more preferably G. X3 is preferably P or A. X4 is preferably T, A, V or C. X4 is preferably T, V or C. X5 is preferably G. X6 is preferably K. X7 is preferably T or S. The RecD helicase preferably comprises Q-(X8)₁₆₋₁₈-X1-X2-X3-G-X4-X5-X6-X7 (hereinafter called the extended RecD-like motif I; SEQ ID NOs: 9, 10 and 11 where there are 16, 17 and 18 X8s respectively), wherein X1 to X7 are as defined above and X8 is any amino acid. There are preferably 16 X8 residues (i.e. (X8)₁₆) in the extended RecD-like motif I (SEQ ID NO. 9) Suitable sequences for (X8)₁₆ can be identified in SEQ ID NOs: 18, 21, 24, 25, 28, 30, 32, 35, 37, 39, 41, 42 and 44.

The RecD helicase preferably comprises the amino acid motif G-G-P-G-Xa-G-K-Xb (hereinafter called the RecD motif I; SEQ ID NO: 12) wherein Xa is T, V or C and Xb is T or S. Xa is preferably T. Xb is preferably T. The Rec-D helicase preferably comprises the sequence G-G-P-G-T-G-K-T (SEQ ID NO: 19; see Table 5). The RecD helicase more preferably comprises the amino acid motif Q-(X8)₁₆₋₁₈-G-G-P-G-Xa-G-K-Xb (hereinafter called the extended RecD motif 1, SEQ ID NOs: 13, 14 and 15 where there are 16, 17 and 18 X8s respectively), wherein Xa and Xb are as defined above and X8 is any amino acid. There are preferably 16 X8 residues (i.e. (X8)₁₆) in the extended RecD motif I (SEQ ID NO: 13). Suitable sequences for (X8)₁₆ can be identified in SEQ ID NOs: 18, 21, 24, 25, 28, 30, 32, 35, 37, 39, 41, 42 and 44.

The RecD helicase typically comprises the amino acid motif X1-X2-X3-X4-X5-(X6)₃-Q-X7 (hereinafter called the RecD-like motif V; SEQ ID NO: 16), wherein X1 is Y, W or F, X2 is A. T, S, M, C or V, X3 is any amino acid, X4 is T, N or S, X5 is A, T, G, S, V or 1, X6 is any amino acid and X7 is G or S. X1 is preferably Y. X2 is preferably A, M, C or V. X2 is more preferably A X3 is preferably I, M or L. X3 is more preferably I or L. X4 is preferably T or S. X4 is more preferably T. X5 is preferably A, V or I. X5 is more preferably V or 1. X5 is most preferably V. (X6)₃ is preferably H-K-S, H-M-A, H-G-A or H-R-S. (X6)₃ is more preferably H-K-S. X7 is preferably G. The RecD helicase preferably comprises the amino acid motif Xa-Xb-Xc-Xd-Xe-H-K-S-Q-G (hereinafter called the RecD motif V; SEQ ID NO: 17), wherein Xa is Y, W or F, Xb is A, M, C or V, Xc is I, M or L, Xd is T or S and Xe is V or I. Xa is preferably Y. Xb is preferably A. Xd is preferably T. Xe is preferably V. The RecD helicase preferably comprises (1) RecD-like motifs I and V (SEQ ID NOs: 8 and 12), (2) RecD motif I and RecD-like motif V (SEQ ID NOs: 12 and 16), (3) RecD motifs I and V (SEQ ID NOs. 12 and 17), (4) extended RecD-like motif I and RecD-like motif V (SEQ ID NOs: 9, 10 or 11 and 16), (5) extended RecD motif I and RecD-like motif V (SEQ ID NOs: 13, 14 or 15 and 16) or (6) extended RecD motif I and RecD motif V (SEQ ID NOs: 13, 14 or 15 and 17).

Preferred RecD motifs I are shown in Table 5 below. Preferred RecD-like motifs I are shown in Table 7 below. Preferred RecD-like motifs V are shown in Tables 5 and 7 below.

The RecD helicase is preferably one of the helicases shown in Table 4 below or a variant thereof.

TABLE 4

Preferred RecD helicases and their Accession numbers

| | | |
|---|---|---|
| 1 | NP 295625.1 | exodeoxyribonuclease V subunit RecD [*Deinococcus radiodurans* R1] |
| 2 | YP 604297.1 | helicase RecD/TraA [*Deinococcus geothermalis* DSM 11300] |
| 3 | YP 002786343.1 | exodeoxyribonuclease V subunit alpha [*Deinococcus deserti* VCD115] |
| 4 | 3E1S A | Chain A, Structure Of An N-Terminal Truncation Of *Deinococcus* |
| 5 | YP 004256144.1 | helicase, RecD/TraA family [*Deinococcus proteolyticus* MRP] |
| 6 | YP 004170918.1 | helicase, RecD/TraA family [*Deinococcus maricopensis* DSM 21211] |
| 7 | YP 004256838.1 | helicase, RecD/TraA family [*Deinococcus proteolyticus* MRP] |
| 8 | YP 003885838.1 | helicase, RecD/TraA family [*Cyanothece* sp. PCC 7822] |
| 9 | ZP 08579275.1 | helicase, RecD/TraA family [*Prevotella multisaccharivorax* DSM 17128] |
| 10 | YP 002377692.1 | helicase, RecD/TraA family [*Cyanothece* sp. PCC 7424] |
| 11 | YP 001519318.1 | RecD/TraA family helicase [*Acaryochloris marina* MBIC11017] |
| 12 | YP 003318882.1 | helicase, RecD/TraA family [*Sphaerobacter thermophilus* DSM 20745] |
| 13 | YP 004671137.1 | hypothetical protein SNE A07690 [*Simkania negevensis* Z] |
| 14 | YP 375364.1 | helicase RecD/TraA [*Chlorobium luteolum* DSM 273] >gb|ABB24321.1| |
| 15 | YP 002418908.1 | RecD/TraA family helicase [*Methylobacterium chloromethanicum* CM4] |
| 16 | YP 003065757.1 | Helicase [*Methylobacterium extorquens* DM4] >emb|CAX21689.1| |
| 17 | ZP 00518989.1 | Helicase RecD/TraA [*Crocosphaera watsonii* WH 8501] |
| 18 | ZP 06973397.1 | helicase, RecD/TraA family [*Ktedonobacter racemifer* DSM 44963] |
| 19 | ZP 08486910.1 | helicase, RecD/TraA family [*Methylomicrobium album* BG8] |
| 20 | YP 002015362.1 | RecD/TraA family helicase [*Prosthecochloris aestuarii* DSM 271] |

TABLE 4-continued

Preferred RecD helicases and their Accession numbers

| # | Accession | Description |
|---|---|---|
| 21 | YP 001130786.1 | RecD/TraA family helicase [*Chlorobium phaeovibrioides* DSM 265] |
| 22 | YP 002961258.1 | Helicase [*Methylobacterium extorquens* AM1] >gb|ACS37981.1| |
| 23 | ZP 08772902.1 | helicase, RecD/TraA family [*Thiocapsa marina* 5811] >gb|EGV16093.1| |
| 24 | YP 001637509.1 | RecD/TraA family helicase [*Methylobacterium extorquens* PA1] |
| 25 | ZP 02062824.1 | helicase, RecD/TraA family [*Rickettsiella grylli*] >gb|EDP46829.1| |
| 26 | ZP 08768753.1 | helicase, RecD/TraA family [*Thiocapsa marina 5811*] >gb|EGV20712.1| |
| 27 | YP 001922739.1 | helicase, RecD/TraA family [*Methylobacterium populi* BJ001] |
| 28 | YP 002018300.1 | helicase, RecD/TraA family [*Pelodictyon phaeoclathratiforme* BU-1] |
| 29 | ZP 06245171.1 | helicase, RecD/TraA family [*Victivallis vadensis* ATCC BAA-548] |
| 30 | ZP 08771217.1 | helicase, RecD/TraA family [*Thiocapsa marina* 5811] >gb|EGV17897.1| |
| 31 | ZP 08769899.1 | helicase, RecD/TraA family [*Thiocapsa marina* 5811] >gb|EGV18833.1| |
| 32 | ZP 03727363.1 | Exodeoxyribonuclease V [*Opitutaceae bacterium* TAV2] |
| 33 | ZP 05027797.1 | helicase, RecD/TraA family [*Microcoleus chthonoplastes* PCC 7420] |
| 34 | YP 001521445.1 | RecD/TraA family helicase [*Acaryochloris marina* MBIC11017] |
| 35 | YP 002606149.1 | RecD3 [*Desulfobacterium autotrophicum* HRM2] >gb|ACN17985.1| |
| 36 | YP 003165615.1 | helicase, RecD/TraA family [*Candidatus Accumulibacter phosphatis*] |
| 37 | ZP 01732265.1 | Helicase RecD/TraA [*Cyanothece* sp. CCY0110] >gb|EAZ88318.1| |
| 38 | YP 901533.1 | RecD/TraA family helicase [*Pelobacter propionicus* DSM 2379] |
| 39 | YP 004121205.1 | helicase, RecD/TraA family [*Desulfovibrio aespoeensis* Aspo-2] |
| 40 | YP 911313.1 | RecD/TraA family helicase [*Chlorobium phaeobacteroides* DSM 266] |
| 41 | YP 002424008.1 | RecD/TraA family helicase [*Methylobacterium chloromethanicum*] |
| 42 | YP 320143.1 | helicase RecD/TraA [*Anabaena variabilis* ATCC 29413] |
| 43 | YP 001603050.1 | exodeoxyribonuclease [*Gluconacetobacter diazotrophicus* PA1 5] |
| 44 | ZP 05054956.1 | helicase, RecD/TraA family [*Octadecabacter antarcticus* 307] |
| 45 | YP 003445164.1 | helicase, RecD/TraA family [*Allochromatium vinosum* DSM 180] |
| 46 | NP 490177.1 | exodeoxyribonuclease V, alpha chain [*Nostoc* sp. PCC 7120] |
| 47 | NP 923575.1 | exodeoxyribonuclease V alpha chain [*Gloeobacter violaceus* PCC 7421] |
| 48 | YP 001601244.1 | exodeoxyribonuclease V alpha chain [*Gluconacetobacter diazotrophicus*] |
| 49 | YP 004748470.1 | exodeoxyribonuclease V subunit alpha [*Acidithiobacillus caldus* SM-1] |
| 50 | YP 004863326.1 | helicase, RecD/TraA family [*Candidatus Chloracidobacterium*] |
| 51 | YP 001520750.1 | RecD/TraA family helicase [*Acaryochloris marina* MBIC11017] |
| 52 | YP 003197384.1 | helicase, RecD/TraA family [*Desulfohalobium retbaense* DSM 5692] |
| 53 | ZP 08900128.1 | helicase, RecD/TraA family protein [*Gluconacetobacter oboediens*] |
| 54 | YP 002275391.1 | helicase, RecD/TraA family [*Gluconacetobacter diazotrophicus* PA1 5] |
| 55 | YP 003156740.1 | RecD/TraA family helicase [*Desulfomicrobium baculatum* DSM 4028] |
| 56 | YP 08821817.1 | helicase, RecD/TraA family [*Thiorhodococcus drewsii* AZ1] |
| 57 | ZP 01731986.1 | Helicase RecD/TraA [*Cyanothece* sp. CCY0110] >gb|EAZ88625.1| |
| 58 | YP 001943002.1 | RecD/TraA family helicase [*Chlorobium limicola* DSM 245] |
| 59 | ZP 08318929.1 | hypothetical protein SXCC 04894 [*Gluconacetobacter* sp. SXCC-1] |
| 60 | YP 002017890.1 | RecD/TraA family helicase [*Pelodictyon phaeoclathratiforme* BU-1] |
| 61 | ZP 07972826.1 | RecD/TraA family helicase [*Synechococcus* sp. CB0101] |
| 62 | YP 003189342.1 | DNA helicase RecD/TraA [*Acetobacter pasteurianus* IFO 3283-01] |
| 63 | YP 001959197.1 | RecD/TraA family helicase [*Chlorobium phaeobacteroides* BS1] |
| 64 | ZP 05064957.1 | helicase, RecD/TraA family [*Octadecabacter antarcticus* 238] |
| 65 | YP 001772290.1 | RecD/TraA family helicase [*Methylobacterium* sp. 4-46] |
| 66 | YP 001998378.1 | RecD/TraA family helicase [*Chlorobaculum parvum* NCIB 8327] |
| 67 | YP 001869949.1 | RecD/TraA family helicase [*Nostoc punctiforme* PCC 73102] |
| 68 | ZP 08109907.1 | helicase, RecD/TraA family [*Desulfovibrio* sp. ND132] |
| 69 | ZP 06965850.1 | helicase, RecD/TraA family [*Ktedonobacter racemifer* DSM 44963] |
| 70 | ZP 05428586.1 | helicase, RecD/TraA family [*Clostridium thermocellum* DSM 2360] |
| 71 | ZP 05404007.1 | helicase, RecD/TraA family [*Mitsuokella multacida* DSM 20544] |
| 72 | YP 002992028.1 | helicase, RecD/TraA family [*Desulfovibrio salexigens* DSM 2638] |
| 73 | ZP 02190744.1 | Helicase RecD/TraA [alpha proteobacterium BAL199] |
| 74 | ZP 08959149.1 | RecD/TraA family helicase [*Halomonas* sp. HAL1] >gb|EHA16215.1| |
| 75 | YP 003709145.1 | exodeoxyribonuclease V, alpha subunit [*Waddlia chondrophila* WSU |
| 76 | YP 003528424.1 | helicase, RecD/TraA family [*Nitrosococcus halophilus* Nc4] |
| 77 | ZP 02191403.1 | Helicase RecD/TraA [alpha proteobacterium BAL199] |
| 78 | YP 004802608.1 | helicase, RecD/TraA family [*Streptomyces* sp. SirexAA-E] |
| 79 | CCB91170.1 | uncharacterized protein yrrC [*Waddlia chondrophila* 2032/99] |
| 80 | YP 289811.1 | helicase RecD/TraA [*Thermobifida fusca* YX] >gb|AAZ55788.1| |
| 81 | YP 07015918.1 | helicase, RecD/TraA family [*Desulfonatronospira thiodismutans* ASO3- |
| 82 | YP 004766648.1 | helicase [*Megasphaera elsdenii* DSM 20460] >emb|CCC73821.1| |
| 83 | ZP 04708454.1 | putative exodeoxyribonuclease V [*Streptomyces roseosporus* NRRL |
| 84 | YP 001039578.1 | RecD/TraA family helicase [*Clostridium thermocellum* ATCC 27405] |
| 85 | YP 594664.1 | exonuclease V subunit alpha [*Lawsonia intracellularis* PHE/MN1-00] |
| 86 | NP 662288.1 | exodeoxyribonuclease V, alpha subunit, putative [*Chlorobium tepidum* |
| 87 | ZP 08423994.1 | helicase, RecD/TraA family [*Desulfovibrio africanus* str. Walvis Bay] |
| 88 | YP 007688.1 | putative exodeoxyribonuclease V [*Candidatus Protochlamydia*] |
| 89 | YP 002953244.1 | helicase RecD/TraA family protein [*Desulfovibrio magneticus* RS-1] |
| 90 | ADW05584.1 | helicase, RecD/TraA family [*Streptomyces flavogriseus* ATCC 33331] |
| 91 | ZP 01385982.1 | Helicase RecD/TraA [*Chlorobium ferrooxidans* DSM 13031] |
| 92 | YP 001716965.1 | RecD/TraA family helicase [*Candidatus Desulforudis audaxviator*] |
| 93 | ADL25833.1 | helicase, RecD/TraA family [*Fibrobacter succinogenes* subsp. |
| 94 | YP 002480970.1 | helicase, RecD/TraA family [*Cyanothece* sp. PCC 7425] |
| 95 | YP 004516136.1 | helicase, RecD/TraA family [*Desulfotomaculum kuznetsovii* DSM |
| 96 | ZP 08778308.1 | exodeoxyribonuclease [*Candidatus Odyssella thessalonicensis* L13] |
| 97 | ZP 06825719.1 | RecD/TraA family helicase [*Streptomyces* sp. SPB741] >gb|EDY42267.2| |
| 98 | ZP 05293745.1 | Exodeoxyribonuclease V alpha chain [*Acidithiobacillus caldus* ATCC |

TABLE 4-continued

Preferred RecD helicases and their Accession numbers

| | | |
|---|---|---|
| 99 | YP 480657.1 | helicase RecD/TraA [*Frankia* sp. CcI3] >gb|ABD10928.1|Helicase |
| 100 | ZP 07017628.1 | helicase, RecD/TraA family [*Desulfonatronospira thiodismutans* ASO3-1] |
| 101 | YP 379155.1 | helicase RecD/TraA [*Chlorobium chlorochromatii* CaD3] |
| 102 | YP 004897355.1 | helicase [*Acidaminococcus intestini* RyC-MR95] >gb|AEQ23215.1| |
| 103 | ZP 03311944.1 | hypothetical protein DESPIG 01864 [*Desulfovibrio piger* ATCC 29098] |
| 104 | YP 004783252.1 | RecD/TraA family helicase [*Acidithiobacillus ferrivorans* SS3] |
| 105 | ZP 03928493.1 | helicase [*Acidaminococcus* sp. D21] >gb|EEH89723.1|helicase |
| 106 | ZP 06530901.1 | RecD/TraA family helicase [*Streptomyces lividans* TK24] |
| 107 | ZP 01667371.1 | helicase, RecD/TraA family [*Thermosinus carboxydivorans* Nor1] |
| 108 | ZP 08942446.1 | helicase, RecD/TraA family [*Thiorhodovibrio* sp. 970] >gb|EGZ54636.1| |
| 109 | NP 626969.1 | deoxyribonuclease [*Streptomyces coelicolor* A3(2)] >emb|CAB66276.1| |
| 110 | ADU73817.1 | helicase, RecD/TraA family [*Clostridium thermocellum* DSM 1313] |
| 111 | YP 001157093.1 | RecD/TraA family helicase [*Salinispora tropica* CNB-440] |
| 112 | ZP 02929767.1 | putative exodeoxyribonuclease [*Verrucomicrobium spinosum* DSM 4136] |
| 113 | ZP 08455023.1 | putative exodeoxyribonuclease V [*Streptomyces* sp. Tu6071] |
| 114 | YP 003022840.1 | helicase, RecD/TraA family [*Geobacter* sp. M21] >gb|ACT19082.1| |
| 115 | YP 003549103.1 | helicase, RecD/TraA family [*Coraliomargarita akajimensis* DSM 45221] |
| 116 | YP 001530229.1 | RecD/TraA family helicase [*Desulfococcus oleovorans* Hxd3] |
| 117 | YP 004461132.1 | helicase, RecD/TraA family [*Tepidanaerobacter* sp. Rel] |
| 118 | ZP 08943153.1 | helicase, RecD/TraA family [*Thiorhodovibrio* sp. 970] >gb|EGZ54097.1| |
| 119 | ZP 06560617.1 | helicase, RecD/TraA family [*Megasphaera* genomosp. type 1 str. 28L] |
| 120 | YP 002138036.1 | helicase, RecD/TraA family [*Geobacter bemidjiensis* Bem] |
| 121 | YP 001300657.1 | exonuclease V subunit alpha [*Bacteroides vulgatus* ATCC 8482] |
| 122 | ZP 07303897.1 | exodeoxyribonuclease V, alpha subunit [*Streptomyces viridochromogenes* |
| 123 | YP 003399141.1 | helicase, RecD/TraA family [*Acidaminococcus fermentans* DSM 20731] |
| 124 | YP 389216.1 | RecD/TraA family helicase [*Desulfovibrio alaskensis* G20] |
| 125 | ZP 01085074.1 | Helicase RecD/TraA [*Synechococcus* sp. WH 5701] >gb|EAQ75130.1| |
| 126 | ZP 07271541.1 | exodeoxyribonuclease V, alpha subunit [*Streptomyces* sp. SPB78] |
| 127 | ZP 02731419.1 | helicase, RecD/TraA family protein [*Gemmata obscuriglobus* UQM 2246] |
| 128 | ZP 08287369.1 | deoxyribonuclease [*Streptomyces griseoaurantiacus* M045] |
| 129 | CBX27215.1 | hypothetical protein N47 A12440 [uncultured *Desulfobacterium* sp.] |
| 130 | YP 001530553.1 | RecD/TraA family helicase [*Desulfococcus oleovorans* Hxd3] |
| 131 | ZP 06707995.1 | RecD/TraA family helicase [*Streptomyces* sp. e14] >gb|EFF91117.1| |
| 132 | ZP 06917215.1 | exodeoxyribonuclease V, alpha subunit [*Streptomyces sviceus* ATCC |
| 133 | YP 002955020.1 | helicase RecD/TraA family protein [*Desulfovibrio magneticus* RS-1] |
| 134 | ZP 07985895.1 | putative exodeoxyribonuclease V [*Streptomyces* sp. SA3 actF] |
| 135 | YP 003103858.1 | helicase, RecD/TraA family [*Actinosynnema mirum* DSM 43827] |
| 136 | YP 001826337.1 | putative exodeoxyribonuclease V [*Streptomyces griseus* subsp. *griseus* |
| 137 | NP 826506.1 | exodeoxyribonuclease V [*Streptomyces avermitilis* MA-4680] |
| 138 | ZP 01048465.1 | Helicase RecD/TraA [*Nitrobacter* sp. Nb-311A] >gb|EAQ33584.1| |
| 139 | YP 003761194.1 | helicase, RecD/TraA family [*Nitrosococcus watsonii* C-113] |
| 140 | YP 003681742.1 | RecD/TraA family helicase [*Nocardiopsis dassonvillei* subsp. *dassonvillei* |
| 141 | ZP 08944617.1 | helicase, RecD/TraA family [*Thiorhodovibrio* sp. 970] >gb|EGZ52593.1| |
| 142 | ZP 08803068.1 | DNA-binding protein [*Streptomyces zinciresistens* K42] |
| 143 | ZP 07740397.1 | helicase, RecD/TraA family [*Aminomonas paucivorans* DSM 12260] |
| 144 | YP 003250238.1 | helicase, RecD/TraA family [*Fibrobacter succinogenes* subsp. |
| 145 | ZP 01903329.1 | Helicase RecD/TraA [*Roseobacter* sp. AzwK-3b] >gb|EDM71427.1| |
| 146 | ZP 03641678.1 | hypothetical protein BACCOPRO 00005 [*Bacteroides coprophilus* DSM |
| 147 | ZP 06578909.1 | exodeoxyribonuclease V [*Streptomyces ghanaensis* ATCC 14672] |
| 148 | YP 004652609.1 | protein yrrC [*Parachlamydia acanthamoebae* UV7] >emb|CCB86755.1| |
| 149 | ZP 06299454.1 | hypothetical protein pah c032o017 [*Parachlamydia acanthamoebae* str. |
| 150 | YP 001771030.1 | RecD/TraA family helicase [*Methylobacterium* sp. 4-46] |
| 151 | ZP 08291769.1 | exodeoxyribonuclease V alpha chain [*Chlamydophila psittaci* Cal10] |
| 152 | CCB74558.1 | Exodeoxyribonuclease V [*Streptomyces cattleya* NRRL 8057] |
| 153 | ZP 08077054.1 | helicase, RecD/TraA family [*Phascolarctobacterium* sp. YIT 12067] |
| 154 | ZP 07297625.1 | RecD/TraA family helicase [*Streptomyces hygroscopicus* ATCC 53653] |
| 155 | ZP 08030087.1 | helicase, RecD/TraA family [*Selenomonas artemidis* F0399] |
| 156 | YP 003300321.1 | helicase, RecD/TraA family [*Thermomonospora curvata* DSM 43183] |
| 157 | YP 001535192.1 | RecD/TraA family helicase [*Salinispora arenicola* CNS-205] |
| 158 | NP 829514.1 | RecD/TraA family helicase [*Chlamydophila caviae* GPIC] |
| 159 | ZP 08843685.1 | RecD/TraA family helicase [*Desulfovibrio* sp. 6 1 46AFAA] |
| 160 | ZP 07331538.1 | helicase, RecD/TraA family [*Desulfovibrio fructosovorans* JJ] |
| 161 | YP 003491438.1 | DNA-binding protein [*Streptomyces scabiei* 87.22] >emb|CBG72898.1| |
| 162 | ZP 08073657.1 | helicase, RecD/TraA family [*Methylocystis* sp. ATCC 49242] |
| 163 | ZP 07829281.1 | helicase, RecD/TraA family [*Selenomonas* sp. oral taxon 137 str. F0430] |
| 164 | YP 899880.1 | RecD/TraA family helicase [*Pelobacter propionicus* DSM 2379] |
| 165 | YP 343034.1 | helicase RecD/TraA [*Nitrosococcus oceani* ATCC 19707] |
| 166 | YP 004817633.1 | helicase, RecD/TraA family [*Streptomyces violaceusniger* Tu 4113] |
| 167 | BAJ31218.1 | putative helicase RecD/TraA family protein [*Kitasatospora setae* KM- |
| 168 | YP 578071.1 | helicase RecD/TraA [*Nitrobacter hamburgensis* X14] >gb|ABE63611.1| |
| 169 | ZP 01873510.1 | ATP-dependent exoDNAse (exonuclease V), alpha subunit-helicase |
| 170 | EFE27709.1 | helicase, RecD/TraA family [*Filifactor alocis* ATCC 35896] |
| 171 | YP 220018.1 | putative exodeoxyribonuclease [*Chlamydophila abortus* S26/3] |
| 172 | ZP 07327131.1 | helicase, RecD/TraA family [*Acetivibrio cellulolyticus* CD2] |
| 173 | YP 002480862.1 | helicase, RecD/TraA family [*Desulfovibrio desulfuricans* subsp. |
| 174 | EGK69360.1 | putative exodeoxyribonuclease V subunit alpha [*Chlamydophila abortus* |
| 175 | YP 001967390.1 | helicase RecD/TraA [*Rickettsia monacensis*] >gb|ABO85878.1|helicase |
| 176 | ZP 03754577.1 | hypothetical protein ROSEINA2194 03004 [*Roseburia inulinivorans* |

TABLE 4-continued

Preferred RecD helicases and their Accession numbers

| | | |
|---|---|---|
| 177 | ZP 04608382.1 | helicase [*Micromonospora* sp. ATCC 39149] >gb|EEP74312.1|helicase |
| 178 | YP 001509194.1 | RecD/TraA family helicase [*Frankia* sp. EAN1pec] >gb|ABW14288.1| |
| 179 | ZP 06771382.1 | Exodeoxyribonuclease V [*Streptomyces clavuligerus* ATCC 27064] |
| 180 | ZP 08838047.1 | RecD/TraA family helicase [*Bilophila* sp. 4 1 30] >gb|EGW42429.1| |
| 181 | CBE67477.1 | Helicase, RecD/TraA family [NC10 bacterium 'Dutch sediment'] |
| 182 | YP 001950493.1 | helicase, RecD/TraA family [*Geobacter lovleyi* SZ] >gb|ACD93973.1| |
| 183 | ZP 02192076.1 | Helicase RecD/TraA [alpha proteobacterium BAL199] >gb|EDP61161.1| |
| 184 | ZP 07943852.1 | RecD/TraA family helicase [*Bilophila wadsworthia* 3 1 6] |
| 185 | YP 003652363.1 | helicase, RecD/TraA family [*Thermobispora bispora* DSM 43833] |
| 186 | ZP 05005893.1 | exodeoxyribonuclease V [*Streptomyces clavuligerus* ATCC 27064] |
| 187 | ZP 05065242.1 | helicase, RecD/TraA family [*Octadecabacter antarcticus* 238] |
| 188 | CBL24549.1 | helicase, putative, RecD/TraA family [*Ruminococcus obeum* A2-162] |
| 189 | YP 002499923.1 | RecD/TraA family helicase [*Methylobacterium nodulans* ORS 2060] |
| 190 | YP 002432033.1 | helicase, RecD/TraA family [*Desulfatibacillum alkenivorans* AK-01] |
| 191 | ZP 07286835.1 | exodeoxyribonuclease V, alpha subunit [*Streptomyces* sp. C] |
| 192 | YP 001105553.1 | helicase RecD/TraA [*Saccharopolyspora erythraea* NRRL 2338] |
| 193 | YP 003639317.1 | helicase, RecD/TraA family [*Thermincola* sp. JR] >gb|ADG81416.1| |
| 194 | CBK63520.1 | helicase, putative, RecD/TraA family [*Alistipes shahii* WAL 8301] |
| 195 | ZP 07940306.1 | RecD/TraA family helicase [*Bacteroides* sp. 4 1 36] >gb|EFV24451.1| |
| 196 | ZP 08905541.1 | helicase RecD/TraA family protein [*Desulfovibrio* sp. FW1012B] |
| 197 | CBL07724.1 | helicase, putative, RecD/TraA family [*Roseburia intestinalis* M50/1] |
| 198 | ZP 03729282.1 | helicase, RecD/TraA family [*Dethiobacter alkaliphilus* AHT 1] |
| 199 | YP 001220283.1 | RecD/TraA family helicase [*Acidiphilium cryptum* JF-5] |
| 200 | ZP 05382244.1 | exodeoxyribonuclease V alpha chain [*Chlamydia trachomatis* D(s)2923] |
| 201 | YP 001654372.1 | exodeoxyribonuclease V alpha chain [*Chlamydia trachomatis* 434/Bu] |
| 202 | ZP 04743359.1 | helicase, RecD/TraA family [*Roseburia intestinalis* L1-82] |
| 203 | ZP 08626355.1 | helicase, RecD/TraA family protein [*Acetonema longum* DSM 6540] |
| 204 | YP 004197836.1 | helicase, RecD/TraA family [*Geobacter* sp. M18] >gb|ADW12560.1| |
| 205 | ZP 06415577.1 | helicase, RecD/TraA family [*Frankia* sp. EUN1f] >gb|EFC81619.1| |
| 206 | YP 001618568.1 | exodeoxyribonuclease V [*Sorangium cellulosum* 'So ce 56'] |
| 207 | ZP 05000079.1 | exodeoxyribonuclease V [*Streptomyces* sp. Mg1] >gb|EDX24590.1| |
| 208 | ZP 05346027.3 | helicase, RecD/TraA family [*Bryantella formatexigens* DSM 14469] |
| 209 | ADI10122.1 | exodeoxyribonuclease V [*Streptomyces bingchenggensis* BCW-1] |
| 210 | YP 001220030.1 | RecD/TraA family helicase [*Acidiphilium cryptum* JF-5] |
| 211 | YP 515278.1 | ATP-dependent dsDNA/ssDNA exodeoxyribonuclease V alpha |
| 212 | ZP 04658601.1 | exodeoxyribonuclease V alpha subunit [*Selenomonas flueggei* ATCC |
| 213 | YP 002887661.1 | exodeoxyribonuclease V alpha chain [*Chlamydia trachomatis* |
| 214 | ADH17723.1 | exodeoxyribonuclease V alpha chain [*Chlamydia trachomatis* G/9768] |
| 215 | YP 327831.1 | exodeoxyribonuclease V alpha chain [*Chlamydia trachomatis* A/HAR- |
| 216 | ZP 06604245.1 | RecD/TraA family helicase [*Selenomonas noxia* ATCC 43541] |
| 217 | YP 004819301.1 | helicase, RecD/TraA family [*Thermoanaerobacter wiegelii* Rt8.B1] |
| 218 | ZP 05353404.1 | exodeoxyribonuclease V alpha chain [*Chlamydia trachomatis* 6276] |
| 219 | YP 003340096.1 | exodeoxyribonuclease V [*Streptosporangium roseum* DSM 43021] |
| 220 | YP 003965592.1 | Helicase RecD/TraA [*Paenibacillus polymyxa* SC2] >gb|ADO59524.1| |
| 221 | CCA55822.1 | RecD DNA helicase YrrC [*Streptomyces venezuelae* ATCC 10712] |
| 222 | NP 296681.1 | exodeoxyribonuclease V, alpha subunit [*Chlamydia muridarum* Nigg] |
| 223 | YP 001126584.1 | exodeoxyribonuclease V subunit alpha [*Geobacillus thermodenitrificans* |
| 224 | YP 004584034.1 | RecD/TraA family helicase [Frankia symbiont of *Datisca glomerata*] |
| 225 | ZP 08710208.1 | helicase, RecD/TraA family [*Megasphaera* sp. UPII 135-E] |
| 226 | NP 219535.1 | exodeoxyribonuclease V alpha chain [*Chlamydia trachomatis* D/UW- |
| 227 | ZP 05899746.1 | helicase, RecD/TraA family [*Selenomonas sputigena* ATCC 35185] |
| 228 | ZP 08502002.1 | RecD/TraA family helicase [*Centipeda periodontii* DSM 2778] |
| 229 | ZP 06590805.1 | exodeoxyribonuclease V [*Streptomyces albus* J1074] >gb|EFE81266.1| |
| 230 | YP 003116724.1 | helicase, RecD/TraA family [*Catenulispora acidiphila* DSM 44928] |
| 231 | YP 002953905.1 | helicase RecD/TraA family protein [*Desulfovibrio magneticus* RS-1] |
| 232 | ZP 06250970.1 | helicase, RecD/TraA family [*Prevotella copri* DSM 18205] |
| 233 | ZP 08634959.1 | RecD/TraA family helicase [*Acidiphilium* sp. PM] >gb|EGO93242.1| |
| 234 | YP 846029.1 | RecD/TraA family helicase [*Syntrophobacter fumaroxidans* MPOB] |
| 235 | YP 003476334.1 | helicase, RecD/TraA family [*Thermoanaerobacter italicus* Ab9] |
| 236 | YP 001665762.1 | RecD/TraA family helicase [*Thermoanaerobacter pseudethanolicus* |
| 237 | YP 001662092.1 | RecD/TraA family helicase [*Thermoanaerobacter* sp. X514] |
| 238 | ZP 01462693.1 | helicase, RecD/TraA family [*Stigmatella aurantiaca* DW4/3-1] |
| 239 | ZP 07396437.1 | RecD/TraA family helicase [*Selenomonas* sp. oral taxon 149 str. |
| 240 | ZP 08211163.1 | helicase, RecD/TraA family [*Thermoanaerobacter ethanolicus* JW 200] |
| 241 | YP 003953494.1 | exodeoxyribonuclease v alpha chain [*Stigmatella aurantiaca* DW4/3-1] |
| 242 | YP 003676322.1 | RecD/TraA family helicase [*Thermoanaerobacter mathranii* subsp. |
| 243 | YP 003252104.1 | helicase, RecD/TraA family [*Geobacillus* sp. Y412MC61] |
| 244 | YP 001918465.1 | helicase, RecD/TraA family [*Natranaerobius thermophilus* JW/NM-WN- |
| 245 | ZP 08880276.1 | helicase RecD/TraA [*Saccharopolyspora spinosa* NRRL 18395] |
| 246 | ZP 03991439.1 | possible exodeoxyribonuclease V alpha subunit [*Oribacterium sinus* |
| 247 | AAG23283.1 | probable exodeoxyribonuclease V [*Saccharopolyspora spinosa*] |
| 248 | YP 148414.1 | ATP-dependent exonuclease V [*Geobacillus kaustophilus* HTA426] |
| 249 | YP 714380.1 | putative exodeoxyribonuclease V [*Frankia alni* ACN14a] |
| 250 | CAJ74974.1 | similar to exodeoxyribonuclease V alpha subunit [Candidatus *Kuenenia* |
| 251 | YP 001936773.1 | exodeoxyribonuclease V alpha subunit [*Orientia tsutsugamushi* str. |
| 252 | YP 001248319.1 | helicase RecD/TraA, ATP-dependent exoDNAse (exonuclease V) |
| 253 | YP 004377643.1 | RecD/TraA family helicase [*Chlamydophila pecorum* E58] |
| 254 | CBL20603.1 | helicase, putative, RecD/TraA family [*Ruminococcus* sp. SR1/5] |

TABLE 4-continued

Preferred RecD helicases and their Accession numbers

| # | Accession | Description |
|---|---|---|
| 255 | YP 004421448.1 | helicase RecD/TraA [*Candidatus Rickettsia amblyommii* AaR/SC] |
| 256 | ZP 04857179.1 | conserved hypothetical protein [*Ruminococcus* sp. 5 1 39B FAA] |
| 257 | YP 003670549.1 | helicase, RecD/TraA family [*Geobacillus* sp. C56-T3] >gb|AD125972.1| |
| 258 | YP 003824777.1 | helicase, RecD/TraA family [*Thermosediminibacter oceani* DSM 16646] |
| 259 | ZP 08812773.1 | hypothetical protein DOT 4190 [*Desulfosporosinus* sp. OT] |
| 260 | ZP 07757395.1 | helicase, RecD/TraA family [*Megasphaera micronuciformis* F0359] |
| 261 | ZP 08131496.1 | helicase, RecD/TraA family [*Clostridium* sp. D5] >gb|EGB91345.1| |
| 262 | ZP 04698234.1 | helicase, RecD/TraA family [*Rickettsia* endosymbiont of Ixodes |
| 263 | AEH95290.1 | putative helicase [*Aplysina aerophoba* bacterial symbiont clone |
| 264 | YP 002464026.1 | helicase, RecD/TraA family [*Chloroflexus aggregans* DSM 9485] |
| 265 | YP 461625.1 | exodeoxyribonuclease V subunit alpha [*Syntrophus aciditrophicus* SB] |
| 266 | YP 010116.1 | RecD/TraA family helicase [*Desulfovibrio vulgaris* str. Hildenborough] |
| 267 | YP 001634449.1 | RecD/TraA family helicase [*Chloroflexus aurantiacus* J-10-fl] |
| 268 | YP 004371330.1 | helicase, RecD/TraA family [*Desulfobacca acetoxidans* DSM 11109] |
| 269 | ZP 02432140.1 | hypothetical protein CLOSCI 02385 [*Clostridium scindens* ATCC |
| 270 | YP 001546377.1 | RecD/TraA family helicase [*Herpetosiphon aurantiacus* DSM 785] |
| 271 | ZP 01995753.1 | hypothetical protein DORLON 01748 [*Dorea longicatena* DSM 13814] |
| 272 | ZP 08602931.1 | RecD/TraA family helicase [*Lachnospiraceae bacterium* 5 1 57FAA] |
| 273 | YP 003409821.1 | helicase, RecD/TraA family [*Geodermatophilus obscurus* DSM 43160] |
| 274 | YP 004839529.1 | helicase, RecD/TraA family protein [*Roseburia hominis* A2-183] |
| 275 | ZP 08864377.1 | helicase, RecD/TraA family [*Desulfovibrio* sp. A2] >gb|EGY27050.1| |
| 276 | ZP 05733053.1 | helicase, RecD/TraA family [*Dialister invisus* DSM 15470] |
| 277 | YP 003270118.1 | helicase, RecD/TraA family [*Haliangium ochraceum* DSM 14365] |
| 278 | YP 001717534.1 | RecD/TraA family helicase [*Candidatus Desulforudis audaxviator* |
| 279 | YP 003317021.1 | helicase, RecD/TraA family [*Thermanaerovibrio acidaminovorans* DSM |
| 280 | NP 622165.1 | exonuclease V subunit alpha [*Thermoanaerobacter tengcongensis* MB4] |
| 281 | ZP 05346627.1 | helicase, RecD/TraA family [*Bryantella formatexigens* DSM 14469] |
| 282 | ZP 04451325.1 | hypothetical protein GCWU000182 00609 [*Abiotrophia defectiva* ATCC |
| 283 | NP 623674.1 | exonuclease V subunit alpha [*Thermoanaerobacter tengcongensis* MB4] |
| 284 | ZP 02037832.1 | hypothetical protein BACCAP 03451 [*Bacteroides capillosus* ATCC |
| 285 | EGS35366.1 | helicase, RecD/TraA family [*Finegoldia magna* SY403409CC001050417] |
| 286 | ZP 05092205.1 | helicase, RecD/TraA family [*Carboxydibrachium pacificum* DSM 12653] |
| 287 | ZP 08419913.1 | helicase, RecD/TraA family [*Ruminococcaceae bacterium* D16] |
| 288 | YP 001692807.1 | ATP-dependent exodeoxyribonuclease subunit alpha [*Finegoldia magna* |
| 289 | ZP 07268899.1 | helicase, RecD/TraA family [*Finegoldia magna* ACS-171-V-Col3] |
| 290 | ZP 06598130.1 | helicase, RecD/TraA family [*Oribacterium* sp. oral taxon 078 str. F0262] |
| 291 | YP 003807812.1 | helicase, RecD/TraA family [*Desulfarculus baarsii* DSM 2075] |
| 292 | ZP 02233368.1 | hypothetical protein DORFOR 00200 [*Dorea formicigenerans* ATCC |
| 293 | ZP 02037912.1 | hypothetical protein BACCAP 03531 [*Bacteroides capillosus* ATCC |
| 294 | ZP 07202886.1 | helicase, RecD/TraA family [delta proteobacterium NaphS2] |
| 295 | YP 003152507.1 | helicase, RecD/TraA family [*Anaerococcus prevotii* DSM 20548] |
| 296 | ZP 04861948.1 | helicase, RecD/TraA family [*Clostridium botulinum* D str. 1873] |
| 297 | ZP 07398794.1 | RecD/TraA family helicase [*Peptoniphilus duerdenii* ATCC BAA-1640] |
| 298 | YP 867272.1 | RecD/TraA family helicase [*Magnetococcus* sp. MC-1] |
| 299 | YP 003852761.1 | helicase, RecD/TraA family [*Thermoanaerobacterium* |
| 300 | ZP 07959337.1 | RecD/TraA family Helicase [*Lachnospiraceae bacterium* 8 1 57FAA] |
| 301 | YP 004020312.1 | helicase, RecD/TraA family [*Frankia* sp. EuI1c] >gb|ADP84442.1| |
| 302 | ZP 05055731.1 | helicase, RecD/TraA family [*Verrucomicrobiae bacterium* DG1235] |
| 303 | YP 002936648.1 | helicase, RecD/TraA family [*Eubacterium rectale* ATCC 33656] |
| 304 | ZP 02620578.1 | helicase, RecD/TraA family [*Clostridium botulinum* C str. Eklund] |
| 305 | CBK80090.1 | helicase, putative, RecD/TraA family [*Coprococcus catus* GD/7] |
| 306 | ZP 08865335.1 | hypothetical protein DA2 1615 [*Desulfovibrio* sp. A2] >gb|EGY26242.1| |
| 307 | YP 004309919.1 | helicase, RecD/TraA family [*Clostridium lentocellum* DSM 5427] |
| 308 | YP 004471588.1 | helicase, RecD/TraA family [*Thermoanaerobacterium xylanolyticum* LX- |
| 309 | CBL21608.1 | helicase, putative, RecD/TraA family [*Ruminococcus* sp. SR1/5] |
| 310 | YP 003844493.1 | helicase, RecD/TraA family [*Clostridium cellulovorans* 743B] |
| 311 | ZP 07321245.1 | helicase, RecD/TraA family [*Finegoldia magna* BVS033A4] |
| 312 | YP 699450.1 | RecD/TraA family helicase [*Clostridium perfringens* SM101] |
| 313 | ZP 03781777.1 | hypothetical protein RUMHYD 01213 [*Blautia hydrogenotrophica* DSM |
| 314 | YP 002435820.1 | helicase, RecD/TraA family [*Desulfovibrio vulgaris* str. 'Miyazaki F'] |
| 315 | ZP 02042737.1 | hypothetical protein RUMGNA 03541 [*Ruminococcus gnavus* ATCC |
| 316 | YP 004003526.1 | helicase, recd/traa family [*Caldicellulosiruptor owensensis* OL] |
| 317 | ZP 04666257.1 | helicase [*Clostridiales bacterium* 1 7 47 FAA] >gb|EEQ62058.1| |
| 318 | YP 004025165.1 | helicase, recd/traa family [*Caldicellulosiruptor kronotskyensis* 2002] |
| 319 | YP 003937377.1 | DNA-binding protein [*Clostridium sticklandii* DSM 519] |
| 320 | ZP 03777575.1 | hypothetical protein CLOHYLEM 04627 [*Clostridium hylemonae* DSM |
| 321 | ZP 02089268.1 | hypothetical protein CLOBOL 06837 [*Clostridium bolteae* ATCC BAA- |
| 322 | ZP 06946532.1 | RecD/TraA family helicase [*Finegoldia magna* ATCC 53516] |
| 323 | ZP 03762681.1 | hypothetical protein CLOSTASPAR 06723 [*Clostridium asparagiforme* |
| 324 | ZP 08933657.1 | RecD/TraA family helicase [*Peptoniphilus indolicus* ATCC 29427] |
| 325 | YP 003759289.1 | UvrD/REP helicase [*Dehalogenimonas lykanthroporepellens* BL-DC-9] |
| 326 | ZP 02865223.1 | helicase, RecD/TraA family [*Clostridium perfringens* C str. JGS1495] |
| 327 | YP 002315104.1 | ATP-dependent exoDNAse (exonuclease V) subunit alpha-helicase |
| 328 | YP 003820655.1 | helicase, RecD/TraA family [*Clostridium saccharolyticum* WM1] |
| 329 | NP 563091.1 | helicase, RecD/TraA family [*Clostridium perfringens* str. 13] |
| 330 | ZP 02631593.1 | helicase, RecD/TraA family [*Clostridium perfringens* E str. JGS1987] |
| 331 | YP 754748.1 | exodeoxyribonuclease V [*Syntrophomonas wolfei* subsp. *wolfei* str. |
| 332 | YP 002574552.1 | RecD/TraA family helicase [*Caldicellulosiruptor bescii* DSM 6725] |

TABLE 4-continued

Preferred RecD helicases and their Accession numbers

| | | |
|---|---|---|
| 333 | ZP 02641429.1 | helicase, RecD/TraA family [*Clostridium perfringens* NCTC 8239] |
| 334 | YP 004121351.1 | ATP-dependent RecD/TraA family DNA helicase [*Desulfovibrio* |
| 335 | EGC82456.1 | helicase, RecD/TraA family [*Anaerococcus prevotii* ACS-065-V-Col13] |
| 336 | YP 004199699.1 | ATP-dependent RecD/TraA family DNA helicase [*Geobacter* sp. M18] |
| 337 | ZP 08616225.1 | RecD/TraA family helicase [*Lachnospiraceae bacterium* 1 4 56FAA] |
| 338 | ZP 06113685.1 | helicase, RecD/TraA family [*Clostridium hathewayi* DSM 13479] |
| 339 | ZP 03799911.1 | hypothetical protein COPCOM 02174 [*Coprococcus comes* ATCC |
| 340 | YP 003841513.1 | helicase, RecD/TraA family [*Caldicellulosiruptor obsidiansis* OB47] |
| 341 | YP 004464342.1 | RecD/TraA family ATP-dependent DNA helicase [*Mahella australiensis* |
| 342 | YP 696854.1 | RecD/TraA family helicase [*Clostridium perfringens* ATCC 13124] |
| 343 | ZP 03167580.1 | hypothetical protein RUMLAC 01253 [*Ruminococcus lactaris* ATCC |
| 344 | YP 847893.1 | hypothetical protein Sfum 3789 [*Syntrophobacter fumaroxidans* MPOB] |
| 345 | ZP 05430222.1 | helicase, RecD/TraA family [*Clostridium thermocellum* DSM 2360] |
| 346 | ZP 02211142.1 | hypothetical protein CLOBAR 00740 [*Clostridium bartlettii* DSM |
| 347 | YP 388414.2 | UvrD/REP helicase [*Desulfovibrio alaskensis* G20] >gb\|ABB38719.2\| |
| 348 | YP 003807790.1 | ATP-dependent RecD/TraA family DNA helicase [*Desulfarculus baarsii* |
| 349 | YP 003993640.1 | helicase, recd/traa family [*Caldicellulosiruptor hydrothermalis* 108] |
| 350 | YP 001038644.1 | ATP-dependent RecD/TraA family DNA helicase [*Clostridium* |
| 351 | ZP 06597516.1 | helicase, RecD/TraA family [*Oribacterium* sp. oral taxon 078 str. F0262] |
| 352 | YP 004799933.1 | helicase, RecD/TraA family [*Caldicellulosiruptor lactoaceticus* 6A] |
| 353 | YP 001179036.1 | RecD/TraA family helicase [*Caldicellulosiruptor saccharolyticus* DSM |
| 354 | ZP 03759537.1 | hypothetical protein CLOSTASPAR 03561 [*Clostridium asparagiforme* |
| 355 | ZP 04564978.1 | exodeoxyribonuclease subunit V alpha [*Mollicutes bacterium* D7] |
| 356 | YP 001557372.1 | RecD/TraA family helicase [*Clostridium phytofermentans* ISDg] |
| 357 | ZP 02094462.1 | hypothetical protein PEPMIC 01228 [*Parvimonas micra* ATCC 33270] |
| 358 | ZP 02428906.1 | hypothetical protein CLORAM 02328 [*Clostridium ramosum* DSM |
| 359 | ZP 07367500.1 | exodeoxyribonuclease V alpha subunit [*Pediococcus acidilactici* DSM |
| 360 | YP 004027603.1 | helicase, recd/traa family [*Caldicellulosiruptor kristjanssonii* 177R1B] |
| 361 | ZP 02420394.1 | hypothetical protein ANACAC 03011 [*Anaerostipes caccae* DSM 14662] |
| 362 | ZP 08707741.1 | helicase, RecD/TraA family [*Veillonella* sp. oral taxon 780 str. F0422] |
| 363 | ZP 08532372.1 | helicase, RecD/TraA family [*Caldalkalibacillus thermarum* TA2.A1] |
| 364 | YP 003119362.1 | helicase, RecD/TraA family [*Catenulispora acidiphila* DSM 44928] |
| 365 | YP 001821497.1 | RecD/TraA family helicase [*Opitutus terrae* PB90-1] >gb\|ACB77897.1\| |
| 366 | YP 003427313.1 | ATP-dependent exoDNAse V [*Bacillus pseudofirmus* OF4] |
| 367 | ZP 07036639.1 | helicase, RecD/TraA family [*Peptoniphilus* sp. oral taxon 386 str. F0131] |
| 368 | YP 004091069.1 | helicase, RecD/TraA family [*Ethanoligenens harbinense* YUAN-3] |
| 369 | ZP 06197663.1 | RecD/TraA family helicase [*Pediococcus acidilactici* 7 4] |
| 370 | ZP 06409626.1 | helicase, RecD/TraA family [*Clostridium hathewayi* DSM 13479] |
| 371 | ZP 08339411.1 | RecD/TraA family helicase [*Lachnospiraceae bacterium* 2 1 46FAA] |
| 372 | YP 004883288.1 | putative nuclease [*Oscillibacter valericigenes* Sjm18-20] |
| 373 | YP 004396914.1 | RecD/TraA family helicase [*Clostridium botulinum* BKT015925] |
| 374 | YP 002950456.1 | helicase, RecD/TraA family [*Geobacillus* sp. WCH70] >gb\|ACS25190.1\| |
| 375 | YP 387402.1 | UvrD/REP helicase [*Desulfovibrio alaskensis* G20] >gb\|ABB37707.1\| |
| 376 | YP 002771377.1 | hypothetical protein BBR47 18960 [*Brevibacillus brevis* NBRC 100599] |
| 377 | ZP 01173819.1 | YrrC [*Bacillus* sp. NRRL B-14911] >gb\|EAR63466.1\|YrrC [*Bacillus* sp. |
| 378 | ZP 02074502.1 | hypothetical protein CLOL250 01272 [*Clostridium* sp. L2-50] |
| 379 | ZP 02951515.1 | helicase, RecD/TraA family [*Clostridium butyricum* 5521] |
| 380 | YP 07326697.1 | helicase, RecD/TraA family [*Acetivibrio cellulolyticus* CD2] |
| 381 | ZP 08662208.1 | helicase, RecD/TraA family [*Streptococcus* sp. oral taxon 056 str. F0418] |
| 382 | ZP 07709630.1 | helicase, RecD/TraA family protein [*Bacillus* sp. m3-13] |
| 383 | ZP 08151018.1 | RecD/TraA family helicase [*Lachnospiraceae bacterium* 4 1 37FAA] |
| 384 | ZP 05855961.1 | helicase, RecD/TraA family [*Blautia hansenii* DSM 20583] |
| 385 | ZP 08333468.1 | RecD/TraA family helicase [*Lachnospiraceae bacterium* 6 1 63FAA] |
| 386 | ZP 01967327.1 | hypothetical protein RUMTOR 00874 [*Ruminococcus torques* ATCC |
| 387 | ZP 07843612.1 | helicase, RecD/TraA family [*Staphylococcus hominis* subsp. *hominis* |
| 388 | ZP 08335292.1 | RecD/TraA family helicase [*Lachnospiraceae bacterium* 9 1 43BFAA] |
| 389 | YP 002425519.1 | helicase, RecD/TraA family [*Acidithiobacillus ferrooxidans* ATCC |
| 390 | ZP 08074741.1 | Exodeoxyribonuclease V [*Methylocystis* sp. ATCC 49242] |
| 391 | ZP 03288021.1 | hypothetical protein CLONEX 00200 [*Clostridium nexile* DSM 1787] |
| 392 | NP 349457.1 | ATP-dependent exoDNAse (exonuclease V), alpha subunit, RecD |
| 393 | YP 535621.1 | exodeoxyribonuclease V alpha chain [*Lactobacillus salivarius* UCC118] |
| 394 | YP 001514053.1 | RecD/TraA family helicase [*Alkaliphilus oremlandii* OhILAs] |
| 395 | ZP 06059658.1 | RecD/TraA family helicase [*Streptococcus* sp. 2 1 36FAA] |
| 396 | ZP 04059935.1 | helicase, RecD/TraA family [*Staphylococcus hominis* SK119] |
| 397 | AEN87514.1 | Exodeoxyribonuclease V-like protein [*Bacillus megaterium* WSH-002] |
| 398 | YP 003988429.1 | helicase, RecD/TraA family [*Geobacillus* sp. Y4.1MC1] |
| 399 | NP 781026.1 | exodeoxyribonuclease V alpha chain [*Clostridium tetani* E88] |
| 400 | YP 004707292.1 | hypothetical protein CXIVA 02230 [*Clostridium* sp. SY8519] |
| 401 | YP 003590771.1 | helicase, RecD/TraA family [*Bacillus tusciae* DSM 2912] |
| 402 | ZP 03708405.1 | hypothetical protein CLOSTMETH 03166 [*Clostridium methylpentosum* |
| 403 | ZP 07904646.1 | RecD/TraA family helicase [*Eubacterium saburreum* DSM 3986] |
| 404 | ZP 08463854.1 | exodeoxyribonuclease V alpha subunit [*Desmospora* sp. 8437] |
| 405 | YP 003339261.1 | exodeoxyribonuclease V [*Streptosporangium roseum* DSM 43021] |
| 406 | ZP 07356412.1 | helicase, RecD/TraA family [*Desulfovibrio* sp. 3 1 syn3] |
| 407 | YP 004310482.1 | helicase, RecD/TraA family [*Clostridium lentocellum* DSM 5427] |
| 408 | YP 003565054.1 | helicase, RecD/TraA family [*Bacillus megaterium* QM B1551] |
| 409 | EGM50608.1 | helicase, RecD/TraA family [*Lactobacillus salivarius* GJ-24] |
| 410 | ZP 07454758.1 | RecD/TraA family helicase [*Eubacterium yurii* subsp. *margaretiae* ATCC |

TABLE 4-continued

Preferred RecD helicases and their Accession numbers

| | | |
|---|---|---|
| 411 | CBL17987.1 | helicase, putative, RecD/TraA family [*Ruminococcus* sp. 18P13] |
| 412 | ZP 03917092.1 | possible exodeoxyribonuclease V alpha subunit [*Anaerococcus* |
| 413 | ZP 08757131.1 | helicase, RecD/TraA family [*Parvimonas* sp. oral taxon 393 str. F0440] |
| 414 | EGL99465.1 | recD-like DNA helicase YrrC [*Lactobacillus salivarius* NIAS840] |
| 415 | ZP 01725995.1 | hypothetical protein BB14905 09550 [*Bacillus* sp. B14905] |
| 416 | YP 003590260.1 | helicase, RecD/TraA family [*Bacillus tusciae* DSM 2912] |
| 417 | ZP 07206301.1 | helicase, RecD/TraA family [*Lactobacillus salivarius* ACS-116-V-Col5a] |
| 418 | YP 001680910.1 | exodeoxyribonuclease V, alpha chain, RecD [*Heliobacterium* |
| 419 | YP 003821341.1 | helicase, RecD/TraA family [*Clostridium saccharolyticum* WM1] |
| 420 | ZP 08005791.1 | YrrC protein [*Bacillus* sp. 2 A 57 CT2] >gb\|EFV77442.1\|YrrC protein |
| 421 | YP 002560662.1 | exodeoxyribonuclease V alpha subunit [*Macrococcus caseolyticus* |
| 422 | ZP 05028653.1 | hypothetical protein MC7420 1174 [*Microcoleus chthonoplastes* PCC |
| 423 | CCC58043.1 | RecD-like DNA helicase YrrC [*Caloramator australicus* RC3] |
| 424 | YP 001699482.1 | exodeoxyribonuclease V-like protein [*Lysinibacillus sphaericus* C3-41] |
| 425 | ZP 02616886.1 | helicase, RecD/TraA family [*Clostridium botulinum* Bf] |
| 426 | XP 001420006.1 | predicted protein [*Ostreococcus lucimarinus* CCE9901] |
| 427 | YP 001779796.1 | RecD/TraA family helicase [*Clostridium botulinum* B1 str. Okra] |
| 428 | YP 001389532.1 | RecD/TraA family helicase [*Clostridium botulinum* F str. Langeland] |
| 429 | ZP 02993715.1 | hypothetical protein CLOSPO 00789 [*Clostridium sporogenes* ATCC |
| 430 | ZP 01964108.1 | hypothetical protein RUMOBE 01832 [*Ruminococcus obeum* ATCC |
| 431 | ZP 03227028.1 | ATP-dependent exonuclease V [*Bacillus coahuilensis* m4-4] |
| 432 | YP 001252714.1 | helicase, RecD/TraA family [*Clostridium botulinum* A str. ATCC 3502] |
| 433 | YP 001307573.1 | RecD/TraA family helicase [*Clostridium beijerinckii* NCIMB 8052] |
| 434 | ZP 08091201.1 | hypothetical protein HMPREF9474 02952 [*Clostridium symbiosum* |
| 435 | CBZ01987.1 | recd-like DNA helicase YrrC [*Clostridium botulinum* H04402 065] |
| 436 | ZP 06620580.1 | helicase, RecD/TraA family [*Turicibacter sanguinis* PC909] |
| 437 | ZP 02612165.1 | helicase, RecD/TraA family [*Clostridium botulinum* NCTC 2916] |
| 438 | ZP 03464124.1 | hypothetical protein BACPEC 03225 [*Bacteroides pectinophilus* ATCC |
| 439 | ZP 05427870.1 | helicase, RecD/TraA family [*Eubacterium saphenum* ATCC 49989] |
| 440 | ZP 04819493.1 | exodeoxyribonuclease V alpha subunit [*Staphylococcus epidermidis* |
| 441 | CBL16176.1 | helicase, putative, RecD/TraA family [*Ruminococcus bromii* L2-63] |
| 442 | CBK73489.1 | helicase, putative, RecD/TraA family [*Butyrivibrio fibrisolvens* 16/4] |
| 443 | XP 003081706.1 | Dehydrogenase kinase (ISS) [*Ostreococcus tauri*] >emb\|CAL56230.1\| |
| 444 | ZP 06425429.1 | helicase, RecD/TraA family [*Peptostreptococcus anaerobius* 653-L] |
| 445 | ZP 08539226.1 | helicase, RecD/TraA family [*Oribacterium* sp. oral taxon 108 str. F0425] |
| 446 | ZP 04008608.1 | exodeoxyribonuclease V alpha chain [*Lactobacillus salivarius* ATCC |
| 447 | ZP 08525848.1 | helicase, RecD/TraA family [*Streptococcus anginosus* SK52] |
| 448 | ZP 08245897.1 | helicase, RecD/TraA family [*Streptococcus parauberis* NCFD 2020] |
| 449 | ZP 06290581.1 | helicase, RecD/TraA family [*Peptoniphilus lacrimalis* 315-B1 |
| 450 | ZP 08680798.1 | RecD/TraA family helicase [*Sporosarcina newyorkensis* 2681] |
| 451 | YP 002802482.1 | helicase, RecD/TraA family [*Clostridium botulinum* A2 str. Kyoto] |
| 452 | YP 001449573.1 | RecD/TraA family helicase [*Streptococcus gordonii* str. Challis substr. |
| 453 | ZP 01862085.1 | hypothetical protein BSG1 18450 [*Bacillus* sp. SG-1] >gb\|EDL62855.1\| |
| 454 | YP 001785497.1 | RecD/TraA family helicase [*Clostridium botulinum* A3 str. Loch Maree] |
| 455 | EFV89168.1 | exodeoxyribonuclease V alpha chain [*Staphylococcus epidermidis* |
| 456 | ZP 07956105.1 | RecD/TraA family helicase [*Lachnospiraceae bacterium* 5 1 63FAA] |
| 457 | ZP 03055915.1 | helicase, RecD/TraA family [*Bacillus pumilus* ATCC 7061] |
| 458 | ZP 04797338.1 | exodeoxyribonuclease V alpha subunit [*Staphylococcus epidermidis* |
| 459 | EGS77340.1 | helicase, RecD/TraA family [*Staphylococcus epidermidis* VCU105] |
| 460 | YP 004478259.1 | hypothetical protein STP 0139 [*Streptococcus parauberis* KCTC 11537] |
| 461 | ZP 08605488.1 | RecD/TraA family helicase [*Lachnospiraceae bacterium* |
| 462 | ZP 08643227.1 | hypothetical protein BRLA c44940 [*Brevibacillus laterosporus* LMG |
| 463 | ZP 06875615.1 | putative exonuclease with DNA/RNA helicase motif [*Bacillus subtilis* |
| 464 | ZP 04678546.1 | helicase, RecD/TraA family [*Staphylococcus warneri* L37603] |
| 465 | ZP 06613101.1 | conserved hypothetical protein [*Staphylococcus epidermidis* |
| 466 | ZP 02441706.1 | hypothetical protein ANACOL 00987 [*Anaerotruncus colihominis* DSM |
| 467 | YP 188759.1 | RecD/TraA family helicase [*Staphylococcus epidermidis* RP62A] |
| 468 | ZP 02440294.1 | hypothetical protein CLOSS21 02797 [*Clostridium* sp. SS2/1] |
| 469 | YP 001919909.1 | helicase, RecD/TraA family [*Clostridium botulinum* E3 str. Alaska E43] |
| 470 | YP 001884722.1 | helicase, RecD/TraA family [*Clostridium botulinum* B str. Eklund 17B] |
| 471 | ZP 02039032.1 | hypothetical protein BACCAP 04681 [*Bacteroides capillosus* ATCC |
| 472 | ZP 07093704.1 | helicase, RecD/TraA family [*Peptoniphilus* sp. oral taxon 836 str. F0141] |
| 473 | YP 001487615.1 | exodeoxyribonuclease V alpha subunit [*Bacillus pumilus* SAFR-032] |
| 474 | NP 764857.1 | deoxyribonuclease [*Staphylococcus epidermidis* ATCC 12228] |
| 475 | YP 804665.1 | ATP-dependent RecD/TraA family DNA helicase [*Pediococcus* |
| 476 | NP 942288.1 | exodeoxyribonuclease V alpha chain [*Synechocystis* sp. PCC 6803] |
| 477 | ZP 07054718.1 | RecD/TraA family helicase [*Listeria grayi* DSM 20601] >gb\|EFI83599.1\| |
| 478 | EHA31059.1 | hypothetical protein BSSC8 15020 [*Bacillus subtilis* subsp. *subtilis* str. |
| 479 | CBL39055.1 | helicase, putative, RecD/TraA family [butyrate-producing bacterium |
| 480 | EGF05416.1 | exodeoxyribonuclease V alpha subunit [*Streptococcus sanguinis* SK1057] |
| 481 | YP 003974155.1 | putative exonuclease [*Bacillus atrophaeus* 1942] >gb\|ADP33224.1\| |
| 482 | ZP 07822731.1 | helicase, RecD/TraA family [*Peptoniphilus harei* ACS-146-V-Sch2b] |
| 483 | ZP 06348052.1 | helicase, RecD/TraA family [*Clostridium* sp. M62/1] >gb\|EFE10725.1\| |
| 484 | ZP 05394746.1 | helicase, RecD/TraA family [*Clostridium carboxidivorans* P7] |
| 485 | YP 004204562.1 | putative exonuclease [*Bacillus subtilis* BSn5] >dbj\|BAI86231.1\| |
| 486 | EGG96535.1 | helicase, RecD/TraA family [*Staphylococcus epidermidis* VCU121] |
| 487 | YP 003471518.1 | Exodeoxyribonuclease V subunit alpha [*Staphylococcus lugdunensis* |
| 488 | ZP 04820712.1 | helicase, RecD/TraA family [*Clostridium botulinum* E1 str. 'BoNT E |

TABLE 4-continued

Preferred RecD helicases and their Accession numbers

| | | |
|---|---|---|
| 489 | EGF05816.1 | exodeoxyribonuclease V alpha subunit [*Streptococcus sanguinis* SK1] |
| 490 | YP 002634323.1 | hypothetical protein Sca 1231 [*Staphylococcus carnosus* subsp. *carnosus* |
| 491 | YP 301232.1 | ATP-dependent exonuclease V alpha subunit [*Staphylococcus* |
| 492 | ZP 07841151.1 | helicase, RecD/TraA family [*Staphylococcus caprae* C87] |
| 493 | NP 846841.1 | helicase [*Bacillus anthracis* str. Ames] >ref|YP 021271.2|helicase |
| 494 | NP 390625.1 | exonuclease with DNA/RNA helicase motif [*Bacillus subtilis* subsp. |
| 495 | ZP 07910981.1 | RecD/TraA family helicase [*Staphylococcus lugdunensis* M23590] |
| 496 | YP 001727916.1 | exonuclease V subunit alpha [*Leuconostoc citreum* KM20] |
| 497 | YP 030537.1 | helicase [*Bacillus anthracis* str. Sterne] >ref|ZP 00394720.1|COG0507: |
| 498 | ZP 04291295.1 | Helicase, RecD/TraA [*Bacillus cereus* R309803] >gb|EEK76998.1| |
| 499 | YP 002751754.1 | putative helicase [*Bacillus cereus* 03BB102] >gb|ACO31219.1|putative |
| 500 | ZP 08091585.1 | hypothetical protein HMPREF9474 03336 [*Clostridium symbiosum* |

The RecD helicase is more preferably one of the helicases shown in Table 5 below or a variant thereof. The RecD helicase more preferably comprises the sequence of one of the helicases shown in Table 5, i.e. one of SEQ ID NOs. 18, 21, 24, 25, 28, 30, 32, 35, 37, 39, 41, 42 and 44, or a variant thereof.

TABLE 5

More preferred RecD helicases

| SEQ ID NO | Name | Source | NCBI ref | % Identity to RecD2 Dra | RecD motif I (SEQ ID NO:) | ReeD-like motif V (SEQ ID NO:) |
|---|---|---|---|---|---|---|
| 18 | RecD 2 Ama | *Acaryochloris marina* | NCBI Reference Sequence: YP 001521445.1 | 29.8 | GGPGTGKT (19) | WAVTIH KSQG (20) |
| 21 | RecD 2 Dde | *Deinococcus deserti* | NCBI Reference Sequence: YP 002786343.1 | 12.3 | GGPGTGKS (22) | YALTVH RAQG (23) |
| 24 | RecD 2 Dge | *Deinococcus geothermalis* | NCBI Reference Sequence: YP_604297.1 | 79 | GGPGTGKS (22) | YALTVH RAQG (23) |
| 25 | RecD 2 Hoc | *Haliangium ochraceum* DSM | NCBI Reference Sequence: YP_003270118.1 | 30 | GGPGVGKT (26) | YAISVH KSQG (27) |
| 28 | RecD 2 Nth | *Natranaerobius thermophilus* | NCBI Reference Sequence: YP_001918465.1 | 28.6 | GGPGTGKT (19) | YCISVH KSQG (29) |
| 30 | RecD 2 Oan | *Octadecabacter antarcticus* | NCBI Reference Sequence: ZP_05054956.1 | 31 | GGPGVGKT (26) | YAATIH KSQG (31) |
| 32 | RecD 2 Str | *Salinispora tropica* | NCBI Reference Sequence: YP_001157093.1 | 31.7 | GGPGCGKS (33) | YAMTIH RSQG (34) |
| 35 | RecD 2 Dth | *Desulfonatronospira thiodismutans* | NCBI Reference Sequence: ZP_07015918.1 | 27.6 | GGPGTGKS (22) | YAVSIH KSQG (36) |
| 37 | RecD 2 Nha | *Nitrosococcus halophilus* | NCBI Reference Sequence: YP_003528424.1 | 29.8 | GGPGVGKT (26) | YATSVH KSQG (38) |
| 39 | RecD 2 Dre | *Desulfohalobium retbaense* | NCBI Reference Sequence: YP_003197384.1 | 32 | GGPGTGKT (19) | YAVSVH KSQG (40) |
| 41 | RecD 2 Dra | *Deinococcus radiidurans* | NCBI Reference Sequence: NP_295625.1 | — | GGPGTGKS (22) | YALTVH RAQG (23) |
| 42 | RecD 2 Cch | *Chlorobium chlorochromatii* | NCBI Reference Sequence: YP_379155.1 | 30.8 | GGPGVGKT (26) | YATSIHK SQG (43) |
| 44 | RecD | *Deinococcus* | NCBI Reference | 67 | GGPGTGKS (22) | YALTVH |

TABLE 5-continued

More preferred RecD helicases

| SEQ ID NO | Name | Source | NCBI ref | % Identity to RecD2RecD Dra | RecD motif I (SEQ ID NO:) | ReeD-like motif V (SEQ ID NO:) |
|---|---|---|---|---|---|---|
| 2 | Dma | *maricopensis* | Sequence: YP_004170918.1 | | | RGQG (45) |

All sequences in the above Table comprise a RecD-like motif V (as shown). Only SEQ ID NOs: 18, 25, 28, 30, 35, 37, 39 and 42 comprise a RecD motif V (as shown).

The RecD helicase is preferably a TraI helicase or a TraI subgroup helicase. TraI helicases and TraI subgroup helicases may contain two RecD helicase domains, a relaxase domain and a C-terminal domain. The TraI subgroup helicase is preferably a TrwC helicase. The TraI helicase or TraI subgroup helicase is preferably one of the helicases shown in Table 6 below or a variant thereof.

The TraI helicase or a TraI subgroup helicase typically comprises a RecD-like motif I as defined above (SEQ ID NO: 8) and/or a RecD-like motif V as defined above (SEQ ID NO. 16). The TraI helicase or a TraI subgroup helicase preferably comprises both a RecD-like motif I (SEQ ID NO: 8) and a RecD-like motif V (SEQ ID NO: 16). The TraI helicase or a TraI subgroup helicase typically further comprises one of the following two motifs:

The amino acid motif H-$(X1)_2$-X2-R-$(X3)_{5-12}$-H-X4-H (hereinafter called the MobF motif III; SEQ ID NOs: 46 to 53 show all possible MobF motifs III (including all possible numbers of X3)), wherein X1 and X3 are any amino acid and X2 and X4 are independently selected from any amino acid except D, E, K and R. $(X1)_2$ is of course X1a-X1b. X1a and X1b can be the same of different amino acid. X1a is preferably D or E. X1b is preferably T or D. $(X1)_2$ is preferably DT or ED. $(X1)_2$ is most preferably DT. The 5 to 12 amino acids in $(X3)_{5-12}$ can be the same or different. X2 and X4 are independently selected from G, P, A, V, L, I, M, C, F, Y, W, H, Q, N, S and T. X2 and X4 are preferably not charged. X2 and X4 are preferably not H. X2 is more preferably N, S or A. X2 is most preferably N. X4 is most preferably F or T. $(X3)_{5-12}$ is preferably 6 or 10 residues in length (SEQ ID NOs: 47 and 51). Suitable embodiments of $(X3)_{5-12}$ can be derived from SEQ ID NOs: 61, 65, 69, 73, 74, 82, 86, 90, 94, 98, 102, 110, 112, 113, 114, 117, 121, 124, 125, 129, 133, 136, 140, 144, 147, 151, 152, 156, 160, 164 and 168 shown in Table 7 below (i.e. all but SEQ ID NOs: 78 and 106). Preferred embodiments of the MobF motif III are shown in Table 7 below.

The amino acid motif G-X1-X2-X3-X4-X5-X6-X7-H-$(X8)_{6-12}$-H-X9 (hereinafter called the MobQ motif III; SEQ ID NOs: 54 to 60 show all possible MobQ motifs III (including all possible numbers of X8)), wherein X1, X2, X3, X5, X6, X7 and X9 are independently selected from any amino acid except D, E, K and R, X4 is D or E and X8 is any amino acid. X1, X2, X3, X5, X6, X7 and X9 are independently selected from G, P, A, V, L, I, M, C, F, Y, W, H, Q, N, S and T. X1, X2, X3, X5, X6, X7 and X9 are preferably not charged X1, X2, X3, X5, X6, X7 and X9 are preferably not H. The 6 to 12 amino acids in $(X8)_{6-12}$ can be the same or different. Suitable embodiments of $(X8)_{6-12}$ can be derived from SEQ ID NOs: 78 and 106 shown in Table 7 below. Preferred embodiments of the MobF motif III are shown in Table 7 below.

TABLE 6

Preferred TraI helicases and TraI subgroup helicases and their Accession Numbers

| | | |
|---|---|---|
| 1 | NP 061483.1 | conjugal transfer nickase/helicase TraI [Plasmid F] |
| 2 | NP 862951.1 | conjugal transfer nickase/helicase TraI [*Escherichia coli*] |
| 3 | ZP 03047597. | type IV secretion-like conjugative transfer relaxase protein TraI |
| 4 | YP 00203889 | conjugal transfer nickase/helicase TraI [*Salmonella enterica* subsp. |
| 5 | YP 00173989 | type IV secretion-like conjugative transfer relaxase protein TraI |
| 6 | YP 190115.1 | conjugal transfer nickase/helicase TraI [*Escherichia coli*] |
| 7 | ZP 08368984. | conjugative transfer relaxase protein TraI [*Escherichia coli* TA271] |
| 8 | EFW76779.1 | IncF plasmid conjugative transfer DNA-nicking and unwinding |
| 9 | YP 00382905 | type IV secretion-like conjugative transfer relaxase protein |
| 10 | EGX11991.1 | conjugative transfer relaxase protein TraI [*Escherichia coli* |
| 11 | YP 00191916 | type IV secretion-like conjugative transfer relaxase protein TraI |
| 12 | ZP 03051102. | type IV secretion-like conjugative transfer relaxase protein TraI |
| 13 | EGH36328.1 | IncF plasmid conjugative transfer DNA-nicking and unwinding |
| 14 | ZP 03030171. | type IV secretion-like conjugative transfer relaxase protein TraI |
| 15 | EGB88794.1 | conjugative transfer relaxase protein TraI [*Escherichia coli* MS 117-3] |
| 16 | YP 00382916 | nickase/helicase [*Escherichia coli*] >gb\|ADL14054.1\|TraI |
| 17 | EFU55615.1 | conjugative transfer relaxase protein TraI [*Escherichia coli* MS 16-3] |
| 18 | EGB69775.1 | conjugative transfer relaxase TraI [*Escherichia coli* TW10509] |
| 19 | YP 00303405 | conjugal transfer nickase/helicase TraI [*Escherichia coli* Vir68] |
| 20 | YP 443956.1 | conjugal transfer nickase/helicase TraI [*Escherichia coli*] |
| 21 | YP 00196541 | oriT-specific relaxase; helicase [*Escherichia coli*] >gb\|ABG29544.1\| |
| 22 | AAQ98619.1 | DNA helicase I [*Escherichia coli*] |
| 23 | YP 00240109 | conjugal transfer nickase/helicase TraI [*Escherichia coli* S88] |
| 24 | YP 00233218 | conjugal transfer nickase/helicase TraI [*Escherichia coli* O127:H6 str. |
| 25 | CBG27820.1 | DNA helicase I [*Escherichia coli*] |
| 26 | YP 00171193 | conjugal transfer nickase/helicase TraI [*Escherichia coli*] |
| 27 | EGI88721.1 | conjugative transfer relaxase protein TraI [*Shigella* dysenteriae 155- |

TABLE 6-continued

Preferred TraI helicases and TraI subgroup helicases and their Accession Numbers

| # | Accession | Description |
|---|---|---|
| 28 | ZP 06661276. | conjugative transfer relaxase TraI [*Escherichia coli* B088] |
| 29 | YP 00148121 | conjugal transfer nickase/helicase TraI [*Escherichia coli* APEC O1] |
| 30 | ZP 03070008. | type IV secretion-like conjugative transfer relaxase protein TraI |
| 31 | YP 00191934 | type IV secretion-like conjugative transfer relaxase protein TraI |
| 32 | YP 00129475 | conjugal transfer nickase/helicase TraI [*Escherichia coli*] |
| 33 | YP 00323254 | conjugal transfer protein TraI [*Escherichia coli* O26:H1] str. 11368] |
| 34 | YP 00323781 | nickase [*Escherichia coli* O111:H-str. 11128] >dbj|BAI39380.1| |
| 35 | ADR29948.1 | conjugative transfer relaxase protein TraI [*Escherichia coli* O83:H1 |
| 36 | YP 00181654 | conjugal transfer nickase/helicase TraI [*Escherichia coli* 1520] |
| 37 | ZP 07104698. | conjugative transfer relaxase protein TraI [*Escherichia coli* MS 119-7] |
| 38 | ZP 06988741. | conjugal transfer nickase/helicase TraI [*Escherichia coli* FVEC1302] |
| 39 | YP 00322510 | putative TraI protein [*Escherichia coli* O103:H2 str. 12009] |
| 40 | AEE59988.1 | IncF transfer nickase/helicase protein TraI [*Escherichia coli* |
| 41 | EFZ76933.1 | conjugative transfer relaxase protein TraI [*Escherichia coli* RN587/1] |
| 42 | YP 00487008 | protein TraI [*Escherichia coli*] >gb|AEP03777.1|TraI [*Escherichia* |
| 43 | ZP 08376536. | conjugative transfer relaxase protein TraI [*Escherichia coli* H591] |
| 44 | YP 538737.1 | DNA helicase I [*Escherichia coli* UTI89] >ref|ZP 03035119.1|type |
| 45 | NP 052981.1 | conjugal transfer nickase/helicase TraI [Plasmid R100] |
| 46 | YP 00329403 | conjugal transfer nickase/helicase [*Escherichia coli* ETEC H10407] |
| 47 | YP 00240597 | conjugal transfer protein TraI [*Escherichia coli* UMN026] |
| 48 | ZP 08344394. | conjugative transfer relaxase protein TraI [*Escherichia coli* H736] |
| 49 | ZP 06648569. | conjugal transfer nickase/helicase TraI [*Escherichia coli* FVEC1412] |
| 50 | CBJ04377.1 | DNA helicase I (TraI) (EC 3.6.1.—) [*Escherichia coli* ETEC H10407] |
| 51 | YP 00332919 | TraI [*Klebsiella pneumoniae*] >gb|ACK98846.1|TraI [*Klebsiella* |
| 52 | ADN74088.1 | conjugal transfer nickase/helicase TraI [*Escherichia coli* UM146] |
| 53 | YP 00351762 | TraI [*Klebsiella pneumoniae*] >gb|ADD63581.1|TraI [*Klebsiella* |
| 54 | YP 788091.1 | conjugal transfer nickase/helicase TraI [*Escherichia coli*] |
| 55 | P22706.1 | RecName: Full = Multifunctional conjugation protein TraI; Includes: |
| 56 | EGC09761.1 | conjugative transfer relaxase TraI [*Escherichia coli* E1167] |
| 57 | EGX11419.1 | conjugative transfer relaxase protein TraI [*Escherichia coli* |
| 58 | YP 00393764 | protein TraI (DNA helicase I) [*Escherichia coli*] >emb|CBX35963.1| |
| 59 | EGW83369.1 | conjugative transfer relaxase protein TraI [*Escherichia coli* |
| 60 | EGB59895.1 | conjugative transfer relaxase TraI [*Escherichia coli* M863] |
| 61 | EFZ69441.1 | conjugative transfer relaxase protein TraI [*Escherichia coli* |
| 62 | EFU44479.1 | conjugative transfer relaxase protein TraI [*Escherichia coli* MS |
| 63 | YP 406350.1 | oriT nicking and unwinding protein, fragment [*Shigella boydii* |
| 64 | NP 085415.1 | oriT nicking and unwinding protein, fragment [*Shigella flexneri* |
| 65 | EGW99614.1 | conjugative transfer relaxase protein TraI [*Escherichia coli* |
| 66 | EGK37046.1 | conjugative transfer relaxase protein TraI [*Shigella flexneri* K- |
| 67 | EFW60434.1 | IncF plasmid conjugative transfer DNA-nicking and unwinding |
| 68 | ZP 07678376.1 | conjugative transfer relaxase protein TraI [*Shigella dysenteriae* |
| 69 | EFW49146.1 | IncF plasmid conjugative transfer DNA-nicking and unwinding |
| 70 | AEG39580.1 | IncF plasmid conjugative transfer DNA-nicking and unwinding |
| 71 | NP 490592.1 | conjugal transfer nickase/helicase TraI [*Salmonella typhimurium* |
| 72 | EFW56310.1 | IncF plasmid conjugative transfer DNA-nicking and unwinding |
| 73 | YP 271768.1 | conjugal transfer nickase/helicase TraI [*Salmonella enterica*] |
| 74 | EGP21913.1 | Protein traI [*Escherichia coli* PCN033] |
| 75 | EGR70911.1 | conjugal transfer nickase/helicase TraI [*Escherichia coli* |
| 76 | EGB84217.1 | conjugative transfer relaxase protein TraI [*Escherichia coli* MS |
| 77 | ZP 07119795.1 | conjugative transfer relaxase protein TraI [*Escherichia coli* MS |
| 78 | YP 313447.1 | oriT nicking and unwinding protein, fragment [*Shigella sonnei* |
| 79 | EFU49447.1 | conjugative transfer relaxase protein TraI [*Escherichia coli* MS |
| 80 | ZP 07197893.1 | conjugative transfer relaxase protein TraI [*Escherichia coli* MS |
| 81 | ZP 08386420.1 | conjugative transfer relaxase protein TraI [*Escherichia coli* |
| 82 | ZP 07246816.1 | conjugative transfer relaxase protein TraI [*Escherichia coli* MS |
| 83 | YP 406123.1 | oriT nicking and unwinding protein, fragment [*Shigella* |
| 84 | EFZ55097.1 | conjugative transfer relaxase protein TraI [*Shigella sonnei* 53G] |
| 85 | YP 002213911.1 | conjugative transfer relaxase protein TraI [*Salmonella enterica* |
| 86 | YP 001716148.1 | conjugative transfer oriT nicking-unwinding protein [*Salmonella* |
| 87 | EGE32684.1 | conjugative transfer oriT nicking-unwinding protein [*Salmonella* |
| 88 | EFZ60917.1 | conjugative transfer relaxase protein TraI [*Escherichia coli* LT- |
| 89 | EGB40000.1 | conjugative transfer relaxase TraI [*Escherichia coli* H120] |
| 90 | CAH64717.1 | putative DNA helicase I [uncultured bacterium] |
| 91 | ZP 08351681.1 | conjugative transfer relaxase protein TraI [*Escherichia coli* |
| 92 | ZP 08351622.1 | conjugative transfer relaxase protein TraI [*Escherichia coli* |
| 93 | YP 001338645.1 | conjugal transfer nickase/helicase TraI [*Klebsiella pneumoniae* |
| 94 | EGK29111.1 | conjugative transfer relaxase protein TraI [*Shigella flexneri* K- |
| 95 | NP 858382.1 | oriT nicking and unwinding protein [*Shigella flexneri* 2a str. |
| 96 | EGT71209.1 | hypothetical protein C22711 5245 [*Escherichia coli* O104:H4 |
| 97 | YP 003560496.1 | oriT nicking-unwinding [*Klebsiella pneumoniae*] |
| 98 | YP 003517517.1 | TraI [*Klebsiella pneumoniae*] >ref|YP 004249929.1|IncF |
| 99 | ZP 06015312.1 | conjugal transfer nickase/helicase TraI [*Klebsiella pneumoniae* |
| 100 | EGJ92351.1 | conjugative transfer relaxase protein TraI [*Shigella flexneri* K- |
| 101 | YP 003754133.1 | conjugal transfer nickase/helicase TraI [*Klebsiella pneumoniae*] |
| 102 | ADA76996.1 | OriT nicking and unwinding protein [*Shigella flexneri* 2002017] |
| 103 | YP 001154759.1 | conjugal transfer nickase/helicase TraI [*Yersinia pestis* Pestoides |
| 104 | YP 093987.1 | conjugal transfer nickase/helicase TraI [*Yersinia pestis*] |
| 105 | EGB74535.1 | conjugative transfer relaxase protein TraI [*Escherichia coli* MS |

TABLE 6-continued

Preferred TraI helicases and TraI subgroup helicases and their Accession Numbers

| | | |
|---|---|---|
| 106 | EGX15096.1 | protein traI domain protein [*Escherichia coli* TX1999] |
| 107 | ZP 07778521.1 | traI domain protein [*Escherichia coli* 2362-75] >gb\|EFR18955.1\| |
| 108 | EGB44795.1 | DNA helicase TraI [*Escherichia coli* H252] |
| 109 | ZP 07192950.1 | putative conjugative transfer relaxase protein TraI [*Escherichia* |
| 110 | ZP 07692602.1 | putative conjugative transfer relaxase protein TraI [*Escherichia* |
| 111 | ZP 07212721.1 | putative conjugative transfer relaxase protein TraI [*Escherichia* |
| 112 | ZP 07122964.1 | putative conjugative transfer relaxase protein TraI [*Escherichia* |
| 113 | ZP 06641688.1 | conjugal transfer nickase/helicase TraI [*Serratia odorifera* DSM |
| 114 | ZP 07213112.1 | putative conjugative transfer relaxase protein TraI [*Escherichia* |
| 115 | ZP 07125330.1 | putative conjugative transfer relaxase protein TraI [*Escherichia* |
| 116 | AAA98086.1 | helicase I [Plasmid F] >gb\|AAC44187.1\|TraI* [*Escherichia* |
| 117 | ZP 07692570.1 | DNA helicase TraI [*Escherichia coli* MS 145-7] |
| 118 | EGB44794.1 | conjugative relaxase domain-containing protein [*Escherichia coli* |
| 119 | CBA76609.1 | conjugal transfer nickase/helicase [*Arsenophonus nasoniae*] |
| 120 | YP 004831100.1 | conjugal transfer nickase/helicase TraI [*Serratia marcescens*] |
| 121 | AEJ60155.1 | conjugal transfer protein TraI [*Escherichia coli* UMNF18] |
| 122 | EGX24402.1 | conjugative transfer relaxase protein TraI [*Escherichia coli* |
| 123 | AAM90727.1 | TraI [*Salmonella enterica* subsp. *enterica* serovar *Typhi*] |
| 124 | ZP 08374850.1 | conjugative transfer relaxase protein TraI [*Escherichia coli* |
| 125 | CBY99022.1 | conjugal transfer nickase/helicase TraI [*Salmonella enterica* |
| 126 | ZP 02347591.1 | conjugative transfer relaxase protein TraI [*Salmonella enterica* |
| 127 | YP 001144265.1 | TraI protein [*Aeromonas salmonicida* subsp. *salmonicida* A449] |
| 128 | YP 001144345.1 | TraI protein [*Aeromonas salmonicida* subsp. *salmonicida* A449] |
| 129 | YP 003717559.1 | putative TraI DNA helicase I [*Escherichia coli* ETEC 1392/75] |
| 130 | ZP 08351623.1 | protein TraI (DNA helicase I) [*Escherichia coli* M605] |
| 131 | ZP 06658914.1 | conjugative transfer relaxase TraI [*Escherichia coli* B185] |
| 132 | YP 002291232.1 | TraI protein [*Escherichia coli* SE11] >dbj\|BAG80410.1\|TraI |
| 133 | EFZ47384.1 | protein traI domain protein [*Escherichia coli* E128010] |
| 134 | EGX19478.1 | protein traI domain protein [*Escherichia coli* STEC S1191] |
| 135 | YP 002527579.1 | hypothetical protein pO103 123 [*Escherichia coli*] |
| 136 | EGX15095.1 | protein traI domain protein [*Escherichia coli* TX1999] |
| 137 | EFZ47387.1 | protein traI domain protein [*Escherichia coli* E128010] |
| 138 | ZP 06193648.1 | protein TraI [*Serratia odorifera* 4Rx13] >gb\|EFA13747.1\|protein |
| 139 | EGB39999.1 | conjugative relaxase domain-containing protein [*Escherichia coli* |
| 140 | YP 003739388.1 | conjugal transfer nickase/helicase [*Erwinia billingiae* Eb661] |
| 141 | YP 002539341.1 | TraI [*Escherichia coli*] >gb\|ACM18376.1\|TraI [*Escherichia coli*] |
| 142 | BAA31818.1 | helicase I [*Escherichia coli* O157:H7 str. Sakai] |
| 143 | ADA76995.1 | OriT nicking and unwinding protein [*Shigella flexneri* 2002017] |
| 144 | EFZ45075.1 | protein traI domain protein [*Escherichia coli* E128010] |
| 145 | ZP 05940744.1 | conjugal transfer protein TraI [*Escherichia coli* O157:H7 str. |
| 146 | NP 858381.1 | oriT nicking and unwinding protein [*Shigella flexneri* 2a str. 301] |
| 147 | YP 325658.1 | DNA helicase [*Escherichia coli* O157:H7 EDL933] |
| 148 | EFZ04572.1 | TraI protein [*Salmonella enterica* subsp. *enterica* serovar |
| 149 | YP 209287.1 | TraI protein [*Salmonella enterica* subsp. *enterica* serovar |
| 150 | YP 001598090.1 | hypothetical protein pOU7519 37 [*Salmonella enterica* subsp. |
| 151 | EGY27955.1 | DNA helicase [*Candidatus Regiella insecticola* R5.15] |
| 152 | ZP 02775703.2 | protein TraI [*Escherichia coli* O157:H7 str. EC4113] |
| 153 | ZP 02802536.2 | protein TraI (DNA helicase I) [*Escherichia coli* O157:H7 str. |
| 154 | ZP 07779988.1 | traI domain protein [*Escherichia coli* 2362-75] >gb\|EFR17488.1\| |
| 155 | ZP 08386421.1 | protein TraI (DNA helicase I) [*Escherichia coli* H299] |
| 156 | 1P4D A | Chain A, F Factor Trai Relaxase Domain >pdb\|1P4D\|B Chain B, |
| 157 | 2A0I A | Chain A, F Factor Trai Relaxase Domain Bound To F Orit |
| 158 | EFZ47389.1 | protein traI domain protein [*Escherichia coli* E128010] |
| 159 | YP 004118615.1 | conjugative transfer relaxase protein TraI [*Pantoea* sp. At-9b] |
| 160 | YP 004119632.1 | conjugative transfer relaxase protein TraI [*Pantoea* sp. At-9b] |
| 161 | EGW99739.1 | protein traI domain protein [*Escherichia coli* G58-1] |
| 162 | YP 004821631.1 | conjugative transfer relaxase protein TraI [*Enterobacter asburiae* |
| 163 | YP 001165588.1 | exonuclease V subunit alpha [*Enterobacter* sp. 638] |
| 164 | YP 003602677.1 | conjugative transfer relaxase protein TraI [*Enterobacter cloacae* |
| 165 | YP 311531.1 | hypothetical protein SSON 2674 [*Shigella sonnei* VSs046] |
| 166 | NP 073254.1 | hypothetical protein pKDSC50 p30 [*Salmonella enterica* subsp. |
| 167 | 2Q7T A | Chain A, Crystal Structure Of The F Plasmid Trai Relaxase |
| 168 | EGB84260.1 | conjugative relaxase domain protein [*Escherichia coli* MS 60-1] |
| 169 | ZP 07119794.1 | conjugative relaxase domain protein [*Escherichia coli* MS 198-1] |
| 170 | EGB74274.1 | conjugative relaxase domain protein [*Escherichia coli* MS 57-2] |
| 171 | ZP 04533197.1 | helicase I [*Escherichia* sp. 3 2 53FAA] >gb\|EEH89372.1\| |
| 172 | EFU49424.1 | conjugative relaxase domain protein [*Escherichia coli* MS 153-1] |
| 173 | EFZ60914.1 | protein traI domain protein [*Escherichia coli* LT-68] |
| 174 | CBK86956.1 | conjugative relaxase domain, TrwC/TraI family [*Enterobacter* |
| 175 | YP 313450.1 | oriT nicking and unwinding protein, fragment [*Shigella sonnei* |
| 176 | EGP22056.1 | hypothetical protein PPECC33 45560 [*Escherichia coli* PCN033] |
| 177 | ZP 04533202.1 | TraI protein [*Escherichia* sp. 3 2 53FAA] >gb\|EEH89366.1\|TraI |
| 178 | ZP 07248320.1 | DNA helicase TraI [*Escherichia coli* MS 146-1] >gb\|EFK88152.1\| |
| 179 | EFZ45103.1 | protein traI domain protein [*Escherichia coli* E128010] |
| 180 | YP 003502675.1 | ATP-dependent exoDNAse (exonuclease V), alpha subunit- |
| 181 | ZP 04533172.1 | predicted protein [*Escherichia* sp. 3 2 53FAA] >gb\|EEH89397.1\| |
| 182 | YP 406124.1 | putative DNA helicase I, fragment [*Shigella dysenteriae* Sd197] |
| 183 | ZP 04533171.1 | conserved hypothetical protein [*Escherichia* sp. 3 2 53FAA] |

TABLE 6-continued

Preferred TraI helicases and TraI subgroup helicases and their Accession Numbers

| | | |
|---|---|---|
| 184 | ZP 07192951.1 | DNA helicase TraI [*Escherichia coli* MS 196-1] >gb|EFI85454.1| |
| 185 | YP 001853797.1 | putative conjugative transfer protein TraI [*Vibrio tapetis*] |
| 186 | YP 002261511.1 | protein TraI (DNA helicase I) [*Aliivibrio salmonicida* LFI1238] |
| 187 | NP 762615.1 | conjugative transfer relaxase protein TraI [*Vibrio vulnificus*] |
| 188 | YP 001393155.1 | putative conjugative transfer protein TraI [*Vibrio vulnificus*] |
| 189 | EGB74536.1 | DNA helicase TraI [*Escherichia coli* MS 57-2] |
| 190 | NP 932226.1 | putative conjugative transfer protein TraI [*Vibrio vulnificus*] |
| 191 | YP 001557030.1 | conjugative transfer relaxase protein TraI [*Shewanella baltica* |
| 192 | ADT96679.1 | conjugative transfer relaxase protein TraI [*Shewanella baltica* |
| 193 | YP 001911094.1 | TraI protein [*Erwinia tasmaniensis* Et1/99] >emb|CAO94972.1| |
| 194 | YP 002360275.1 | conjugative transfer relaxase protein TraI [*Shewanella baltica* |
| 195 | AEG13610.1 | conjugative transfer relaxase protein TraI [*Shewanella baltica* |
| 196 | EFZ04571.1 | TraI protein [*Salmonella enterica* subsp. *enterica* serovar |
| 197 | ZP 01813760.1 | putative conjugative transfer protein TraI [*Vibrionales bacterium* |
| 198 | YP 002360333.1 | conjugative transfer relaxase protein TraI [*Shewanella baltica* |
| 199 | YP 001557007.1 | conjugative transfer relaxase protein TraI [*Shewanella baltica* |
| 200 | YP 002364244.1 | conjugative transfer relaxase protein TraI [*Shewanella baltica* |
| 201 | YP 209286.1 | TraI protein [*Salmonella enterica* subsp. *enterica* serovar |
| 202 | YP 015476.1 | DNA helicase TraI [*Photobacterium profundum* SS9] |
| 203 | YP 001355447.1 | conjugative transfer relaxase protein TraI [*Shewanella baltica* |
| 204 | EHC04201.1 | conjugative transfer relaxase protein TraI [*Shewanella baltica* |
| 205 | ZP 06188936.1 | conjugative transfer relaxase protein TraI [*Legionella* |
| 206 | ZP 06157867.1 | IncF plasmid conjugative transfer DNA-nicking and unwinding |
| 207 | ZP 06157920.1 | IncF plasmid conjugative transfer DNA-nicking and unwinding |
| 208 | ZP 08351743.1 | protein TraI (DNA helicase I) [*Escherichia coli* M605] |
| 209 | ZP 08738328.1 | putative conjugative transfer protein TraI [*Vibrio tubiashii* ATCC |
| 210 | YP 003993727.1 | incf plasmid conjugative transfer DNA-nicking and unwinding |
| 211 | ZP 06157811.1 | IncF plasmid conjugative transfer DNA-nicking and unwinding |
| 212 | YP 003915110.1 | putative conjugative transfer protein TraI [*Legionella* |
| 213 | YP 122194.1 | hypothetical protein plpp0039 [*Legionella pneumophila* str. Paris] |
| 214 | ZP 07197892.1 | conjugative relaxase domain protein [*Escherichia coli* MS 185-1] |
| 215 | ZP 05884791.1 | putative conjugative transfer protein TraI [*Vibrio coralliilyticus* |
| 216 | ZP 07222592.1 | type-F conjugative transfer system pilin acetylase TraX |
| 217 | 3FLD A | Chain A, Crystal Structure Of The TraI C-Terminal Domain |
| 218 | EGT71207.1 | hypothetical protein C22711 5243 [*Escherichia coli* O104:H4 str. |
| 219 | ZP 05440093.1 | conjugal transfer nickase/helicase TraI [*Escherichia sp.* 4 1 40B] |
| 220 | EGX24451.1 | protein traI domain protein [*Escherichia coli* TX1999] |
| 221 | EFZ55098.1 | traI domain protein [*Shigella sonnei* 53G] |
| 222 | YP 003933505.1 | DNA methylase [*Pantoea vagans* C9-1] >gb|ADO08159.1| |
| 223 | AAA83930.1 | traI [Plasmid F] |
| 224 | ADQ53972.1 | putative conjugative transfer protein [*Vibrio harveyi*] |
| 225 | ZP 07778522.1 | traI domain protein [*Escherichia coli* 2362-75] >gb|EFR18956.1| |
| 226 | ZP 07192561.1 | conserved domain protein [*Escherichia coli* MS 196-1] |
| 227 | AAW64824.1 | oriT nicking and unwinding protein [*Shigella flexneri*] |
| 228 | NP 085414.1 | oriT nicking and unwinding protein, fragment [*Shigella flexneri* |
| 229 | ADA76994.1 | OriT nicking and unwinding protein [*Shigella flexneri* 2002017] |
| 230 | ZP 07197891.1 | conjugative relaxase domain protein [*Escherichia coli* MS 185-1] |
| 231 | EFU44520.1 | conjugative relaxase domain protein [*Escherichia coli* MS 110-3] |
| 232 | ZP 07222591.1 | conjugative relaxase domain protein [*Escherichia coli* MS 78-1] |
| 233 | YP 406349.1 | oriT nicking and unwinding protein, fragment [*Shigella boydii* |
| 234 | YP 406122.1 | oriT nicking and unwinding protein, fragment [*Shigella* |
| 235 | EFW49145.1 | conjugal transfer nickase/helicase TraI [*Shigella dysenteriae* CDC |
| 236 | ZP 07246817.1 | conjugative relaxase domain protein [*Escherichia coli* MS 146-1] |
| 237 | YP 004250852.1 | putative protein traI (DNA helicase I) [*Vibrio nigripulchritudo*] |
| 238 | EFZ60915.1 | protein traI domain protein [*Escherichia coli* LT-68] |
| 239 | YP 617529.1 | TrwC protein [*Sphingopyxis alaskensis* RB2256] |
| 240 | ZP 01813650.1 | ATP-dependent exoDNAse, alpha subunit [*Vibrionales bacterium* |
| 241 | ZP 01813651.1 | ATP-dependent exoDNAse, alpha subunit [*Vibrionales bacterium* |
| 242 | NP 052850.1 | hypothetical protein QpDV p09 [*Coxiella burnetii*] |
| 243 | CAA75825.1 | hypothetical protein [*Coxiella burnetii*] |
| 244 | YP 002302593.1 | DNA helicase [*Coxiella burnetii* CbuK Q154] >gb|ACJ21266.1| |
| 245 | YP 003502676.1 | TraI [*Escherichia coli* O55:H7 str. CB9615] >gb|ADD59692.1| |
| 246 | YP 001649308.1 | putative protein traI [*Coxiella burnetii* 'MSU Goat Q177'] |
| 247 | YP 001423428.2 | DNA helicase [*Coxiella burnetii* Dugway 5J108-111] |
| 248 | YP 001595803.1 | putative protein traI [*Coxiella burnetii* RSA 331] |
| 249 | NP 052342.1 | hypothetical protein QpH1 p10 [*Coxiella burnetii*] |
| 250 | ZP 01863208.1 | hypothetical protein ED21 17597 [*Erythrobacter sp.* SD-21] |
| 251 | ZP 08645753.1 | conjugal transfer protein TraA [*Acetobacter tropicalis* NBRC |
| 252 | YP 497456.1 | TrwC protein [*Novosphingobium aromaticivorans* DSM 12444] |
| 253 | AAL78346.1 | DNA helicase I [*Escherichia coli*] |
| 254 | EFW60435.1 | conjugal transfer nickase/helicase TraI [*Shigella flexneri* CDC |
| 255 | YP 001235537.1 | exonuclease V subunit alpha [*Acidiphilium cryptum* JF-5] |
| 256 | ZP 05038212.1 | hypothetical protein S7335 4654 [*Synechococcus sp.* PCC 7335] |
| 257 | ZP 08897263.1 | exonuclease V subunit alpha [*Gluconacetobacter oboediens* |
| 258 | NP 049139.1 | DNA helicase [*Novosphingobium aromaticivorans*] |
| 259 | YP 004390567.1 | conjugative relaxase domain-containing protein [*Alicycliphilus* |
| 260 | ZP 07678069.1 | TrwC protein [*Ralstonia sp.* 5 7 47FAA] >ref|ZP 08896172.1| |
| 261 | YP 974028.1 | TrwC protein [*Acidovorax sp.* JS42] >gb|ABM44293.1|TrwC |

TABLE 6-continued

Preferred TraI helicases and TraI subgroup helicases and their Accession Numbers

| # | Accession | Description |
|---|---|---|
| 262 | YP 001869867.1 | mobilization protein TraI-like protein [*Nostoc punctiforme* PCC |
| 263 | YP 718086.1 | DNA helicase [*Sphingomonas* sp. KA1] >dbj|BAF03374.1|DNA |
| 264 | YP 004534199.1 | TrwC protein [*Novosphingobium* sp. PP1Y] >emb|CCA92381.1| |
| 265 | ZP 08701842.1 | TrwC protein [*Citromicrobium* sp. JLT1363] |
| 266 | YP 003602886.1 | hypothetical protein ECL B116 [*Enterobacter cloacae* subsp. |
| 267 | ZP 06861556.1 | TrwC protein [*Citromicrobium bathyomarinum* JL354] |
| 268 | NP 542915.1 | putative TraC protein [*Pseudomonas putida*] >emb|CAC86855.1| |
| 269 | YP 457045.1 | TrwC protein [*Erythrobacter litoralis* HTCC2594] |
| 270 | YP 122325.1 | hypothetical protein plpl0032 [*Legionella pneumophila* str. Lens] |
| 271 | YP 004030608.1 | DNA helicase I TraI [*Burkholderia rhizoxinica* HKI 454] |
| 272 | YP 457732.1 | TrwC protein [*Erythrobacter litoralis* HTCC2594] |
| 273 | ZP 01039301.1 | TrwC protein [*Erythrobacter* sp. NAP1] >gb|EAQ29772.1|TrwC |
| 274 | YP 737083.1 | TrwC protein [*Shewanella* sp. MR-7] >gb|ABI42026.1|TrwC |
| 275 | ZP 05040239.1 | hypothetical protein S7335 1207 [*Synechococcus* sp. PCC 7335] |
| 276 | AAP57243.1 | putative TraC protein [*Pseudomonas putida*] |
| 277 | NP 942625.1 | TrwC [*Xanthomonas citri*] >ref|ZP 06705283.1|TraI protein |
| 278 | 1OMH A | Chain A, Conjugative Relaxase Trwc In Complex With Orit Dna. |
| 279 | ZP 06485934.1 | TrwC protein [*Xanthomonas campestris* pv. *vasculorum* |
| 280 | 1OSB A | Chain A, Conjugative Relaxase Trwc In Complex With Orit Dna. |
| 281 | ZP 08207479.1 | conjugative relaxase region-like protein [*Novosphingobium* |
| 282 | 2CDM A | Chain A, The Structure Of Trwc Complexed With A 27-Mer Dna |
| 283 | ZP 01731779.1 | hypothetical protein CY0110 01035 [*Cyanothece* sp. CCY0110] |
| 284 | NP 644759.1 | TrwC protein [*Xanthomonas axonopodis* pv. *citri* str. 306] |
| 285 | ZP 06732867.1 | TraI protein [*Xanthomonas fuscans* subsp. *aurantifolii* str. ICPB |
| 286 | YP 361538.1 | putative TraI protein [*Xanthomonas campestris* pv. *vesicatoria* str. |
| 287 | CBJ36129.1 | putative traC, type IV secretion system [*Ralstonia solanacearum* |
| 288 | YP 001260099.1 | conjugative relaxase region-like protein [*Sphingomonas wittichii* |
| 289 | YP 001451611.1 | putative type IV conjugative transfer system coupling protein |
| 290 | ZP 08208941.1 | conjugative relaxase region-like protein [*Novosphingobium* |
| 291 | AAO84912.1 | DNA helicase I [*Escherichia coli*] |
| 292 | YP 002515847.1 | DNA relaxase/conjugal transfer nickase-helicase TrwC |
| 293 | YP 001260037.1 | conjugative relaxase region-like protein [*Sphingomonas wittichii* |
| 294 | ZP 04629294.1 | hypothetical protein yberc0001 36240 [*Yersinia bercovieri* ATCC |
| 295 | CAZ15897.1 | probable conjugal transfer protein [*Xanthomonas albilineans*] |
| 296 | YP 315578.1 | TrwC protein [*Thiobacillus denitrificans* ATCC 25259] |
| 297 | ZP 01770026.1 | TrwC protein [*Burkholderia pseudomallei* 305] |
| 298 | YP 001869963.1 | exonuclease V subunit alpha [*Nostoc punctiforme* PCC 73102] |
| 299 | ZP 08210392.1 | TrwC protein [*Novosphingobium nitrogenifigens* DSM 19370] |
| 300 | YP 001692976.1 | mobilization protein TraI [*Yersinia enterocolitica*] |
| 301 | YP 003455306.1 | conjugative transfer protein TraI [*Legionella longbeachae* |
| 302 | YP 745335.1 | traI protein (DNA helicase I) [*Granulibacter bethesdensis* |
| 303 | YP 001911166.1 | TrwC [*Salmonella enterica* subsp. *enterica* serovar Dublin] |
| 304 | YP 001874877.1 | mobilisation protein [*Providencia rettgeri*] >emb|CAQ48354.1| |
| 305 | YP 001552064.1 | trwC protein [*Salmonella enterica* subsp. *enterica* serovar |
| 306 | CAA44853.2 | TrwC [*Escherichia coli* K-12] |
| 307 | YP 096090.1 | hypothetical protein lpg2077 [*Legionella pneumophila* subsp. |
| 308 | YP 534815.1 | putative plasmid transfer protein TraC [*Pseudomonas putida*] |
| 309 | FAA00039.1 | TPA: TrwC protein [*Escherichia coli*] |
| 310 | NP 863125.1 | putative TraC protein [*Pseudomonas putida*] |
| 311 | ZP 04868849.1 | conserved hypothetical protein [*Staphylococcus aureus* subsp. |
| 312 | ZP 01304707.1 | TrwC protein [*Sphingomonas* sp. SKA58] >gb|EAT07464.1| |
| 313 | ZP 05040124.1 | TrwC relaxase family [*Synechococcus* sp. PCC 7335] |
| 314 | YP 001798665.1 | putative TrwC/TraI protein [*Cyanothece* sp. ATCC 51142] |
| 315 | YP 002235496.1 | putative conjugative transfer protein [*Burkholderia* |
| 316 | CAZ15872.1 | probable mobilization protein traI [*Xanthomonas albilineans*] |
| 317 | YP 840564.1 | TrwC protein [*Burkholderia cenocepacia* HI2424] |
| 318 | ZP 08207332.1 | TrwC protein [*Novosphingobium nitrogenifigens* DSM 19370] |
| 319 | YP 001966297.1 | TraI [*Pseudomonas* sp. CT14] >gb|ABA25997.1|TraI |
| 320 | 3L6T A | Chain A, Crystal Structure Of An N-Terminal Mutant Of The |
| 321 | YP 001736290.1 | DNA helicase, TrwC and TraI like protein [*Synechococcus* sp. |
| 322 | 3L57 A | Chain A, Crystal Structure Of The Plasmid Pcu1 Trai Relaxase |
| 323 | ZP 04532999.1 | F pilin acetylation protein [*Escherichia* sp. 3 2 53FAA] |
| 324 | CAA40677.1 | DNA helicase I [*Escherichia coli*] |
| 325 | NP 478459.1 | hypothetical protein alr8034 [*Nostoc* sp. PCC 7120] |
| 326 | YP 001893556.1 | conjugative relaxase domain protein [*Burkholderia* |
| 327 | YP 001033863.1 | hypothetical protein RSP 3904 [*Rhodobacter sphaeroides* |
| 328 | ZP 06064648.1 | TrwC protein [*Acinetobacter johnsonii* SH046] |
| 329 | YP 003829308.1 | nickase/helicase [*Escherichia coli*] >gb|ADL14202.1|TraI |
| 330 | YP 002332893.1 | conjugal transfer protein [*Klebsiella pneumoniae*] |
| 331 | YP 002286896.1 | TraI [*Klebsiella pneumoniae*] >gb|ACI63157.1|TraI |
| 332 | YP 003813077.1 | TraI [*Klebsiella pneumoniae*] >gb|ADG84846.1|TraI |
| 333 | YP 002286953.1 | TraI [*Klebsiella pneumoniae*] >ref|YP 003675776.1|TraI |
| 334 | YP 001096334.1 | hypothetical protein pLEW517 p09 [*Escherichia coli*] |
| 335 | YP 724504.1 | hypothetical protein pMUR050 047 [*Escherichia coli*] |
| 336 | NP 511201.1 | hypothetical protein R46 023 [IncN plasmid R46] |
| 337 | ADH30046.1 | conjugal transfer protein [*Escherichia coli* O25b:H4-ST131 str. |
| 338 | YP 002913254.1 | TrwC protein [*Burkholderia glumae* BGR1] >gb|ACR32934.1| |
| 339 | YP 004362462.1 | TrwC protein [*Burkholderia gladioli* BSR3] >gb|AEA65432.1| |

TABLE 6-continued

Preferred TraI helicases and TraI subgroup helicases and their Accession Numbers

| # | Accession | Description |
|---|---|---|
| 340 | ZP 02468056.1 | TrwC protein [*Burkholderia thailandensis* MSMB43] |
| 341 | YP 001840913.1 | TrwC protein [*Acinetobacter baumannii* ACICU] |
| 342 | ZP 07239267.1 | TrwC protein [*Acinetobacter baumannii* AB059] |
| 343 | YP 003853339.1 | TrwC protein [*Parvularcula bermudensis* HTCC2503] |
| 344 | ZP 07237891.1 | TrwC protein [*Acinetobacter baumannii* AB058] |
| 345 | YP 002491522.1 | conjugative relaxase domain-containing protein |
| 346 | YP 002907678.1 | TrwC protein [*Burkholderia glumae* BGR1] >gb|ACR32827.1| |
| 347 | YP 004350971.1 | TrwC protein [*Burkholderia gladioli* BSR3] >gb|AEA65648.1| |
| 348 | ZP 02834825.2 | protein TraD [*Salmonella enterica* subsp. *enterica* serovar |
| 349 | ADX05370.1 | TrwC protein [*Acinetobacter baumannii* 1656-2] |
| 350 | YP 003552078.1 | TrwC protein [*Candidatus Puniceispirillum marinum* |
| 351 | EGB59894.1 | traI protein [*Escherichia coli* M863] |
| 352 | YP 001522461.1 | hypothetical protein AM1 F0157 [*Acaryochloris marina* |
| 353 | ZP 05738733.1 | protein TraI [*Silicibacter* sp. TrichCH4B] >gb|EEW61008.1| |
| 354 | AEM77047.1 | putative conjugative relaxase [*Escherichia coli*] |
| 355 | EHC71302.1 | IncW plasmid conjugative relaxase protein TrwC [*Salmonella* |
| 356 | YP 004765041.1 | TraI [*Escherichia coli*] >gb|AEK64833.1|TraI [*Escherichia coli*] |
| 357 | YP 004553102.1 | conjugative relaxase domain-containing protein [*Sphingobium* |
| 358 | NP 073253.1 | hypothetical protein pKDSC50 p29 [*Salmonella enterica* subsp. |
| 359 | YP 004535774.1 | DNA relaxase/conjugal transfer nickase-helicase TrwC |
| 360 | AEA76430.1 | VirD2 [*Klebsiella pneumoniae*] |
| 361 | YP 001806422.1 | putative TrwC/TraI protein [*Cyanothece* sp. ATCC 51142] |
| 362 | ZP 08138981.1 | TrwC protein [*Pseudomonas* sp. TJI-51] >gb|EGB99721.1|TrwC |
| 363 | YP 394134.1 | exonuclease V subunit alpha [*Sulfurimonas denitrificans* DSM |
| 364 | EGQ61142.1 | conjugative relaxase domain protein [*Acidithiobacillus* sp. GGI- |
| 365 | ZP 06732944.1 | TraI protein [*Xanthomonas fuscans* subsp. *aurantifolii* str. ICPB |
| 366 | YP 004218965.1 | conjugative relaxase domain protein [*Acidobacterium* sp. |
| 367 | YP 001941994.1 | relaxase [*Burkholderia multivorans* ATCC 17616] |
| 368 | EDZ39520.1 | Protein of unknown function [*Leptospirillum* sp. Group II '5-way |
| 369 | YP 004415459.1 | TrwC protein [*Pusillimonas* sp. T7-7] >gb|AEC18835.1|TrwC |
| 370 | YP 003545248.1 | traI/trwC-like protein [*Sphingobium japonicum* UT26S] |
| 371 | YP 004184501.1 | conjugative relaxase domain-containing protein [*Terriglobus* |
| 372 | EGD06685.1 | relaxase [*Burkholderia* sp. TJI49] |
| 373 | ADQ53945.1 | putative conjugative transfer protein [*Vibrio harveyi*] |
| 374 | YP 004089509.1 | conjugative relaxase domain protein [*Asticcacaulis excentricus* |
| 375 | YP 004183694.1 | conjugative relaxase domain-containing protein [*Terriglobus* |
| 376 | YP 003900289.1 | conjugative relaxase domain-containing protein [*Cyanothece* sp. |
| 377 | EDZ40407.1 | Putative mobilization protein TraA [*Leptospirillum* sp. Group II |
| 378 | YP 004534918.1 | TrwC protein [*Novosphingobium* sp. PP1Y] >emb|CCA93100.1| |
| 379 | YP 004210530.1 | conjugative relaxase domain protein [*Acidobacterium* sp. |
| 380 | YP 003642130.1 | conjugative relaxase domain protein [*Thiomonas intermedia* K12] |
| 381 | YP 004277247.1 | putative relaxase TrwC [*Acidiphilium multivorum* AIU301] |
| 382 | NP 857772.1 | DNA helicase I [*Yersinia pestis* KIM] >gb|AAC62598.1|DNA |
| 383 | EGB74534.1 | hypothetical protein HMPREF9532 05052 [*Escherichia coli* MS |
| 384 | ZP 08138968.1 | putative TraC protein [*Pseudomonas* sp. TJI-51] |
| 385 | YP 002756187.1 | conjugative relaxase domain protein [*Acidobacterium capsulatum* |
| 386 | ZP 07392869.1 | conjugative relaxase domain protein [*Shewanella baltica* OS183] |
| 387 | YP 004210680.1 | conjugative relaxase domain protein [*Acidobacterium* sp. |
| 388 | EAY56629.1 | probable TrwC protein [*Leptospirillum rubarum*] |
| 389 | YP 068423.1 | hypothetical protein pYV0010 [*Yersinia pseudotuberculosis* IP |
| 390 | NP 995413.1 | hypothetical protein YP pCD97 [*Yersinia pestis* biovar *Microtus* |
| 391 | ZP 08634947.1 | Conjugative relaxase domain protein [*Acidiphilium* sp. PM] |
| 392 | ZP 01301850.1 | hypothetical protein SKA58 02210 [*Sphingomonas* sp. SKA58] |
| 393 | YP 002754293.1 | conjugative relaxase domain protein [*Acidobacterium capsulatum* |
| 394 | YP 001818827.1 | conjugative relaxase domain-containing protein [*Opitutus terrae* |
| 395 | EGT71208.1 | hypothetical protein C22711 5244 [*Escherichia coli* O104:H4 str. |
| 396 | YP 001522273.1 | hypothetical protein AM1 E0190 [*Acaryochloris marina* |
| 397 | YP 003891048.1 | conjugative relaxase domain protein [*Cyanothece* sp. PCC 7822] |
| 398 | YP 001521867.1 | hypothetical protein AM1 D0057 [*Acaryochloris marina* |
| 399 | YP 004748378.1 | TraI protein [*Acidithiobacillus caldus* SM-1] >gb|AEK57678.1| |
| 400 | YP 002380579.1 | relaxase [*Cyanothece* sp. PCC 7424] >gb|ACK74122.1| |
| 401 | ZP 08634902.1 | Conjugative relaxase domain protein [*Acidiphilium* sp. PM] |
| 402 | ZP 05738878.1 | TraI [*Silicibacter* sp. TrichCH4B] >gb|EEW61153.1|TraI |
| 403 | YP 001821352.1 | conjugative relaxase domain-containing protein [*Opitutus terrae* |
| 404 | ZP 02733385.1 | TrwC protein [*Gemmata obscuriglobus* UQM 2246] |
| 405 | YP 004183160.1 | conjugative relaxase domain-containing protein [*Terriglobus* |
| 406 | YP 001522155.1 | TrwC protein, putative [*Acaryochloris marina* MBIC11017] |
| 407 | YP 002478348.1 | conjugative relaxase domain protein [*Cyanothece* sp. PCC 7425] |
| 408 | YP 002756241.1 | conjugative relaxase domain protein [*Acidobacterium capsulatum* |
| 409 | YP 001521036.1 | hypothetical protein AM1 A0387 [*Acaryochloris marina* |
| 410 | YP 004416953.1 | TrwC protein [*Pusillimonas* sp. T7-7] >gb|AEC20329.1|TrwC |
| 411 | YP 001521806.1 | hypothetical protein AM1 C0379 [*Acaryochloris marina* |
| 412 | YP 001357151.1 | hypothetical protein NIS 1688 [*Nitratiruptor* sp. SB155-2] |
| 413 | ZP 07030639.1 | conjugative relaxase domain protein [*Acidobacterium* sp. |
| 414 | YP 530542.1 | putative ATP-dependent exoDNAse (exonuclease V) subunit |
| 415 | NP 052442.1 | hypothetical protein pYVe227 p65 [*Yersinia enterocolitica*] |
| 416 | YP 004783051.1 | conjugative relaxase domain-containing protein [*Acidithiobacillus* |
| 417 | YP 003262832.1 | relaxase [*Halothiobacillus neapolitanus* c2] >gb|ACX95785.1| |

TABLE 6-continued

Preferred TraI helicases and TraI subgroup helicases and their Accession Numbers

| | | |
|---|---|---|
| 418 | ADQ53973.1 | putative conjugative transfer protein [*Vibrio harveyi*] |
| 419 | EDZ37984.1 | Conjugal transfer protein, TraA [*Leptospirillum* sp. Group II '5- |
| 420 | YP 001522591.1 | hypothetical protein AM1 G0097 [*Acaryochloris marina* |
| 421 | EAY56417.1 | putative conjugal transfer protein (TraA) [*Leptospirillum* |
| 422 | YP 459829.1 | hypothetical protein ELI 14700 [*Erythrobacter litoralis* |
| 423 | YP 001818081.1 | conjugative relaxase domain-containing protein [*Opitutus terrae* |
| 424 | ZP 07745472.1 | conjugative relaxase domain protein [*Mucilaginibacter paludis* |
| 425 | CBA73957.1 | conjugal transfer nickase/helicase TraI [*Arsenophonus nasoniae*] |
| 426 | YP 002248140.1 | hypothetical protein THEYE A0292 [*Thermodesulfovibrio* |
| 427 | ZP 06641691.1 | conserved hypothetical protein [*Serratia odorifera* DSM 4582] |
| 428 | ZP 05056614.1 | TrwC relaxase family [*Verrucomicrobiae bacterium* DG1235] |
| 429 | ZP 03723740.1 | conjugative relaxase domain protein [*Opitutaceae bacterium* |
| 430 | YP 004210579.1 | conjugative relaxase domain protein [*Acidobacterium* sp. |
| 431 | YP 001522671.1 | hypothetical protein AM1 H0004 [*Acaryochloris marina* |
| 432 | YP 001573657.1 | conjugative relaxase domain-containing protein [*Burkholderia* |
| 433 | EDZ39038.1 | Conjugal protein, TraA [*Leptospirillum* sp. Group II '5-way CG'] |
| 434 | YP 001632380.1 | conjugal transfer protein [*Bordetella petrii* DSM 12804] |
| 435 | ZP 06242489.1 | conjugative relaxase domain protein [*Victivallis vadensis* ATCC |
| 436 | EDZ37956.1 | Conjugal protein, TraA [*Leptospirillum* sp. Group II '5-way CG'] |
| 437 | YP 004488214.1 | conjugative relaxase domain-containing protein [*Delftia* sp. Cs1- |
| 438 | ZP 00208504.1 | COG0507: ATP-dependent exoDNAse (exonuclease V), alpha |
| 439 | ACJ47794.1 | TraI [*Klebsiella pneumoniae*] |
| 440 | ZP 02730551.1 | TrwC protein [*Gemmata obscuriglobus* UQM 2246] |
| 441 | ZP 06244759.1 | TrwC relaxase [*Victivallis vadensis* ATCC BAA-548] |
| 442 | YP 003022160.1 | relaxase [*Geobacter* sp. M21] >gb|ACT18402.1|conjugative |
| 443 | YP 001521304.1 | hypothetical protein AM1 B0272 [*Acaryochloris marina* |
| 444 | ZP 01091846.1 | hypothetical protein DSM3645 02833 [*Blastopirellula marina* |
| 445 | CAZ88117.1 | putative ATP-dependent exoDNAse (exonuclease V), alpha |
| 446 | YP 004718365.1 | conjugative relaxase domain-containing protein [*Sulfobacillus* |
| 447 | YP 002553030.1 | conjugative relaxase domain-containing protein [*Acidovorax* |
| 448 | YP 003386820.1 | conjugative relaxase domain-containing protein [*Spirosoma* |
| 449 | YP 001119893.1 | exonuclease V subunit alpha [*Burkholderia vietnamiensis* G4] |
| 450 | YP 315444.1 | putative ATP-dependent exoDNAse (exonuclease V) subunit |
| 451 | YP 003071370.1 | hypothetical protein p2METDI0024 [*Methylobacterium* |
| 452 | YP 003125939.1 | conjugative relaxase [*Chitinophaga pinensis* DSM 2588] |
| 453 | ZP 08495729.1 | TrwC relaxase [*Microcoleus vaginatus* FGP-2] >gb|EGK83455.1| |
| 454 | EFZ53417.1 | traI domain protein [*Shigella sonnei* 53G] |
| 455 | EGR70910.1 | conjugal transfer nickase/helicase TraI [*Escherichia coli* O104:H4 |
| 456 | YP 002912178.1 | ATP-dependent exoDNAse (exonuclease V) subunit alpha |
| 457 | ZP 01089566.1 | hypothetical protein DSM3645 27912 [*Blastopirellula marina* |
| 458 | YP 002753784.1 | DNA helicase domain protein [*Acidobacterium capsulatum* ATCC |
| 459 | EFZ60916.1 | protein traI domain protein [*Escherichia coli* LT-68] |
| 460 | ZP 08262009.1 | protein traI [*Asticcacaulis biprosthecum* C19] >gb|EGF93811.1| |
| 461 | AEI11045.1 | TrwC relaxase [[*Cellvibrio*] gilvus ATCC 13127] |
| 462 | ZP 05040209.1 | hypothetical protein S7335 1177 [*Synechococcus* sp. PCC 7335] |
| 463 | YP 001840830.1 | ATP-dependent exoDNAse (exonuclease V) [*Mycobacterium* |
| 464 | YP 001700713.1 | TraA/ATP-dependent exoDNAse/relaxase [*Mycobacterium* |
| 465 | CAC86586.1 | conjugal transfer protein [*Agrobacterium tumefaciens*] |
| 466 | NP 355808.2 | conjugation protein [*Agrobacterium tumefaciens* str. C58] |
| 467 | YP 001120496.1 | hypothetical protein Bcep1808 2669 [*Burkholderia vietnamiensis* |
| 468 | EGW76304.1 | protein traI domain protein [*Escherichia coli* STEC B2F1] |
| 469 | YP 002979543.1 | Ti-type conjugative transfer relaxase TraA [*Rhizobium* |
| 470 | EHB44041.1 | TrwC relaxase [*Mycobacterium rhodesiae* JS60] |
| 471 | YP 002984810.1 | Ti-type conjugative transfer relaxase TraA [*Rhizobium* |
| 472 | ZP 06848350.1 | ATP-dependent exoDNAse (exonuclease V) [*Mycobacterium* |
| 473 | YP 001972793.1 | putative conjugal transfer protein TraA [*Stenotrophomonas* |
| 474 | ZP 06760230.1 | putative conjugative relaxase domain protein [*Veillonella* sp. |
| 475 | YP 001840914.1 | TrwC protein [*Acinetobacter baumannii* ACICU] |
| 476 | YP 003311407.1 | TrwC relaxase [*Veillonella parvula* DSM 2008] |
| 477 | ZP 08208016.1 | TrwC protein [*Novosphingobium nitrogenifigens* DSM 19370] |
| 478 | XP 003342708.1 | hypothetical protein SMAC 10304 [*Sordaria macrospora* k-hell] |
| 479 | YP 004074482.1 | TrwC relaxase [*Mycobacterium* sp. Spyr1] >gb|ADU02001.1| |
| 480 | YP 935511.1 | exonuclease V subunit alpha [*Mycobacterium* sp. KMS] |
| 481 | YP 004100308.1 | TrwC relaxase [*Intrasporangium calvum* DSM 43043] |
| 482 | YP 003326911.1 | TrwC relaxase [*Xylanimonas cellulosilytica* DSM 15894] |
| 483 | YP 001136860.1 | exonuclease V subunit alpha [*Mycobacterium gilvum* PYR- |
| 484 | YP 001776789.1 | conjugative relaxase domain-containing protein |
| 485 | NP 862296.1 | transfer protein homolog TraA [*Corynebacterium glutamicum*] |
| 486 | YP 001851874.1 | ATP-dependent exoDNAse (exonuclease V) [*Mycobacterium* |
| 487 | AAS20144.1 | TraA-like protein [*Arthrobacter aurescens*] |
| 488 | YP 949993.1 | putative TraA-like protein [*Arthrobacter aurescens* TC1] |
| 489 | YP 004271377.1 | TrwC relaxase [*Planctomyces brasiliensis* DSM 5305] |
| 490 | YP 001243088.1 | putative ATP-dependent exoDNAse [*Bradyrhizobium* sp. |
| 491 | YP 771309.1 | putative conjugal transfer protein TraA [*Rhizobium* |
| 492 | ZP 02730298.1 | TrwC protein [*Gemmata obscuriglobus* UOM 2246] |
| 493 | EGO61143.1 | conjugative relaxase domain protein [*Acidithiobacillus* sp. GGI- |
| 494 | YP 002978744.1 | Ti-type conjugative transfer relaxase TraA [*Rhizobium* |
| 495 | YP 002973152.1 | Ti-type conjugative transfer relaxase TraA [*Rhizobium* |

TABLE 6-continued

Preferred TraI helicases and TraI subgroup helicases and their Accession Numbers

| | | |
|---|---|---|
| 496 | ZP 06846967.1 | ATP-dependent exoDNAse (exonuclease V) [*Mycobacterium* |
| 497 | YP 003377696.1 | TraA [*Corynebacterium glutamicum*] >dbj|BAI66031.1|TraA, |
| 498 | ZP 06846356.1 | Ti-type conjugative transfer relaxase TraA [*Burkholderia* sp. |
| 499 | YP 001136826.1 | exonuclease V subunit alpha [*Mycobacterium gilvum* PYR- |
| 500 | YP 949954.1 | putative TraA-like conjugal transfer protein [*Arthrobacter* |

The TraI helicase or TraI subgroup helicase is more preferably one of the helicases shown in Table 7 below or a variant thereof. The TraI helicase or TraI subgroup helicase more preferably comprises the sequence of one of the helicases shown in Table 7, i.e. one of SEQ ID NOs: 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168, or a variant thereof.

TABLE 7

More preferred TraI helicase and TraI subgroup helicases

| SEQ ID NO | Name | Strain | NCBI ref | % Identity to TraI Eco | RecD-like motif I (SEQ ID NO:) | RecD-like motif V (SEQ ID NO:) | Mob F or Q motif III (SEQ ID NO:) |
|---|---|---|---|---|---|---|---|
| 61 | TraI Eco | *Escherichia coli* | NCBI Reference Sequence: NP_061483.1 Genbank AAQ98619.1 | — | GYAGV GKT (62) | YAITA HGAQG (63) | HDTSR DQEPQ LHTH (64) |
| 65 | TrwC Cba | *Citromicrobium bathyomarinum* JL354 | NCBI Reference Sequence: ZP_06861556.1 | 15% | GIAGA GKS (66) | YALNV HMAQG (67) | HDTNR NQEPN LHFH (68) |
| 69 | TrwC Hne | *Halothiobacillus neopolitanus* c2 | NCBI Reference Sequence: YP_003262832.1 | 11.5% | GAAGA GKT (70) | YCITIH RSQG (71) | HEDAR TVDDI ADPQL HTH (72) |
| 73 | TrwC Eli | *Erythrobacter litoralis* HTCC2594 | NCBI Reference Sequence: YP_457045.1 | 16% | GIAGA GKS (66) | YALNA HMAQG (67) | HDTNR NQEPN LHFH (68) |
| 74 | TrwC Eco | *E. coli* | CAA44853.2 | 11.998% | GFAGT GKS (75) | YATTV HSSQG (76) | HETSRE RDPQL HTH (77) |
| 78 | TraA Atu | *Agrobacterium tumefaciens* C58 | AAC17212.1 | 12.68% | GRAGA GKT (79) | YATTIH KSQG (80) | GMVAD WVYH DNPGN PHIH (81) |
| 82 | TrwC Sac | *Sulfobacillus acidophilus* TPY | YP_004718365.1 | 9.487% | GAAGT GKT (83) | YASTA HKSQG (84) | HSTSR AQDPH LHSH (85) |
| 86 | TrwC Afe | *Acidithiobacillus ferrivorans* SS3 | YP_004783051.1 | 10.247% | GHAGA GKT (87) | YAGTT HRNQG (88) | HASSR EQDPQI HSH (89) |
| 90 | TrwC Tsa | *Terriglobus saanensis* SP1PR4 | YP_004184501.1 | 14.689% | GLAGT GKT (91) | YAVTS HSSQG (92) | HDTAR PVNGY AAPQL HTH (93) |
| 94 | TrwC Mph | *Microlunatus phosphovorus* NM-1 | YP_004574196.1 | 11.467% | GPAGA GKT (95) | YAITA HRAQG (96) | HYDSR AGDPQ LHTH (97) |

TABLE 7-continued

More preferred TraI helicase and TraI subgroup helicases

| SEQ ID NO | Name | Strain | NCBI ref | % Identity to TraI Eco | RecD-like motif I (SEQ ID NO:) | RecD-like motif V (SEQ ID NO:) | Mob F or Q motif III (SEQ ID NO:) |
|---|---|---|---|---|---|---|---|
| 98 | TrwC Tye | Thermodesulfovibrio yellowstonii DSM 11347 | YP_002248140.1 | 8.487% | GWAG VGKT (99) | YAVTA DHMQG (100) | HLCGR LDPQIH NH (101) |
| 102 | TrwC Rma | Rhodothermus marinus SG0.5JP17-172 | YP_004826542.1 | 11.909% | GVAGA GKT (103) | YALTID SAQG (104) | HMTSG DGSPH LHVH (105) |
| 106 | TraA Oma | Oceanicaulis alexandrii HTCC2633 | ZP_00953568.1 | 12.099% | GYAGT GKS (107) | YAATI HKAQG (108) | GMIAD LVNVH WDIGE DGKAK PHAH (109) |
| 110 | TrwC Cjlt | Citromicrobium sp. JLT1363 | ZP_08701842.1 | 12.371% | GIAGA GKS (66) | YALNA HMAQG (67) | HDTNR NQEPN LHFH (111) |
| 112 | TrwC Esd | Erythrobacter sp. SD-21 | ZP_01863208.1 | 12.907% | GIAGA GKS (66) | YALNA HMAQG (67) | HDTNR NQEPN LHFH (111) |
| 113 | Trw Enap | Erythrobacter sp. NAP1 | ZP_01039301.1 | 12.969% | GIAGA GKS (66) | YALNA HMAQG (67) | HDTNR NQEPN LHFH (111) |
| 114 | TrwC Npe | Novosphingobium pentaromativorans US6-1 | ZP_09190449.1 | 12.765% | GVAGA GKS (115) | YALNA HMAQG (67) | HDTNR NQEPN AHFH (116) |
| 117 | TrwC Nni | Novosphingobium nitrogenifigens DSM 19370 | ZP_08210392.1 | 11.82% | GGAGV GKS (118) | YAINV HIAQG (119) | HDVSR NNDPQ LHVH (120) |
| 121 | TrwC Swi | Sphingomonas wittichii RW1 | YP_001260099.1 | 13.945% | GIAGA GKS (66) | YALNM HMAQG (122) | HDTSR ALDPQ GHIH (123) |
| 124 | TrwC Ska | Sphingomonas sp. KA1 | YP_718086.1 | 14.119% | GVAGA GKS (115) | YALNA HMAQG (67) | HDTSR ALDPQ GHIH (123) |
| 125 | TrwC Pma | Candidatus Puniceispirillum marinum IMCC1322 | YP_003552078.1 | 12.91% | GRAGT GKT (126) | FASTA HGAQG (127) | HEASR NLDPQ LHSH (128) |
| 129 | TrwC Pbe | Parvularcula bermudensis HTCC2503 | YP_003853339.1 | 13.141% | GYAGT GKT (130) | YAMTS HAAQG (131) | HDISRD KDPQL HTH (132) |
| 133 | TrwC Ajs | Acidovorax sp. JS42 | YP_974028.1 | 12.52% | GLAGT GKT (91) | YAQTV HASQG (134) | HNTSR DLDPQ THTH (135) |
| 136 | TrwC Ccr | Caulobacter crescentus NA1000 | YP_002515847.1 | 13.137% | GFAGT AKT (137) | YVQTA FAAQG (138) | HETSR AQDPQ LHTH (139) |

TABLE 7-continued

More preferred TraI helicase and TraI subgroup helicases

| SEQ ID NO | Name | Strain | NCBI ref | % Identity to TraI Eco | RecD-like motif I (SEQ ID NO:) | RecD-like motif V (SEQ ID NO:) | Mob F or Q motif III (SEQ ID NO:) |
|---|---|---|---|---|---|---|---|
| 140 | TrwC Sal | Sphingopyxis alaskensis RB2256 | YP_617529.1 | 14.193% | GYAGT AKT (141) | YVDTA FAAQG (142) | HGTSR AQDPQ LHTH (143) |
| 144 | TrwC Atr | Acetobacter tropicalis NBRC 101654 | ZP_08645753.1 | 13.171% | GYAGT AKT (141 | YASTA FAAQG (145) | HGTSR ALDPQ LHSH (146) |
| 147 | TrwC Aca | Acidobacterium capsulatum | YP_002756241.1 | 11.338% | GSAGS GKT (148) | YAVTS YSAQG (149) | HDTAR PVGGY AAPQL HTH (150) |
| 151 | TrwC Gtu | Granulicella tundricola | YP_004218965.1 | 14.12% | GLAGT GKT (91) | YAVTS HSSQG (92) | HDTAR PVNGY AAPQL HTH (93) |
| 152 | TrwC Bmu | Burkholderia multivorans ATCC 17616 | YP_001941994.1 | 13.347% | GEAGT GKT (153) | YAHTS YKEQG (154) | HETNR ENEPQ LHNH (155) |
| 156 | TrwC Llo | Legionella longbeachae NSW150 | YP_003455306.1 | 11.612% | GYAGV AKT (157) | YVLTN YKVQG (158) | QPSSRA NDPAL HTH (159) |
| 160 | TrwC Aex | Asticcacaulis excentricus CB 48 | YP_004089509.1 | 11.86% | GSAGT GKT (161) | YSLTA NRAQG (162) | HSMSR AGDPE MHNH (163) |
| 164 | TrwC mRA | Methylobacterium radiotolerans JCM 2831 | YP_001776789 | 11.565% | AGAGT GKT (165) | YAGTV YAAQG (166) | HYTTR EGDPNI HTH (167) |
| 168 | TrwC Mpa | Mycobacterium parascrofulaceum ATCC BAA-614 | ZP_06848350 | 11.394% | APAGA GKT (169) | YAVTV HAAQG (170) | HETSR AGDPH LHTH (171) |

SEQ ID NOs: 78 and 106 comprise a MobQ motif III, whereas the other sequences in Table 7 comprise a MobF motif III.

The TraI helicase preferably comprises the sequence shown in SEQ ID NO: 61 or a variant thereof.

A variant of a RecD helicase is an enzyme that has an amino acid sequence which varies from that of the wild-type helicase and which retains polynucleotide binding activity. In particular, a variant of any one of SEQ ID NOs: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168 is an enzyme that has an amino acid sequence which varies from that of any one of SEQ ID NOs: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168 and which retains polynucleotide binding activity. A variant of SEQ ID NO: 18 or 61 is an enzyme that has an amino acid sequence which varies from that of SEQ ID NO: 18 or 61 and which retains polynucleotide binding activity. The variant retains helicase activity. Methods for measuring helicase activity are known in the art. Helicase activity can also be measured as described in the Examples. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of the motifs discussed above. However, variants may include modifications within these motif(s).

Over the entire length of the amino acid sequence of any one of SEQ ID NOs: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168, such as SEQ ID NO: 18 or 61, a variant will preferably be at least 10% homologous to that sequence based on amino acid identity. More preferably, the variant polypeptide may be at least 20%, at least 25%, at least 30%, at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168, such as SEQ ID NO: 18 or 61, over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NOs: 2 and 4.

In particular, variants may include fragments of SEQ ID NOs: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168. Such fragments retain polynucleotide binding activity. Fragments may be at least about 200, at least about 300, at least about 400, at least about 500, at least about 600, at least about 650, at least about 700, at least about 800, at least about 900 or at least about 1000 amino acids in length. The length of the fragment will depend on the length of the wild-type sequence. As discussed in more detail below, fragments preferably comprise the RecD-like motif I and/or the RecD-like motif V of the relevant wild-type sequence.

As discussed above, TraI helicases and TraI subgroup helicases comprise a relaxase domain. The relaxase domain comprises the MobF motif III or the MobQ motif III and is typically found at the amino (N) terminus of the TraI helicase or TraI subgroup helicase. Preferred fragments of TraI helicases and TraI subgroup helicases, such as preferred fragments of SEQ ID NOs: 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168, lack the N terminal domain of the wild-type sequence. The N-terminal domain typically corresponds to the about the N terminal third of the protein. In SEQ ID NO: 61 (which is 1756 amino acids in length), the N-terminal domain is typically from about 500 to about 700 amino acids in length, such as from about 550 to about 600 amino acids in length. In SEQ ID NOs: 65, 69 and 73 (which are 970, 943 and 960 amino acids in length respectively), the N-terminal domain is typically from about 300 to about 350 amino acids in length, such as from about 320 to about 340 amino acids in length.

Amino acid substitutions may be made to the amino acid sequence of SEQ ID NO: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168, for example up to 1, 2, 3, 4, 5, 10, 20 or 30 substitutions. The substitutions are preferably conservative substitutions as discussed above. One or more substitutions may be made at amino acid positions K555, R554, T644, R647, P666, M667, H646, N604, N596, Y598, V470, G391, H409, T407, R410 and Y414 of SEQ ID NO: 41. In SEQ ID NOs: 18, 21, 24, 25, 28, 30, 32, 35, 37, 39, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168, substitutions may be made at one or more amino acid positions which correspond to amino acid positions K555, R554, T644, R647, P666, M667, H646, N604, N596, Y598, V470, G391, H409, T407, R410 and Y414 of SEQ ID NO: 41. It is straightforward to determine corresponding amino acid positions in different protein sequences. For instance, the proteins may be aligned based on their homology. Homology may be determined as discussed above.

A variant, such as a fragment, of any one of SEQ ID NOs: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168 preferably comprises the RecD-like motif I (or RecD motif I) and/or RecD-like motif V (or RecD motif V) of the relevant wild-type sequence. A variant, such as a fragment, of any one of SEQ ID NOs: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168 preferably comprises the RecD-like motif I (or RecD motif I) and the RecD-like motif V (or RecD motif V) of the relevant wild-type sequence. For instance, a variant of SEQ ID NO: 18 preferably comprises the RecD motif I GGPGTGKT (SEQ ID NO: 19) and the RecD motif V WAVTIHKSQG (SEQ ID NO: 20). The RecD-like motifs I and V (or RecD motifs I and V) of each of SEQ ID NOs: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168 are shown in Tables 5 and 7. However, a variant of any one SEQ ID NOs: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168 may comprise the RecD-like motif I (or RecD motif I) and/or RecD-like motif V (or RecD motif V) from a different wild-type sequence. For instance, a variant of SEQ ID NO: 28 or SEQ ID NO: 35 may comprise the RecD motif I and RecD-like motif V of SEQ ID NO: 21 (GGPGTGKS and YALTVHRAQG respectively; SEQ ID NOs: 22 and 23). A variant of any one SEQ ID NOs: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168 may comprise any one of the preferred motifs shown in Tables 5 and 7. Variants of any one of SEQ ID NOs: 18, 21, 24, 25, 28, 30, 32, 35, 37, 39, 41, 42, 44, 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168 may also include modifications within the RecD-like motifs I and V of the relevant wild-type sequence. Suitable modifications are discussed above when defining the two motifs. The discussion in the paragraph equally applies to the MobF motif III in SEQ ID NOs: 61, 65, 69, 73, 74, 82, 86, 90, 94, 98, 102, 110, 112, 113, 114, 117, 121, 124, 125, 129, 133, 136, 140, 144, 147, 151, 152, 156, 160, 164 and 168 and MobQ motif III in SEQ ID NOs: 78 and 106. In particular, a variant, such as a fragment, of any one of SEQ ID NOs: 61, 65, 69, 73, 74, 82, 86, 90, 94, 98, 102, 110, 112, 113, 114, 117, 121, 124, 125, 129, 133, 136, 140, 144, 147, 151, 152, 156, 160, 164 and 168 preferably comprises the MobF motif III of the relevant wild-type sequence. A variant, such as a fragment, of SEQ ID NO: 78 or 106 preferably comprises the MobQ motif III of the relevant wild-type sequence. A variant, such as a fragment, of any one of SEQ ID NOs: 61, 65, 69, 73, 74, 78, 82, 86, 90, 94, 98, 102, 106, 110, 112, 113, 114, 117, 121, 124, 125, 129, 133, 136, 140, 144, 147, 151, 152, 156, 160, 164 and 168 preferably comprises the RecD-like motif I (or RecD motif I), RecD-like motif V (or RecD motif V) and MobF or MobQ motif Ill of the relevant wild-type sequence.

The helicase may be covalently attached to the pore. The helicase is preferably not covalently attached to the pore. The application of a voltage to the pore and helicase typically results in the formation of a sensor that is capable of sequencing target polynucleotides. This is discussed in more detail below.

Any of the proteins described herein, i.e. the transmembrane protein pores or RecD helicases, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or helicase. An example of this would be to react a gel-shift reagent to a cysteine engineered on the outside of the pore. This has been demonstrated as a method for separating hemolysin hetero-oligomers (Chem Biol. 1997 July; 4(7): 497-505).

The pore and/or helicase may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

Proteins may be made synthetically or by recombinant means. For example, the pore and/or helicase may be synthesized by in vitro translation and transcription (IVTT). The amino acid sequence of the pore and/or helicase may be modified to include non-naturally occurring amino acids or to increase the stability of the protein. When a protein is produced by synthetic means, such amino acids may be introduced during production. The pore and/or helicase may also be altered following either synthetic or recombinant production.

The pore and/or helicase may also be produced using D-amino acids. For instance, the pore or helicase may comprise a mixture of L-amino acids and D-amino acids. This is conventional in the art for producing such proteins or peptides.

The pore and/or helicase may also contain other non-specific modifications as long as they do not interfere with pore formation or helicase function. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

The pore and helicase can be produced using standard methods known in the art. Polynucleotide sequences encoding a pore or helicase may be derived and replicated using standard methods in the art. Polynucleotide sequences encoding a pore or helicase may be expressed in a bacterial host cell using standard techniques in the art. The pore and/or helicase may be produced in a cell by in situ expression of the polypeptide from a recombinant expression vector. The expression vector optionally carries an inducible promoter to control the expression of the polypeptide. These methods are described in described in Sambrook, J. and Russell, D. (2001). Molecular Cloning: A Laboratory Manual, 3rd Edition. Cold Spring Harbor Laboratory Press, Cold Spring Harbor, N.Y.

The pore and/or helicase may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured using the number of interactions between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem. Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interation with each nucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined 10 with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:
(a) contacting the target polynucleotide with a transmembrane pore and a RecD helicase such that the target polynucleotide moves through the pore and the RecD helicase controls the movement of the target polynucleotide through the pore; and
(b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from M to 1.4 M. The salt concentration is preferably from 150 mM to 1 M. As discussed above, RecD helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method is typically carried out in the presence of free nucleotides or free nucleotide analogues and an enzyme cofactor that facilitate the action of the helicase. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The target polynucleotide may be contacted with the RecD helicase and the pore in any order. In is preferred that, when the target polynucleotide is contacted with the RecD helicase and the pore, the target polynucleotide firstly forms a complex with the helicase. When the voltage is applied across the pore, the target polynucleotide/helicase complex then forms a complex with the pore and controls the movement of the polynucleotide through the pore.

As discussed above, RecD helicases may work in two modes with respect to the pore. First, the method is preferably carried out using the RecD helicase such that it moves the target sequence through the pore with the field resulting from the applied voltage. In this mode the 5' end of the DNA is first captured in the pore, and the enzyme moves the DNA into the pore such that the target sequence is passed through the pore with the field until it finally translocates through to the trans side of the bilayer. Alternatively, the method is preferably carried out such that the enzyme moves the target sequence through the pore against the field resulting from the applied voltage. In this mode the 3' end of the DNA is first captured in the pore, and the enzyme moves the DNA through the pore such that the target sequence is pulled out of the pore against the applied field until finally ejected back to the cis side of the bilayer.

The method of the invention most preferably involves a pore derived from MspA and a helicase comprising the sequence shown in SEQ ID NO: 61 or a variant thereof. Any of the embodiments discussed above with reference to MspA and SEQ ID NO: 61 may be used in combination.

Other Methods

The invention also provides a method of forming a sensor for characterising a target polynucleotide. The method comprises forming a complex between a pore and a RecD helicase. The complex may be formed by contacting the pore and the helicase in the presence of the target polynucleotide and then applying a potential across the pore. The applied potential may be a chemical potential or a voltage potential as described above. Alternatively, the complex may be formed by covalently attaching the pore to the helicase. Methods for covalent attachment are known in the art and disclosed, for example, in International Application Nos. PCT/GB09/001679 (published as WO 2010/004265) and PCT/GB10/000133 (published as WO 2010/086603). The complex is a sensor for characterising the target polynucleotide. The method preferably comprises forming a complex between a pore derived from Msp and a RecD helicase. Any of the embodiments discussed above with reference to the method of the invention equally apply to this method.

Kits

The present invention also provides kits for characterising a target polynucleotide. The kits comprise (a) a pore and (b) a RecD helicase. Any of the embodiments discussed above with reference to the method of the invention equally apply to the kits.

The kit may further comprise the components of a membrane, such as the phospholipids needed to form an amphiphilic layer, such as a lipid bilayer.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising a target polynucleotide. The apparatus comprises a plurality of pores and a plurality of a RecD helicase. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention.

The apparatus is preferably set up to carry out the method of the invention.

The apparatus preferably comprises:

a sensor device that is capable of supporting the membrane and plurality of pores and being operable to perform polynucleotide characterising using the pores and helicases;

at least one reservoir for holding material for performing the characterising;

a fluidics system configured to controllably supply material from the at least one reservoir to the sensor device; and a plurality of containers for receiving respective samples, the fluidics system being configured to supply the samples selectively from the containers to the sensor device. The apparatus may be any of those described in International Application No. PCT/GB08/004127 (published as WO 2009/077734), PCT/GB10/000789 (published as WO 2010/122293), International Application No. PCT/GB10/002206 (not yet published) or International Application No. PCT/US99/25679 (published as WO 00/28312).

Characterisation without a Pore

In some embodiments, the target polynucleotide is characterised, such as partially or completely sequenced, using a RecD helicase, but without using a pore. In particular, the invention also provides a method of characterising a target polynucleotide which comprises contacting the target polynucleotide with a RecD helicase such that the RecD helicase controls the movement of the target polynucleotide. In this method, the target polynucleotide is preferably not contacted with a pore, such as a transmembrane pore. The method involves taking one or more measurements as the RecD helicase controls the movement of the polynucleotide and thereby characterising the target polynucleotide. The measurements are indicative of one or more characteristics of the target polynucleotide. Any such measurements may be taken in accordance with the invention. They include without limitation: electrical measurements and optical measurements. These are discussed in detail above. Any of the embodiments discussed above with reference to the pore-based method of the invention may be used in the method lacking a pore. For instance, any of the RecD helicases discussed above may be used.

The invention also provides an analysis apparatus comprising a RecD helicase. The invention also provides a kit for characterising a target polynucleotide comprising (a) an analysis apparatus for characterising target polynucleotides and (b) a RecD helicase. These apparatus and kits preferably do not comprise a pore, such as a transmembrane pore. Suitable apparatus are discussed above.

The following Examples illustrate the invention.

Example 1

This example illustrates the use of a TraI helicase (TraI Eco; SEQ ID NO: 61) to control the movement of intact DNA strands through a nanopore. The general method and substrate employed throughout this example is shown in FIGS. 1A and 1B and described in the figure caption Materials and Methods Primers were designed to amplify a ~400 bp fragment of PhiX 174. Each of the 5'-ends of these primers included a 50 nucleotide non-complimentary region, either a homopolymeric stretch or repeating units of 10 nucleotide homopolymeric sections. These serve as identifiers for controlled translocation of the strand through a nanopore, as well as determining the directionality of translocation. In addition, the 5'-end of the forward primer was "capped" to include four 2'-O-Methyl-Uracil (mU) nucleotides and the 5'-end of the reverse primer was chemically phosphorylated. These primer modifications then allow for the controlled digestion of predominantly only the antisense strand, using lambda exonuclease. The mU capping protects the sense strand from nuclease digestion whilst the PO4 at the 5' of the antisense strand promotes it. Therefore after incubation with lambda exonuclease only the sense strand of the duplex remains intact, now as single stranded DNA (ssDNA). The generated ssDNA was then PAGE purified as previously described.

The DNA substrate design used in all the experiments described here is shown in FIG. 1B. The DNA substrate consists of a 400 base section of ssDNA from PhiX, with a 50T 5'-leader to aid capture by the nanopore (SEQ ID NO: 172). Annealed to this strand just after the 50T leader is a primer (SEQ ID NO: 173) containing a 3' cholesterol tag to enrich the DNA on the surface of the bilayer, and thus improve capture efficiency. An additional primer (SEQ ID NO: 174) is used towards the 3' end of the strand to aid the capture of the strand by the 3' end.

Buffered Solution: 400 mM NaCl, 10 mM Hepes, pH 8.0, 1 mM ATP, 1 mM $MgCl_2$, 1 mM DTT Nanopore: E. coli MS (B2)8 MspA ONLP3476 MS-(L88N/D90N/D91N/D93N/D118R/D134R/E139K)8

Enzyme: TraI Eco (SEQ ID NO: 61; ONLP3572, ~4.3 µM) 23.3 µl→100 nM final.

Electrical measurements were acquired from single MspA nanopores inserted in 1,2-diphytanoyl-glycero-3-phosphocholine lipid (Avanti Polar Lipids) bilayers. Bilayers were formed across ~100 µm diameter apertures in 20 µm thick PTFE films (in custom Delrin chambers) via the Montal-Mueller technique, separating two 1 mL buffered solutions. All experiments were carried out in the stated buffered solution. Single-channel currents were measured on Axopatch 200B amplifiers (Molecular Devices) equipped with 1440A digitizers. Ag/AgCl electrodes were connected to the buffered solutions so that the cis compartment (to which both nanopore and enzyme/DNA are added) is connected to the ground of the Axopatch headstage, and the trans compartment is connected to the active electrode of the headstage. After achieving a single pore in the bilayer, DNA polynucleotide and helicase were added to 50 µL of buffer and pre-incubated for 5 mins (DNA=12.0 nM, Enzyme=2 µM). This pre-incubation mix was added to 950 µL of buffer in the cis compartment of the electrophysiology chamber to initiate capture of the helicase-DNA complexes in the MspA nanopore (to give final concentrations of DNA=0.6 nM, Enzyme=0.1 µM). Helicase ATPase activity was initiated as required by the addition of divalent metal (1 mM $MgCl_2$) and NTP (1 mM ATP) to the cis compartment. Experiments were carried out at a constant potential of +140 mV.

Results and Discussion

The addition of Helicase-DNA substrate to MspA nanopores as shown in FIGS. 1A and 1B produces characteristic current blocks as shown in FIGS. 2, and 3A-3B. DNA without helicase bound interacts transiently with the nanopore producing short-lived blocks in current (<<1 second). DNA with helicase bound and active (ie. moving along the DNA strand under ATPase action) produces long characteristic block levels with stepwise changes in current as shown in FIGS. 2 and 3. Different DNA motifs in the nanopore give rise to unique current block levels. For a given substrate, we observe a characteristic pattern of current transitions that reflects the DNA sequence (examples in FIGS. 3A and 3B).

In the implementation shown in FIGS. 1A and 1B, the DNA strand is sequenced from a random starting point as the DNA is captured with a helicase at a random position along the strand.

Salt Tolerance

Nanopore strand sequencing experiments of this type generally require ionic salts. The ionic salts are necessary to create a conductive solution for applying a voltage offset to capture and translocate DNA, and to measure the resulting sequence dependent current changes as the DNA passes through the nanopore. Since the measurement signal is dependent on the concentration of the ions, it is advantageous to use high concentration ionic salts to increase the magnitude of the acquired signal. For nanopore sequencing salt concentrations in excess of 100 mM KCl are ideal, and salt concentrations of 400 mM KCl and above are preferred.

However, many enzymes (including some helicases and DNA motor proteins) do not tolerate high salt conditions. Under high salt conditions the enzymes either unfold or lose structural integrity, or fail to function properly. The current literature for known and studied helicases shows that almost all helicases fail to function above salt concentrations of approximately 100 mM KCl/NaCl, and there are no reported helicases that show correct activity in conditions of 400 mM KCl and above. While potentially halophilic variants of similar enzymes from halotolerant species exist, they are extremely difficult to express and purify in standard expression systems (e.g. E. coli).

We surprisingly show in this Example that TraI displays salt tolerance up to very high levels of salt. We find that the enzyme retains functionality in salt concentrations of 400 mM KCl through to 1 M KCl, either in fluorescence experiments or in nanopore experiments.

Forward and Reverse Modes of Operation

Most helicases move along single-stranded polynucleotide substrates in uni-directional manner, moving a specific number of bases for each NTPase turned over. Helicase movement can be exploited in different modes to feed DNA through the nanopore in a controlled fashion. FIGS. 1A and 1B illustrate two basic 'forward' and 'reverse' modes of operation. In the forward mode, the DNA is fed into the pore by the helicase in the same direction as the DNA would move under the force of the applied field. This direction is shown by the trans arrows. For TraI, which is a 5'-3' helicase, this requires capturing the 5' end of the DNA in the nanopore until a helicase contacts the top of the nanopore, and the DNA is then fed into the nanopore under the control of the helicase with the field from the applied potential, ie. moving from cis to trans. The reverse mode requires capturing the 3' end of the DNA, after which the helicase proceeds to pull the threaded DNA back out of the nanopore against the field from the applied potential, ie. moving from trans to cis. FIGS. 1A and 1B show these two modes of operation using TraI Eco.

Example 2

This example illustrates the salt tolerance of RecD helicases using a fluorescence assay for testing enzyme activity.

A custom fluorescent substrate was used to assay the ability of the helicase to displace hybridised dsDNA (FIG. 4A). As shown in 1) of FIG. 4A, the fluorescent substrate strand (50 nM final) has a 5' ssDNA overhang, and a 40 base section of hybridised dsDNA. The major upper strand has a carboxyfluorescein base at the 3' end, and the hybrised complement has a black-hole quencher (BHQ-1) base at the 5' end. When hybrised the fluorescence from the fluorescein is quenched by the local BHQ-1, and the substrate is essentially non-fluorescent. 1 µM of a capture strand that is complementary to the shorter strand of the fluorescent substrate is included in the assay. As shown in 2), in the presence of ATP (1 mM) and MgCl$_2$ (10 mM), helicase (100 nM) added to the substrate binds to the 5' tail of the fluorescent substrate, moves along the major strand, and displaces the complementary strand as shown. As shown in 3), once the complementary strand with BHQ-1 is fully displaced the fluorescein on the major strand fluoresces. As shown in 4), an excess of capture strand preferentially anneals to the complementary DNA to prevent re-annealing of initial substrate and loss of fluorescence.

Substrate DNA: SEQ ID NO: 175 with a carboxyfluorescein near the 3' end and SEQ ID NO: 176 with a Black Hole Quencher-1 at the 5' end Capture DNA: SEQ ID NO: 177

The graph in FIG. 4B shows the initial rate of activity of two RecD helicases (RecD Nth and Dth, SEQ IDs 28 and 35) in buffer solutions (100 mM Hepes pH 8.0, 1 mM ATP, 10 mM MgCl$_2$, 50 nM fluorescent substrate DNA, 1 µM capture DNA) containing different concentrations of KCl from 100 mM to 1 M. The helicase works at 1 M.

Example 3

In this Example, a different TraI helicase was used, namely TrwC Cba (SEQ ID NO: 65). All experiments were carried out as previously described in Example 1 under the same experimental conditions (pore=MspA B2, DNA=400mer SEQ ID NO: 172, 173 and 174, buffer-400 mM KCl, 10 mM Hepes pH 8.0, 1 mM DTT, 1 mM ATP, 1 mM MgCl$_2$). FIGS. 5A and 5B show two typical examples of helicase controlled DNA events using this enzyme.

Example 4

In this Example a number of different TrwC helicases (TrwC (Atr) (SEQ ID NO: 144), TrwC (Sal) (SEQ ID NO: 140), TrwC (Ccr) (SEQ ID NO: 136) and TrwC (Eco) (SEQ ID NO: 74)) were investigated for their ability to control the movement of DNA (SEQ ID NOs: 178, 179 (with/iSp18// iSp18//iSp18//iSp18//iSp18//iSp18/TT/3CholTEG/ at the 3' end) and 180) through an MspA nanopore (MS-(G75S/ G77S/L88N/D90N/D91N/D93N/D118R/Q126R/D134R/ E139K)8, i.e. 8×SEQ ID NO: 2 with G75S/G77S/L88N/ Q126R.

Materials and Methods

Buffered Solution: 625 mM KCl, 75 mM K Ferrocyanide, 25 mM K Ferricyanide, 100 mM Hepes at pH 8.0 for TrwC (Atr), TrwC (Eco) and TrwC (CcR), and at pH 9.0 for TrwC (Sal).

Enzyme: TrwC (Atr) (100 nM) or TrwC (Sal) (100 nM) or TrwC (Ccr) (100 nM) or TrwC (Eco) (100 nM) all at a final concentration of 100 nM Electrical measurements were acquired from single MspA nanopores inserted in 1,2-diphytanoyl-glycero-3-phosphocholine lipid (Avanti Polar Lipids) bilayers as described in Example 1, except platinum electrodes were used instead of Ag/AgCl. After achieving a single pore in the bilayer, MgCl$_2$ (10 mM) and dTTP (5 mM, for TrwC (Atr), TrwC (Ccr) and TrwC (Eco)) or ATP (1 mM for TrwC (Sal)) were added to the cis chamber and a control experiment was run for 5 mins at an applied potential of +120 mV. DNA polynucleotide (SEQ ID NO: 178 hybridized to 179 and 180, 0.1 nM) was added to the cis chamber and another control experiment was run for 5 mins at an applied potential of +120 mV. Finally, the appropriate helicase (TrwC (Atr), TrwC (Sal), TrwC (Ccr) or TrwC (Eco) all added at a final concentration of 100 nM) was added to the cis compartment of the electrophysiology chamber to initiate capture of the helicase-DNA complexes in the MspA nanopore. Experiments were carried out at a constant potential of +120 mV.

Results and Discussion

Helicase controlled DNA movement was observed for each of the helicases investigated. Example traces are shown in FIGS. 6 to 9 respectively.

Example 5

In this example, a number of different TrwC helicases (TrwC (Oma) (SEQ ID NO: 106), TrwC (Afe) (SEQ ID NO: 86), and TrwC (Mph) (SEQ ID NO: 94)) were investigated for their ability to control the movement of DNA (SEQ ID NOs: 172 to 174 for TrwC (Oma), and SEQ ID NO: 181 hybridized to SEQ ID NO: 182 (with a cholesterol tag at the 3' end) for TrwC (Afe) and TrwC (Mph)) through an MspA nanopore (MS-(G75S/G77S/L88N/D90N/D91N/D93N/ D118R/Q126R/D134R/E139K)8 i.e. 8×SEQ ID NO: 2 with G75S/G77S/L88N/Q126R.

Buffered Solution: 625 mM KCl, 75 mM K Ferrocyanide, 25 mM K Ferricyanide, 100 mM Hepes. pH8.0

Enzyme: TrwC (Oma), TrwC (Afe), and TrwC (Mph) all at a final concentration of 100 nM Electrical measurements were acquired from single MspA nanopores inserted in 1,2-diphytanoyl-glycero-3-phosphocholine lipid (Avanti Polar Lipids) bilayers as described in Example 1, except platinum electrodes were used instead of Ag/AgCl. After achieving a single pore in the bilayer, MgCl$_2$ (10 mM) were added to the cis chamber and a control experiment was run for 5 mins at an applied potential of 120 mV. 0.15 nM final of DNA polynucleotide (SEQ ID NOs: 172 to 174 (as in Example 1) for TrwC (Oma), or SEQ ID NO: 181 hybridized to 182 for TrwC (Afe) and TrwC (Mph)) and 100 nM final of the appropriate helicase (TrwC (Oma), TrwC (Afe), and TrwC (Mph) were added to the cis chamber and another control experiment was run for 10 mins at an applied potential of +120 mV. Finally, helicase ATPase activity was initiated by the addition of ATP (1 mM) to the cis compartment of the electrophysiology chamber. Experiments were carried out at a constant potential of +120 mV.

Results and Discussion

Helicase controlled DNA movement was observed for each of the helicases investigated. Example traces are shown in FIGS. 10 to 12 respectively.

The invention claimed is:

1. A method of directing the movement of a target polynucleotide through a transmembrane pore in an aqueous solution, the method comprising:
   (a) providing the transmembrane pore and a membrane in the aqueous solution, wherein the transmembrane pore is present in the membrane, and wherein the aqueous solution comprises a salt at a concentration in a range of 0.3 M to 1 M; and
   (b) combining in the aqueous solution of step (a) the target polynucleotide and a RecD helicase under conditions in which the helicase binds to the target polynucleotide and directs the movement of the target polynucleotide through the pore upon application of an electric potential difference across the pore.

2. A method according to claim 1, further comprising measuring ion flow through the transmembrane pore as the target polynucleotide moves through the pore.

3. A method according to claim 2, wherein the ion flow measurements comprise a current measurement, an impedance measurement, a tunneling measurement or a field effect transistor (FET) measurement.

4. A method according to claim 1, wherein the method further comprises the step of applying a voltage across the pore to form a complex between the pore and the helicase.

5. A method according to claim 1, wherein at least a portion of the polynucleotide is double stranded.

6. A method according to claim 1, wherein the pore is a protein pore or a solid state pore, optionally wherein the protein pore is selected from α-hemolysin, leukocidin, *Mycobacterium smegmatis* porin A (MspA), outer membrane porin F (OmpF), outer membrane porin G (OmpG), outer membrane phospholipase A, *Neisseria* autotransporter lipoprotein (NalP) and WZA.

7. A method according to claim 1, wherein the RecD helicase comprises an amino acid sequence selected from any one of SEQ ID NOs: 19, 20, 22, 23, 26, 27, 29, 31, 33, 34, 36, 38, 40, and 43.

8. A method according to claim 1, wherein the RecD helicase is a TraI helicase or TraI subgroup helicase, optionally wherein the TraI helicase or TraI subgroup helicase further comprises an amino acid sequence selected from any one of SEQ ID NOs: 62-64, 66, 68, 70-72, 75-77, 79-81, 83-85, 87-89, 91-93, 95-97, 99-101, 103-105, 107-109, 111, 115, 116, 118-120, 122, 123, 126-128, 130-132, 134, 135, 137-139, 141-143, 145, 146, 148-150, 153-155, 157-159, 161-163, 165-167, and 169-171.

9. A method according to claim 8, wherein the TraI helicase or TraI subgroup helicase comprises the following motifs:
   (a) GYAGVGKT (SEQ ID NO: 62), YAITAHGAQG (SEQ ID NO: 63) and HDTSRDQEPQLHTH (SEQ ID NO: 64).

10. A method according to claim 1, wherein the salt is KCl.

* * * * *